(12) United States Patent
Karp et al.

(10) Patent No.: US 11,052,221 B2
(45) Date of Patent: Jul. 6, 2021

(54) INFANT CALMING/SLEEP-AID DEVICE

(71) Applicant: Happiest Baby, Inc., Los Angeles, CA (US)

(72) Inventors: Harvey Neil Karp, Los Angeles, CA (US); Ted Larson, Los Angeles, CA (US); Robert Garbanati, Los Angeles, CA (US); Saryan Mikayel, Los Angeles, CA (US); Peter Fornell, Los Angeles, CA (US); Roy Kosuge, Los Angeles, CA (US); Joe Kopp, Los Angeles, CA (US)

(73) Assignee: HB Innovations, Inc., Los Angeles, CA (US)

( * ) Notice: Subject to any disclaimer, the term of this patent is extended or adjusted under 35 U.S.C. 154(b) by 259 days.

(21) Appl. No.: 16/342,050

(22) PCT Filed: Oct. 17, 2017

(86) PCT No.: PCT/US2017/057055
§ 371 (c)(1),
(2) Date: Apr. 15, 2019

(87) PCT Pub. No.: WO2018/075566
PCT Pub. Date: Apr. 26, 2018

(65) Prior Publication Data
US 2019/0247611 A1    Aug. 15, 2019

Related U.S. Application Data

(60) Provisional application No. 62/409,307, filed on Oct. 17, 2016.

(51) Int. Cl.
*A61M 21/02*    (2006.01)
*A47D 9/02*    (2006.01)
(Continued)

(52) U.S. Cl.
CPC .............. *A61M 21/02* (2013.01); *A47D 9/02* (2013.01); *A47D 13/063* (2013.01);
(Continued)

(58) Field of Classification Search
CPC ...... A61M 2240/00; A61M 2021/0022; A61M 2021/0027; A61M 2205/50; A61M 21/02;
(Continued)

(56) References Cited

U.S. PATENT DOCUMENTS

| 1,332,400 A | 3/1920 | Johnson |
| 1,897,258 A | 2/1933 | Jenne |

(Continued)

FOREIGN PATENT DOCUMENTS

| CA | 2459037 | 8/2005 |
| CA | 2760609 | 11/2010 |

(Continued)

OTHER PUBLICATIONS

Edge Banding, Kreg Newsletter, Nov. 2014, site visited Jun. 15, 2017, available online <URL:http://www.popularwoodworking.com/projects/iron-on-edge-banding>.
(Continued)

*Primary Examiner* — Christine H Matthews
*Assistant Examiner* — Joshua Daryl D Lannu
(74) *Attorney, Agent, or Firm* — Akerman LLP

(57) ABSTRACT

An infant calming/sleep-aid device that includes a moving platform and a sound generator, the sound and motion adapted to calm a fussy baby, induce sleep, and maintain sleep under normal conditions. The device makes a determination as to whether sound signals represent sound coming from inside the device or outside the device. If the sound signals are coming from the inside the device, then the signals are evaluated in a specified frequency band to determine whether the sound is a baby cry. If a determina-
(Continued)

tion is made that there is a baby cry, then a threshold analysis is performed to quantify the cry and compare it to a threshold value. If the cry is above a specified threshold, the device moves the platform and/or generates sound.

9 Claims, 80 Drawing Sheets

(51) Int. Cl.
  *G16H 50/30* (2018.01)
  *A47D 15/00* (2006.01)
  *G01H 17/00* (2006.01)
  *A47D 13/06* (2006.01)
  *A61M 21/00* (2006.01)

(52) U.S. Cl.
  CPC .......... *A47D 15/008* (2013.01); *G01H 17/00* (2013.01); *G16H 50/30* (2018.01); *A61M 2021/0022* (2013.01); *A61M 2021/0027* (2013.01); *A61M 2205/3375* (2013.01); *A61M 2205/50* (2013.01); *A61M 2240/00* (2013.01)

(58) Field of Classification Search
  CPC ............. A61M 2205/3375; A47D 9/02; A47D 15/008; A47D 13/063; G01H 17/00; G16H 50/30
  See application file for complete search history.

(56) References Cited

U.S. PATENT DOCUMENTS

| | | |
|---|---|---|
| D90,696 S | 9/1933 | Caldwell |
| D128,488 S | 7/1941 | Buckner |
| D158,030 S | 4/1950 | Wagner |
| 2,508,110 A | 5/1950 | Hansen |
| 2,523,422 A | 9/1950 | Dunn |
| 2,808,828 A | 10/1957 | Rubin |
| 2,873,458 A | 2/1959 | Adamson |
| 2,974,325 A | 3/1961 | Mango |
| 2,992,440 A | 7/1961 | Revolt |
| 3,146,736 A | 9/1964 | Hetrick |
| 3,536,067 A | 10/1970 | Sternagel |
| D224,822 S | 9/1972 | Lee, Jr. |
| 3,789,439 A | 2/1974 | Berg |
| D232,279 S | 8/1974 | White |
| 3,886,607 A | 6/1975 | Dunn |
| D244,890 S | 7/1977 | Adams |
| 4,196,484 A | 4/1980 | Harris |
| 4,553,485 A | 11/1985 | Lee |
| 4,611,353 A | 9/1986 | Als et al. |
| 4,619,270 A | 10/1986 | Margolis |
| 4,750,223 A | 6/1988 | D'Arcy |
| 4,934,997 A | 6/1990 | Skakas |
| 4,975,997 A | 12/1990 | Misiura et al. |
| D316,339 S | 4/1991 | Taylor |
| 5,037,375 A | 8/1991 | Gatts |
| D320,316 S | 10/1991 | Arnold |
| 5,129,406 A | 7/1992 | Magnuson et al. |
| 5,183,457 A | 2/1993 | Gatts et al. |
| 5,228,155 A | 7/1993 | Shultz |
| 5,295,490 A | 3/1994 | Dodakian |
| 5,311,622 A | 5/1994 | Allen |
| 5,381,569 A | 1/1995 | Church |
| 5,384,922 A | 1/1995 | Jobe |
| 5,385,153 A | 1/1995 | Jamieson et al. |
| 5,398,353 A | 3/1995 | Sachathamakul |
| D367,979 S | 3/1996 | Lewis |
| 5,577,450 A | 11/1996 | Huang |
| 5,640,717 A | 6/1997 | Ray |
| 5,668,780 A | 9/1997 | Hsieh |
| 5,684,460 A | 11/1997 | Scanlon |
| 5,706,533 A | 1/1998 | Opheim |
| 5,711,045 A | 1/1998 | Caster et al. |
| 5,806,113 A | 9/1998 | McMahan et al. |
| D401,454 S | 11/1998 | De Blaay |
| 5,845,350 A | 12/1998 | Beemiller et al. |
| 5,852,827 A | 12/1998 | Lear et al. |
| 5,855,031 A | 1/1999 | Swift |
| 5,881,408 A | 3/1999 | Bashista et al. |
| 5,931,534 A | 8/1999 | Flutter |
| D413,454 S | 9/1999 | Kasem |
| D417,090 S | 11/1999 | Reynolds |
| D418,440 S | 1/2000 | Dallaire |
| 6,009,576 A | 1/2000 | Gramme et al. |
| 6,011,477 A | 1/2000 | Teodorescu et al. |
| 6,068,566 A | 5/2000 | Kim |
| 6,146,332 A | 11/2000 | Pinsonneault |
| 6,148,455 A | 11/2000 | Kasem |
| 6,155,976 A | 12/2000 | Sackner et al. |
| 6,280,392 B1 | 8/2001 | Yoshimi et al. |
| 6,343,994 B1 | 2/2002 | Clarke |
| 6,386,986 B1 | 5/2002 | Sonner |
| 6,393,612 B1 | 5/2002 | Thach et al. |
| 6,415,442 B1 | 7/2002 | Smith et al. |
| 6,498,652 B1 | 12/2002 | Varshneya et al. |
| 6,588,033 B1 | 7/2003 | Welsh, Jr. |
| 6,594,834 B2 | 7/2003 | Fenty |
| 6,652,469 B2 | 11/2003 | Pinsonnault |
| 6,662,390 B1 | 12/2003 | Berger et al. |
| 6,839,924 B2 | 1/2005 | Sims et al. |
| 6,868,566 B2 | 3/2005 | Gatten et al. |
| 6,907,626 B1 | 6/2005 | Welsh |
| 6,916,249 B2 | 7/2005 | Meade |
| 6,928,674 B2 | 8/2005 | Blackburn |
| 6,966,082 B2 | 11/2005 | Bloemer et al. |
| D512,466 S | 12/2005 | White |
| 6,978,479 B2 | 12/2005 | Thach et al. |
| D518,942 S | 4/2006 | Dandrea |
| 7,043,783 B2 | 5/2006 | Gatten et al. |
| 7,076,819 B2 | 7/2006 | Trani et al. |
| D526,133 S | 8/2006 | Song |
| 7,100,724 B2 | 9/2006 | Haigh et al. |
| 7,123,758 B2 | 10/2006 | Mostafavi et al. |
| D536,191 S | 2/2007 | Kasem |
| D536,550 S | 2/2007 | Kasem |
| 7,181,789 B2 | 2/2007 | Gatten et al. |
| 7,203,981 B1 | 4/2007 | Cowgill et al. |
| 7,246,392 B2 | 7/2007 | Schmid et al. |
| D561,978 S | 2/2008 | Soulides |
| 7,337,482 B2 | 3/2008 | Byrne et al. |
| 7,347,806 B2 | 3/2008 | Nakano et al. |
| 7,406,725 B2 | 8/2008 | Martin et al. |
| 7,427,921 B2 | 9/2008 | Van |
| 7,485,086 B2 | 2/2009 | Dickie et al. |
| 7,587,769 B1 | 9/2009 | McDermott et al. |
| 7,587,772 B2 | 9/2009 | Ward et al. |
| D605,870 S | 12/2009 | Bergkvist |
| D606,282 S | 12/2009 | Chen |
| 7,685,657 B1 | 3/2010 | Hernandez et al. |
| D613,091 S | 4/2010 | Taylor |
| 7,722,118 B2 | 5/2010 | Bapst et al. |
| D616,665 S | 6/2010 | Dumais |
| 7,743,442 B2 | 6/2010 | Maloney et al. |
| 7,774,875 B1 | 8/2010 | Zeidman et al. |
| 7,785,257 B2 | 8/2010 | Mack et al. |
| 7,857,677 B2 | 12/2010 | Kamm |
| 7,918,505 B2 | 4/2011 | King et al. |
| D640,483 S | 6/2011 | Daley et al. |
| 7,954,187 B1 | 6/2011 | Earnest et al. |
| D644,413 S | 9/2011 | Keall |
| 8,011,037 B1 | 9/2011 | Earnest et al. |
| 8,032,958 B2 | 10/2011 | Pieta et al. |
| D650,153 S | 12/2011 | Chopak et al. |
| 8,083,601 B2 | 12/2011 | Speedie et al. |
| 8,096,960 B2 | 1/2012 | Loree et al. |
| 8,112,835 B2 | 2/2012 | Eirich et al. |
| 8,141,186 B2 | 3/2012 | Jackson et al. |
| 8,191,188 B2 | 6/2012 | Kaplan et al. |
| 8,197,005 B2 | 6/2012 | Hopke et al. |
| 8,239,984 B2 | 8/2012 | Hopke et al. |
| 8,269,625 B2 | 9/2012 | Hoy et al. |
| D669,659 S | 10/2012 | Barski |

(56) References Cited

U.S. PATENT DOCUMENTS

| | | |
|---|---|---|
| 8,302,225 B1 | 11/2012 | Earnest et al. |
| 8,321,980 B2 | 12/2012 | Maloney et al. |
| D674,614 S | 1/2013 | Morand |
| 8,347,432 B2 | 1/2013 | Schmid et al. |
| 8,365,325 B2 | 2/2013 | Schneider et al. |
| 8,375,486 B2 | 2/2013 | Earnest et al. |
| D678,693 S | 3/2013 | Bergkvist |
| 8,395,510 B1 | 3/2013 | Kirk |
| 8,398,538 B2 | 3/2013 | Dothie et al. |
| 8,429,771 B2 | 4/2013 | Long et al. |
| 8,522,375 B2 | 9/2013 | Conrad et al. |
| 8,539,620 B1 | 9/2013 | Wynh et al. |
| D692,209 S | 10/2013 | Dragu |
| 8,555,414 B2 | 10/2013 | Davis et al. |
| 8,561,227 B2 | 10/2013 | Jenkins et al. |
| D696,486 S | 12/2013 | Barski |
| 8,607,364 B2 | 12/2013 | Barski et al. |
| 8,607,366 B2 | 12/2013 | Austin |
| 8,661,582 B2 | 3/2014 | Sclare et al. |
| 8,667,631 B2 | 3/2014 | Coates et al. |
| 8,695,133 B2 | 4/2014 | Christensen et al. |
| 8,726,437 B2 | 5/2014 | Hardesty et al. |
| 8,745,794 B1 | 6/2014 | McDermott |
| 8,756,731 B1 | 6/2014 | Huttner et al. |
| 8,769,737 B1 | 7/2014 | Duggins et al. |
| 8,776,265 B2 | 7/2014 | Neveu et al. |
| 8,777,311 B1 | 7/2014 | Laurel et al. |
| 8,782,831 B2 | 7/2014 | Houston et al. |
| 8,784,227 B2 | 7/2014 | Speedie et al. |
| D715,027 S | 9/2014 | Haut et al. |
| 8,827,366 B2 | 9/2014 | Daley et al. |
| 8,832,880 B2 | 9/2014 | Sheard et al. |
| 8,845,440 B2 | 9/2014 | Hayt et al. |
| 8,863,329 B2 | 10/2014 | Sofia-Mcintire et al. |
| D718,017 S | 11/2014 | Barski |
| 8,898,833 B2 | 12/2014 | Coates et al. |
| 8,904,580 B1 | 12/2014 | Christensen et al. |
| 8,910,332 B2 | 12/2014 | Buckson |
| 8,942,783 B2 | 1/2015 | Cervantes et al. |
| 8,943,625 B2 | 2/2015 | Gotel et al. |
| 9,003,564 B2 | 4/2015 | Wynh |
| 9,020,622 B2 | 4/2015 | Shoham et al. |
| D728,198 S | 5/2015 | Barski |
| D728,199 S | 5/2015 | Barski |
| 9,032,963 B2 | 5/2015 | Grissom |
| 9,069,549 B2 | 6/2015 | Buckson |
| D734,592 S | 7/2015 | Castillo et al. |
| 9,119,423 B2 | 9/2015 | Gotel et al. |
| 9,131,734 B2 | 9/2015 | Daugherty et al. |
| D741,046 S | 10/2015 | Pelekanou |
| 9,155,403 B2 | 10/2015 | Mountz et al. |
| D742,097 S | 11/2015 | Dunn |
| 9,179,711 B2 | 11/2015 | Krawchuk |
| D751,847 S | 3/2016 | Brown |
| 9,392,881 B1 | 7/2016 | Schmelzle |
| D780,472 S | 3/2017 | Behar |
| 9,962,012 B1 | 5/2018 | Schmid et al. |
| D825,219 S | 8/2018 | Karp et al. |
| 2002/0016991 A1 | 2/2002 | Brown |
| 2002/0100116 A1 | 8/2002 | Richards et al. |
| 2003/0229942 A1 | 12/2003 | Dilascio |
| 2004/0070254 A1 | 4/2004 | Conlon et al. |
| 2004/0078895 A1 | 4/2004 | Elling et al. |
| 2005/0022284 A1 | 2/2005 | Thach |
| 2005/0091743 A1 | 5/2005 | Bloemer et al. |
| 2005/0120459 A1 | 6/2005 | McConnell et al. |
| 2005/0210592 A1 | 9/2005 | Littlehorn et al. |
| 2005/0283908 A1 | 12/2005 | Wong et al. |
| 2006/0025226 A1 | 2/2006 | Nakano et al. |
| 2006/0042013 A1 | 3/2006 | Madsen |
| 2006/0084514 A1 | 4/2006 | Speedie et al. |
| 2006/0096031 A1 | 5/2006 | Foster |
| 2006/0225206 A1 | 10/2006 | Kasem |
| 2007/0056109 A1 | 3/2007 | Forshpan et al. |
| 2007/0060015 A1 | 3/2007 | Glatt et al. |
| 2007/0061968 A1 | 3/2007 | Fader |
| 2007/0085695 A1 | 4/2007 | Nerurkar et al. |
| 2007/0111809 A1 | 5/2007 | Bellows et al. |
| 2007/0267904 A1 | 11/2007 | Clapper et al. |
| 2008/0077020 A1 | 3/2008 | Young et al. |
| 2008/0136236 A1 | 6/2008 | Kincaid et al. |
| 2008/0196164 A1 | 8/2008 | Calilung |
| 2008/0217150 A1 | 9/2008 | Chen |
| 2008/0314665 A1 | 12/2008 | Sanders et al. |
| 2009/0062622 A1 | 3/2009 | Lin et al. |
| 2009/0064390 A1 | 3/2009 | Beiring et al. |
| 2009/0131185 A1 | 5/2009 | Speedie |
| 2009/0206642 A1 | 8/2009 | Raphael et al. |
| 2010/0044164 A1 | 2/2010 | Thorne |
| 2010/0201171 A1 | 8/2010 | Velderman et al. |
| 2010/0218299 A1 | 9/2010 | Damir |
| 2010/0228315 A1 | 9/2010 | Nielsen |
| 2010/0231421 A1 | 9/2010 | Rawls-Meehan |
| 2010/0253504 A1 | 10/2010 | Lliteras et al. |
| 2010/0257654 A1 | 10/2010 | Waters et al. |
| 2010/0275373 A1 | 11/2010 | Kaplan |
| 2010/0298742 A1 | 11/2010 | Perlman |
| 2010/0328075 A1 | 12/2010 | Rahamim et al. |
| 2011/0025915 A1 | 2/2011 | Daban et al. |
| 2011/0032103 A1 | 2/2011 | Bhat et al. |
| 2011/0078855 A1 | 4/2011 | Buckson et al. |
| 2011/0099719 A1 | 5/2011 | Hardesty et al. |
| 2011/0116549 A1 | 5/2011 | Riddiford et al. |
| 2011/0179546 A1* | 7/2011 | Millette ............... A41B 13/06 2/75 |
| 2011/0277210 A1 | 11/2011 | Hardesty et al. |
| 2011/0308011 A1 | 12/2011 | Cheng |
| 2012/0025992 A1 | 2/2012 | Tallent et al. |
| 2012/0083670 A1 | 4/2012 | Rotondo |
| 2012/0125347 A1 | 5/2012 | Soileau et al. |
| 2012/0216349 A1 | 8/2012 | Kaplan et al. |
| 2012/0297518 A1 | 11/2012 | Aiken et al. |
| 2012/0311762 A1 | 12/2012 | Aiken et al. |
| 2013/0123654 A1 | 5/2013 | Rahamim et al. |
| 2013/0139290 A1 | 6/2013 | Barski et al. |
| 2013/0165809 A1 | 6/2013 | Abir |
| 2013/0185867 A1 | 7/2013 | Long et al. |
| 2014/0059762 A1 | 3/2014 | Bonczek |
| 2014/0068834 A1 | 3/2014 | Skinner |
| 2014/0130254 A1 | 5/2014 | Jeong |
| 2014/0163343 A1 | 6/2014 | Heneghan et al. |
| 2014/0173822 A1 | 6/2014 | Doering et al. |
| 2014/0249382 A1 | 9/2014 | Bhat et al. |
| 2014/0250558 A1 | 9/2014 | Russo |
| 2014/0250592 A1* | 9/2014 | Karp ..................... A47D 9/02 5/108 |
| 2014/0265480 A1 | 9/2014 | Perrin et al. |
| 2014/0339867 A1 | 11/2014 | Daley et al. |
| 2014/0345042 A1 | 11/2014 | Morand |
| 2015/0026886 A1 | 1/2015 | Gangan |
| 2015/0045608 A1 | 2/2015 | Karp et al. |
| 2015/0059089 A1 | 3/2015 | Falkiner |
| 2015/0126819 A1 | 5/2015 | Cervantes |
| 2015/0196137 A1 | 7/2015 | Zhao et al. |
| 2015/0250330 A1 | 9/2015 | Mountz et al. |
| 2015/0250419 A1 | 9/2015 | Cooper et al. |
| 2016/0128392 A1 | 5/2016 | Krawchuk |
| 2016/0165961 A1 | 6/2016 | Karp |
| 2016/0166081 A1 | 6/2016 | Karp et al. |
| 2016/0174619 A1 | 6/2016 | Waters |
| 2016/0174728 A1 | 6/2016 | Karp et al. |
| 2016/0310067 A1 | 10/2016 | Heinrich et al. |
| 2017/0043117 A1 | 2/2017 | Karp et al. |
| 2017/0043118 A1 | 2/2017 | Karp et al. |

FOREIGN PATENT DOCUMENTS

| | | |
|---|---|---|
| CA | 2848529 | 3/2013 |
| CA | 2918029 | 4/2016 |
| CN | 1701732 A | 11/2005 |
| CN | 1759897 A | 4/2006 |
| CN | 101036556 A | 9/2007 |
| CN | 201042329 A | 4/2008 |
| CN | 2018085348 Y | 7/2008 |

(56) References Cited

FOREIGN PATENT DOCUMENTS

| | | |
|---|---|---|
| CN | 101756556 A | 6/2010 |
| CN | 201664114 U | 12/2010 |
| CN | 201718870 U | 1/2011 |
| CN | 102727004 A | 10/2012 |
| EP | 0617907 | 6/1997 |
| EP | 1435810 | 7/2004 |
| EP | 1748711 | 2/2007 |
| EP | 2617329 | 7/2013 |
| EP | 2197322 | 2/2014 |
| EP | 2292124 | 7/2014 |
| EP | 2768345 | 8/2014 |
| EP | 2915459 | 9/2015 |
| EP | 292812 | 10/2015 |
| EP | 2756136 | 8/2016 |
| EP | 3081117 | 10/2016 |
| FR | 2669201 | 5/1992 |
| GB | 2312374 | 10/1997 |
| JP | 07275091 | 10/1995 |
| JP | 07289394 | 11/1995 |
| JP | 2000510022 | 8/2000 |
| KR | 1020040097883 | 11/2004 |
| KR | 20060019024 A | 3/2006 |
| KR | 1020060079587 | 7/2006 |
| KR | 20090121797 A | 11/2009 |
| KR | 1020120081799 | 7/2012 |
| NO | 2013038248 | 3/2013 |
| NO | 2016055946 | 4/2016 |
| WO | 199817150 A2 | 4/1998 |
| WO | 2004107927 A1 | 12/2004 |
| WO | 2007062499 | 6/2007 |
| WO | 2010098702 | 9/2010 |
| WO | 2013059625 | 4/2013 |
| WO | 2013087955 | 6/2013 |
| WO | 2013135975 | 9/2013 |
| WO | 2013188810 | 12/2013 |
| WO | 2014078442 | 5/2014 |
| WO | 2015017709 | 2/2015 |
| WO | 2015-078937 A1 | 6/2015 |
| WO | 2015143430 | 9/2015 |
| WO | 2016096518 | 6/2016 |
| WO | 2016123619 | 8/2016 |
| WO | 2016138441 | 9/2016 |

OTHER PUBLICATIONS

Iron-on Edge Banding, Popular Woodworking Magazine, Sep. 19, 2008, site visited Jun. 15, 2017, available online <URL:http://www.popularwoodworking.com/projects/iron-on-edge-banding>.
Oval Crib, Fine Woodworking, http://www.finewoodworking.com/readerprojectJ2009/11/11/oval-crib, Nov. 11, 2009.
SNOO Bassinet, Can this High-Tech Bassinet Keep Sleep-Deprived Parents Sane?, The Wall Street Journal, http://www.wsj.com/articles/can-this-high-tech-bassinet-keep-sleep-deprived-parents-sane, Oct. 18, 2018.
Office Action issued in Australian Application No. 2012325947, dated Aug. 22, 2016.
Office Action issued in Mexican Patent Application No. MX/a/2014/004648, dated Mar. 24, 2017.
Extended European search report issued in European Patent Application No. 14831425.5, dated Feb. 24, 2017.
Putting Baby in SNOO Sack, https://www.youtube.com/watch?v=NvTIOzWxG80, Oct. 28, 2016.
About SUID and SIDS, Centers for Disease Control and Prevention, http://www.cdc.gov/sids/ aboutsuidandsids.htm, Oct. 3, 2016, (accessed Nov. 3, 2016), 2 pages.
'Infant Sleep Forum Posting, http://www.sleepnet.com/ infant/messages/501.html, (accessed Mar. 16, 2015), 2 pages.
Safety Standard for Bassinets and Cradles; Correction, Federal Register, vol. 78, No. 247, https://www.bderalregistergov/documents/2013/12/24/2013-30527/safety-standard-for-bassinets-and-cradles-correction (accessed Nov. 10, 2016), Consumer Product Safety Commission, Dec. 24, 2013, 1 page.
Safety Standard for Bassinets and Cradles; Correction, Federal Register, vol. 78, No. 205, https://www.bderalregistergov/documents/2013/10/23/2013-24203/safety-standard-for-bassinets-and-cradles (accessed Nov. 10, 2016), Consumer Product Safety Commission, Oct. 23, 2013, 18 pages.
Safety Standard for Bedside Sleepers, Federal Register, vol. 79, No. 10, https://www.federalregister.gov/documents/2014/01/15/2014-00597/safety-standard-for-bedside-sleepers, (accessed Nov. 10, 2016), Consumer Product Safety Commission, Jan. 15, 2014, 9 pages.
SIDS and Other Sleep-Related Infant Deaths: Expansion of Recommendations for a Safe Infant Sleeping Environment, Task Force on Sudden Infant Death Syndrome, Pediatrics, vol. 128, No. 5, Nov. 2011, pp. e1341, 29 pages.
EP Application No. 12781007.5, Examination Notification Art. 94(3) dated May 5, 2015, Unacuna, LLC, 3 Pages.
AAP Task Force on SIDS, The Changing Concept of Sudden Infant Death Syndrome: Diagnostic Coding Shifts, Controversies Regarding the Sleeping Environment, and New Variables to Consider in Reducing Risk, Peds, vol. 116, 2005, pp. 1245-1255.
Ariagno, et al., Fewer spontaneous arousals during prone sleep in preterm infants at 1 and 3 months corrected age, Journal of Perinatology, vol. 26, 2006, pp. 306-312.
Carpenter, et al., Sudden unexplained infant death in 20 regions in Europe: case control study, The Lancet, vol. 363, No. 9404, 2004, pp. 185-191.
Colvin, et al., Sleep Environment Risks for Younger and Older Infants, Pediatrics, vol. 134, Jul. 2014, pp. e406-e412.
Galland, et al., Prone versus supine sleep position: a review of the physiological studies in SIDS research, J Paediatr Child Health. vol. 38, No. 4, Aug. 2002, pp. 332-338.
Groswasser, et al., Reduced arousals following obstructive apneas in infants sleeping prone, Pediatric Research, vol. 49, No. 3, 2001, pp. 402-406.
Horne, et al., Effects of body position on sleep and arousal characteristics in infants, Early Human Development, vol. 69, iss. 1-2, Oct. 2002, pp. 25-33.
Horne, et al., The prone sleeping position impairs arousability in term infants, The Journal of Pediatrics, vol. 138, No. 6, 2001, pp. 811-816.
Kato, et al., Spontaneous Arousability in Prone and Supine Position in Healthy Infants, Sleep, vol. 29, No. 6, 2006, pp. 785-790.
L'Hoir, et al., Risk and preventive factors for cot death in The Netherlands, a low-incidence country, Eur J Pediatr, fol. 157, 1998, pp. 681-688.
Li et al., Infant Sleeping Position and the Risk of Sudden Infant Death Syndrome in California, 1997-2000, Am J Epidemiol, vol. 157, No. 5, 2003, pp. 446-455.
McDonnell, et al., Infant Deaths and Injuries Associated with Wearable Blankets, Swaddle Wraps, and Swaddling, J. Pediatr., vol. 164, No. 5, May 2014, pp. 1152-1156.
Mitchell, et al., Changing Infants' Sleep Position Increases Risk of Sudden Infant Death Syndrome, Arch Ped Adol Med., vol. 153, 1999, pp. 1136-1141.
Oyen, et al., Combined effects of sleeping position and prenatal risk factors in sudden infant death syndrome: the Nordic Epidemiological SIDS Study, Pediatrics, vol. 100, No. 4, 1997, pp. 613-621.
International Preliminary Report on Patentability With Written Opinion for PCT/US2012/061069, dated May 1, 2014.
International Search Report and Written Opinion for PCT/US2012/061069, dated Mar. 11, 2012.
International Preliminary Report on Patentability for PCT/US2014/049253, dated Feb. 11, 2016.
International Search Report and Written Opinion for PCT/US2014/049253, dated Nov. 24, 2014.
International Search Report and Written Opinion for PCT/US2016/019878. dated May 6, 2016.
Pease, et al., Swaddling and the Risk of Sudden Infant Death Syndrome: A Meta-analysis, Pediatrics, vol. 137, No. 3, Jun. 2016, pp. e20153275 (11 pages).
Ponsonby, et al., Factors potentiating the risk of Sudden Infant Death Syndrome associated with the Prone Position, NEJM, vol. 329, 1993, pp. 377-382.

(56) References Cited

OTHER PUBLICATIONS

Shapiro-Mendoza, et al., Trends in Infant Bedding Use: National Infant Sleep Position Study, 1993-2010, Pediatrics, vol. 135, 2015, pp. 10-17.
Tuladhar, et al., Effects of sleep position, sleep state and age on heart rate responses following provoked arousal n term infants, Early human development, vol. 71, iss. 2, Apr. 2003, pp. 157-169.
Vennemann, et al., Sleep Environment Risk Factors for Sudden Infant Death Syndrome: The German Sudden Infant Death Syndrome Study, Pediatrics, vol. 123, No. 4, Apr. 2009, pp. 1162-1170.
International Search Report and Written Opinion for PCT/US2019/019010, dated May 24, 2019.
Internal Search Report dated Feb. 1, 2018 issued in connection with PCT/US17/57055.
Written Opinion dated Jan. 24, 2018 issued in connection with PCT/US17/57055.
Office Action issued in KR 10-2019-7011162 dated Sep. 22, 2020.
Office Action issued in EP 17861301.4 dated Nov. 24, 2020.

* cited by examiner

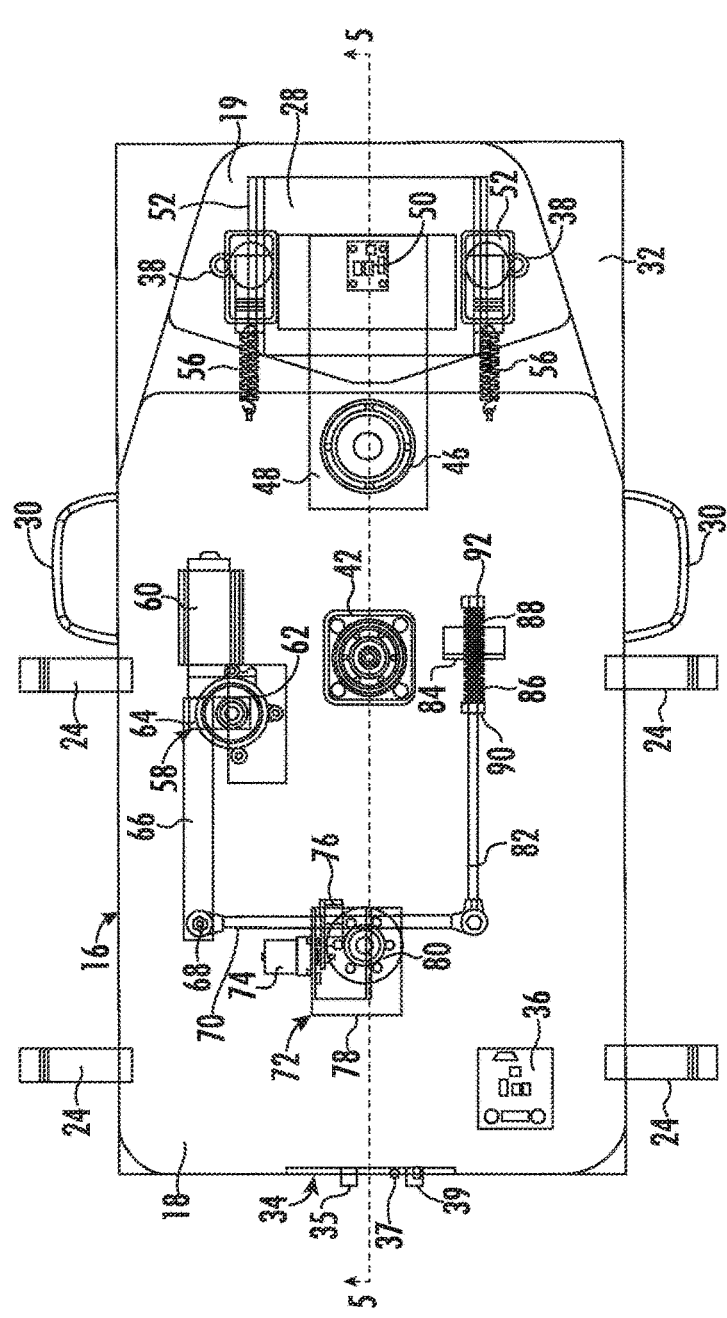

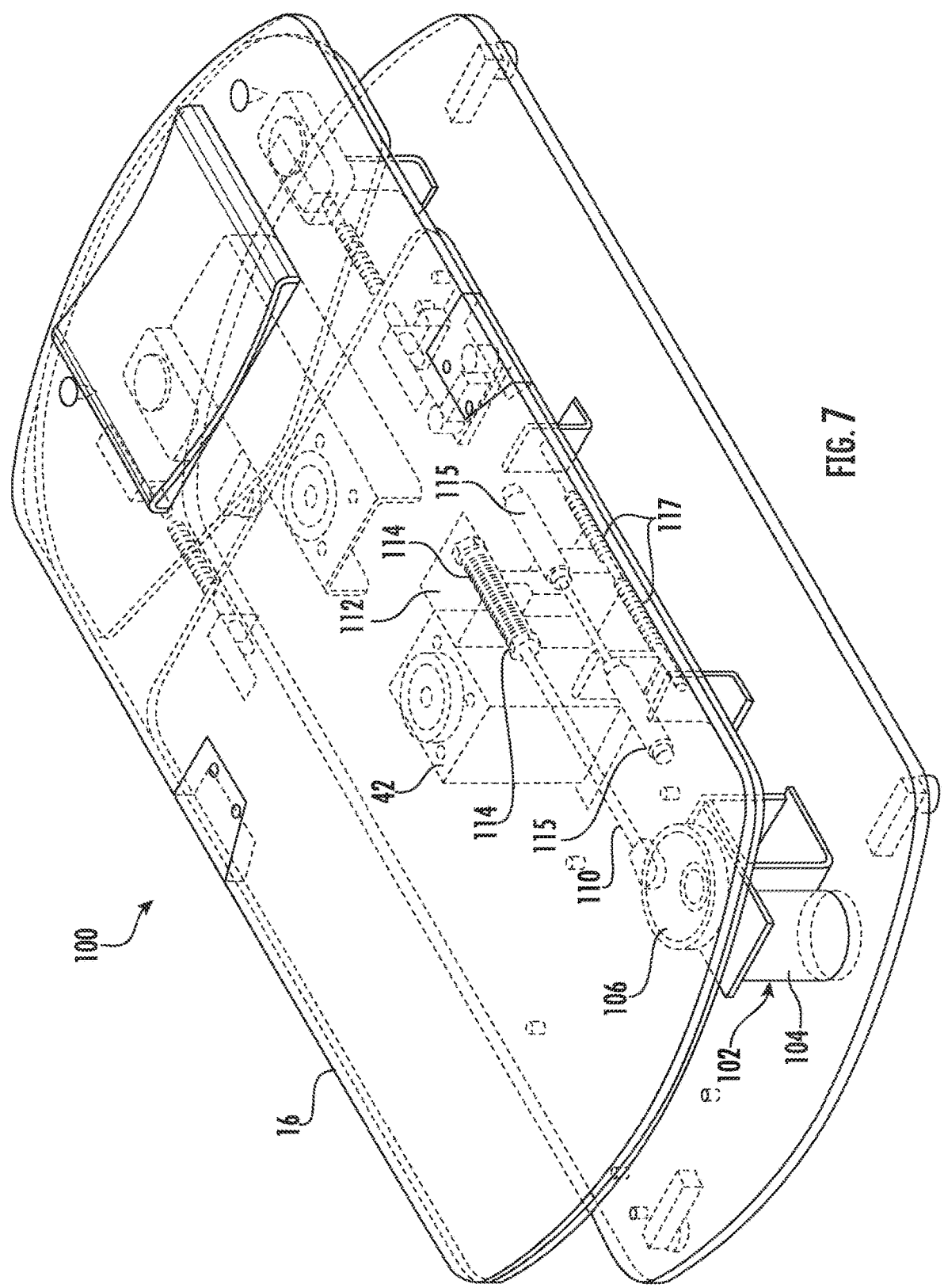

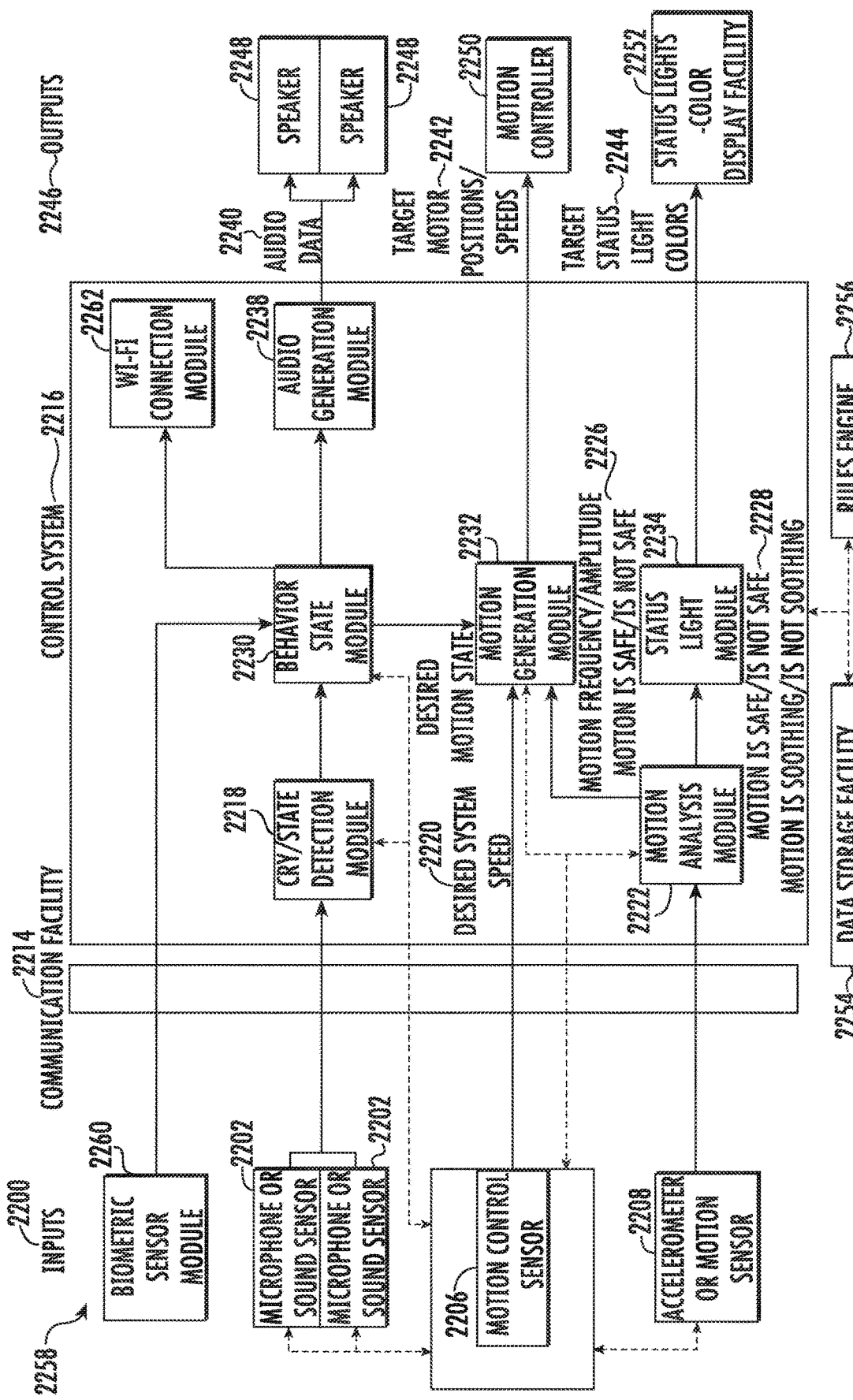

EXAMPLE OF FREQUENCY WINDOW REMOVED FROM
WHITE NOISE FILE

IF AVERAGE OVER ROLLING 6 SECONDS
GREATER THAN PREDETERMINED THRESHOLD
VALUE AT EACH STATE;
THEN REPORT CRY

| START AGE | <0-0.5 MO. | 0.5-4 MO.* | 4+ MO. | |
|---|---|---|---|---|
| HOURS OF SLEEP/DAY | 16.00 | 15.50 | 14.25 | |
| % OF SLEEP TIME IN SLEEPER | 90% | 90% | 85% | |
| ESTIMATED DAYS OF USE* | 30.00 | 105.00 | 90.00 | 225.00 |
| MOTION VALUES (Hz) | | | | LED COLOR |
| BASELINE | 0.50 | 0.50 | | BLUE |
| LEVEL 1 | 1.00 | 1.00 | | PURPLE |
| LEVEL 2 | 1.75 | 1.75 | 1.75 | GREEN |
| LEVEL 3 | 2.80 | 2.80 | 2.80 | YELLOW |
| LEVEL 4 | | 3.50 | 3.50 | ORANGE |
| PRETIMEOUT | | 3.50 | 3.50 | ORANGE |
| TIMEOUT | | | | RED |
| AMPLITUDE (INCHES EACH SIDE) | | | | |
| BASELINE | 1.00 | 1.00 | | |
| LEVEL 1 | 1.00 | 1.00 | | |
| LEVEL 2 | 0.70 | 0.70 | 0.70 | |
| LEVEL 3 | 0.50 | 0.50 | 0.50 | |
| LEVEL 4 | | 0.30 | 0.30 | |
| PRETIMEOUT | | 0.30 | 0.30 | |
| TIMEOUT | | | | |
| AUDIO VALUES (dB) | | | | |
| BASELINE | RoR1:65 | RoR1:65 | RoR1:65 | |
| LEVEL 1 | RoR2:70 | RoR2:70 | RoR2:70 | |
| LEVEL 2 | SHD1:74 | SHD1:74 | SHD1:74 | |
| LEVEL 3 | SHD2:78 | SHD2:78 | SHD2:78 | |
| LEVEL 4 | | FnV 85 | FnV 85 | |
| PRETIMEOUT | | FnV 85 | FnV 85 | |
| TIMEOUT | | | | |

*USED FOR DEFAULT, IF NO BABY AGE IS SET

FIG. 22I

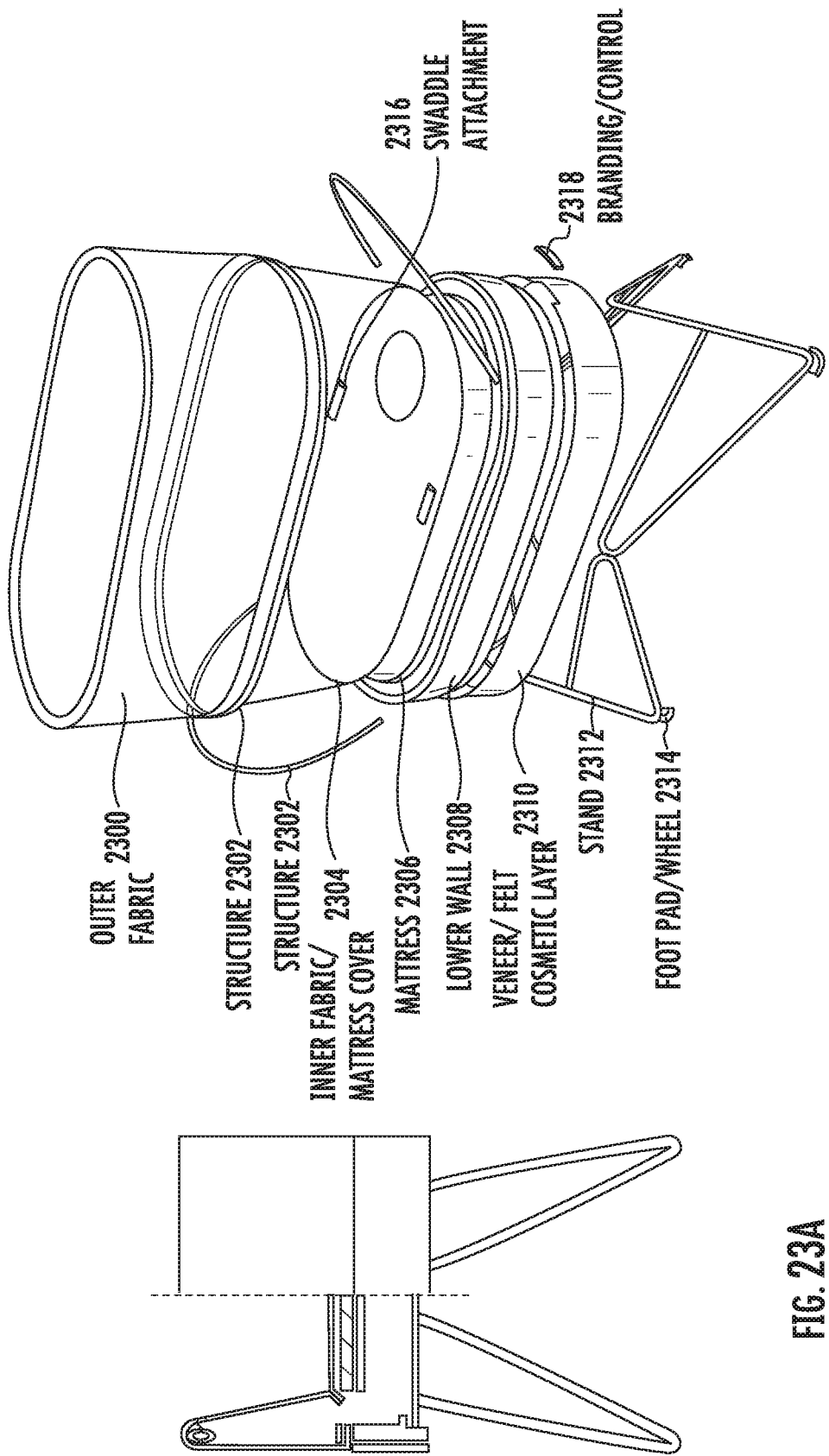

LOW POSITION

HIGH POSITION

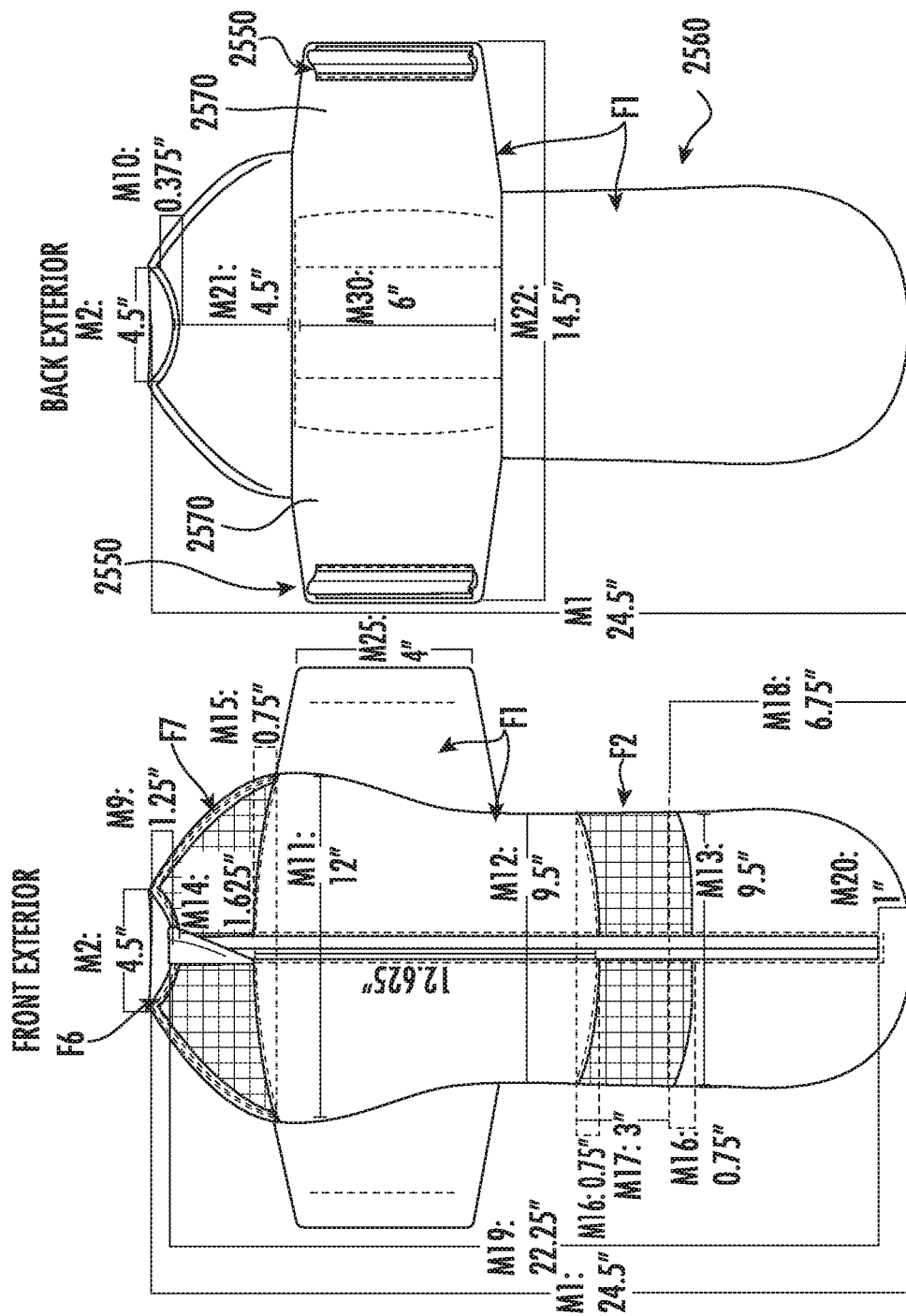

INTERIOR WRAP

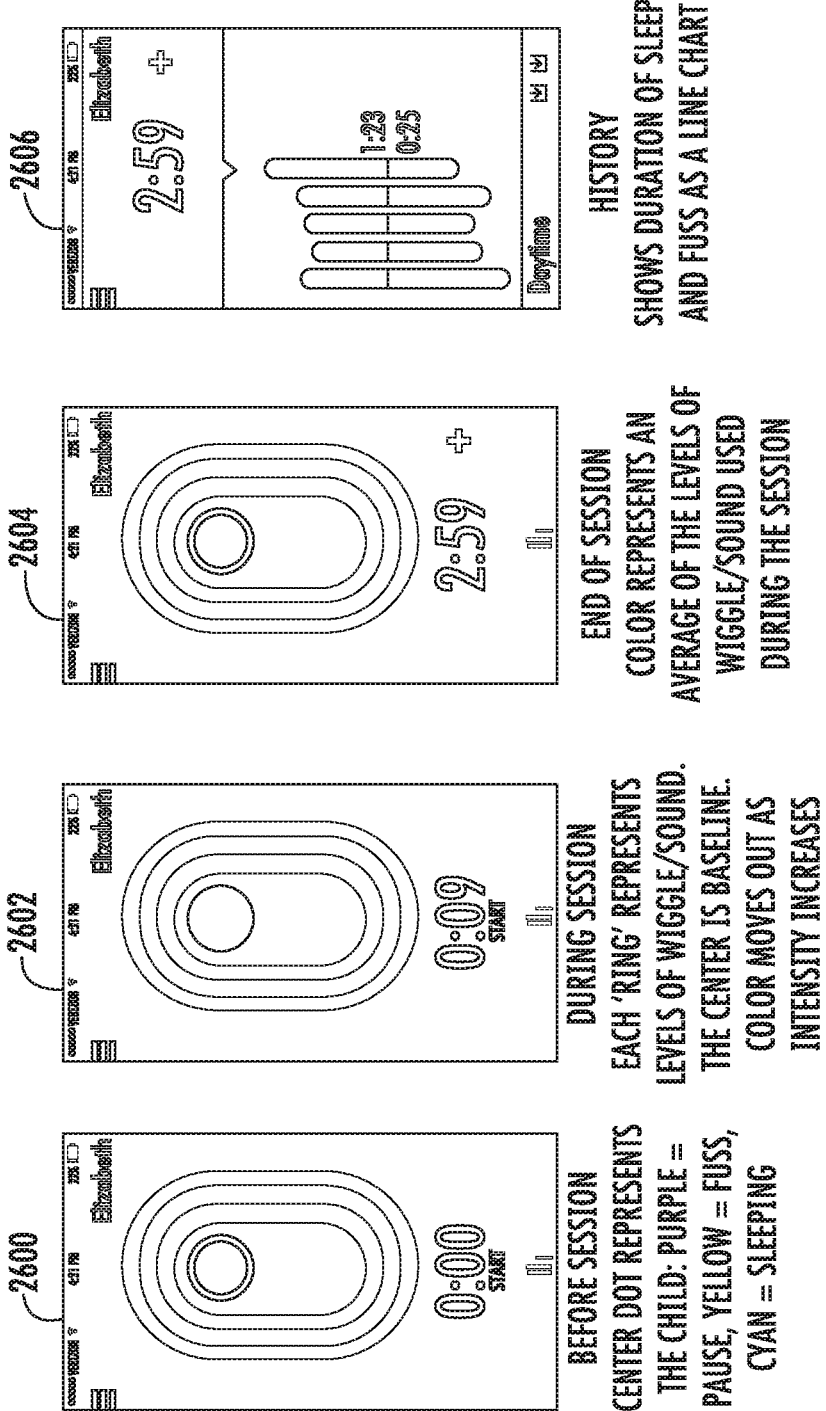

FIG. 27E

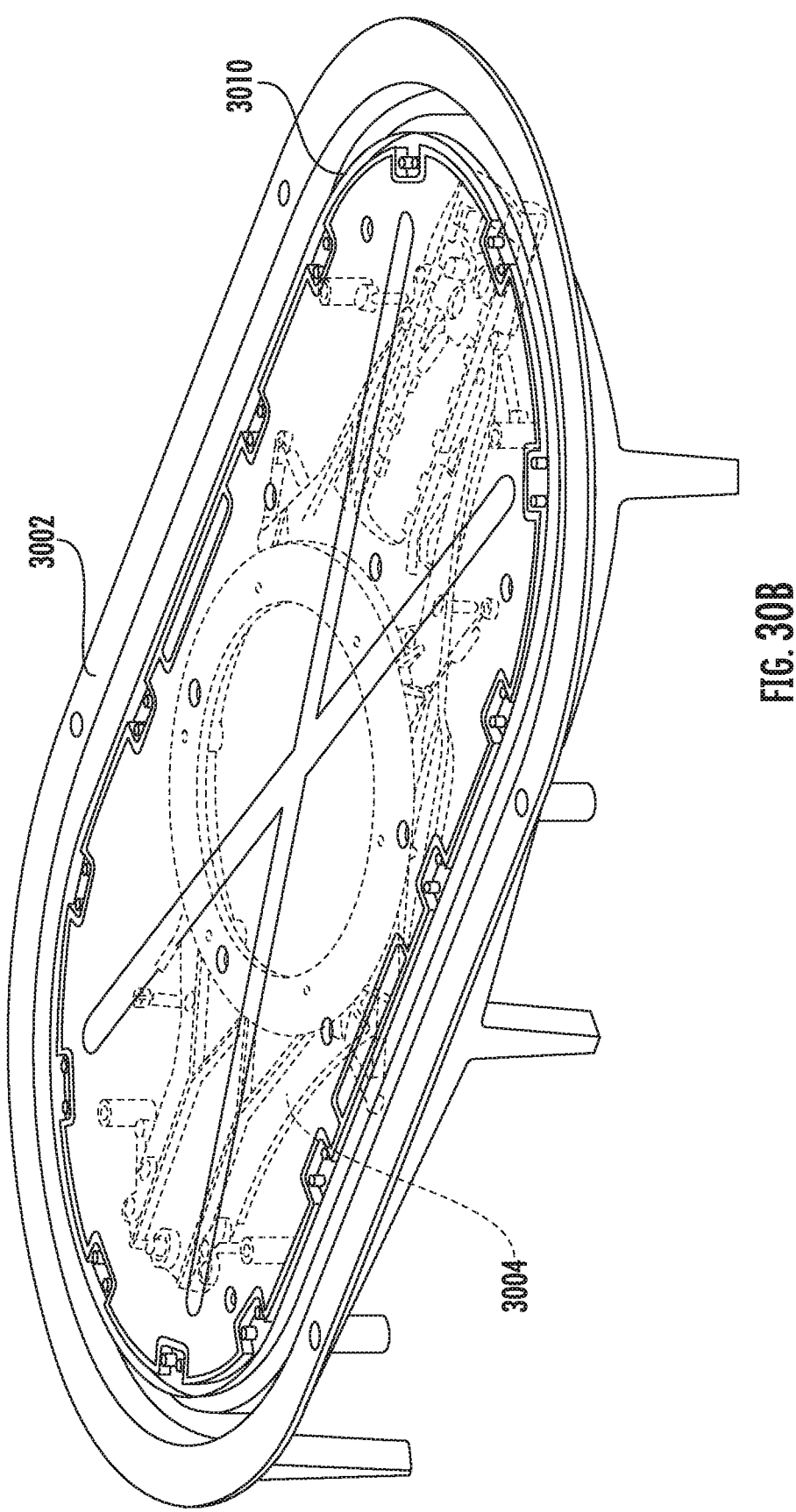

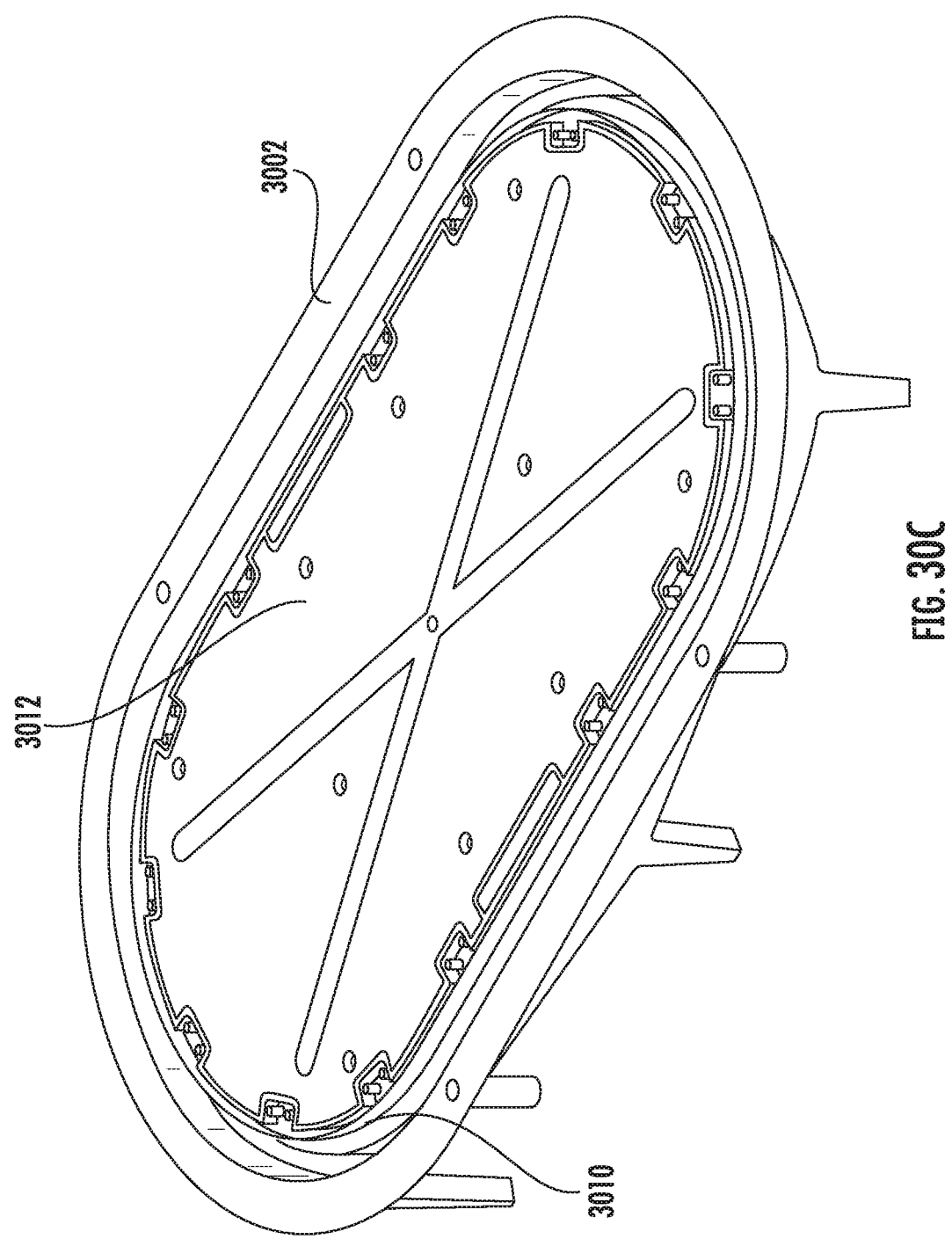

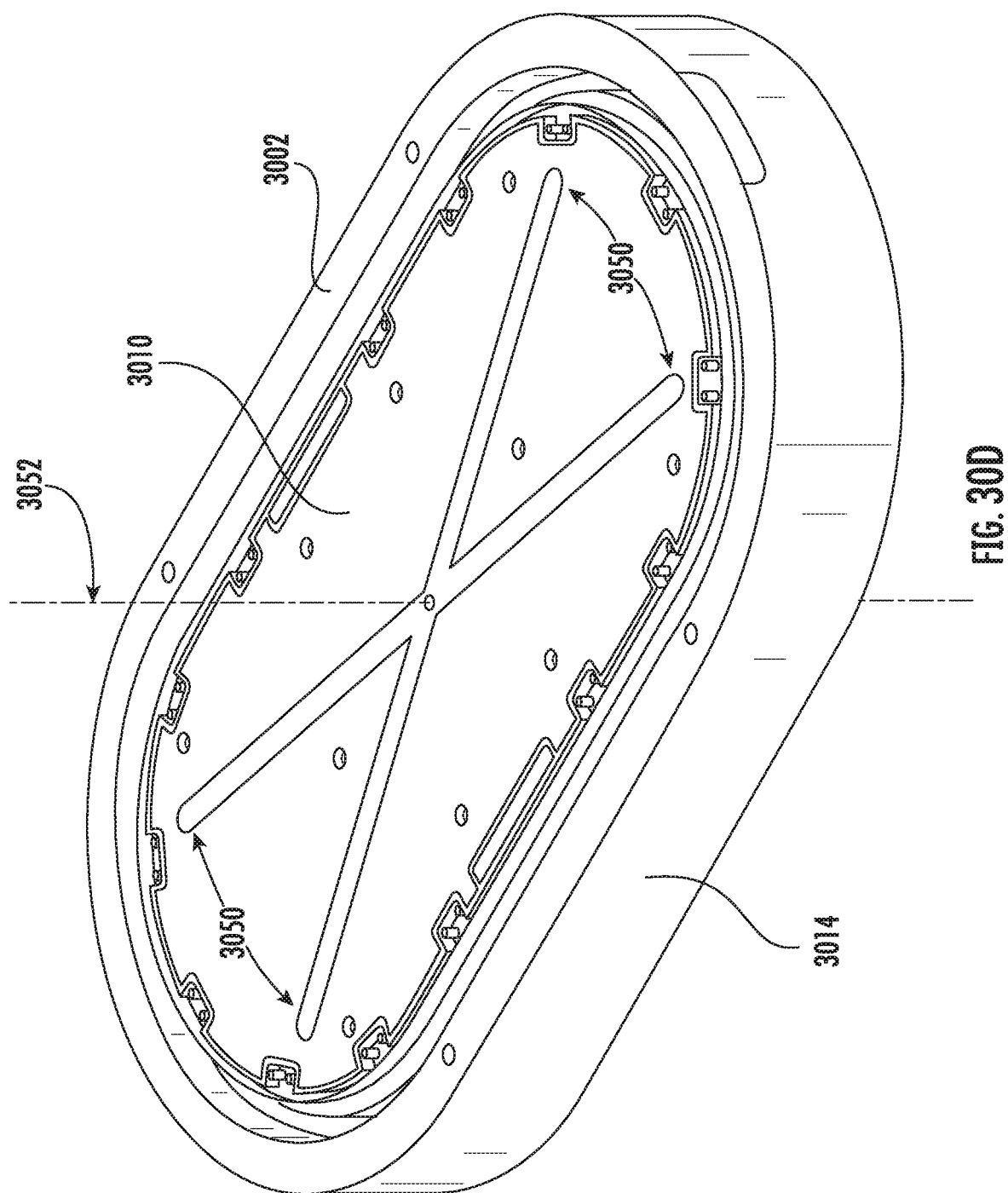

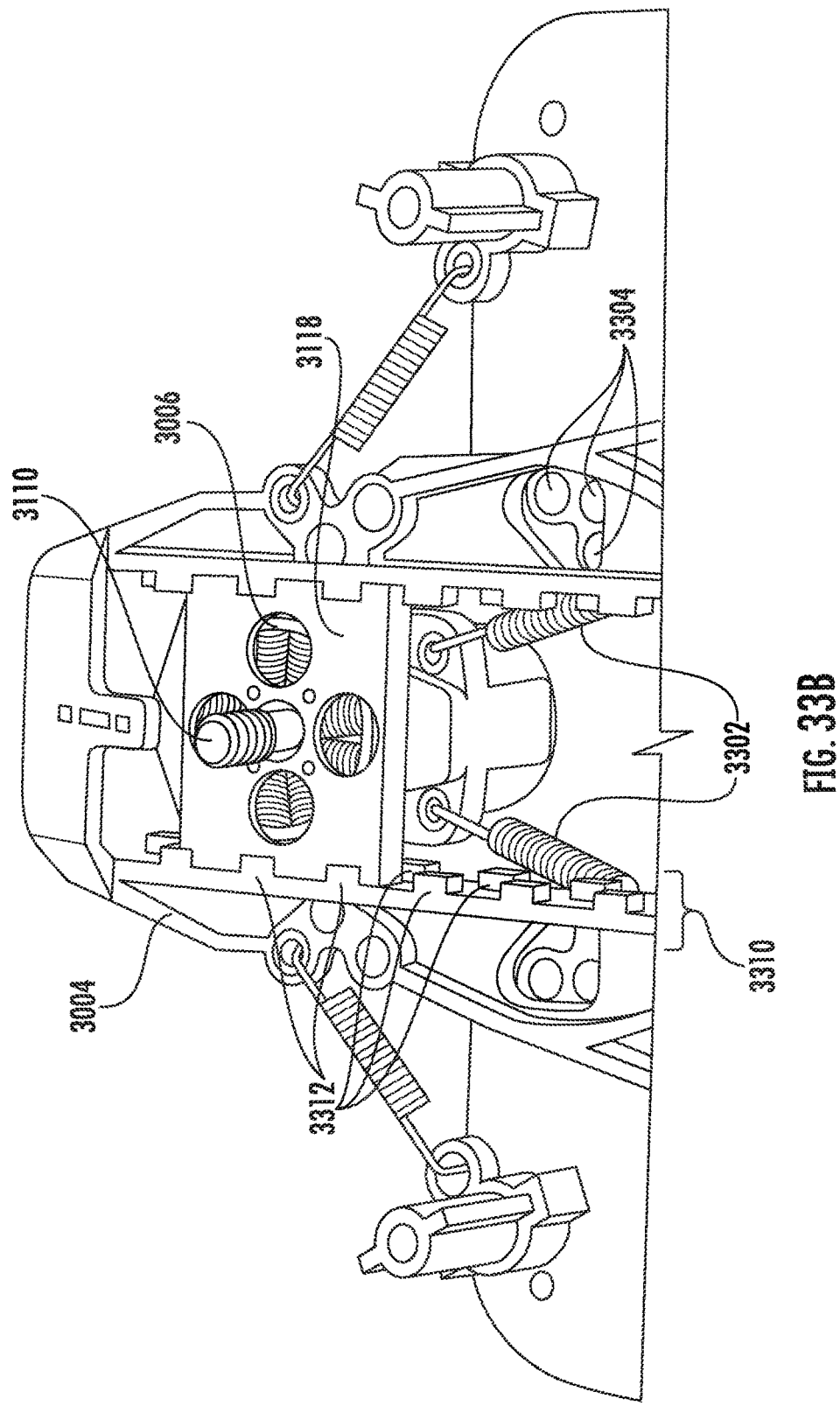

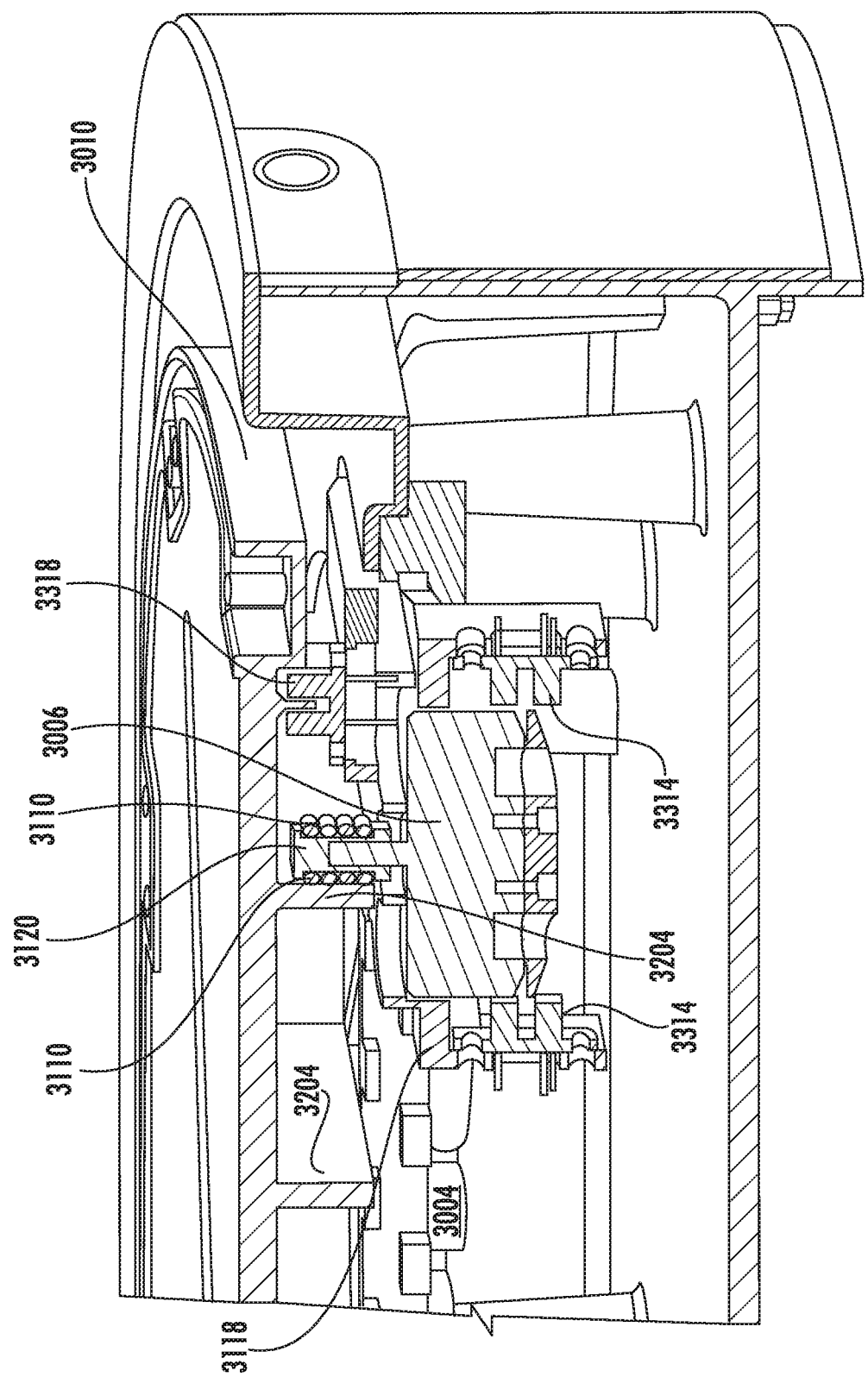

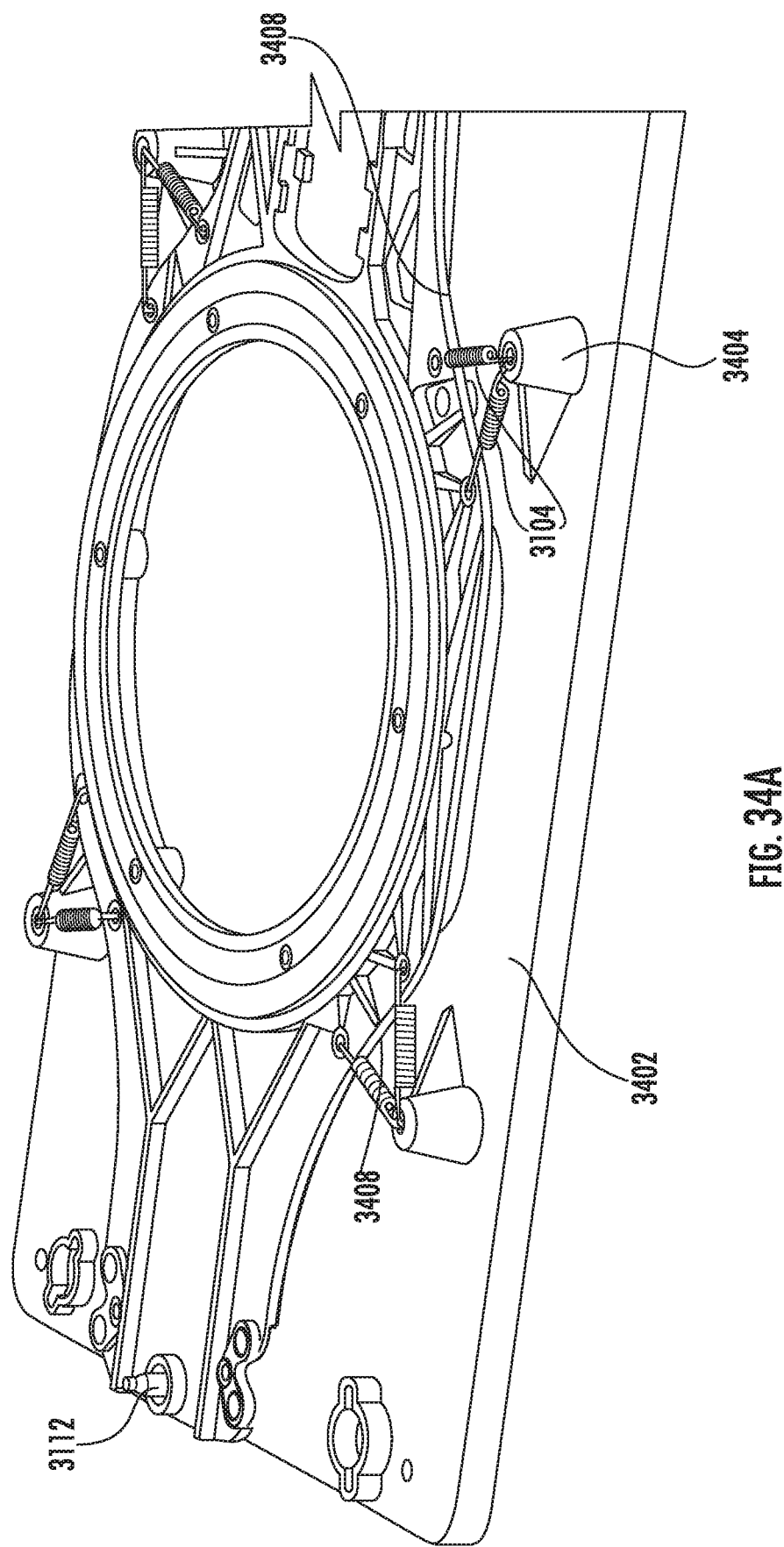

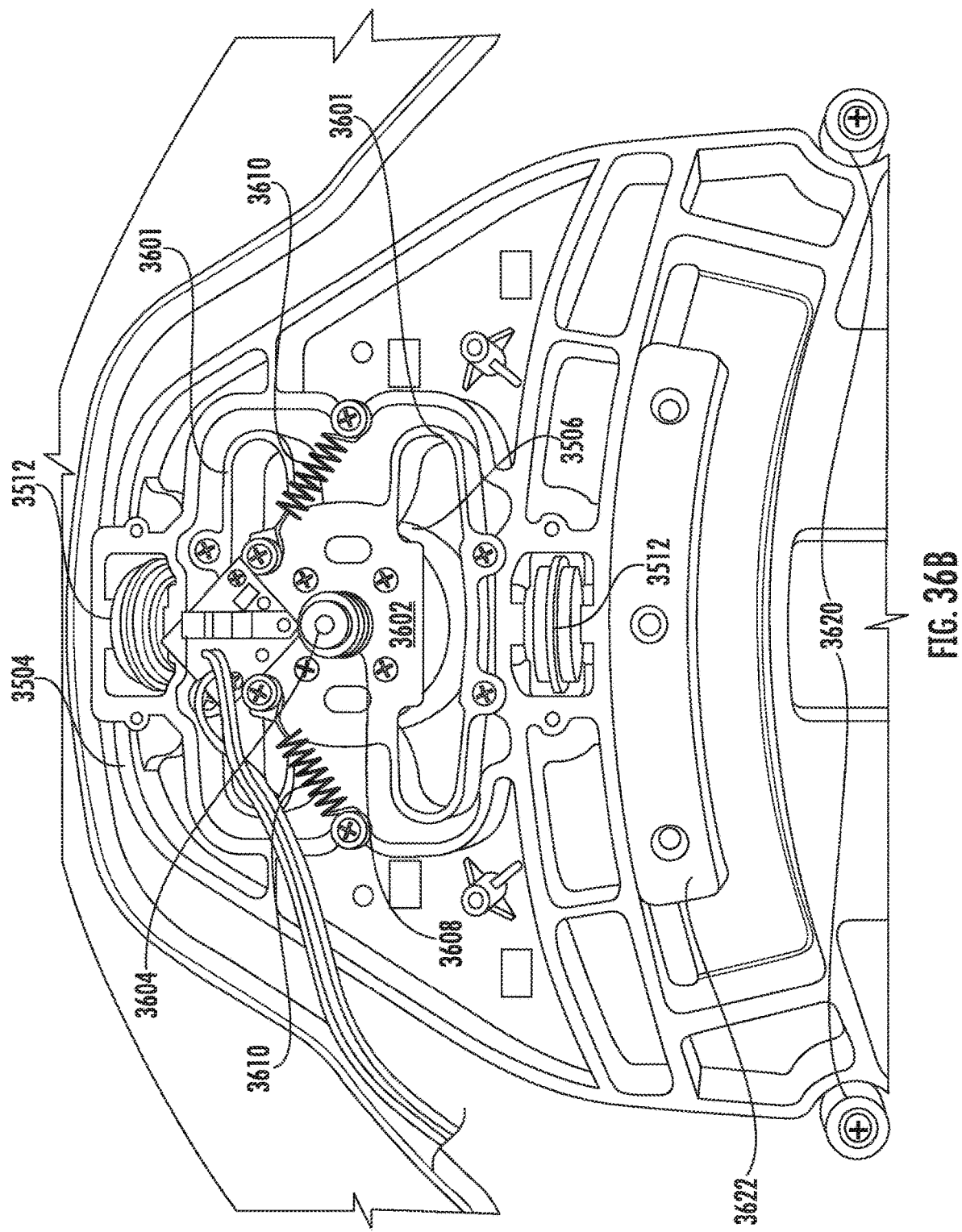

INFANT CALMING/SLEEP-AID DEVICE

This application is a national phase of PCT/US2017/057055, filed Oct. 17, 2017, and claims priority to U.S. Provisional Application No. 62/409,307, filed Oct. 17, 2016, the entire contents of both of which are hereby incorporated by reference.

RELATED FIELD

This disclosure relates to devices with a control system that includes a cry/state detection module that may be infant calming, sleep promoting, or SIDS preventing.

BACKGROUND

Persistent crying and poor infant sleep are perennial and ubiquitous causes of parent frustration. During the first months of life, babies fuss/cry an average of about two hours/day and wake two to three times a night. One in six infants is brought to a medical professional for evaluation for sleep/cry issues.

Infant crying and parental exhaustion are often demoralizing and directly linked to marital conflict, anger towards the baby, and impaired job performance. In addition, they are primary triggers for a cascade of serious/fatal health sequelae, including postpartum depression (which affects about 15% of all mothers and about 25 to about 50% of their partners), breastfeeding failure, child abuse and neglect, infanticide, suicide, unsafe sleeping practices, SIDS/suffocation, cigarette smoking, excessive doctor visits, overtreatment of infants with medication, automobile accidents, dysfunctional bonding, and perhaps maternal and infant obesity.

Traditional parenting practices have utilized swaddling, rhythmic motion and certain sounds to soothe fussing infants and promote sleep (by reducing sleep latency and increasing sleep efficiency). "Sleep latency" may be defined as the length of time between going to bed and falling asleep. "Sleep efficiency" may be defined as the ratio of time spent asleep (total sleep time) to the amount of time spent in bed.

Swaddling, rhythmic motion and certain sounds imitate elements of a baby's in utero sensory milieu and activate a suite of subcortical reflexes, called the "calming reflex," during the first 4-6 months of a baby's life. After that time, these stimuli can still promote infant sleep, but they do so by activating a conditioned response.

Swaddling is a method of snug wrapping with the arms restrained at the baby's sides. This imitates the confinement babies experience in the womb and the continual touch they experience from the soft lining of the uterine walls. Swaddling also inhibits startling and flailing, which often interrupts sleep and starts/exacerbates crying.

A rhythmic, jiggling motion replicates the movement fetuses experience when the mother is walking. The motion stimulates the vestibular apparatus in the semicircular canals of the inner ear. A specific, rumbling noise imitates the sound created by the turbulence of the blood flowing through the uterine and umbilical arteries. In utero, the sound level babies hear has been measured at between 75 and 92 dB. Each baby has a specific and distinctive unique mix of motion and sound that most efficiently activates his or her calming reflex. This preferred mix stays consistent through the first months of life (i.e. babies who respond best to swaddling plus jiggling continue to respond to those modalities over time and don't abruptly switch their preference to swaddling plus sound).

The calming reflex has several constant characteristics. It is triggered by a stereotypical sensory input; produces a stereotypical behavioral output; demonstrates a threshold phenomenon (i.e. stimuli that are too mild may not be sufficient to activate a response); has a threshold that varies between individuals (i.e. is higher or lower for any given child); the threshold varies by state (e.g. fussing and crying raise the level of stimulation required to exceed threshold and bring about reflex activation); the reflex is almost irresistible at first, but wanes after 3-4 months of age.

Since the nominal level of a stimulus needed to reach the triggering threshold of the calming reflex differs from one child to the next, failure to exceed a particular child's threshold level often results in a total absence of a calming response. For example, slow smooth motion may calm one upset infant, yet be too subdued to calm another. Likewise, moderately loud sound (e.g., at a level of about 78 dB) sound may reach the calming threshold for one child, but be insufficient to calm another. Once triggered, the stereotypical output of the calming reflex is a reduction of motor output and a more tranquil state (quiet alert state or sleep). In this context, the word "state" describes an infant's level of attention to and interaction with the environment. Infants experience at least six identifiable states in this context: quiet sleep, active sleep, drowsiness, quiet alert, fussing and crying. The intensity of sound and motion needed to trigger any particular baby's calming reflex is substantially greater than the levels needed to keep the calming reflex activated.

However, despite the convenience, efficacy, and availability of swaddling, rhythmic motion, and sound, these methods fail to calm and promote sleep in a large portion of the infant population because they are not being applied correctly. When parents fail to reduce infant crying and promote sleep, they often bring the baby into their own bed. However, this is problematic because sharing a bed with a parent has been proven to raise an infant's risk of Sudden Infant Death Syndrome (SIDS) and accidental suffocation (which the US Centers for Disease Control reports has been increasing by 14% per year for approximately twenty years). The hazard of bed sharing is further elevated if the parent is extremely fatigued. Like inebriation, exhaustion reduces adult judgment and responsiveness. As many as 50% of new parents report sleeping fewer than 6 hours/night, the level demonstrated in adults to cause a level of impairment of attention and cognition comparable to inebriation. For this reason, bed sharing with an exhausted parent increases the SIDS risk and the suffocation risk (from accidental overlaying of the parents' body over the infant's head, pulling bedding over the baby, etc.).

Other behaviors that stressed, exhausted parents engage in also directly raise the risk of SIDS and suffocation (e.g. cigarette smoking, cessation of breast feeding, falling asleep with the baby on a couch, placing the baby on the stomach to sleep). Medical authorities recommend parents avoid bed sharing. However, cribs too can be problematic. Babies sleeping supine in cribs have a higher risk of plagiocephaly (flattening of the skull), which may require expensive and inconvenient medical treatment, and may result in permanent deformity. A crib's flat, quiet, nonmoving surface is devoid of the swaddling, rhythmic motion and sound that can activate the calming reflex or conditioned response and reduce crying and sleep latency and increase sleep efficiency.

In an attempt to improve infant sleep in cribs, parents have employed several methods (prone sleeping, swaddling, rocking motion, sound), however each is problematic. For example, the prone position is associated with a 3-4 fold increased risk of SIDS. Unswaddled babies can roll to the stomach position (prone), which is associated with an 8-19 fold increased risk of SIDS. Swaddled babies can roll prone, which is associated with a 12-fold increased risk of SIDS. Rocking motion delivery systems (e.g. swings, cradles and hammocks) may all present problems. The motion of infant swings is often insufficient to calm a fussy baby and induce sleep. When sitting in a swing, a baby's head can roll forward and create an airway obstruction, leading to death. Cradles and hammocks require parents to be the motion-powering energy source, and thus can be done for only a limited part of the sleep period. Also, they can accidentally cause a supine baby to roll to the side or stomach or become wedged into the side wall of the sleeper. Sound delivery devices (e.g. fans, air filters, hair driers, sound machines and white noise CDs) may be cumbersome and expensive and the volume, quality or frequency profile of the sound they produce may be excessive or too different from in utero sound to be effective.

Over the past twenty years, attempts have been made to engineer technological methods to create infant calming/sleep devices to deliver sound and motion more conveniently. These current infant calming/sleep devices typically deliver fixed and unchangeable motion and sound. This is a problem because each baby has a different mix of sound and motion that most efficiently calms the child's crying. For example, some babies respond best to swaddling plus motion, while others are not calmed unless they have swaddling, motion plus white noise sound. Another problem with fixed motion and sound infant calming/sleep devices is that each baby has a unique level of motion and sound that induces calming and sleep most efficiently. For example, slow rocking may reduce sleep latency for one infant, yet be too subdued to do so in another infant. And, quiet sound may be sufficient to increase sleep efficiency for one baby, but not another. Devices that deliver constant sound may also expose a baby to unhealthy levels of sound, if they are set at too high a volume.

Still another problem with fixed motion and sound infant calming/sleep devices is that the intensity of the stimuli needed to activate the calming reflex and induce calm and sleep varies substantially as a child's state changes. For example, most fussy babies require more vigorous, jiggling motion (with rapid acceleration-deceleration) and more vigorous sound inputs (as loud as a vacuum cleaner or hair drier—75 to 95 dB). On the other hand, calm, sleepy babies need less vigorous inputs. Further, current infant calming/sleep devices do not continue all night long; do not deliver optimal sound and motion for triggering the calming reflex; do not increase and decrease their sensory input in a step-wise fashion to vary the sensory input intensity to give the baby the most effective level of stimulation with the minimum exposure to high levels of sound; lack the ability to gradually increased the sensory input over the first weeks of life and to gradually wean a baby off the stimuli as he or she ages.

In addition, crib death or SIDS (Sudden Infant Death Syndrome) is a leading cause of infant mortality. Approximately 2500 US babies die each year from SIDS during the first year of life. The peak occurrence is from 2-4 months of age, with 80% of the victims being under 4 months and 90% being under 6 months of age.

In the 1990's, a program to reduce SIDS deaths called "Back to Sleep" was introduced. At that time, it was discovered that sleeping on the stomach was a key triggering factor in SIDS, so caregivers were instructed to place babies on their backs for sleeping. Within less than a decade, the rate of SIDS dropped in half, however, since that time, the SIDS incidence has been not diminished. Furthermore, while the exact cause of SIDS is unknown, the primary cause is believed to be immaturity of the breathing regulatory system in the brain. In essence, it seems that babies "forget" to breath and their internal alarm system does not reliably arouse them to recommence breathing. Once breathing stops, the body becomes more and more hypoxemic and acidotic, leading to a downward spiral of reduced heart rate, dropping blood pressure, cardiovascular collapse and death. Studies have indicated that the risk of stomach sleeping may indeed predispose babies to SIDS by reducing infant arousability.

In the hospital setting, the use of an infant monitor immediately alerts the healthcare workers if an infant stops breathing. The health care workers can often resuscitate the infant with simple stimulation (e.g. vigorous jiggling), without the need of oxygen or formal CPR.

In the home setting, however, studies have not shown that using a cardiorespiratory monitor reduces the incidence of SIDS. This lack of effect may be because, 1) the parent responding to the alarm may not know how to resuscitate the baby; 2) the parent may be panicked and incapable of resuscitating the baby; 3) the baby may be so hypoxic and acidotic, that, by time the parent arrives at the scene, an irreversible cardiorespiratory collapse has already been precipitated.

However, a device that can begin vigorous stimulation of the baby within seconds of the baby stopping breathing (apnea) may be able to arouse the minimally depressed baby and reinitiate the breathing sequence before a downward cardiovascular spiral has occurred. The "Back to Sleep" program has proven that simple interventions can lead to a profound reduction in mortality by virtue of helping babies be slightly more aroused, as they are in the supine position. In other words, it may not take a great amount of sensory input maintain the baby in a mode of regular breathing or to return the baby to normal breathing after a brief, transient cessation. Also, two studies have shown that supine swaddling is associated with a reduction in SIDS. Swaddling has been shown to increase arousability, especially during active sleep.

In addition, many babies fall out of their bassinet during the first 6 months of life. Federal reports reveal that 69% of recent bassinet/cradle incidents have been attributed to falling. All falls resulted in head injury. Alarmingly, 45% of falls occurred in infants five months old or less.

Therefore, a need exists for an infant calming/sleep system that overcomes or minimizes the above-mentioned problems.

SUMMARY

This disclosure is generally directed to devices and methods for aiding calming and safe sleep of an infant. In embodiments, an infant calming/sleep-aid device is provided that includes a main moving platform that moves in a variable manner with accompanying variable sound generation, each adapted to calm a baby, induce sleep, and maintain sleep. This device can be independently controlled, from the device itself, or via communication with a mobile device application that also delivers users various forms of information about sleep, their baby, etc. Also, a secure sleep sack design may be provided which prevents accidental rolling to the potentially risky prone position or accidental falls. Furthermore, this device may contain a sensor to monitor one or more of the baby's biometrics to detect when the baby has temporarily stopped breathing. In that case, the device will sound an alarm to summons the caregiver and commence vigorous motion and sound to perform a resuscitation function—similar to the intervention used by medical personnel to arouse apneic infants in the hospital—before the baby becomes acidotic and bradycardic. The device can also be programmed by the parent to call 911 or local emergency services in case of cessation of breathing of the infant.

In an embodiment, a device in accordance with the present disclosure may include a movable platform configured to support an infant inside the device; a sound output device configured to provide a sound for soothing the infant; a sensor system disposed proximate to the movable platform such that the sensor system is operable to detect a noise, wherein the sensor system is configured to generate measurement data for the noise detected; and a control system communicatively connected to the sensor system, the control system being configured to receive the measurement data generated by the sensor system and to determine, based at least on a first parameter of the measurement data, whether the noise detected originates from inside or outside the device. If the noise detected is determined to originate from inside the device, the control system is further configured to determine, based at least on a second parameter of the measurement data, whether the noise detected comprises an infant cry. If the noise detected is determined to comprise the infant cry, the control system is further configured to determine, based at least on a third parameter of the measurement data, a state of infant cry. The control system is further configured to provide, based on the state of infant cry, a control signal to operate at least one of the movable platform and the sound output device to soothe the infant.

In an embodiment, a system device in accordance with the present disclosure may include a movable platform configured to support an infant inside the system; a sleep sack connected to the movable platform, the sleep sack configured to secure the infant's head at a position inside the system; a sound output device configured to provide a sound for soothing the infant; a sensor system disposed proximate to the movable platform such that the sensor system is operable to detect a noise, wherein the sensor system is configured to generate measurement data for the noise detected; and a control system communicatively connected to the sensor system. In an embodiment, the control system is configured to receive the measurement data generated by the sensor system and to determine, based at least on a first parameter of the measurement data, whether the noise detected originates from inside or outside the system. If the noise detected is determined to originate from inside the system, the control system is further configured to determine, based at least on a second parameter of the measurement data, whether the noise detected comprises an infant cry. If the noise detected is determined to comprise the infant cry, the control system is further configured to determine, based at least on a third parameter of the measurement data, a state of infant cry. The control system is further configured to provide, based on the state of infant cry, a control signal to operate at least one of the movable platform and the sound output device to soothe the infant.

In an embodiment, an infant calming/sleep-aid device may include a movable platform configured to support an infant inside the device; inner and outer mesh layers extending upwardly from an outer periphery portion of the movable platform, the inner and out mesh layers being spaced apart thereby creating a gap therebetween; a sound output device configured to provide a sound towards the infant; a sensor system disposed proximate to the movable platform; and a control system communicatively connected to the sensor system. The control system is configured to receive measurement data generated by the sensor system and to determine, based the measurement data, a distress status of the infant. The control system is further configured to provide, based on the distress status of the infant, a control signal to operate at least one of the movable platform and the sound output device.

In an embodiment, an infant calming/sleep aid device is disclosed, the device comprising a base, a carrier connected to and above the base, a moving platform above the carrier and in contact with at least one bearing between the carrier and the moving platform, wherein the moving platform is rotatable in a plane substantially parallel to a major plane of the carrier in an oscillatory manner relative to the carrier and about an axis of rotation, and a control system for controlling a motor that controls movement of the moving platform about the center of rotation of the at least one bearing relative to the carrier, to cause oscillatory movement of the moving platform, wherein the control system includes a cry detection module. The cry detection module includes a directional filter, a frequency filter, a threshold filter, and a plurality of microphones, wherein the cry detection module detects infant cries originating from within the infant calming/sleep aid device above a threshold in order to detect a cry state and cry threshold of an infant on the moving platform and control movement of the moving platform in accordance with the detected cry state and cry threshold.

In an embodiment, a method is disclosed for controlling movement of an infant calming/sleep aid device providing the device, wherein the device includes a base, a carrier connected to and above the base, a moving platform above the carrier and in contact with at least one bearing between the carrier and the moving platform, wherein the moving platform is rotatable in a plane substantially parallel to a major plane of the carrier in an oscillatory manner relative to the carrier and about an axis of rotation, and a control system for controlling a motor that controls movement of the moving platform about the center of rotation of the at least one bearing relative to the carrier, to cause oscillatory movement of the moving platform, wherein the control system includes a cry detection module. The cry detection module includes a directional filter, a frequency filter, a threshold filter, and a plurality of microphones. Next, the device receives sound signals from the plurality of microphones, determines whether the sound signals from the plurality of microphones originate within the device with the directional filter, evaluates whether sound signals originating within the device are in a specified frequency of infant cries with the frequency filter, analyzes the detected infant cries, determines if the infant cries are at or above a threshold with the cry detection module, and controls movement of the moving platform in accordance with a detected cry state and cry threshold if the sound signals within the device are infant cries and are above the threshold.

In an embodiment, a method is disclosed for controlling an infant calming/sleep aid device comprising providing an infant calming/sleep-aid device comprising a platform for supporting an infant, a control system for receiving at least one input relating to the infant from a user and for generating at least one output that controls at least one of a motion of the platform and a sound directed to the infant, and a communication facility for linking the at least one input with the control system, providing a plurality of selectable operational modes for the infant calming/sleep-aid device, each operational mode comprising at least one of a defined motion range of the platform and a sound range, selecting an operational mode based at least in part on the user provided input, and activating the operational mode based on the selection.

An embodiment is directed to a connector for attaching a sleep sack configured to receive at least a portion of an infant's body therein, the sleep sack having an attachment mechanism. The connector may include a lower portion configured to be disposed beneath a mattress, the lower portion slidably extendible in a lateral direction; first and second upper portions configured to be removably coupled to the attachment mechanism of the sleep sack; and first and second side portions extending generally in a direction perpendicular to the lateral direction and connecting the respective first and second upper portions to the lower portion. A lateral adjustment of an extension of the lower portion adjusts lateral positions of the first and second side portions whereby the mattress fits between the first and second side portions.

In an embodiment, a method in accordance with the present disclosure includes providing a device configured to receive an infant therein, the device comprising a movable platform and a sound output device configured to provide a sound for soothing the infant within the device; detecting a noise with a sensor system of the device; generating measurement data for the noise detected; providing the measurement data to a control system of the device; determining, based at least on a first parameter of the measurement data, whether the noise detected originates from inside or outside the device; if the noise detected is determined to originate from inside the device, determining, based at least on a second parameter of the measurement data, whether the noise detected comprises an infant cry; if the noise detected is determined to comprise the infant cry, determining, based at least on a third parameter of the measurement data, a state of infant cry; and providing, based on the state of infant cry, a control signal from the control system to operate at least one of the movable platform and the sound output device to soothe the infant.

BRIEF DESCRIPTION OF FIGURES

FIG. 4 is a plan view illustrating components supporting the main moving platform of the infant calming/sleep-aid device of FIG. 3, with the rigid base and main moving platform shown in outline.

FIG. 5 is a side view of the infant calming/sleep-aid device shown in FIG. 4, taken along line 5-5.

FIG. 7 is a perspective view of yet another exemplary embodiment of the calming/sleep-aid device of the disclosure, showing components of the device beneath the main moving platform in broken lines.

FIG. 22A is schematic diagram of control system related components of an exemplary infant calming/sleep-aid device.

FIG. 22I illustrates exemplary amplitude and frequency of movement of the platform at various levels for various age ranges.

FIG. 23A illustrates another exemplary embodiment in a perspective partially cut-away view of an infant calming/sleep-aid device viewed from one end of the device, and which can incorporate the control system of FIG. 22A.

FIG. 23B is an exploded perspective view of the infant calming/sleep-aid device of FIG. 23A, showing individual components of the infant calming/sleep-aid device.

FIGS. 25P-S illustrate another exemplary sleep sack.

FIG. 26A illustrates views of layers displayed by a user interface for use with the infant calming/sleep-aid device of FIG. 22A.

Figure 27E:
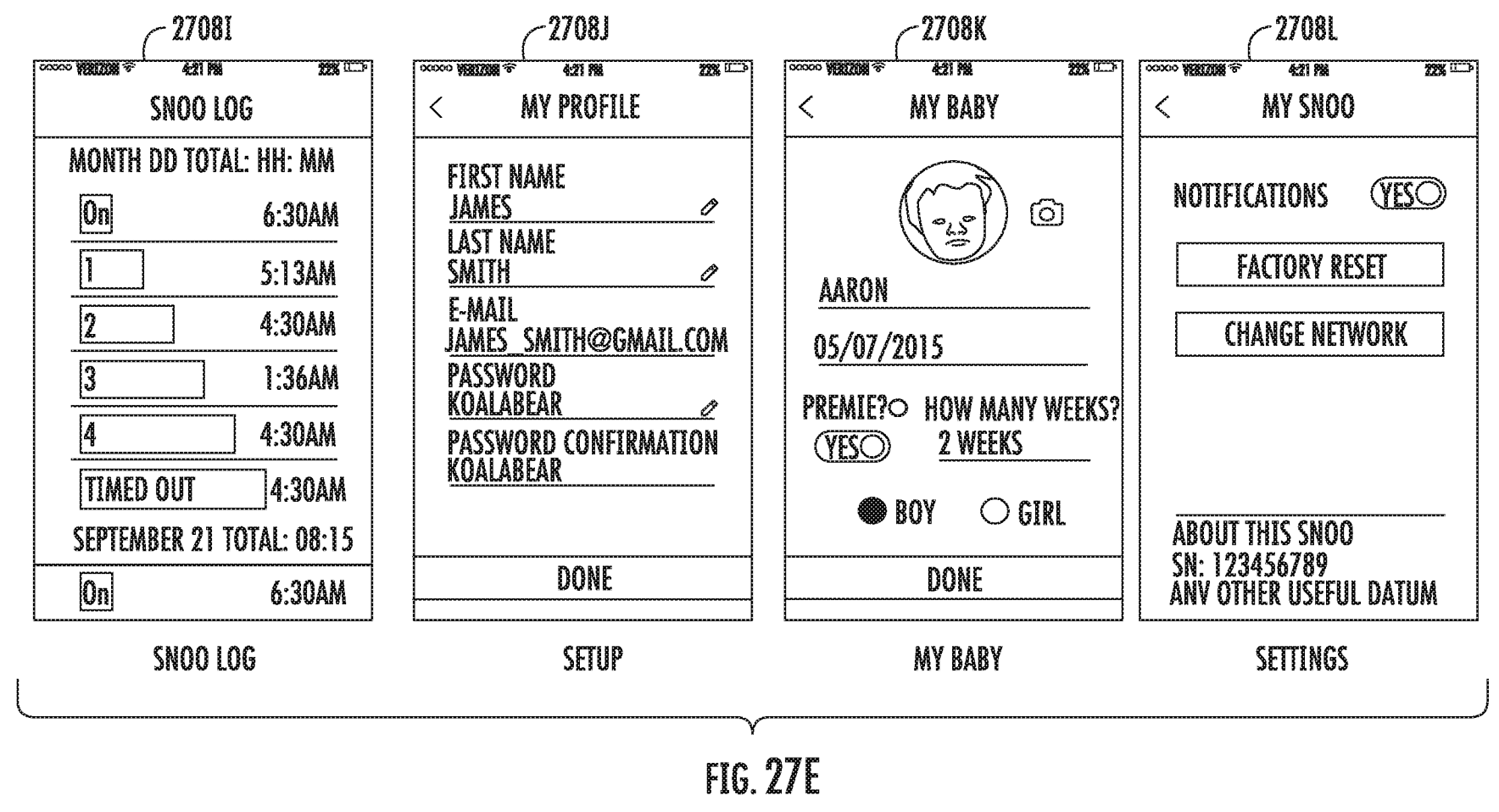

FIGS. 27B-E illustrate further views displayed by an exemplary mobile device application user interface for use with the infant calming device.

FIG. 30B is a transparent view of a partially assembled drive train system.

FIG. 30C is an assembled view of the exemplary drive train system.

FIG. 30D is an illustration of a drive train system with an enclosure.

FIGS. 33B-33C are perspective views of a central carrier and motor.

FIG. 33D is a cross-sectional view of a portion of a drive train system.

FIGS. 34A-34E are perspective views of a rigid base supporting a central carrier.

FIGS. 36A-36C are perspective views of a central carrier and motor.

DETAILED DESCRIPTION

Figure 1:
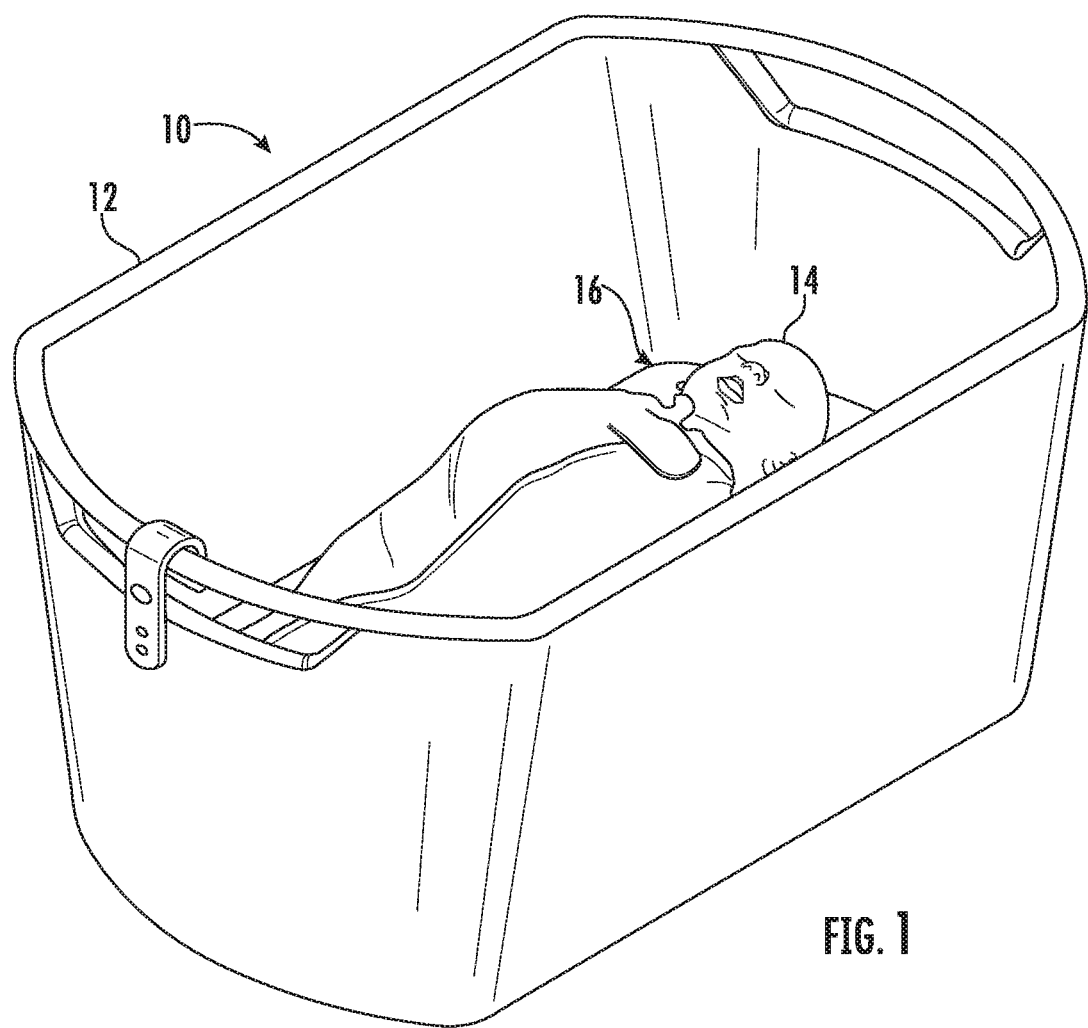
FIG. 1 is a perspective view of an exemplary embodiment of an infant calming/sleep-aid device, with a depiction of an infant asleep inside the device.
Figure 2:
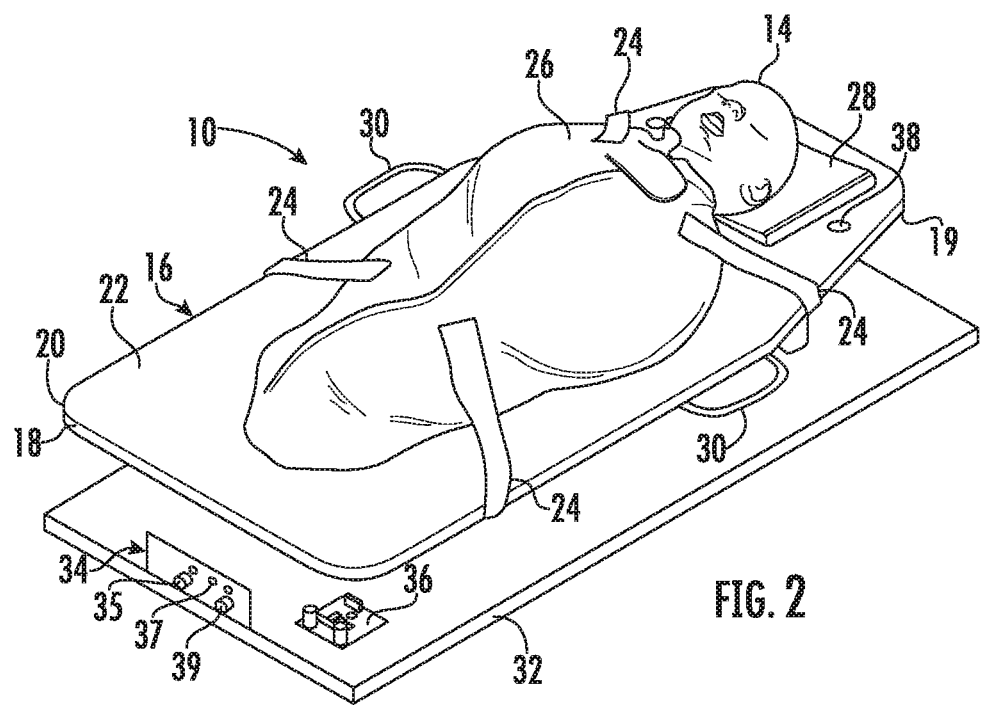
FIG. 2 is a perspective view of the infant calming/sleep-aid device of FIG. 1 with swaddle fastening straps and without an enclosure.
Figure 2A:
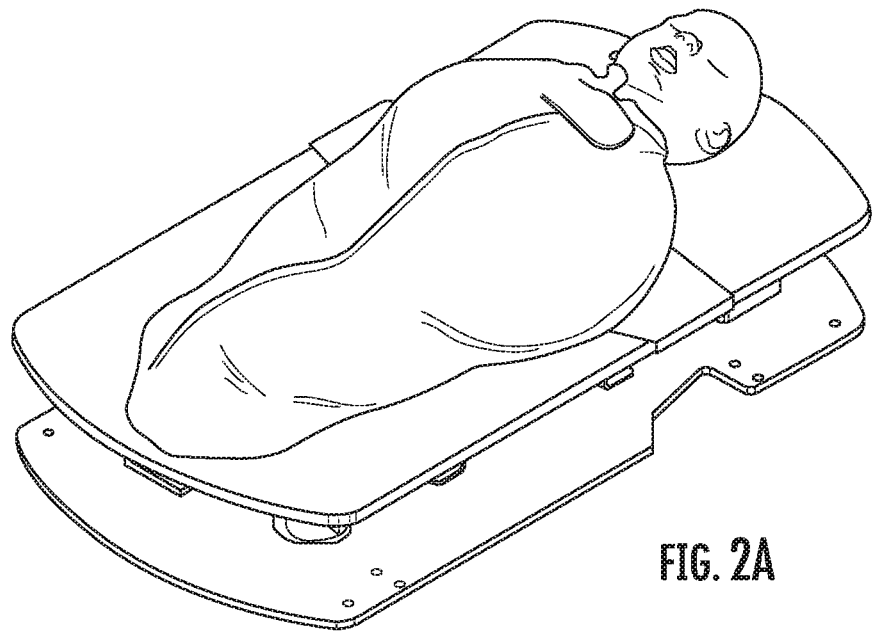
FIG. 2A is a perspective view of the infant calming/sleep-aid device of FIG. 1 with swaddle fastening clips integral to the swaddle and without an enclosure.

In an exemplary embodiment, shown in FIGS. 1 through 6, an infant calming/sleep-aid device 10 includes an enclosure 12 about an infant 14. Enclosure 12 surrounds main moving platform 16. Main moving platform 16 may be made from wood-based particleboard with an injection molded support tray or the entire platform may be injection molded. The injection molded support tray may provide stiffening ribs, attaching features, and the like. As can be seen in FIG. 2, main moving platform 16 includes base 18, moving head platform 19, padding 20 and cloth covering 22. Secure sleep sack fastening straps 24 extend from main moving platform 16 for securing infant 14 in suitable secure sleep sack 26. As can be seen in FIG. 2A, sleep sack fastening straps may take other forms such as attachment clips and may be integral to the sleep sack 26. This embodiment includes a head pad insert 28 that supports the head of infant 14. Preferably, head pad insert 28 includes a gel in order to reduce the risk of plagiocephaly. Handles 30 extend laterally from main moving platform 16. Main moving platform 16 is supported and rotatable about a main support shaft (not shown) that is fixed to rigid base 32. Rigid base 32 may be made from molded plastic, stamped metal, and the like. Control panel 34, which includes speed control knobs 35, status lights 37 and controls 39 for microphone 38. Rigid base control electronics 36 may include drive electronics of the infant calming/sleep-aid device 10, as well as other sensors, such as an accelerometer or biometric sensor (not shown). In embodiments, the biometric sensor could be an accelerometer, and act to measure the breathing of an infant by measuring the movement of the mattress of the infant calming device.

Figure 3:
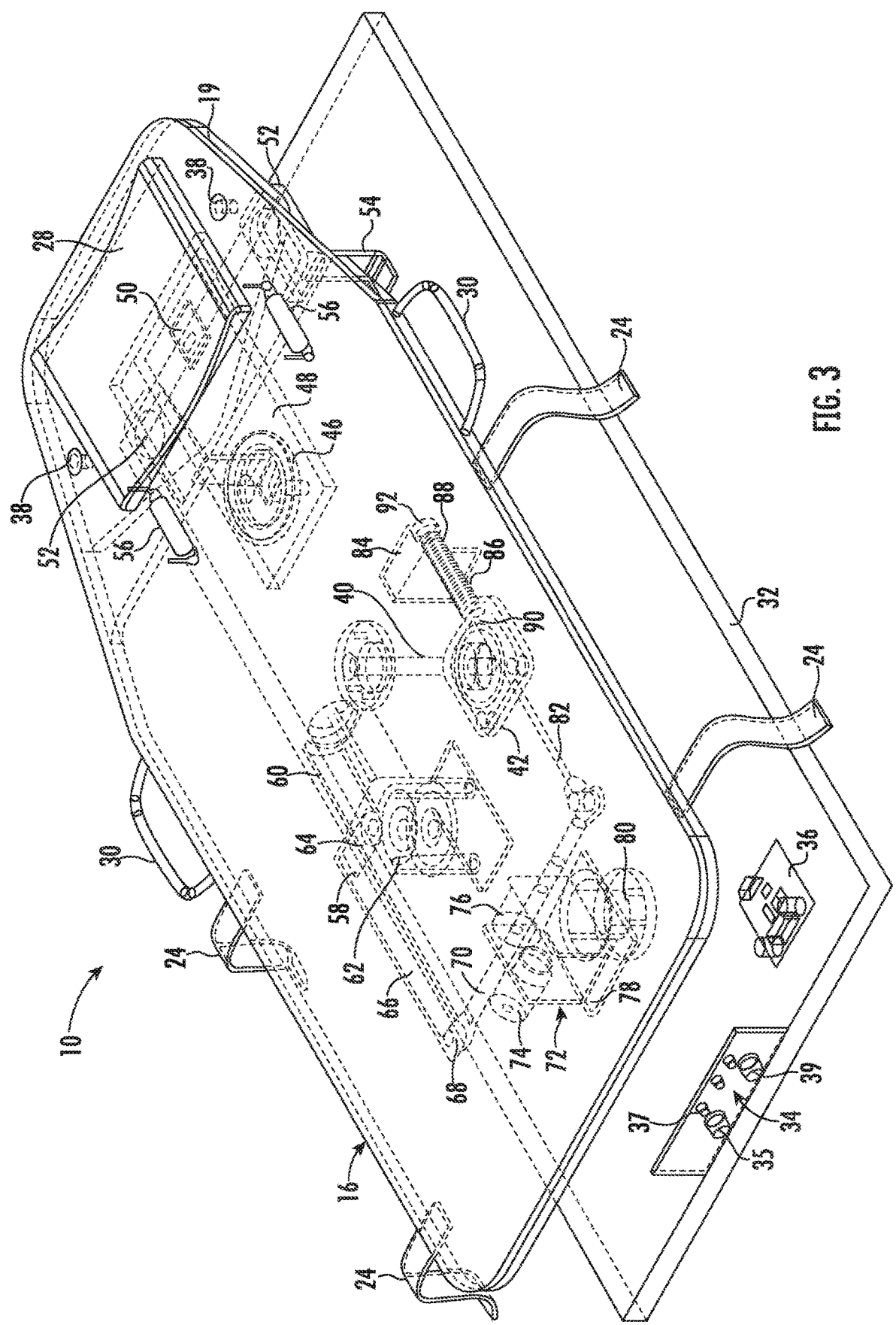
FIG. 3 is a perspective view of the infant calming/sleep-aid device of FIG. 2, showing apparatus beneath the main moving platform in broken lines.

In another representative view of infant calming/sleep-aid device 10 of FIG. 2, shown in FIG. 3, main moving platform 16 is supported by main support shaft 40 at main rotation bearing 42. Moving head platform 19 supports head pad insert 28 and is rotatable about head rotation bearing 46 through arm 48 extending between head rotation bearing 46 and moving head platform 19. Motion sensing device 50, such as an accelerometer, at moving head platform 44 detects motion of moving head platform 19. Microphones 38 at moving head platform 19 detect sound emitted by the infant (not shown) when supported by infant aid sleep device 10. One or more speakers 52, supported by brackets 54 mounted on rigid base 18, are located directly beneath moving head platform 19. Springs 56 linking either side of moving head platform 19 to main moving platform 16 dampen motion of moving head platform 19 relative to main moving platform 16 during reciprocal motion of moving head platform 19 induced by reciprocating motion of main moving platform 16.

Reciprocating motion of main moving platform 16 about main support shaft 40 is about an axis that is orthogonal to a major plane of main moving platform 16. Reciprocating motion of main moving platform 16 is driven by actuator assembly 58.

In some embodiments, the body and the head of the infant can be out of phase. For example, at relatively slow speeds, the motion of the head of the infant can be in the same direction as that of the motion of the upper body of the infant. At relatively high speeds, the reciprocal motion of the head of the infant can be in the opposite direction as that of the upper body of the infant. In another embodiment of the disclosure (not shown), reciprocal motion of the head of the infant can be in some other direction, such as orthogonally relative to the plane of the main support platform.

Actuator assembly 58 includes assembly drive motor 60 mounted to rigid base 32 and gear assembly 62 linked to assembly drive motor 60 and also mounted to rigid base 32. Assembly drive motor 60 may be an electric motor with a reciprocating drive disk and push/pull rod.

Actuation of assembly drive motor 60 causes rotation gear assembly 62 to drive eccentric drive plate 64 about an axis normal to a major plane of rigid base 32. Eccentric drive plate 64 is linked to swing arm plate 66 of actuator assembly 58 that extends from eccentric drive plate 64 to rod end 68 of screw 70 and is pivotally mounted to rod end 68 of screw 70. Screw 70 is mounted to amplitude modulation assembly 72. Amplitude modulation assembly 72 includes amplitude modulation motor 74, nut 76, mounted on nut frame 78, which swivels on rotation bearing 80 mounted to rigid base 32. The axis of rotation of nut frame 78 on rotation bearing 80 is, like that of eccentric drive plate 64, normal to a major plane of rigid base 32. Actuation of amplitude modulation assembly 72 causes movement of screw 70 along its major longitudinal axis to thereby cause rod end 68 to become more proximate or less proximate to amplitude modulation assembly 72. Arm 82 extends from an end of screw 70 opposite to rod end 68 to elastic actuator catch bracket 84, which is mounted on base 18 of main moving platform 16. Arm 82 extends through an opening defined by elastic actuator catch bracket 84 and is linked to main moving platform 16 by springs 86, 88 held in place on either side of elastic actuator catch bracket 84 by nuts 90, 92, respectively.

Actuation of actuation assembly drive motor 60 causes rotation of eccentric drive plate 64 about an axis normal to a major plane of rigid base 32 which, in turn, causes reciprocal motion of swing arm plate 66 roughly along a major longitudinal axis of swing arm plate 66. Such reciprocal motion of swing arm plate 66 causes rod end 68 to move in a reciprocal motion from side-to-side of a major longitudinal axis of screw 70 which causes reciprocal rotation of nut frame 78 about an axis normal to major plane rigid base 18 and side-to-side motion of the opposite end of screw 70 opposite that of rod end 68 of screw 70. Such side-to-side movements of the opposite end of screw 70 causes reciprocal longitudinal movement of arm 82 extending through the opening defined by elastic actuator catch bracket 84.

Resistance to such reciprocal motion of arm 82 causes alternating reciprocal compression and relaxation of springs 86, 88, which thereby causes reciprocal motion of main moving platform 16 about main support shaft 40 linking main moving platform 16 to rigid base 32.

The amplitude of reciprocal motion of main moving platform 16 about main support shaft 40 is controlled by the location of screw 70 relative to amplitude modulation assembly 72. For example, if actuation of amplitude modulation assembly 72 causes rod end 68 to become more proximate to amplitude modulation assembly 72, the side-to-side motion of the opposite end of screw 70 will become greater, thereby causing the amplification of reciprocal motion of main moving platform 16 about main support shaft 40 to increase. Conversely, actuation of amplitude modulation assembly 72 to cause rod end 68 of screw 70 to become more remote from amplitude modulation assembly 72 will diminish the side-to-side motion of opposite end of screw 70, thereby reducing the amplitude of reciprocal motion of main moving platform 16 about main support shaft 40.

Reciprocal motion of main moving platform 16 may cause a delayed reciprocal motion of moving head platform 44 about head rotation bearing 46. The reciprocal motion of moving head platform 44, although delayed, may have greater amplitude about main support shaft 40 because of the rotation of moving head platform 44 about head rotation bearing 46. However, the amplitude of reciprocal motion of moving head platform 44 about head rotation bearing 46 may be dampened by springs 56.

Nevertheless, the reciprocal motion of main moving platform 16 and moving head platform 44 about main support shaft 40 is measured by motion sensing device 50 at moving head platform 44. Measurements by motion sensing device 50 are relayed back to control panel 34 and rigid base control electronics 36 which, alone, or optionally, in combination with external computer software programming, modulate actuator assembly drive motor 60 and amplitude modulation motor 74. Motion detection by motion sensing device 50 can also, optionally, modulate computer programming to affect selection and volume of sounds emitted by one or more speakers 52. Microphones 38, in addition, or optionally, receive acoustical signals that can be fed back through rigid base control electronics 36 or/and control panel 34 to software, either on-board or remote from infant calming/sleep-aid device 10, that further modulates actuator assembly drive motor 60, amplitude modulation motor 74 and/or sounds emitted from one or more speakers 52. Various control algorithms associated with modulation of actuator assembly drive motor 60, amplitude modulation motor 74 and speakers 52 will be more fully discussed below.

In one embodiment, the device allows for a reciprocating motion at 0.5-1.5 cycles per second (cps) of ~2" excursions, but if the baby is fussy the device responds by delivering a smaller excursion (e.g. <1.3") at a faster rate (~2-4.5 cps). This fast and small motion delivers the specific degree of rapid acceleration-deceleration force to the semicircular canals in the vestibular mechanism of the inner ear that is required to activate the calming reflex.

Also, the reciprocating motion typically has a maximum amplitude of less than 1.3 inches during the rapid phase of motion (~2-4.5 cps), further ensuring safety of the infant.

In one embodiment, the biometric sensor monitors the infant and generates a signal indicative of a respiration status or a cardiovascular status of the infant, such as to detect when the baby has paused breathing for a predetermined period of time, or has a cardiovascular collapse, such as indicated by a heart rate below a predetermined threshold, or the like. The sensor signal can be fed back through rigid base control electronics 36 or/and control panel 34 to a control system such as software, either on-board or remote from infant calming/sleep-aid device 10. The control system may receive and analyze the signal to determine whether a distressed status of the infant exists, and further may act, such as to generate an output to control modulation of the actuator assembly drive motor 60, amplitude modulation motor 74, or generate a telephone call to emergency services via Wi-Fi connection, and/or generate alerting and stimulating sounds that may be emitted from one or more speakers 52. An alarm can be directed to the infant's caretakers as well. In an embodiment, a distressed status of the infant may also include a cry state, which may be determined in accordance with embodiment of the present disclosure to be discussed below.

In some embodiments, in response to detection of infant distress, both vigorous motion of the platform and a loud sound can be provided. For example, providing motion of the platform at a frequency greater than 0.5 Hz and an amplitude that is greater than 1 inch, along with sound having an intensity of at least 65 dB, may provide appropriate stimulation of the infant. Of course, other amounts of stimulation are also envisioned.

Figure 6:
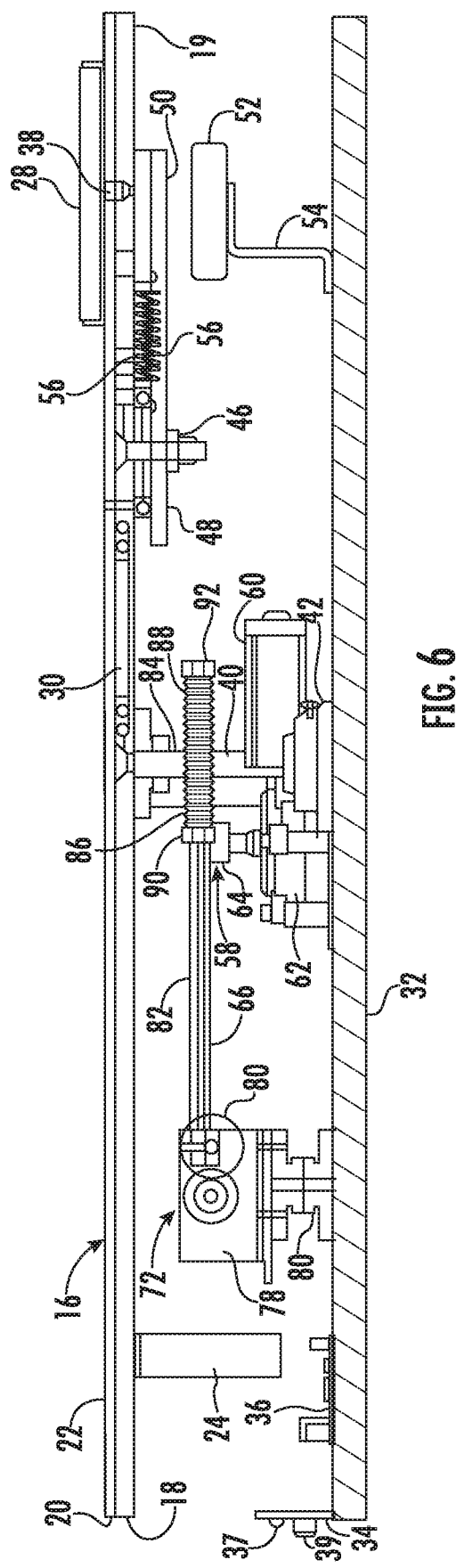
FIG. 6 is a side view of the infant calming/sleep-aid device shown in FIG. 4.
Figure 6A:
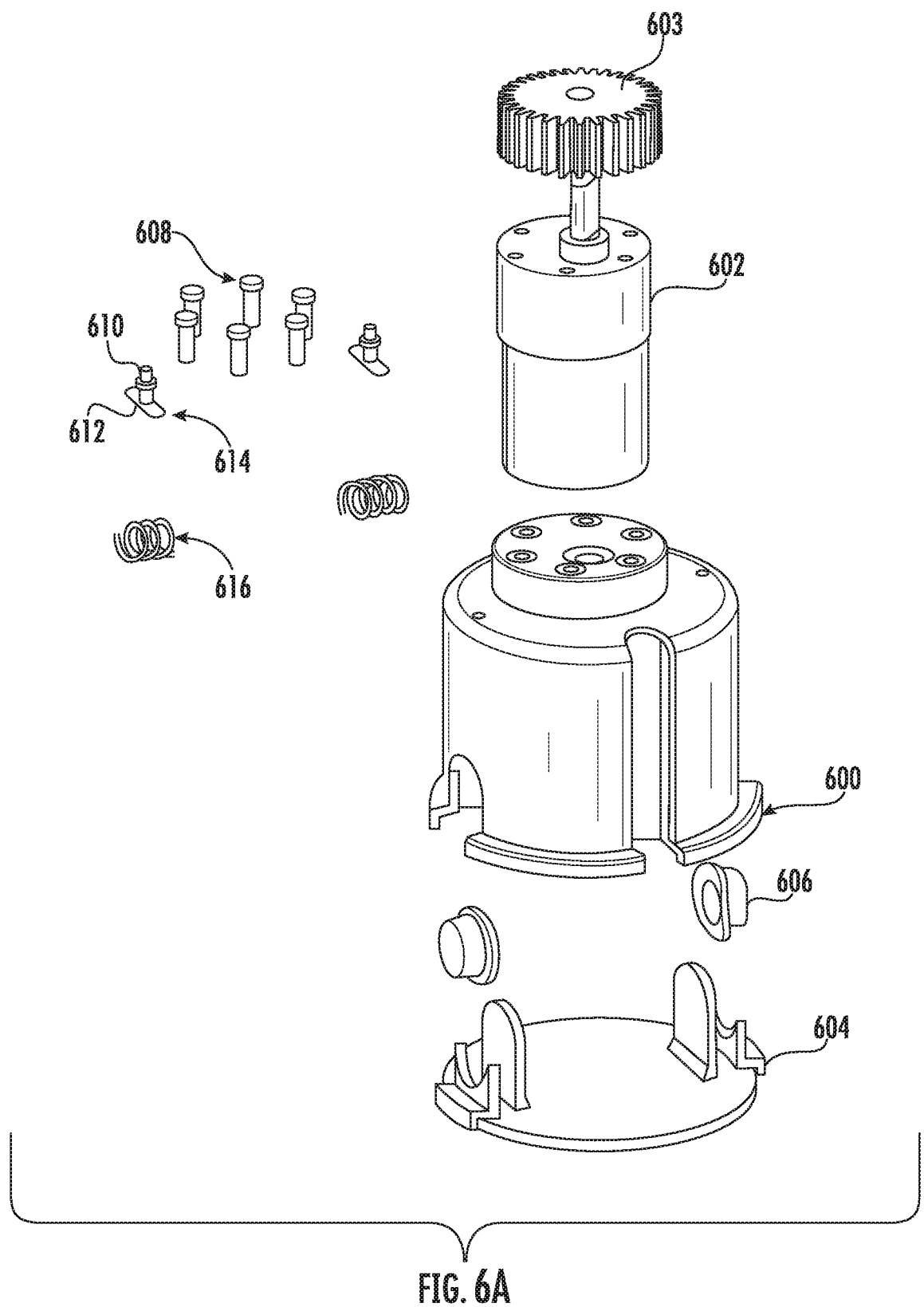
FIG. 6A illustrates a drive motor of the infant calming/sleep-aid device shown in FIG. 4 or of other embodiments of the infant calming/sleep-aid device.

FIG. 6A illustrates an exemplary and non-limiting embodiment of a drive motor 60. Assembly drive motor 60 may include motor case 600, motor 602, motor gear 603, motor case bottom 604, release button 606, button springs 616, screw 608, contact pin 610, metal plate 612, and the like. Motor case 600 may be made from an acrylonitrile butadiene styrene (ABS) plastic and the like. Motor 602 may be a 12V 300 RPM motor and the like. Motor gear may be made from polyoxymethylene (POM) plastic and the like. Motor case bottom 604 may be made from ABS plastic and the like. Release button 606 may be made from ABS plastic and the like. Button spring 616 may be made from stainless steel and the like. Screw 608 may be M3 HEX flat head 15 mm long screw, made from stainless steel, and the like. Contact pin 610 may be made from stainless steel and the like. Metal plate 612 may be made from stainless steel and the like.

Figure 6B:
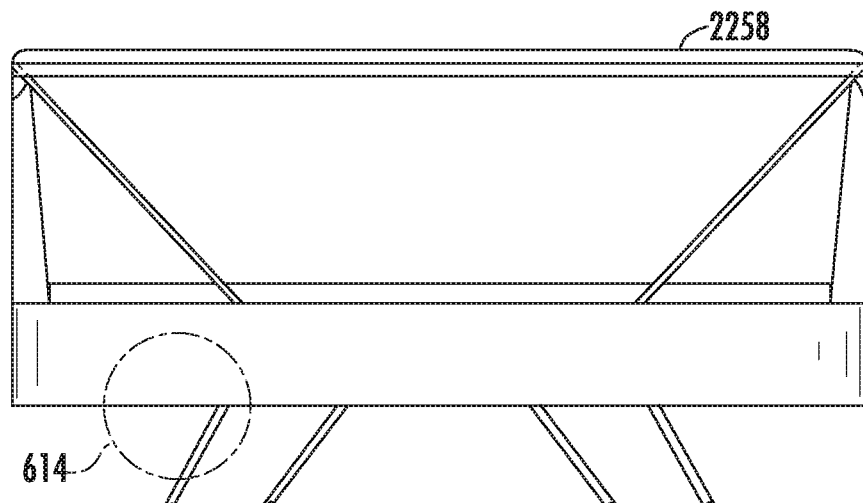
FIG. 6B illustrates an exemplary location of a drive motor on another exemplary embodiment of an infant calming/sleep-aid device.
Figure 6C:
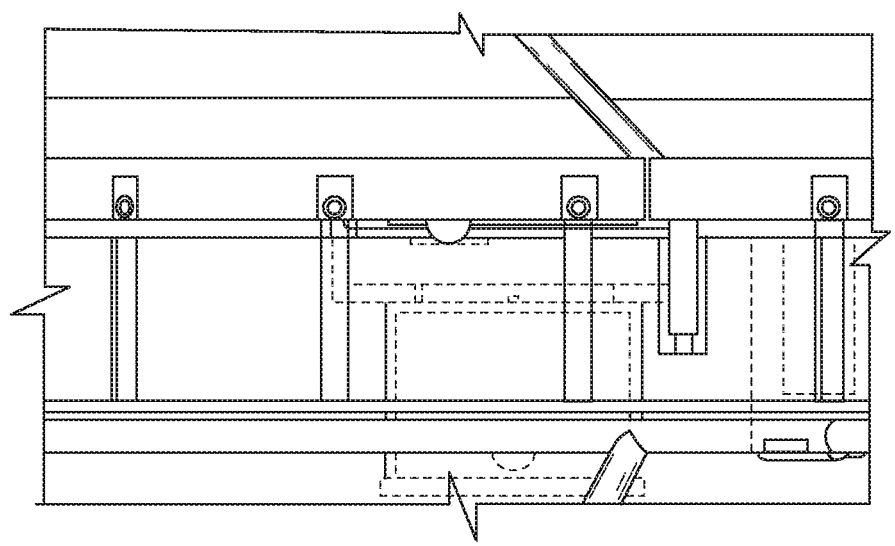
FIG. 6C illustrates a cross sectional view of an embodiment of the infant calming device/sleep-aid device showing the drive motor.

FIG. 6B illustrates the drive motor location 614 of the assembly drive motor 60 in an embodiment of the infant calming/sleep-aid device 2258. FIG. 6C illustrates a cross sectional view of an embodiment of the infant calming device/sleep-aid device showing the drive motor.

Figure 8:
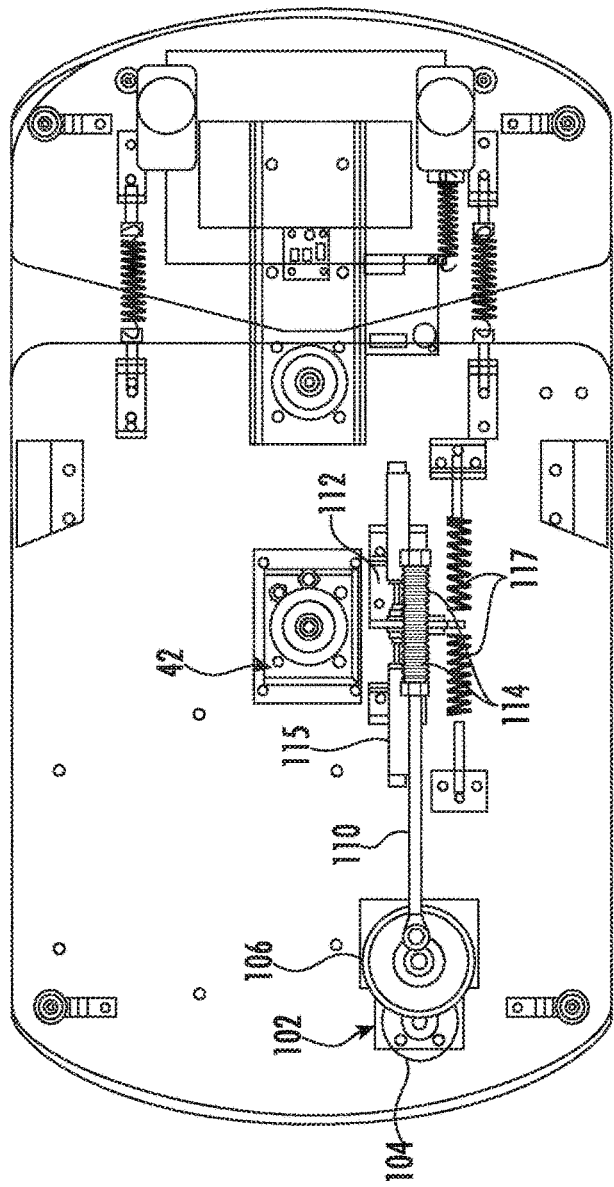
FIG. 8 is a plan view of components supporting the main moving platform of the calming/sleep-aid device of FIG. 7, with the rigid base and main moving platform shown in outline.
Figure 9:
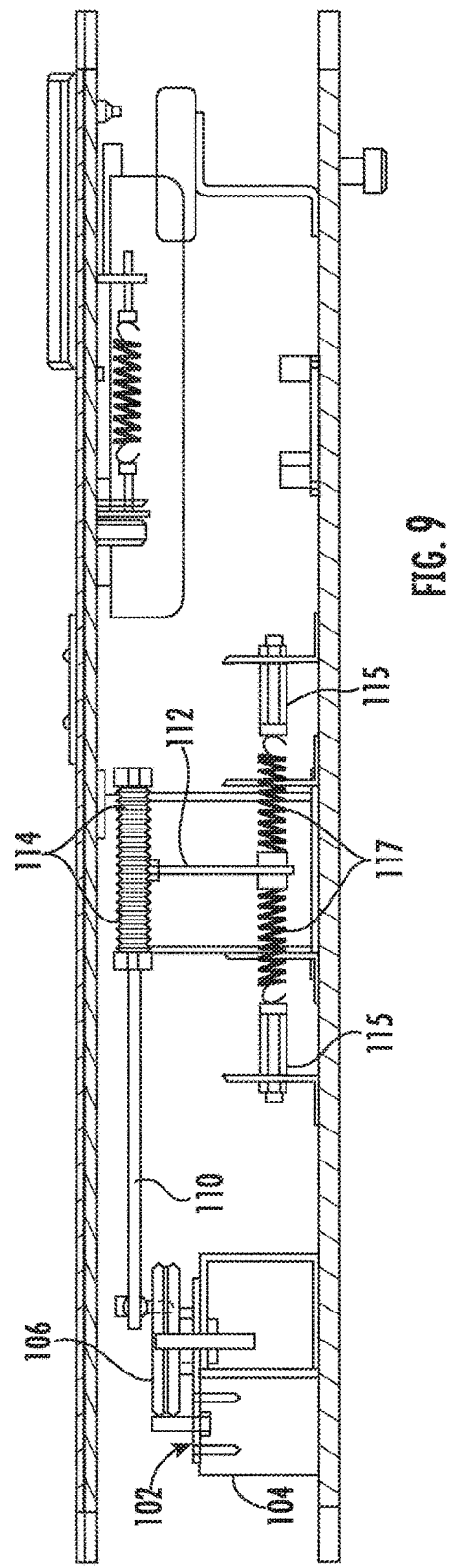
FIG. 9 is a side view of the embodiment of the device shown in FIG. 7.

In another embodiment, shown in FIGS. 7 through 9 calming/sleep-aid device 100 includes actuator assembly 102, which substitutes for actuator assembly 58 of the embodiment shown in FIGS. 2 through 6. Specifically, as shown in FIGS. 7 through 9, drive motor 104 of calming/sleep-aid device 100 is linked to bearing 106, which is, in turn, leads to the eccentric drive plate 108. Eccentric drive plate 108 is connected to push/pull rod 110 that extends through an opening defined by elastic actuator catch bracket 112. Springs 114 about push/pull rod 110 link push/pull rod 110 to main moving platform 16 through elastic actuator catch bracket 112. Springs 114 are series elastic actuator push-springs; they transfer force from actuator assembly 102 to elastic actuator catch bracket 112. Balancing dampers 115 beneath push/pull rod 110 dampen the motion of moving platform 16. Springs 117 are pull-balancing springs; they pull on elastic actuator catch bracket 112 in parallel with balancing dampers 115 to create the desired smooth sinusoidal motion of moving platform 16 at low frequencies and the more square wave, rapid accelerating/decelerating motion at high frequencies. Injection-molded plastic features that are parts of the main moving platform 16 may be used to create the desired smooth sinusoidal motion of main moving platform 16 at low frequencies and the rapid accelerating/decelerating motion at high frequencies.

Actuation of drive motor 104 causes reciprocal longitudinal movement of push/pull rod 110 through the opening defined by elastic actuator catch bracket 112 and translates that reciprocal movement into reciprocal motion of main moving platform 16 about main rotation bearing 42, as does reciprocal motion of arm 82 through elastic actuator catch bracket 84 of the embodiment shown in FIGS. 2 through 6. Other components of the embodiments shown in FIGS. 7 through 9 operate in the same manner as those of infant calming/sleep-aid device 10 represented in FIGS. 2 through 6.

Figure 10:
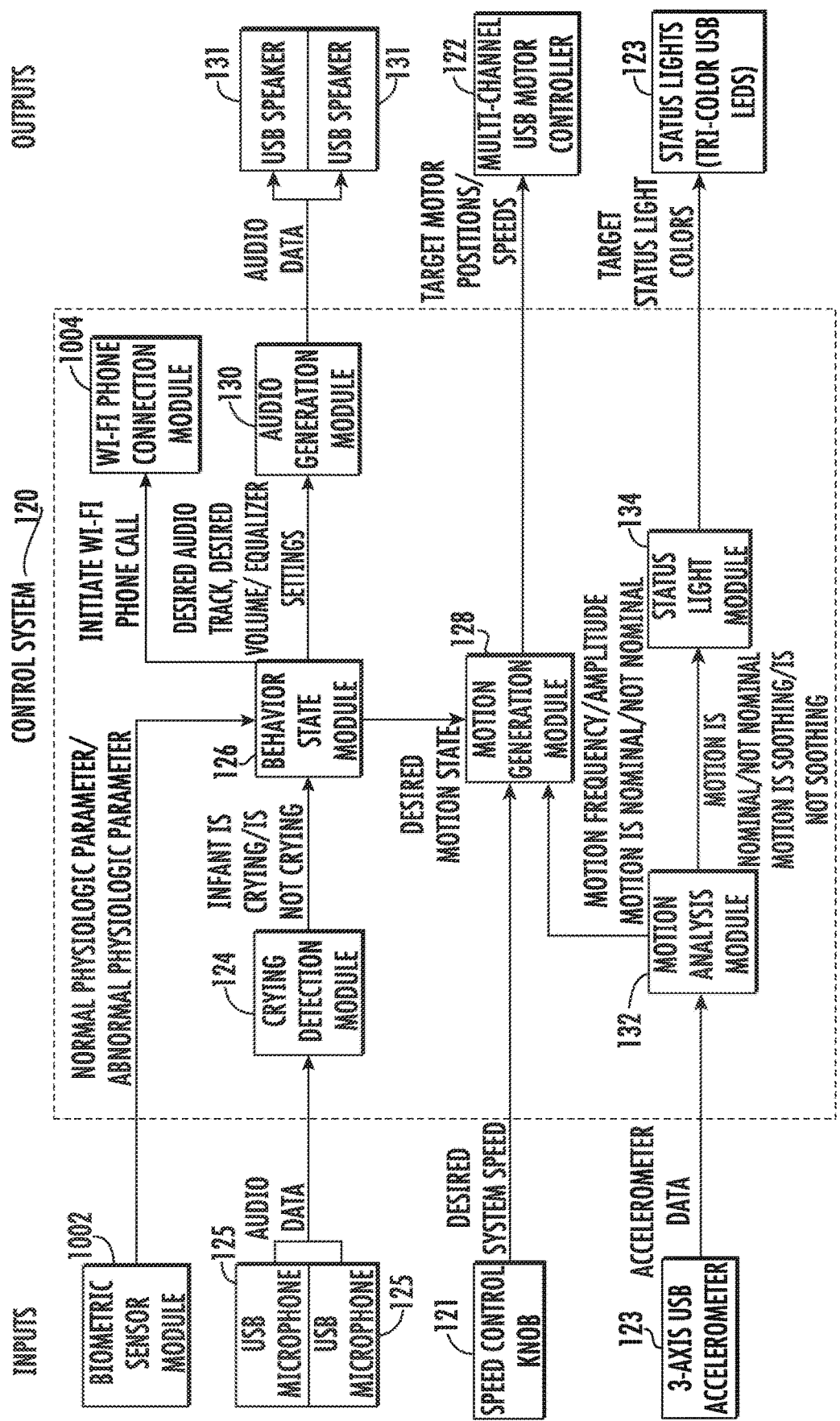
FIG. 10 is a schematic representation of one embodiment of a control system of the calming/sleep-aid device, along with inputs and outputs of the control system.

As shown FIG. 10, control system 120 receives various inputs from a variety of sensors or control input devices representing desired settings or the like and, based on one or more of these inputs, acts to control one or more of various devices, such as to control sound, motion, and/or lights of the sleep aid device, or to initiate an emergency call or alarm. As shown, the control system 120 processes inputs from microphones 125, from speed control knob 121 (also shown as element 35 in FIG. 2), and from a three-axis USB accelerometer 123 (represented as motion sensing device 50 in FIG. 3), and from a biometric sensor module 1002, such as a wireless sensor for detecting one or more of motion, cardiac and respiratory status. Control system 120 generates one or more output signals, such as to control one or more speakers 131 (or one or more speakers 52 as shown in FIG. 3), and to multichannel USB motor controller 122, which controls actuator assembly drive motor (such as assembly drive motor 60 shown in FIG. 3) and amplitude modulation motor (motor 73 of FIG. 3 or drive motor 104 of FIG. 7-9). Status lights, such as tricolor USB DEs 121 (or status lights 37 such as shown in FIG. 3) can also be controlled. Logic or control modules of control system 120 can be located on-board or remotely from the embodiments of infant calming/sleep-aid devices 10, 100 shown in FIGS. 2 through 9. The modules may include a crying detection module 124 that receives data from microphones 125, and relays to a behavior state machine module 126 whether or not an infant on infant calming/sleep-aid device is crying or not crying. Microphones 125 may be mounted on the infant calming/sleep-aid device, integrated into the infant calming/sleep-aid device, included in a sensor that may be located at some distance or placed on or attached to the infant, and the like. Biometric sensor module 1002 may relay one or more of an infant's physiologic parameters (e.g., breathing status, temperature, motion status, etc.) to the behavior state machine module 126, or depending on the signal provided by the sensor, directly to a Wi-Fi phone connection module 1004. An accelerometer may be used to measure the breathing of an infant by measuring mattress movement. Depending upon the input received by behavior state machine module 126, output signals will control motion generation module 128 or audio generation module 130 or a Wi-Fi connection module 1004. Alternatively, or in addition, output signals from behavior state machine module 126 will modulate generation of audio data output from audio generation module 130 to one or more speakers 131, represented as speakers 52 in FIGS. 2 through 9. Control system 120 may receive inputs from other sensors or devices and employ various control algorithms for control of different components of the device, as discussed below.

Motion generation module 128 receives input from speed control knob 121 and information regarding motion of the device 10, 100 from motion analysis module 132. Actuation of motion generation module 128 will modulate the actuator assemblies of the embodiments shown in FIGS. 2 through 9.

In embodiments, data received from accelerometer 123 is processed by motion analysis module 132 to thereby modulate the actuator assembly through motion generation module 128 and/or audio generation module 130 to thereby control the actuators assemblies or one or more speakers, respectively. In addition, motion analysis module 132 controls status light module 134 to alert, through the status lights, whether motions of the main moving platform and the head platform are nominal or not nominal, or alternatively, through feedback, soothing or not soothing to the infant. "Nominal", as that term is defined herein, refers to any and all motion for which the filtered acceleration signal does not exceed a specified, or predetermined maximum motion threshold for a specific length of time. The process by which the motion analysis module classifies motion as nominal or not nominal is detailed in FIG. 12 and in the accompanying text below.

In one embodiment, the rate of the reciprocating rotation is controlled to be within a range of between about one and about four and one-half cycles per second (cps) and with an amplitude of the reciprocating motion at a center of a head of the infant of between about 0.2 inches and about 1.3 inches. In another embodiment, the rate of reciprocating motion is within a range of between about 0.5 and about 1.5 cycles per second and an amplitude of the reciprocating rotation at a center of the head of the infant is in a range of between about 0.25 inches and about 2.0 inches. In differing embodiments, this motion may be parallel to, or orthogonal to the platform supporting the infant's body and head.

Figure 30A:
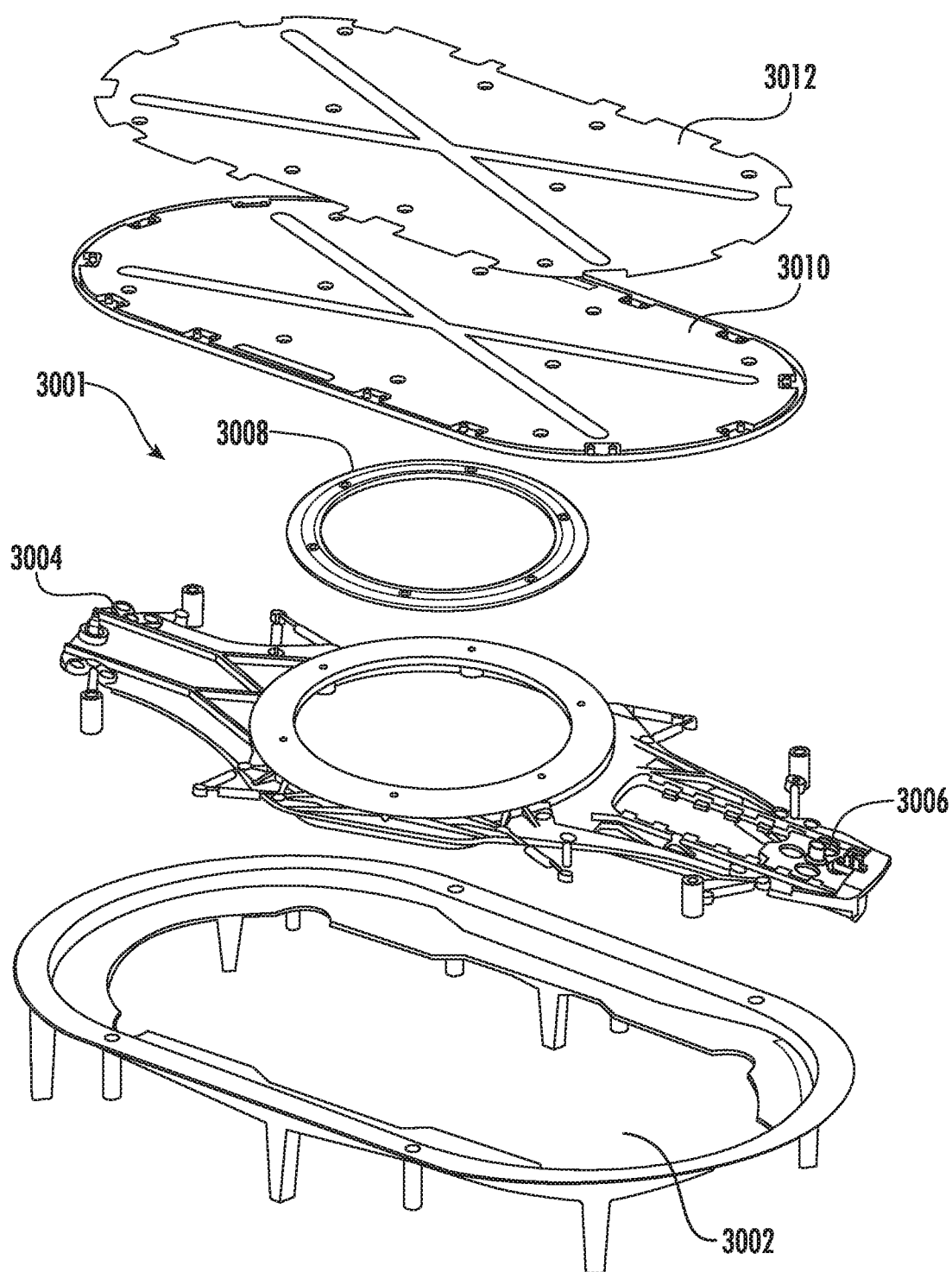
FIG. 30A is an exploded perspective view of an exemplary drive train system.

In embodiments, the infant calming/sleep aid device may comprise a single moving platform, which supports both the infant's body and head. This moving platform may be driven by a drive train system, such as exemplary drive train system 3001 shown in FIG. 30A, which may include a central carrier 3004 that supports a moving platform 3010, with a bearing 3008 between the central carrier 3004 and moving platform 3010, a motor 3006 for moving the moving platform 3010 with respect to the central carrier 3004 in an oscillatory manner. Other components include a top trim component 3002, and an EMI shield 3012. Although the exemplary embodiment being described shows a circular, lazy-Susan bearing, this is non-limiting and other embodiments are contemplated, such that references to bearing 3008 may indicate one or more of a lazy-Susan bearing, a slide bearing, a low-friction load-carrying component such as a Teflon and the like.

FIG. 30B shows a perspective assembled view of the exemplary drive train system 3001 with moving platform 3010 in solid lines and central carrier 3004 in dashed lines, FIG. 30C shows a partially assembled version of the exemplary drive train system 3001, and FIG. 30D also shows an enclosure 3014 that may enclose the internal components of the drive train system 3001. An infant may be placed on a sleeping surface on the moving platform 3010, and may experience the oscillatory movement about a vertical axis 3052 (shown in FIG. 30D) through a center of rotation 3308 (shown in FIG. 30D and also FIG. 33A), which may be at the center of the bearing 3008. The oscillatory movement or rotation of the moving platform 3010 in a horizontal plane is indicated by double-sided arrows 3050 in FIG. 30D and described elsewhere herein, and includes movement that is adaptively changed, with various amplitudes and frequencies of movement according to detected conditions of the infant or other factors.

In embodiments, this movement may be a jiggly, approximately square wave type motion, such as a clipped sinusoidal wave (that is, a position vs. time graph is a clipped sinusoidal wave), rather than being purely sinusoidal. In embodiments, the frequency of the movement of the moving platform may be varied, and/or the amplitude of the movement may be varied according to a desired motion pattern, feedback received regarding the infant, or other factors. In embodiments, the movement of the moving platform 3010 may be increased in frequency and decreased in amplitude to simulate a jiggly motion or a vibration when an infant is detected to not be soothed, not to be breathing or according to other factors.

Figure 31:
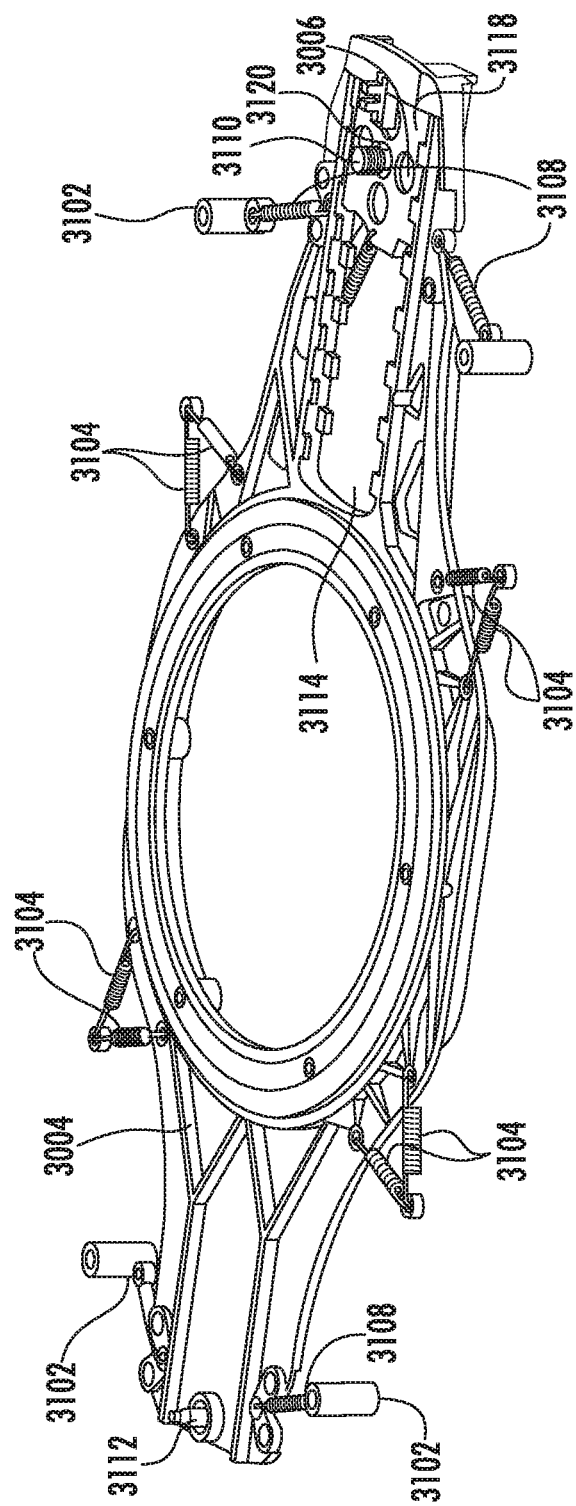
FIG. 31 is a perspective view of a central carrier.

FIG. 31 provides a perspective view of the central carrier 3004 in more detail. In particular, the central carrier 3004 may support the motor 3006 partially enclosed in a motor bracket 3118. A center post 3110 of the motor 3006 may extend upward beyond the motor bracket 3118 and be encircled by one or more motor O-rings 3120, with oscillation of the center post 3110 (see also FIG. 33B) causing back and forth movement of the moving platform 3010 in a horizontal plane about vertically extending axis 3052 with respect to central carrier, as explained more fully elsewhere herein. The motor 3006 held by the motor bracket 3118 may be positioned at various locations within a channel 3114 to correspond with one of several guide tracks 3204 (shown in FIG. 32A and in FIG. 33D), in order to change a corresponding mechanical advantage of the motor. The central carrier 3004 may be suspended from a plurality of suspension springs 3104 that attach to a rigid base 3402 (see also FIG. 34A). The central carrier 3004 may include one or more rotational stop bumpers 3112 to prevent over-rotation of the overlying moving platform 3010. The central carrier 3004 may be attached to a plurality of kinetic helper springs 3108 each attached to an assembly puller 3102. Each assembly puller 3102 may be attached to the underside of the moving platform 3010.

Figure 32A:
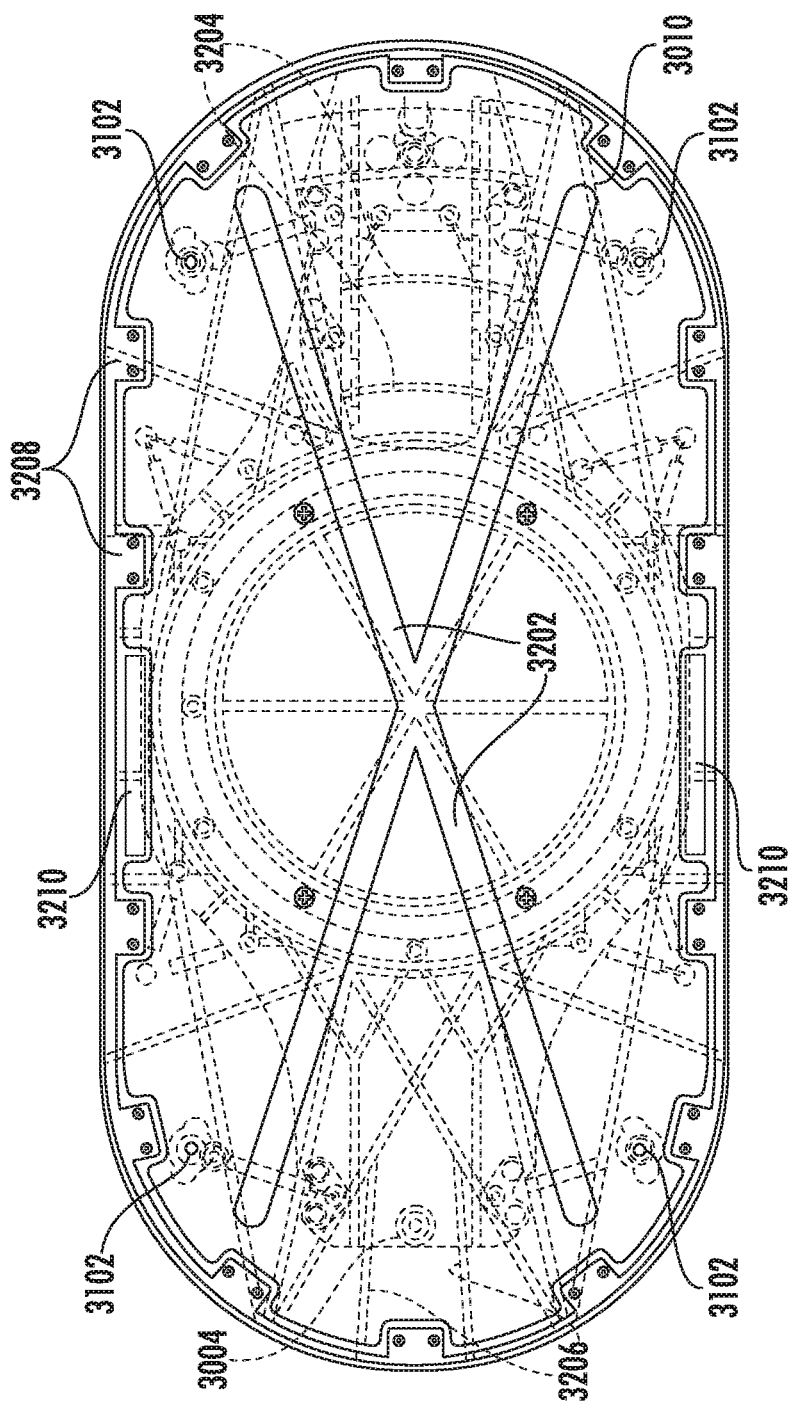
FIG. 32A-32B are plan views of the top of a main moving platform of the exemplary drive train system.
Figure 32B:
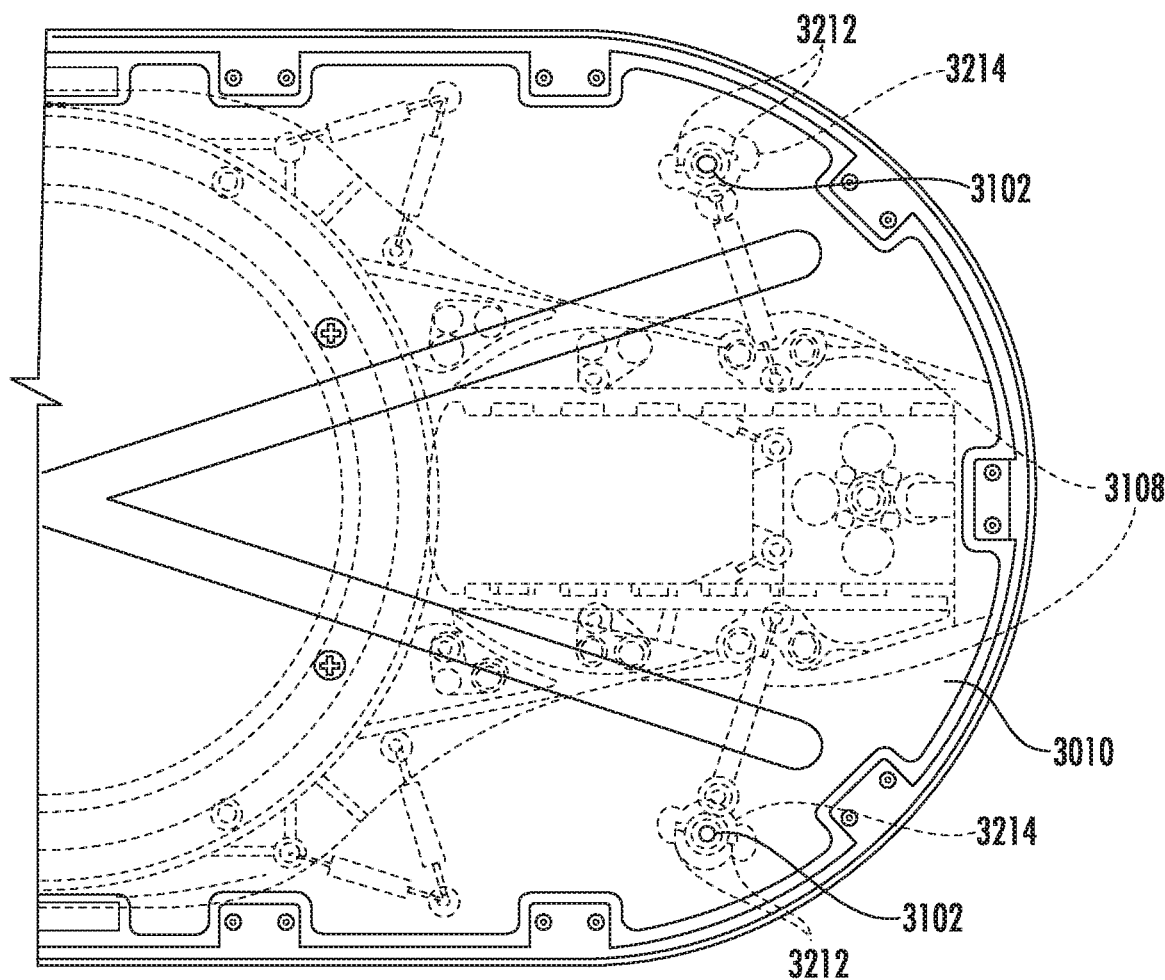

FIGS. 32A and 32B are plan views from the top of the moving platform 3010 of exemplary drive train system 3001 for an infant calming/sleep aid device, with the elements on the underside of the moving platform and the central carrier 3004 shown in dashed lines. The moving platform 3010 supports an infant and may include support structures 3202, which may be integral to the moving platform and may enhance rigidity of the moving platform 3010. The platform support structures 3202 may include channels to act as guides for any moisture collected on the moving platform, directing the moisture away from openings that might allow the moisture to contact moisture sensitive components of the drive train system. As mentioned, the underside of the moving platform 3010 may include one or more guide tracks 3204 (see also FIG. 33D), which interact with the center post 3110 of the motor and guide the movement of the moving platform 3010. Moving platform 3010 may also include rotational stop structures 3206 to keep the platform from over-rotating. There may also be a plurality of openings along the outer portion of the moving platform 3010 providing access for sleeping sack attachments 3210, mesh attachment points 3208, and the like, for attaching a sleeping sack. In embodiments, the control system renders the motor inoperable if a sleeping sack in which the infant is placed is not appropriately attached to the platform 3010.

As shown in FIG. 32B, the moving platform 3010 may include a plurality of assembly puller positioning guides 3214 to aid in the manufacturing and assembly of the device. The assembly puller positioning guides 3214 are shaped to accommodate the assembly puller wings 3212 which extend out from the assembly puller 3102. The assembly puller wings 3212 in combination with the assembly puller positioning guides 3214 prevent the attached assembly puller 3102 from rotating and allow the device to be assembled quickly and easily. The kinetic helper springs 3108 link the assembly pullers 3102 attached to the underside of the moving platform 3010 to the central carrier 3004. As the moving platform 3010 is rotated back and forth, each kinetic helper spring 3108 is under tension as the platform is moved away from that spring, and these kinetic helper springs aid in the movement of the moving platform back to its centered position.

Figure 18:
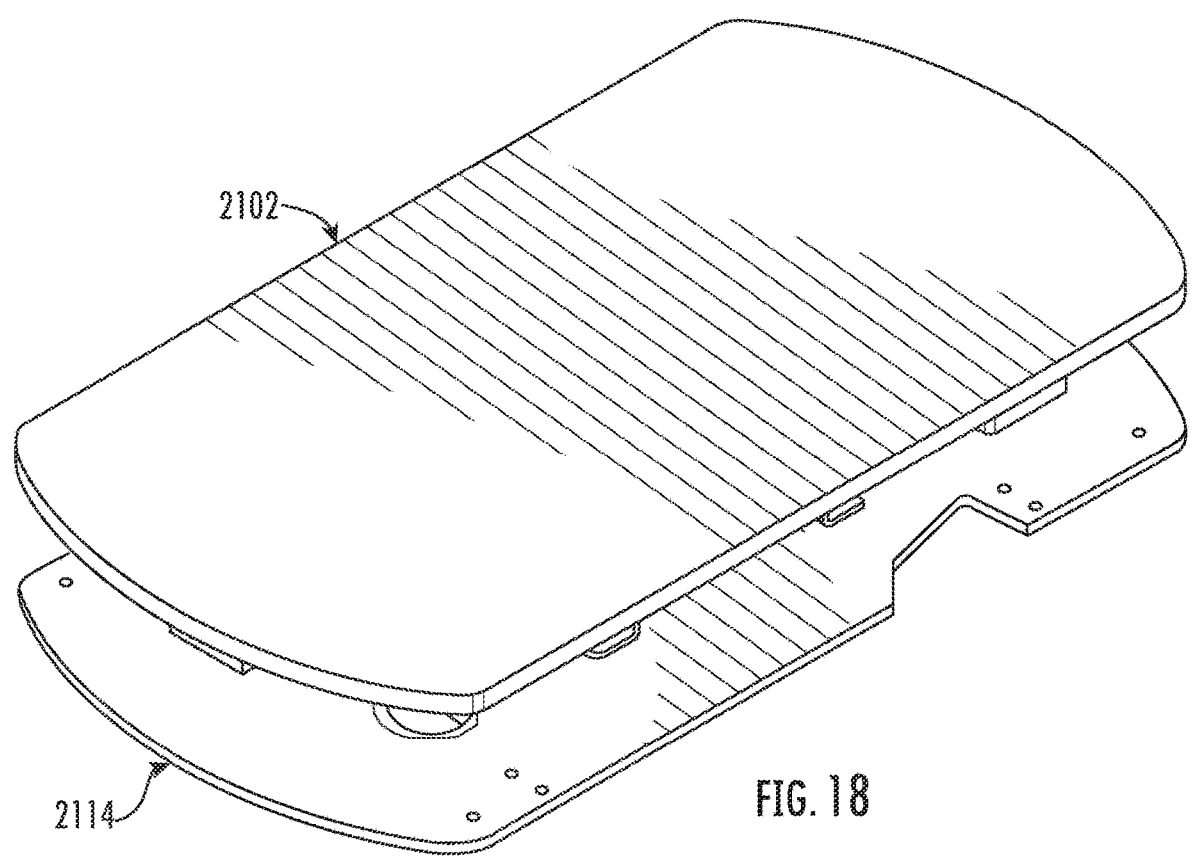
Figure 33A:
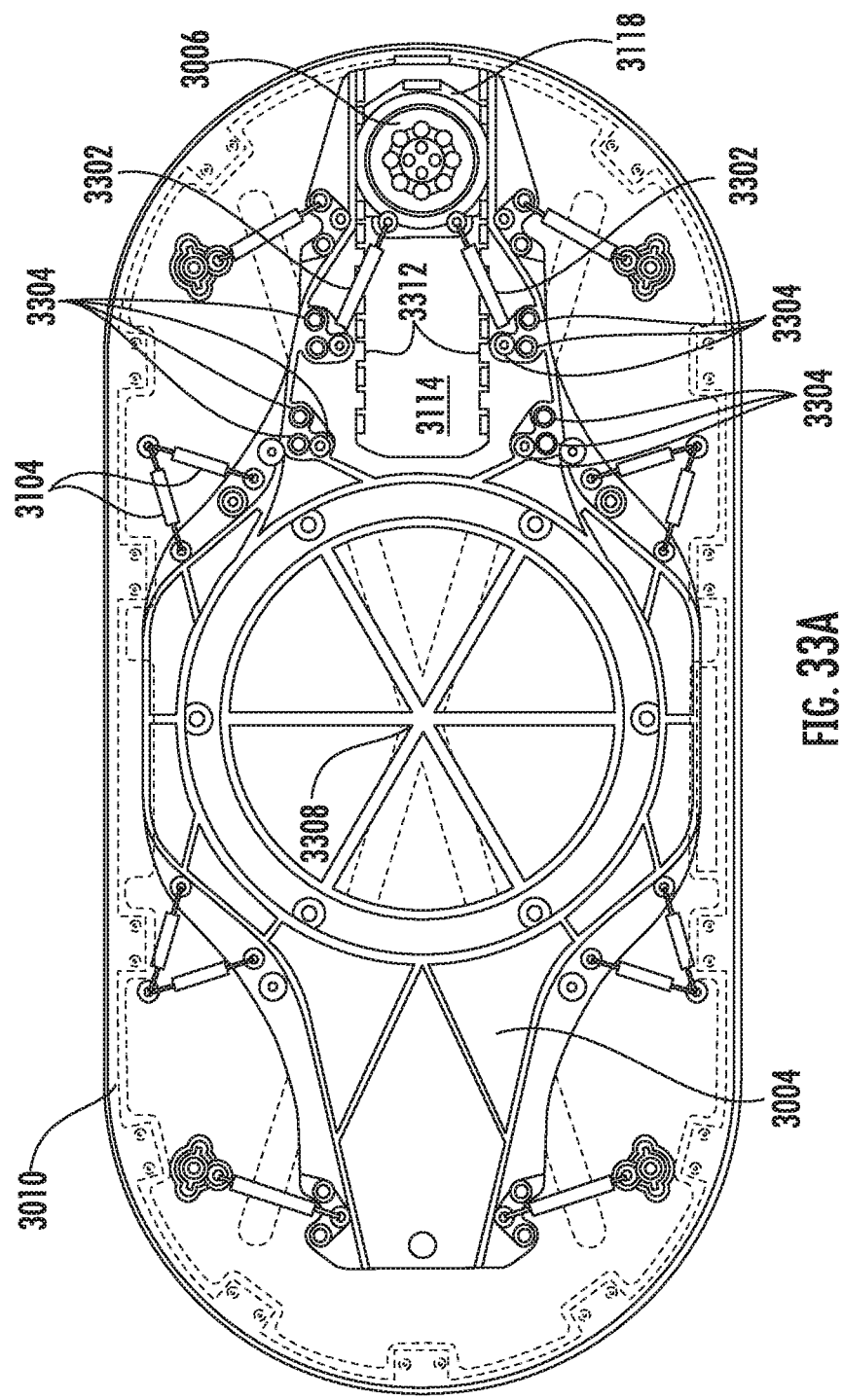
FIG. 33A is a plan view of the underside of a central carrier of the exemplary drive train system.

FIG. 33A is a plan view of the underside of the central carrier 3004 of the drive train system 3001 for infant calming/sleep aid device 10 of FIG. 1 or the sleep aid device of FIG. 18, with the moving platform 3010 partially shown is dashed lines. From this view of the central carrier 3004, motor positioning springs 3302 and motor spring attachment points 3304 are visible. Tension in the motor positioning springs 3302 may act to pull the motor bracket 3118 along the channel 3114 toward vertical axis 3052 (shown in FIG. 30D) through the center of rotation 3308 of the moving platform 3010 to keep the motor 3006 correctly aligned.

Figure 33C:
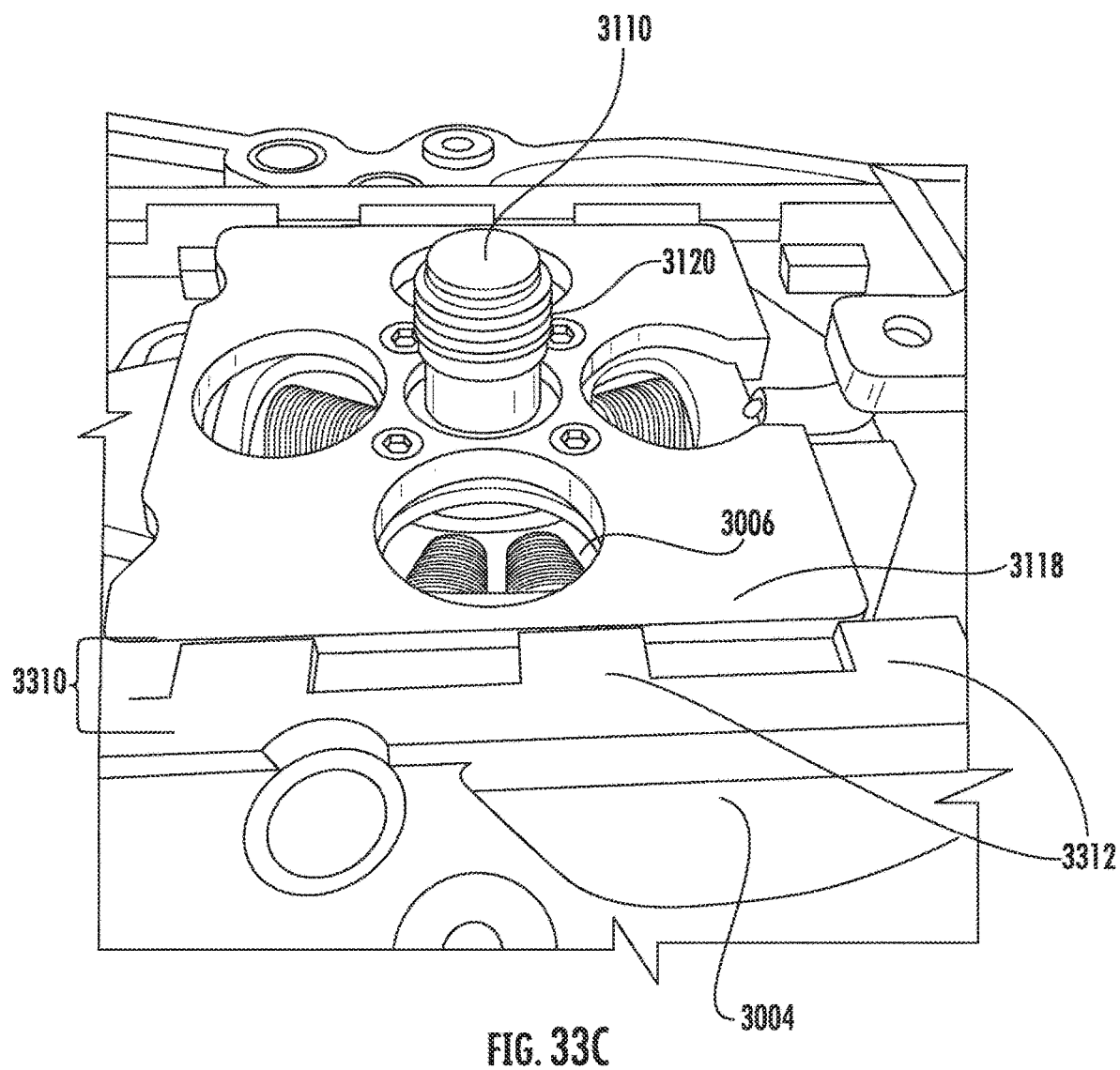

FIG. 33B is a perspective view of the motor 3006, channel 3114, a motor channel guide 3310 and motor channel teeth 3312. FIG. 33C is a close-up view of the motor 3006 in the motor bracket 3118 sitting in the motor channel guide 3110. These figures illustrate how the motor channel guide 3310 created by the motor channel teeth 3312 supports the motor bracket 3118 as it moves along the channel 3114. In particular, motor channel guide 3310 runs along the longitudinal sides of the channel 3114. The motor channel guide 3310 may be comprised of a plurality of non-overlapping motor channel teeth 3312. On each side of channel 3114, the motor channel teeth 3312 may alternate between aligning with the top of the motor channel guide 3310 and aligning with the bottom of the motor channel guide 3310. The arrangement of the motor channel teeth 3312 so that there is no overlap of the motor channel teeth 3312 aligning with the top of the motor channel guide 3310 and those aligning with the bottom of the motor channel guide 3310 may facilitate the manufacturing of the motor channel guide 3310 and motor channel teeth 3312 using a simple core/cavity injection molding tool.

FIG. 33D shows a cross-sectional view of a portion of the motor 3006, the central carrier 3004, the moving platform 3010 and the top trim component 3002. The central carrier 3004 may include a sensor 3318 for detecting the position of the moving platform 3010, as well as a sensor 3314 for detecting the position of the motor 3006. Information related to the position of the moving platform 3010 and the motor 3006 may be used to verify that the motion of the moving platform 3010 is consistent with motion requested by a control algorithm. Motion that is inconsistent with that requested by the control algorithm may be used to identify failures with the motor drive mechanism, blockage of the moving platform 3010, motor 3006 failure, loss of motor power supply, unintended slip between the motor 3006 and the moving platform 3010, and the like. Motion that is inconsistent with that requested by a control algorithm may also be caused by caregiver interaction with the infant and/or moving platform, such as the parent rocking or patting the infant, and over-riding the expected movement of the system. Information related to the position of the moving platform 3010 together with the motor 3006 position may be used by the control algorithm to self-correct any deviations in expected alignment by adjusting the amplitude and frequency of the motor to realign the moving platform 3010 with the central carrier 3004 and the motor 3006. The self-correction may occur over a number of motion cycles, in order to make the change less abrupt and less noticeable or unnoticeable by the infant.

In embodiments, the motor bracket 3118 may be under tension from the motor positioning springs 3302 that extend between the motor and the central carrier and may be pulled toward the axis in line with the center of rotation 3308 of the moving platform 3010. As illustrated, the motor O-rings 3120 are in contact with the guide track 3204 of the moving platform 3010. Because the motor positioning springs 3302 are pulling the motor 3006 in the direction of the center of rotation 3308, there is a pressure being applied by the motor O-rings 3120 on the guide track 3204 of the moving platform 3010. The pressure applied by the motor O-rings 3120 on the guide track 3204 may be in the range of 1 psi to 25 psi. As the motor 3006 oscillates, the center post 3110 and the motor O-rings 3120 are rotated. The friction between the motor O-rings 3120 and the guide track 3204 cause the moving platform 3010 to rotate around the center of rotation 3308. In embodiments, the oscillating movement of the moving platform may be from approximately 0 to +/−5 degrees from a centered position, 0 to +/−10 degrees, or 0 to +/−20 degrees, at frequencies of up to 4 Hz.

The moving platform 3010 may be prevented from over-rotating relative to the central carrier 3004 by the presence of the rotation stop bumper 3112 which will come in contact with the rotational stop structure 3206 on the underside of the moving platform 3010 if the moving platform 3010 rotates too far beyond the preferred maximum rotation of approximately 5 degrees. The rotation stop bumper 3112 may be comprised of a soft rubber such as a 35-45 SHORE A rubber. The rotation stop bumper 3112 may have a screw coming up from the bottom part way through the interior thereof. This composition of the rotation stop bumper may contribute to the comfortable "feel" of the motion dampening from a small initial dampening as the rubber portion of the rotational stop bumper 3112 initially compresses through the rubber to a hard stop provided when the rotational stop bumper 3112 is fully compressed against the rigid internal screw.

The motor O-rings 3120 may be comprised of: buna-N, a synthetic copy of natural rubber; high abrasion polyurethane; polysilicone; silicone; Viton, a synthetic copy of natural rubber; EPDM, neoprene, polyurethane-elastomers, or the like. There may be one or more motor O-rings 3120 encircling the center post 3110. The presence of more than one motor O-ring 3120 may provide redundancy and increased frictional area between the motor O-rings 3120 and a guide track 3204. The moving platform 3010 may be comprised of material such as a poly carbonate, Acrylonitrile butadiene styrene (ABS), a blend of poly carbonate and ABS, and the like, selected to provide adequate traction with respect to the motor O-rings 3120.

Referring to FIGS. 33A-D, in embodiments, the motor 3006, positioned within the motor bracket 3118, may be moved up and down the channel 3114 to various positions such that the motor O-rings 3120 are in contact with various ones of the guide tracks 3204 or other drive surface of the moving platform 3010. In embodiments, there may be a friction optimization device to optimize the friction between the motor O-rings 3120 and the guide track 3204 or other drive surface of the moving platform 3010. Friction optimization devices may include springs pushing and/or pulling on one of more of the guide track 3204, the motor 3006, the motor bracket 3118, and the like. Friction optimization devices may comprise springs or other geometric features integrated directly into the motor bracket 3118, the moving platform 3010, the channel 3114, and the like so as to maintain desired contact of motor O-rings 3120 to guide track 3204 or other drive surface of the moving platform 3010. In one embodiment, friction optimization devices, the motor positioning springs 3302, are attached to the motor bracket 3118 and to various of the motor spring attachment points 3304 as required to achieve the desired pressure, and associated friction, by the motor O-rings 3120 on the selected guide track 3204 given the position of the motor bracket 3118 within the channel 3114 and the tensile characteristics of the motor positioning springs 3302. The mechanical advantage provided by the motor 3006 may vary with the distance of the guide track 3204 in contact with the motor O-rings 3120 from the axis aligned with center of rotation 3308 of the moving platform 3010.

The motor 3006 may be selected to provide smooth, low noise operation with high torque at low rpm that may be precisely controlled for both position and speed. For example, the motor 3006 may be a 3-phase permanent magnet synchronous motor (PMSM), a 3-phase brushless DC motor (BLDC), and the like which may be driven by sinusoidal currents. For controlling speed and position of the motor 3006, a motor driver may synthesize three independent sinusoidal voltages with controllable frequency and amplitude for each phase. The synthesized voltages may have a constant phase offset of 120°, which reflects the position offset of three motor windings. The motor driver may comprise three half-bridges, one for each of the three phases, which generate three independent sinusoidal voltages. Each half-bridge may comprise two MOSFET transistors acting like low resistance electronic switches. By applying two mutually inverted pulse-width modulated (PWM) signals on those switches, the average voltage output from half-bridge may be set anywhere from 0 V to 12 V DC. These voltages are connected to the motor 3006 terminals in order to create sinusoidal currents in the motor 3006 windings and appropriate magnetic flux in motor 3006 stator.

The use of a BLDC motor is advantageous as it enables direct control of both amplitude and frequency without the need for an additional motor or additional gears to manipulate amplitude. The elimination of gears may enable quieter operation, which is an advantage in this application. It also reduces the number of moving mechanical parts, which may lead to an improvement in robustness. The use of a brushless motor may also extend the life of the motor by eliminating brush wear. Typical inductive motors have an optimum RPM and achieve lower speeds with gearing. Applications with continuous change of direction tend to be difficult for these motors. An advantage of the BLDC motor is that it operates well at a wide range of frequencies (RPMs) and has high torque at low RPMs, which facilitate the rapid change of direction needed by this application.

In order to achieve silent operation, the PWM frequency, i.e., the frequency at which the half-bridges are turned on and off, may be set above 20 kHz and preferably around 40 kHz. The PWM frequency is unrelated to the frequency at which the motor 3006 rotates the moving platform 3010. Required PWM signals for a driver stage may be generated by a microcontroller (MCU) based on a control algorithm. The control algorithm may determine the desired amplitude and frequency of motion based on input from an infant motion sensing device, an infant noise sensing device, an infant vital sign sensing device such as a sensor for heart rate, breathing, oxygenation and the like as discussed elsewhere herein. An open-loop control method which relies on the ability of the motor rotor to stay locked with the stator magnetic flux may be used such that control of the position and rotational speed of the center post 3110, may be achieved by control of the three winding currents alone. As long as external disturbances and inertial forces of moving platform 3010 do not overcome the motor 3006 torque, then the rotor will stay locked to the stator magnetic flux. To enable this operation, the drive mechanism may be designed to allow controlled slippage between motor O-rings 3120 and the guide track 3204. Torque at which this slippage occurs may be designed to be lower than the torque of the motor 3006. Thus, if the moving platform 3010 is blocked, the motor O-rings 3120 will slip against the guide track 3204 allowing the motor 3006 to continue to turn and keep the rotor locked to stator magnetic flux. When the moving platform 3010 is again able to move, the system may self-correct the alignment of the moving platform 3010 and the motor center post 3110 as described elsewhere herein.

At low frequencies, such as those below approximately 1.5 Hz, the motor 3006 may be able to provide sufficient torque to enable the motor O-rings 3120 to provide sufficient friction on the guide track 3204 to rotate the moving platform 3010. At higher operating frequencies, such as those above approximately 1.5 Hz, an extremely high torque would be required from the motor 3006 to change the rotational direction of the moving platform 3010. The kinetic helper springs 3108 assist the motor 3006 in returning the moving platform 3010 to a non-rotated position. As the moving platform 3010 is rotated back and forth relative to the central carrier 3004, a subset of the kinetic helper springs 3108, which are attached between the moving platform 3010 and the central carrier 3004, are put under tension. When the motor 3006 changes the rotational direction of the center post 3110, those kinetic helper springs 3108 under tension provide additional spring force to return the moving platform 3010 to a non-rotated position relative to the central carrier 3004.

FIG. 34A is a view of a rigid base 3402 supporting the central carrier 3004. The rigid base 3402 may include a plurality of support structures 3404 from which suspension springs 3104 support the central carrier 3004. In some embodiments, there may be a support structure 3404 in each quadrant of the rigid base 3402. The use of the suspension springs 3104 enables the central carrier 3004 and the supported moving platform 3010 to move with respect to the rigid base 3402. This movement may allow the moving platform 3010 and supported sleep surfaces to have a slight give when an infant positioned on the supported sleep surface is in motion. This slight give may increase the comfort of the baby. In some embodiments, more than one suspension spring 3104 may be attached to a single support structure 3404 where the suspension springs 3104 each have an end attached to the support structure 3404 and another end attached to the central carrier 3004. The ends of the suspension springs 3104 attached to the central carrier may be located such that an angle of approximately 70-90 degrees is created between the two suspension springs attached to a single support structure 3404 helping to dampen any rotational movement of the central carrier 3004 caused by the baby.

Figure 34B:
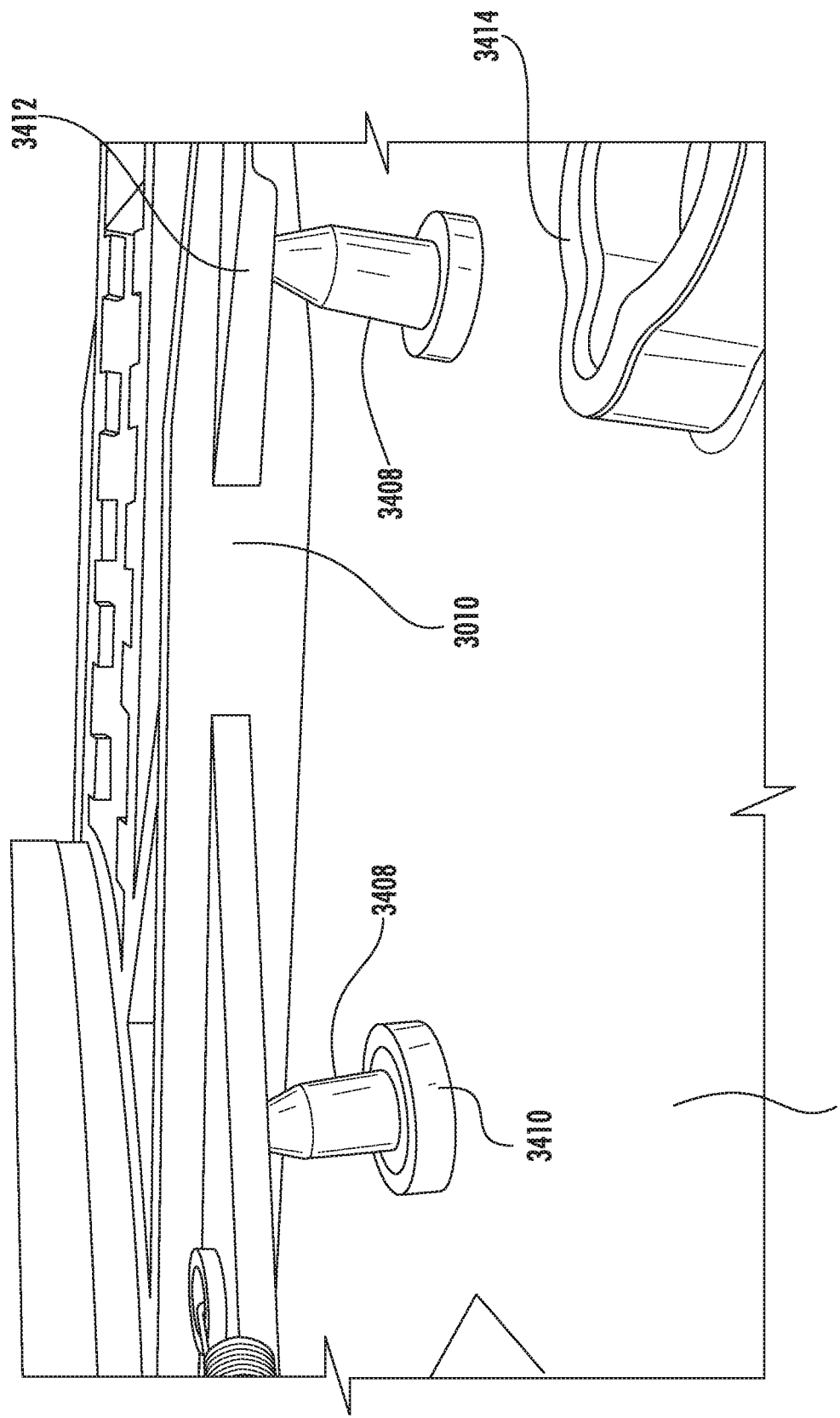
Figure 34C:
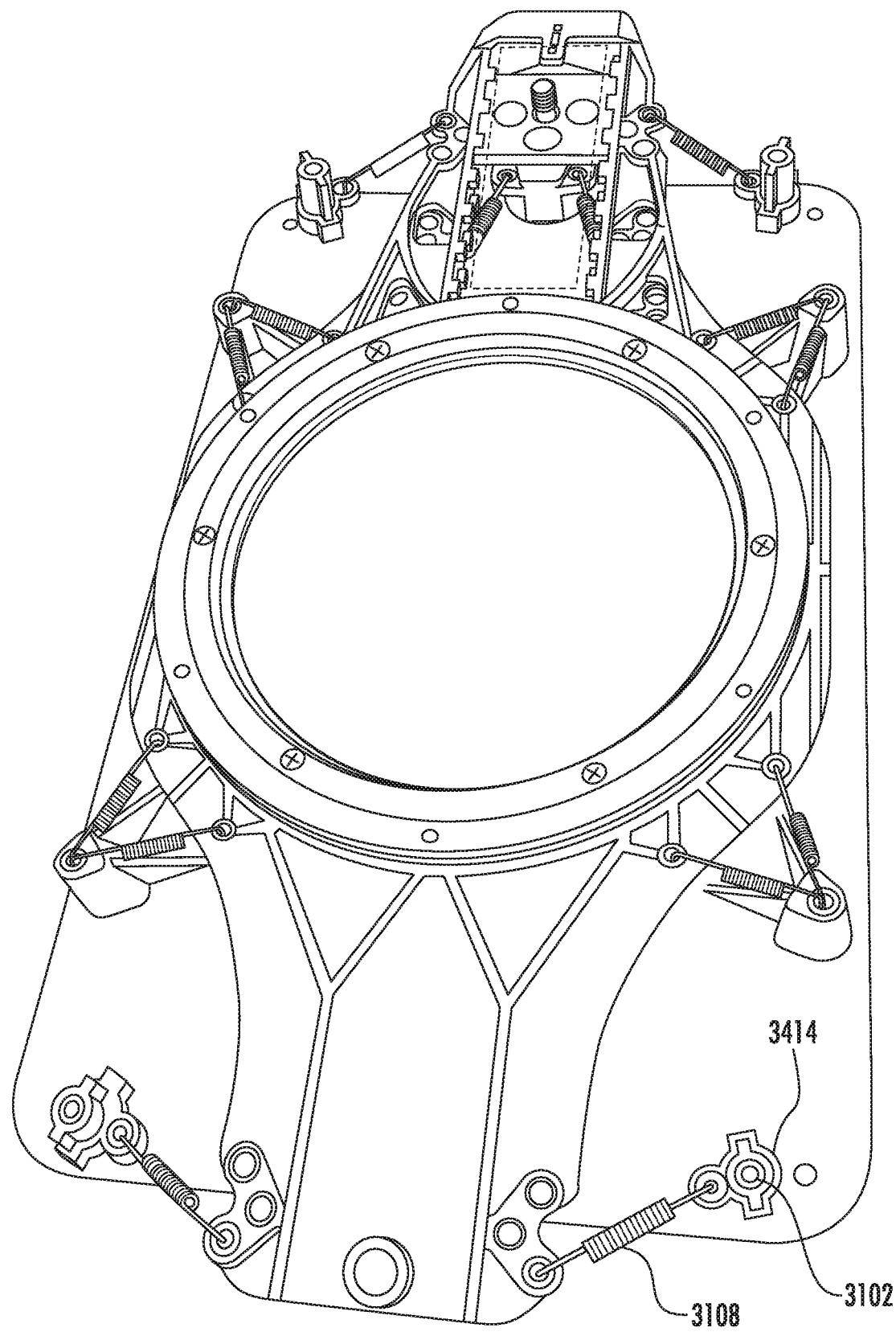
Figure 34D:
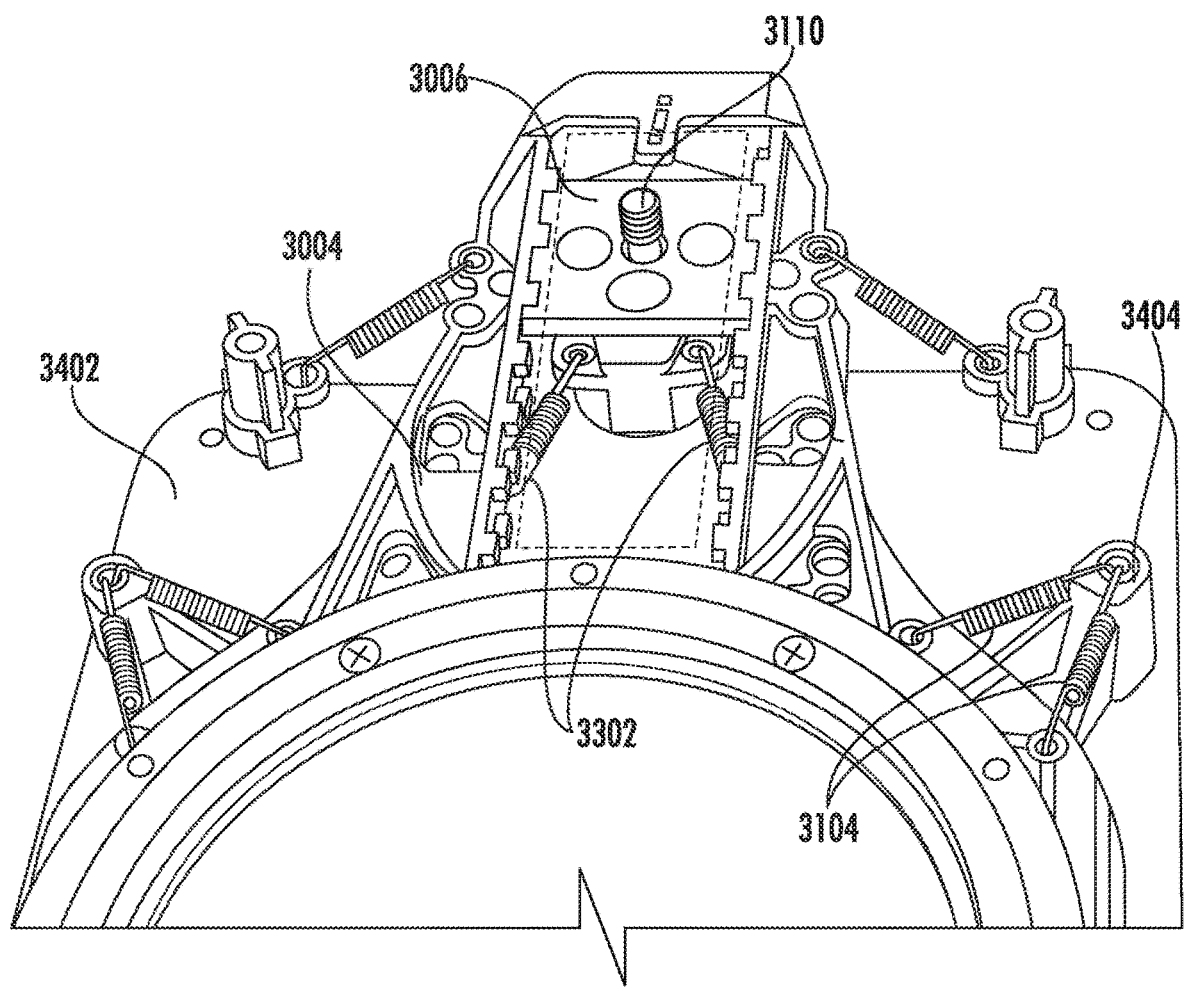
Figure 34E:
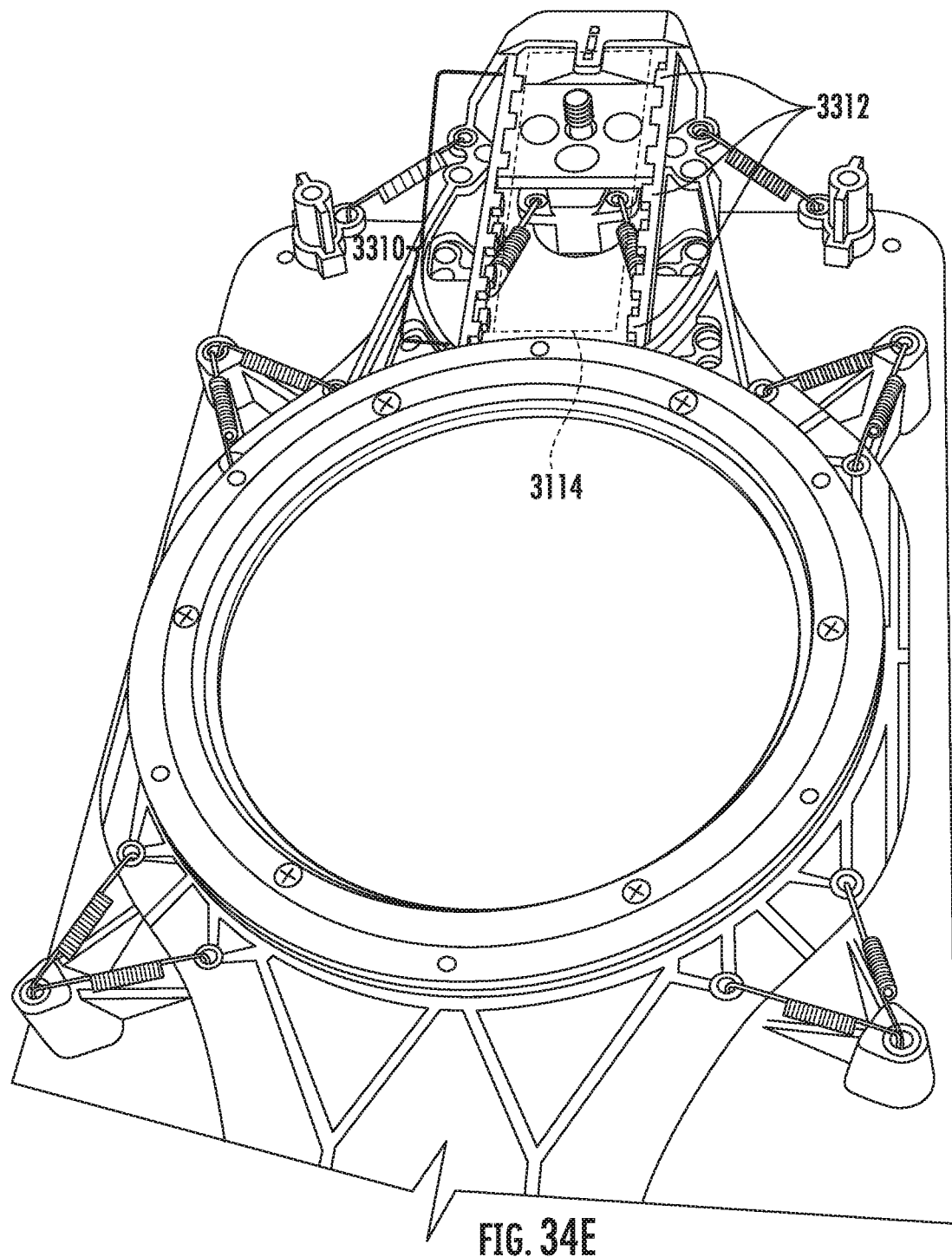

As shown in FIG. 34B, the rigid base 3402 may also comprise a plurality of bumpers 3408 and bumper guides 3410. The bumpers 3408 may act as dampers to prevent the movement of an infant on the moving platform 3010 from bottoming out the central carrier 3004 onto the rigid base 3402. The dampening function of the bumpers 3408 may provide a comfortable "feel" for the infant. The bumpers 3408 may be comprised of a soft rubber such as a 35-45 SHORE A rubber, and may each be partially conical in shape with the top of the bumper being more narrow than the lower part of the bumper. The bumpers 3408 may be attached to the rigid base 3402 via a screw from the bottom part through the interior of the bumper 3408. This composition may contribute to the comfortable "feel" of the movement of the moving platform 3010 by providing a gradual increase in the dampening from a small initial dampening by the narrow upper portions of the bumpers 3408 through a hard stop provided when the bumpers 3408 are fully compressed against the rigid internal screw. The rigid base 3402 may also comprise one or more bumper guides 3410 to be used in positioning bumpers 3408. Bumpers 3408 may be positioned within a bumper guide 3410. Additional bumpers 3408 may be positioned elsewhere across the rigid base to accommodate a desired distribution of weight. The central carrier 3004 may comprise one or more central carrier extensions 3412, which extend from the rim of the central carrier 3004 and interact with one or more bumpers 3408 to modify the "feel" of the motion of the moving platform 3010.

The rigid base 3402 may also comprise a plurality of assembly puller bases 3414. The assembly puller bases 3414 are designed to hold the assembly pullers 3102 perpendicular to the rigid base 3402 during assembly. The shape of the assembly puller bases 3414 may be designed so as to accommodate the assembly puller wings 3212 while preventing rotation of the assembly puller 3102. In this position, the kinetic helper springs 3108 may be attached between the assembly pullers 3102 and the central carrier 3004. During manufacturing, the moving platform 3010 may be fastened to the bearing 3008 positioned over the central carrier 3004. The assembly puller bases 3414 hold the assembly pullers 3102 in such a position that it is easy to tighten a screw and move the assembly pullers 3102 between the assembly puller bases 3414 on the rigid base 3402 to the assembly puller positioning guides 3214 on the underside of the moving platform 3010. The interaction of the assembly puller wings 3212 with the shapes of the assembly puller bases 3414 and the assembly puller positioning guides 3214 prevents the assembly pullers 3102 from rotating as they are repositioned from the rigid base 3402 to the underside of the moving platform 3010. The lack of rotation enables the kinetic helper springs 3108 to be attached between the central carrier while access to the assembly puller 3102 and the central carrier 3004 is good, prior to the addition of the moving platform 3010 to the drive train assembly 3000.

Figure 35:
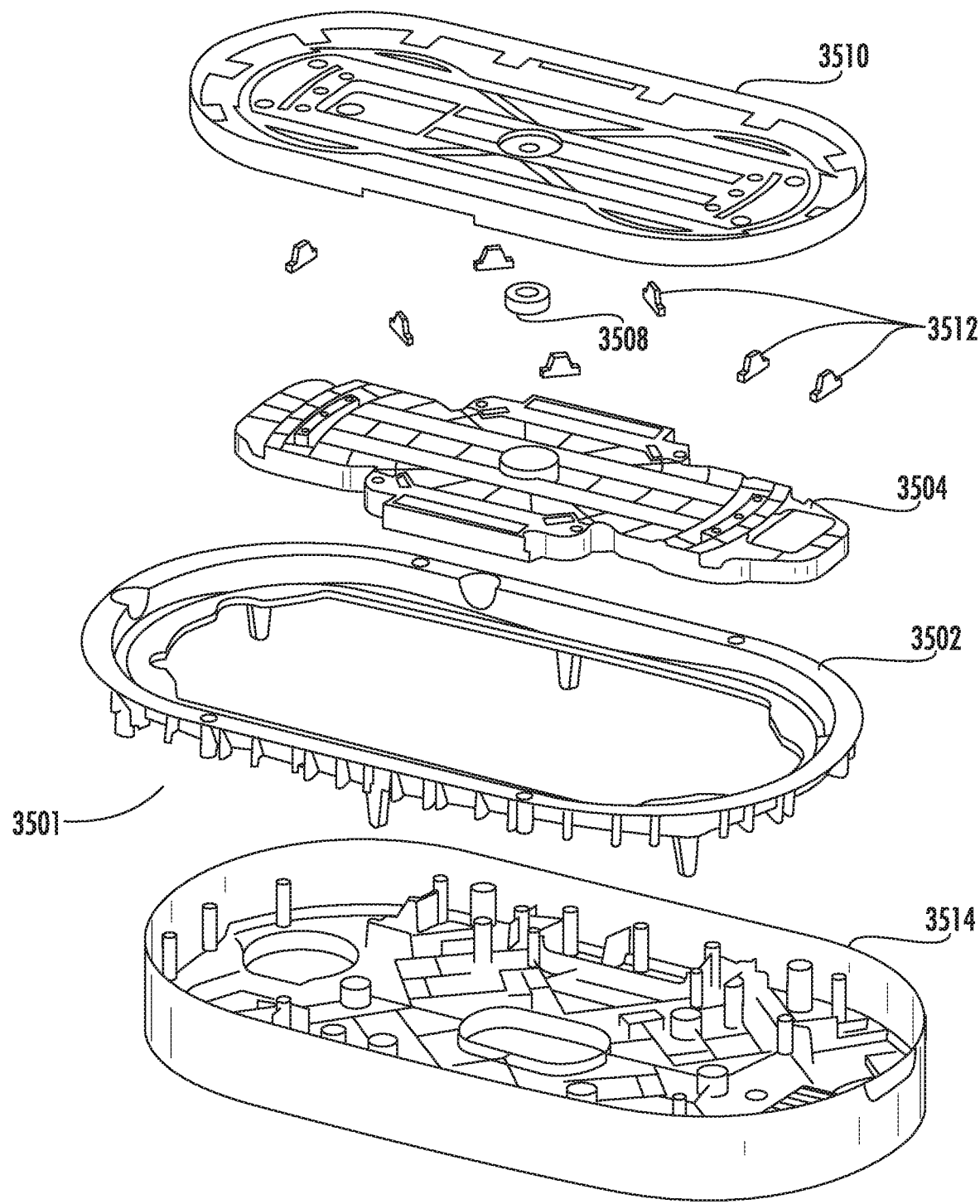
FIG. 35 is an exploded perspective view of an exemplary drive train system.

In embodiments, the drive train system for an infant calming/sleep aid device with a single moving platform, which supports both the infant's body and head, may take other forms. With reference to FIG. 35, the infant calming/sleep aid device may include a base 3514, trim component 3502, a moving platform 3510 driven by a drive train system 3501 that may include a central carrier 3504 that supports the moving platform 3510 on base 3514, with a central thrust bearing 3508 and a plurality of perimeter bearings 3512 between the central carrier 3504 and moving platform 3510. A motor 3506 (see FIG. 36C) is operable for moving the moving platform 3510 with respect to the central carrier 3504 in an oscillatory manner about a vertical axis through center of rotation 3518 (FIG. 36A), at the center of the central thrust bearing 3508.

Figure 36A:
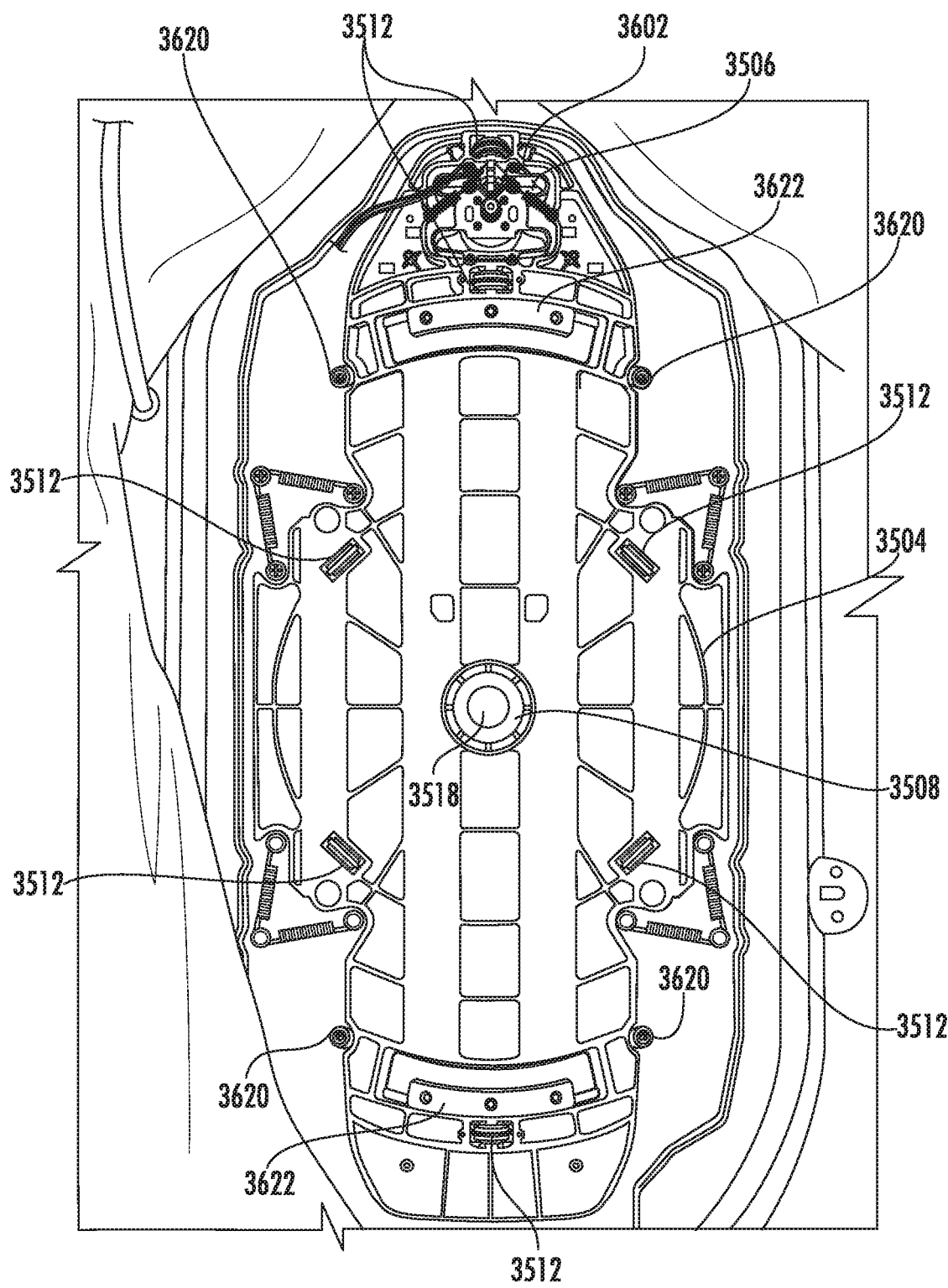
Figure 36C:
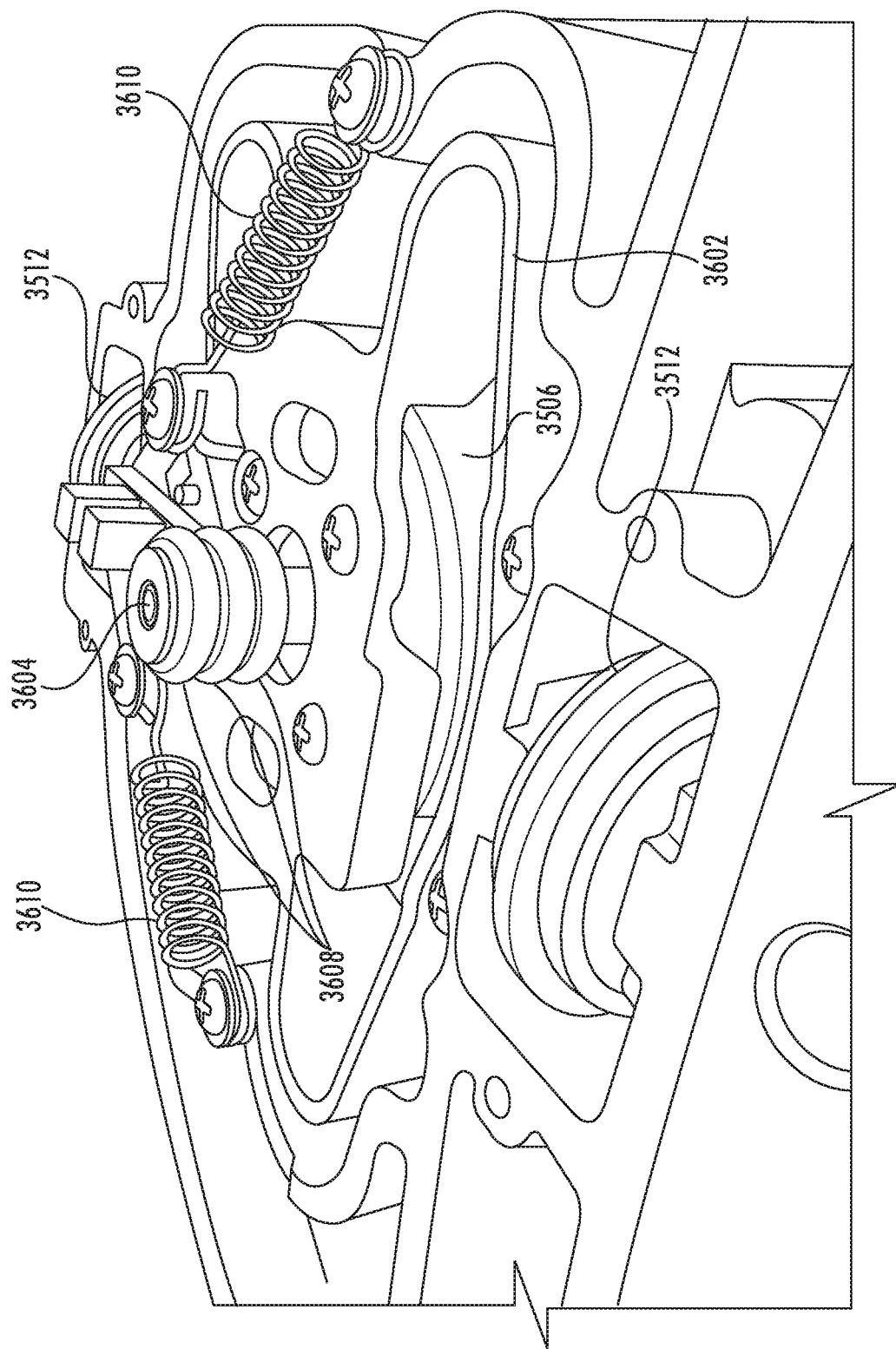

FIG. 36A provides a top view of the central carrier 3504 while FIGS. 36B-36C provide additional detail. In particular, the central carrier 3504 may include the motor 3506 partially enclosed in a motor bracket 3602. A center post 3604 (see FIG. 36B) of the motor 3506 may extend upward beyond the motor bracket 3602 and be encircled by one or more motor O-rings 3608, with oscillation of the center post 3604 causing movement of the moving platform 3510 with respect to central carrier 3504, as explained more fully elsewhere herein. There may be two or more traction springs 3610 causing the motor to move toward the center of rotation 3518 to facilitate contact between the O-rings 3608 and the moving platform 3510, as also explained elsewhere herein.

The central carrier 3504 may be suspended from a plurality of suspension springs that attach to a rigid base, as previously described. The central carrier 3504 may include one or more rotational stop bumpers 3620 to prevent over-rotation of the overlying moving platform 3510. The central carrier 3504 may include one or more lifters 3622 at the longitudinal edges of the central carrier 3504 to help engage the central carrier 3504 with the moving platform 3510.

The central thrust bearing 3508 centralizes the movement of the moving platform 3510 over the central carrier 3504, repeatably aligning the guide track 3712 (FIG. 37B) with the motor O-rings 3608. The guide track 3712 may comprise a steel guide track, a magnesium guide track, a plastic guide track or the like. The plurality of perimeter bearings 3512 are distributed across the central carrier 3504 underneath the main moving platform 3510 to provide support and insure balanced load distribution for the main moving platform 3510. For example, there may be more bearings near where the head of the infant will be on the moving platform as compared to where the feet will be. Each perimeter bearing 3512 may have an axis of motion that is radial to the axis of movement of the central thrust bearing 3508.

The motor bracket 3602 may be composed of a high temperature engineering resin that is molded, and include a plurality of outwardly extending arms 3601. The configuration of the motor bracket 3602 may be such that, when the system is assembled, the combination of the force applied by the traction springs 3610 pulling the motor bracket toward the center of rotation 3518 and the pressure between the motor O-rings 3608 and the steel guide track 3712 (shown in FIG. 37B) pushing the motor bracket 3602 away from the center of rotation 3518, results in little to no strain on the motor bracket 3602, such that it is not deformed from its originally molded shape. This may reduce long-term strain and plastic deformation (creep) under load of the polymer comprising the motor bracket.

Figure 37A:
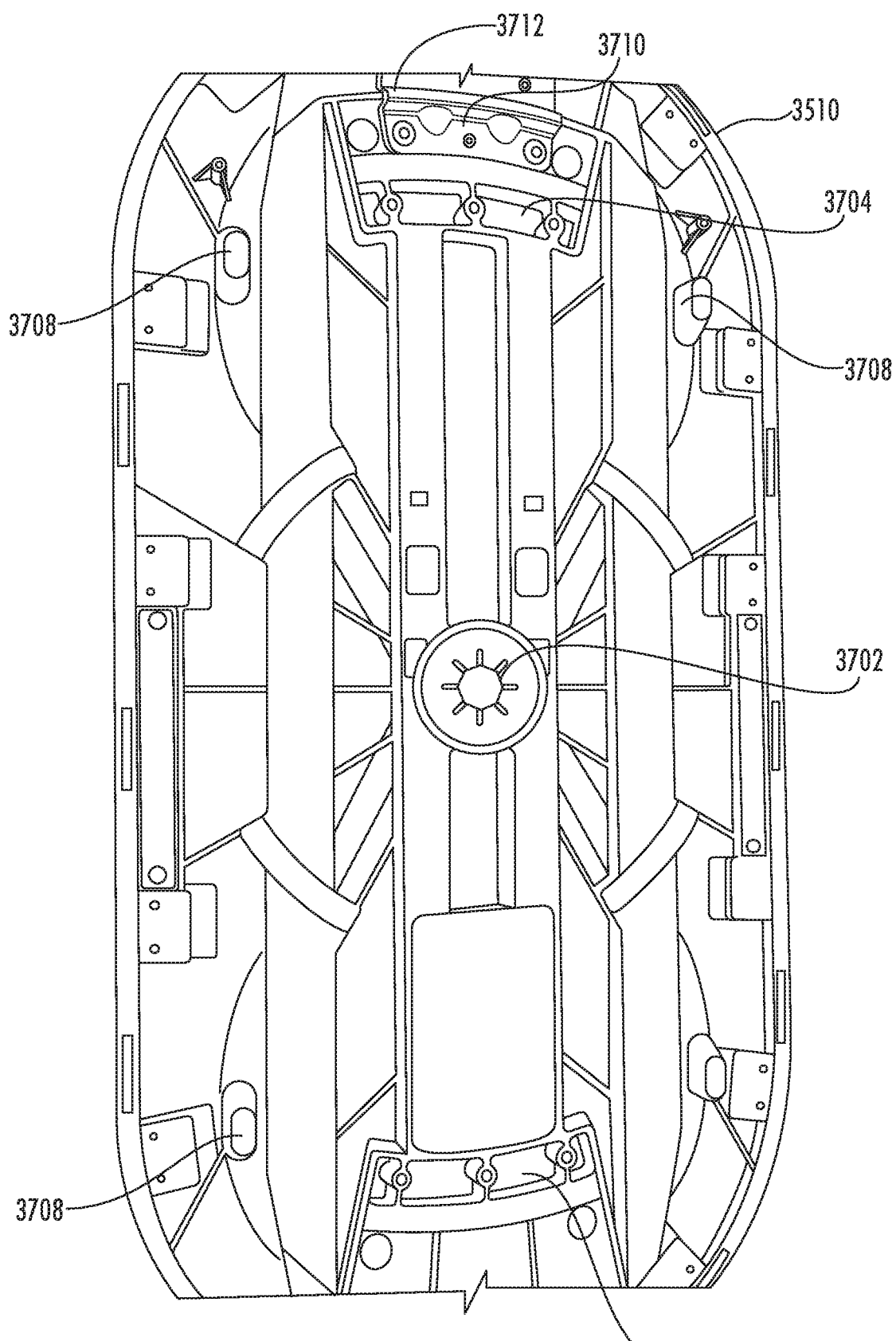
FIG. 37A is a view of the underside of a moving platform.

The motor 3506 may be a 3-phase brushless DC motor (BLDC motor) with the noise and robustness advantages described elsewhere herein. FIG. 37A shows the underside of the moving platform 3510 including, among other features, a central thrust engagement feature 3702 which engages with the central thrust bearing 3508 to repeatably and reliably align the central carrier 3504 and the moving platform 3510, lifter engagement features 3704 for engaging with the lifters 3622 on the central carrier 3504 for alignment purposes, a steel plate 3710, and a plurality of stoppers 3708 which interact with the bumpers 3620 on the central carrier 3504 to prevent over travel of the moving platform 3510. The stoppers 3708 and bumpers 3620, further described elsewhere herein, act to keep the movement of the moving platform within a desired range.

Figure 37B:
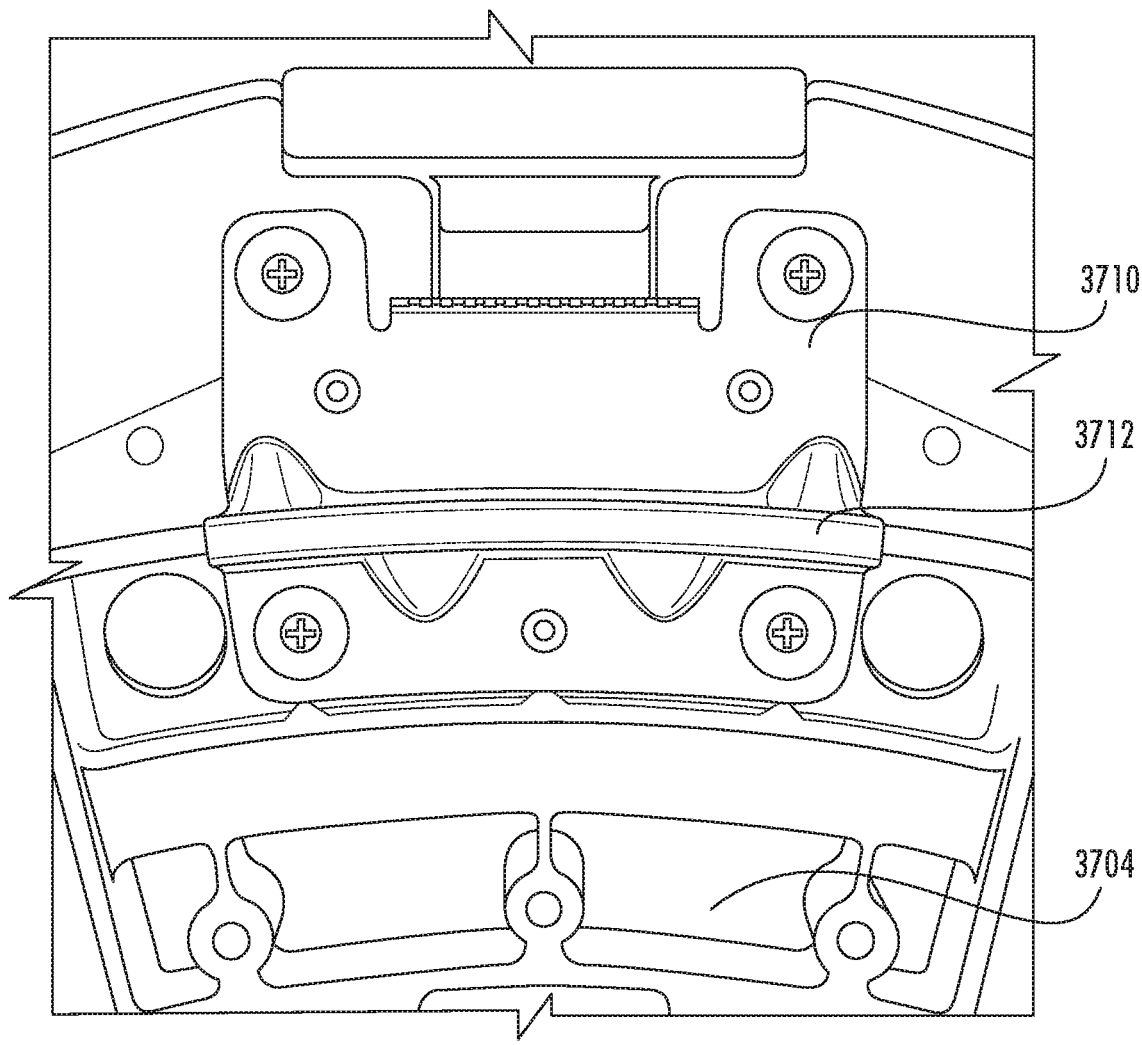
FIG. 37B is a detailed view of a guide track on a moving platform.

FIG. 37B shows a detailed view of the underside of the moving platform 3510 and in particular steel plate 3710 forming a guide track 3712 which engages with the Motor O-rings 3608 and rotates the moving platform 3510 in response to the motor 3506 rotating the center post 3604 and the encircling Motor O-rings 3608. The steel plate 3710 diminishes the amount of wear between the center post and guide track. The motor drive system may self-correct any misalignment between the moving platform 3510 and the center post 3604 as described elsewhere herein.

In embodiments, the control system 120 may operate in a manner wherein the intensity of maximum stimulation is increased over the course of the first weeks and subsequently weans the infant off the device's motion by incorporating the infant age as a variable used in the behavior state machine module 126. For example, modulation of motion and/or sound may be further controlled by at least one of the weight of the infant, the age of the infant, and the duration of the detected sounds made by the infant.

Figure 11:
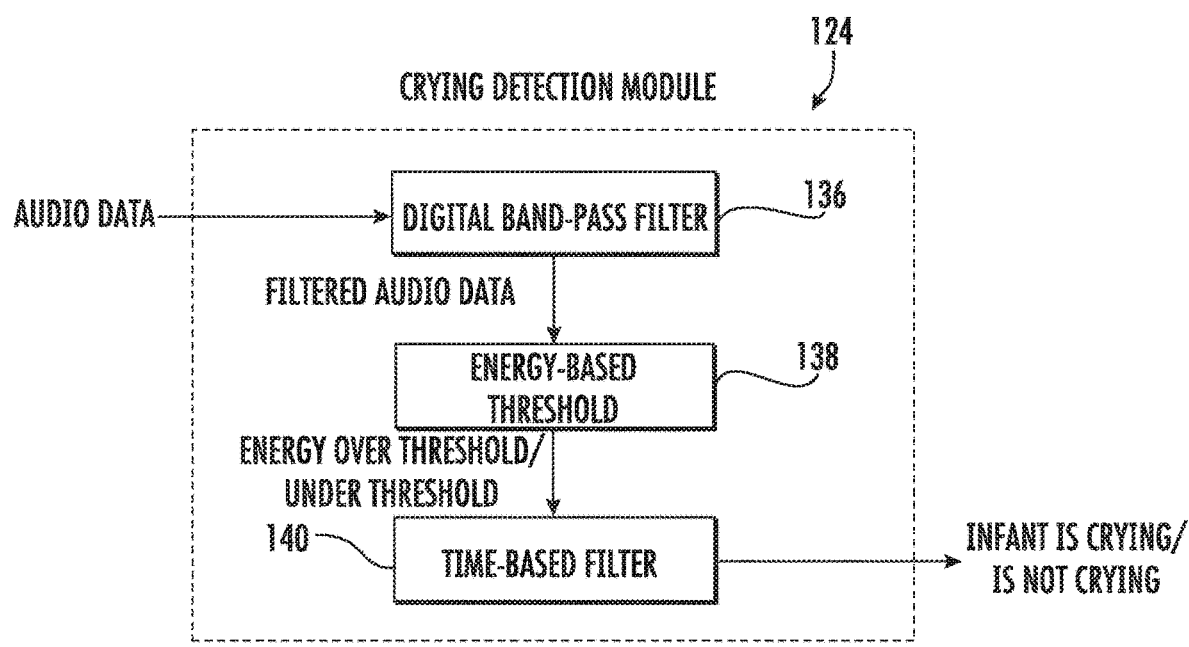
FIG. 11 is a schematic representation of one embodiment of a crying detection module of the calming/sleep-aid device.

Referring to FIG. 11, crying detection module 124 receives audio data from the microphones of infant calming/sleep-aid devices 10, 100, which is processed through a digital band-pass filter 136 to generate filtered audio data. Energy-based threshold 138 receives filtered audio data to determine whether the audio energy is over threshold or under threshold. Time-based filter 140 receives data from energy-based threshold 138 to provide an indication as to whether the infant is crying or not crying. The information, as discussed above with respect to control system 120 (FIG. 10), is received from crying detection module 124 by behavior state machine module 126 that will then provide signals to control motion generation module 128 or audio generation module 130 or both.

Figure 12:
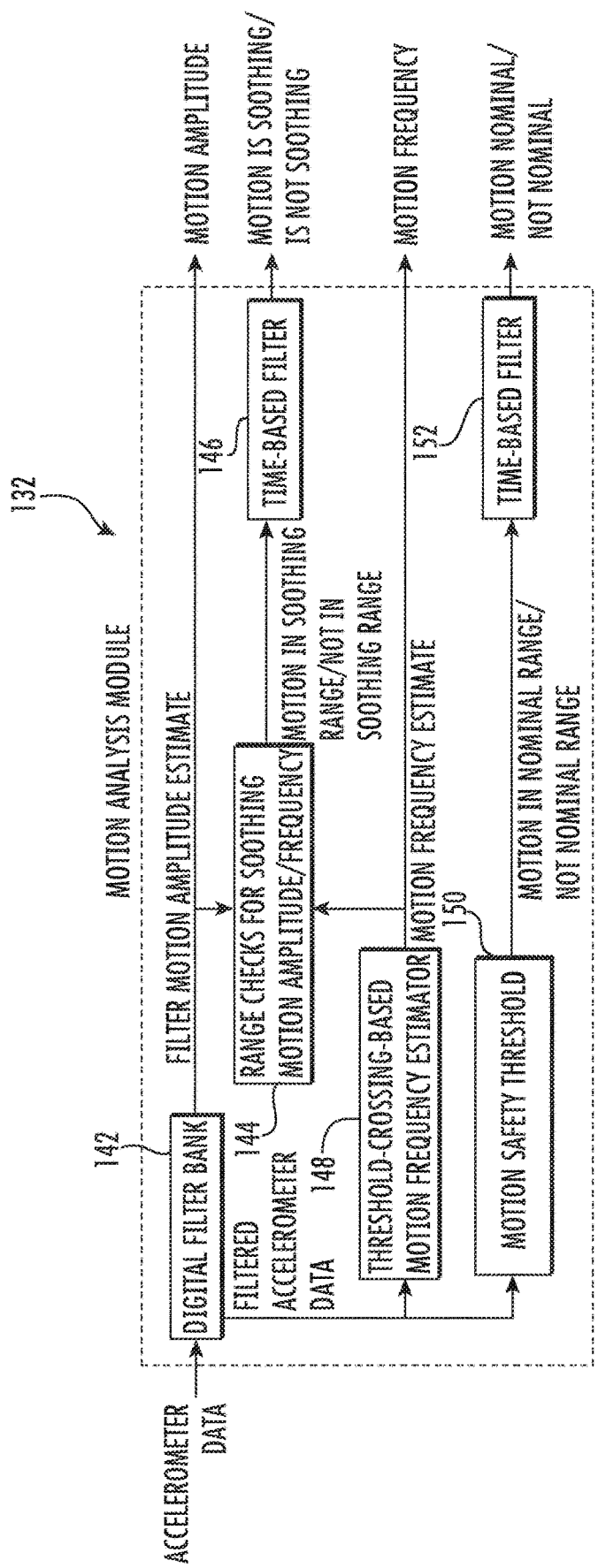
FIG. 12 is a schematic representation of one embodiment of a motion analysis module of the calming/sleep-aid device.

Motion analysis module 132, shown and represented in more detail in FIG. 12, receives a signal from the motion-sensing device of infant calming/sleep-aid devices 10, 100, at digital filter bank 142. Digital filter bank 142 filters the signal to generate a filtered motion amplitude estimate that is used as input to motion generation module 128 (FIG. 10). In addition, the filtered motion amplitude estimate passes through a range check 144 to determine whether the motion is within a soothing or known soothing range, which is provided to time-based filter 146 and provides an indication as to whether a motion is soothing or not soothing to motion generation module 128 (FIG. 10).

Filtered motion sensor, or accelerometer, data from digital filter bank 142 also passes through threshold crossing-based motion frequency estimator 148 to provide an estimate of motion frequency, which is provides to motion generation module 128.

Outputted data from threshold-crossing-based motion frequency estimator 148 also passes through range check 144 for indicating whether the motion is or is not soothing, Filtered accelerometer data from digital filter bank 142 also is processed to determine whether or not the acceleration exceeds a specific maximum motion threshold 150 and, depending on the result, processes that data through time-based filter 152 to provide an indication as to whether the motion is nominal or not nominal. This indication as to whether the motion is nominal or not nominal is used as input to motion generation module 128 (FIG. 10), and is additionally used to control status lights 37 (FIG. 2) via status light module 134 (FIG. 10).

Figure 13:
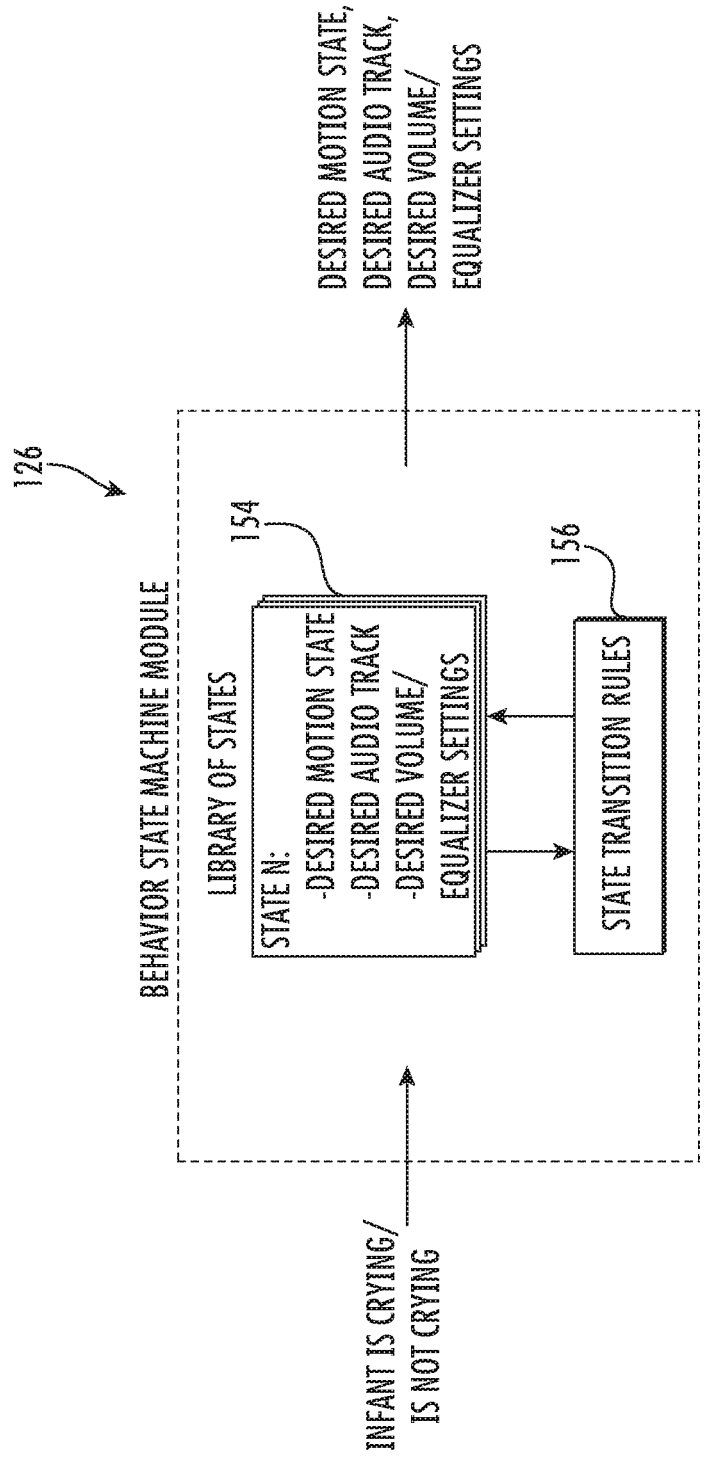
FIG. 13 is a schematic representation of one embodiment of a behavior state machine module.

As can be seen in FIG. 13, behavior state machine module 126 receives information from crying detection module 124 (FIG. 11) as to whether the infant is in a state of crying or not crying. This information is used by the state machine's state transition rules 156 to select an active state from a library of states 154, thereby outputting a desired motion state, a desired audio track and/or desired volume/equalizer settings to audio generation module 130 of FIG. 10.

Figure 13A:
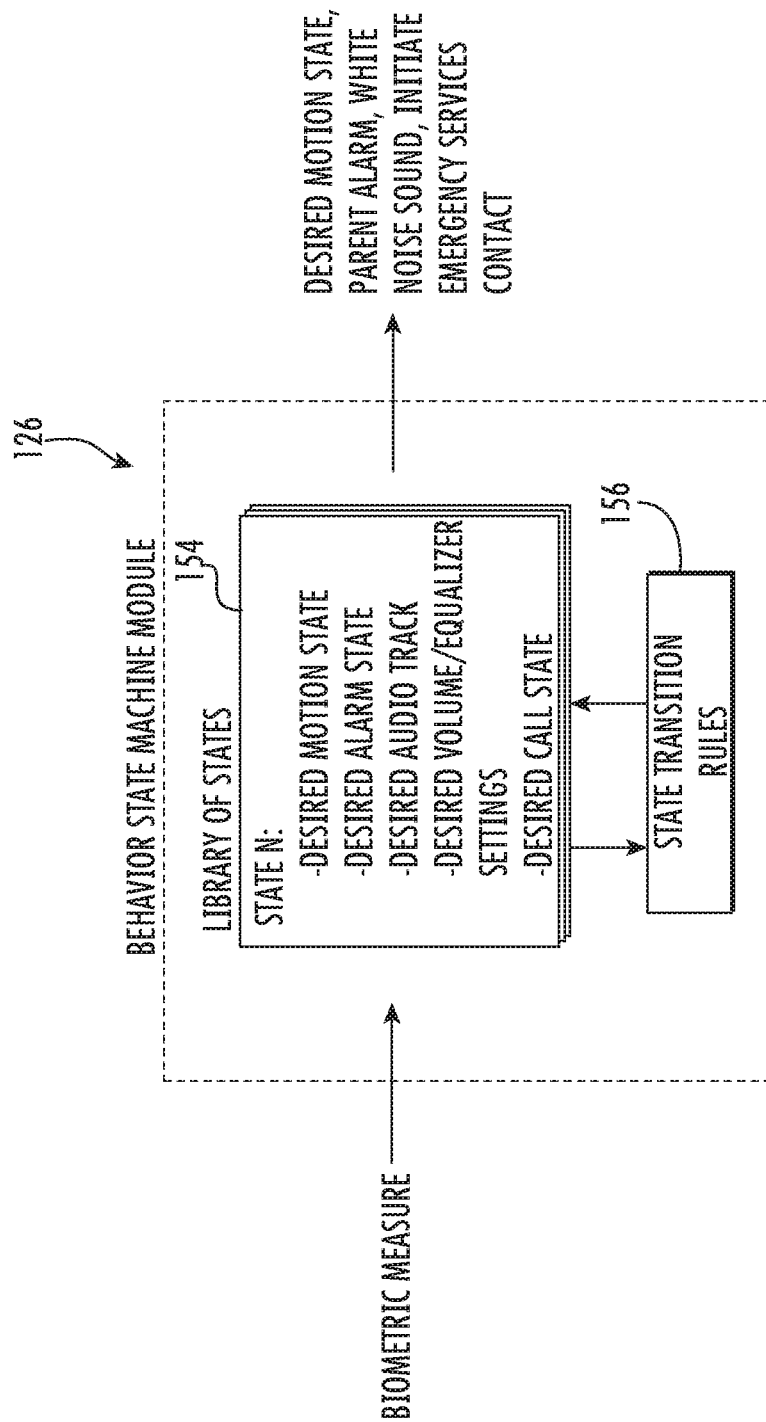
FIG. 13A is a schematic representation of one embodiment of a biometric sensor module interacting with a behavior state machine module.

As can be seen in FIG. 13A, behavior state machine module 126 of FIG. 10 receives a biometric measure from biometric sensor module 1002 (FIG. 10), which is indicative of a monitored parameter of the baby. (Note that a similar analysis applies with respect to the device of FIG. 22A). One measure may be whether respiration is normal, slowing down, or not normal, or whether heart rate is normal, slowing down, or not normal, or categorized in other ways. The biometric measure may be normal if an infant is breathing, not normal if an infant stops breathing for a predetermined amount of time, and the like. This information may be used by the state machine's state transition rules 156 to select an active state from a library of states 154, thereby outputting a desired motion state, a desired audio track and/or desired volume/equalizer settings, a desired call state, or the like to audio generation module 130 (FIG. 10) in order to encourage breathing. A desired alarm state may be a parent alarm state and the like. A desired audio track may be a special vigorous white noise track and the like. A desired call state may be to initiate a call to emergency services using Wi-Fi connection and the like.

Figure 14:
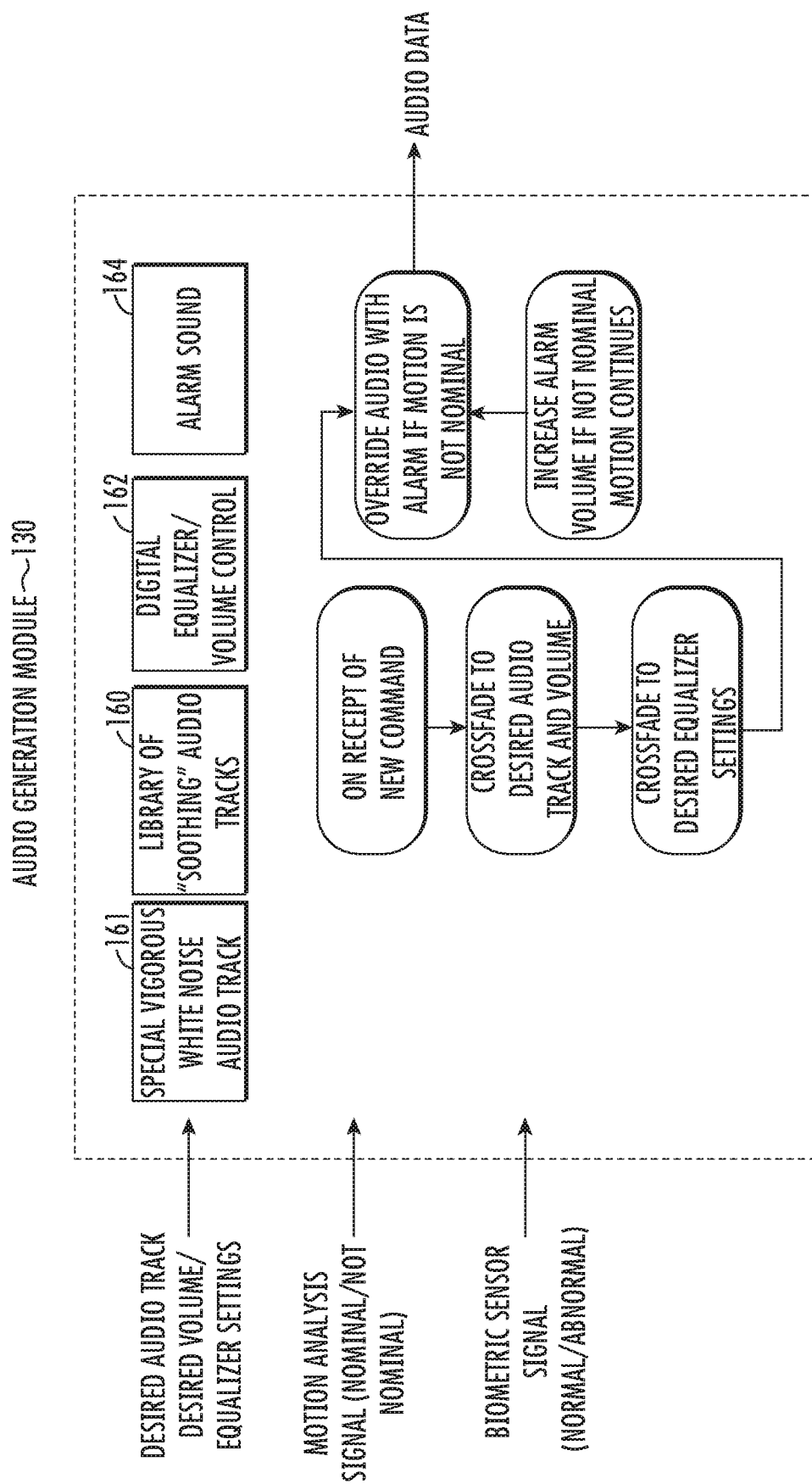
FIG. 14 is a schematic representation of one embodiment of an audio generation module.

Audio generation module 130, represented in FIG. 14, receives signals of a desired audio track and desired volume/equalizer settings from behavior state machine module 126 (FIG. 10) and signals of motion analysis, specifically, whether the motion is nominal or not nominal, from motion analysis module 132 (FIG. 10). Desired audio track may be a sound audio track, music audio track, special vigorous white sound audio track, and the like. Audio generation module 130 includes a special vigorous white noise audio track 161, a library of "soothing" audio tracks 160, a digital equalizer/volume control 162 and alarm sound 164. Upon receipt of a new command from motion analysis module 132 (FIG. 10), audio generation module 130 will cross-fade to a desired audio track and volume, and crossfade to desired equalizer settings. If the motion is not nominal, then an alarm signal may be output to override the audio signal with an alarm. The audio signal from the audio generation module 130 (FIG. 10) is output to the USB speakers 131 (FIG. 10) of infant calming/sleep-aid device 10, 100.

At baseline, the audio generator will produce an output of a low-pitch, rumbling sound at about 65 dB to 74 dB. Upon receipt of a new command from crying detection module 124 (FIG. 11), audio generation module 130 will cross-fade to a more high-pitched audio track and louder volume, at about 75 dB to 95 dB.

Upon receipt of a new command from behavior state machine module 126 (FIG. 10), audio generation module 130 will cross-fade to a desired audio track and volume, and crossfade to desired equalizer settings. If the signal received from the behavior state machine module 126 is indicative of an abnormal biometric signal that has been detected by the biometric sensor module 1002 (FIG. 10), for example that an infant is not breathing, then an alarm signal and special vigorous white sound audio track will be output to override the audio signal with an alarm and special vigorous white sound audio track. The special vigorous white sound audio track signal from the audio generation module 130 (FIG. 10) is output to the USB speakers 131 (FIG. 10) of infant calming/sleep-aid device 10, 100.

Audio generation module 130 (FIG. 14) receives signals from the biometric sensor module 1002 (FIG. 10). An abnormal reading, such as a reading indicating that an infant is not breathing, will activate a desired audio track, such as a special vigorous white sound audio track, parent alarm and desired volume/equalizer settings. Upon receipt of a new command from biometric sensor module 1002 (FIG. 10), audio generation module 130 will cross-fade to a desired audio track and volume, and crossfade to desired equalizer settings.

Audio generation module 130 (FIG. 14) may receive mild signals that indicate an infant is awakening. Mild signals may detect that an infant is mildly awakened. Mild signals may be mild motion signals, mild sound signals, and the like. Mild signals may be sent from a sensor not attached to, attached to or worn by an infant. Mild signals may be detected from an infant before the infant begins to cry. Audio generation module 130 (FIG. 14) may begin to increase sound levels when mild signals are received.

Figure 15:
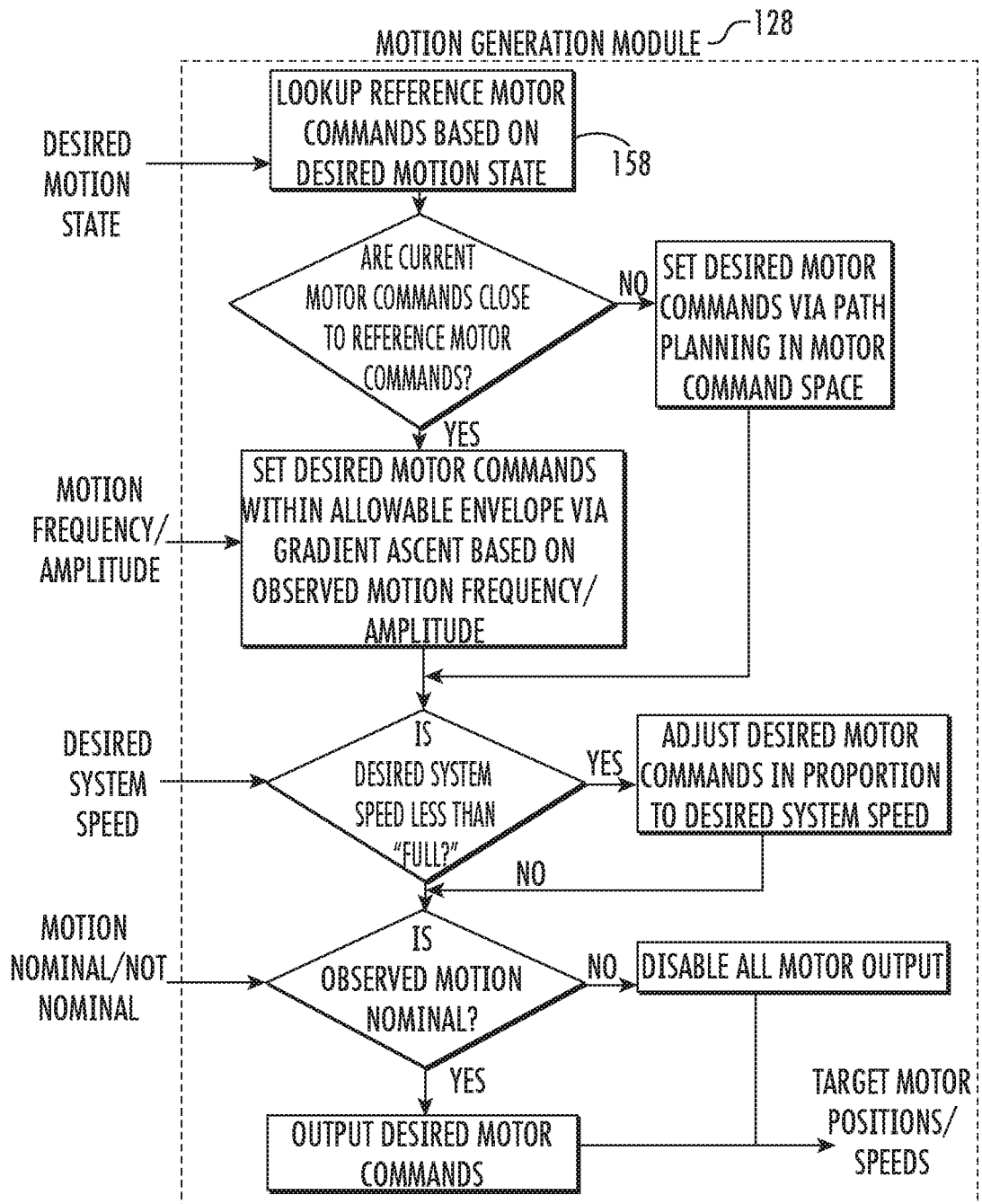
FIG. 15 is a schematic representation of a motion generation module.
Figure 16:
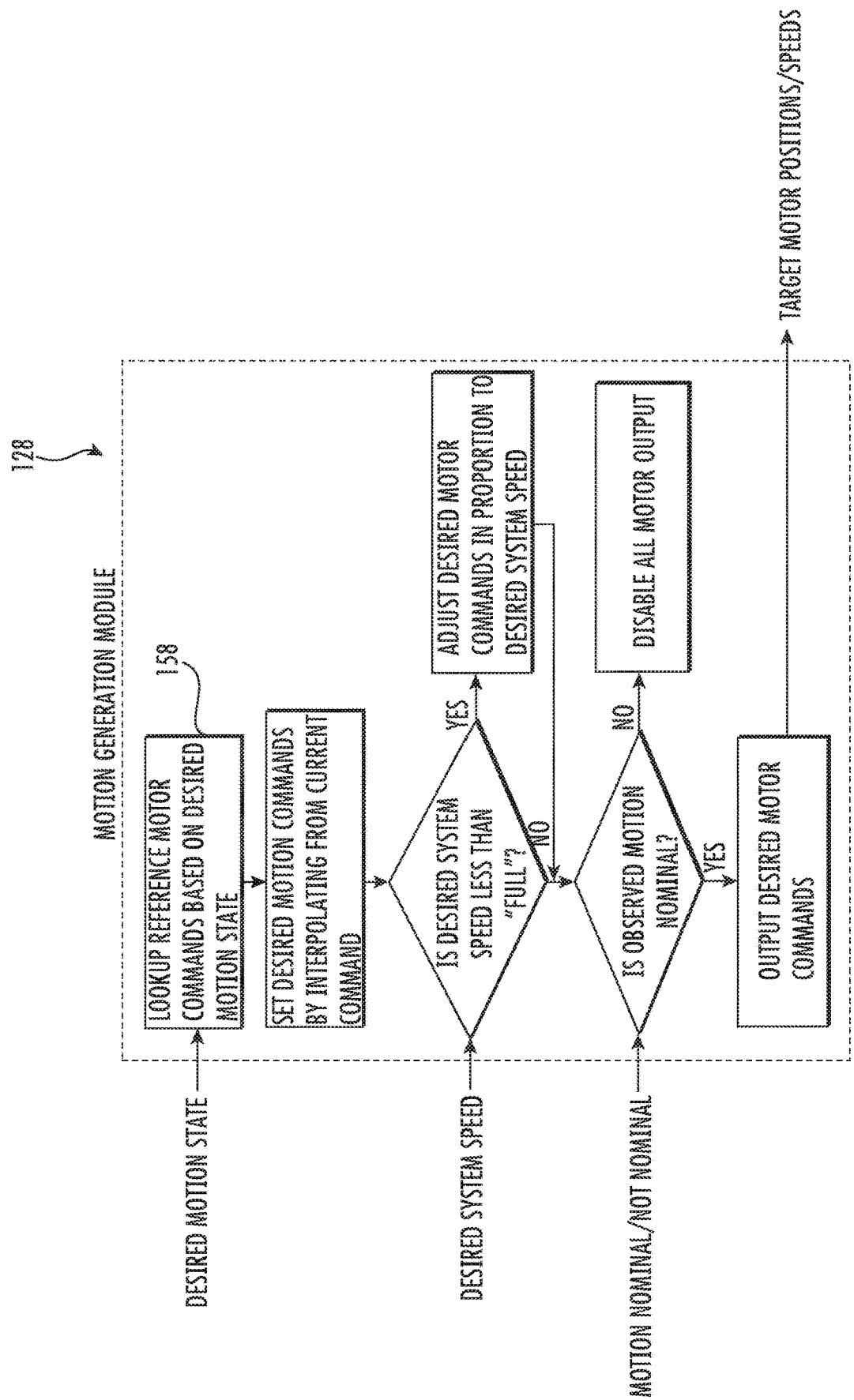
FIG. 16 is a schematic representation of a motion generation module.

Two variations of motion generation module are represented in FIGS. 15 and 16. In the first embodiment of motion generation module 128, shown in FIG. 10, motion generation module 128 receives a desired motion state input from behavior state machine module 126 (FIG. 10), a motion frequency/amplitude signal from motion analysis module 132 (FIG. 10), a desired system speed signal from speed control knob 121 (FIG. 10), and a signal as to whether a motion is nominal or is not nominal. The "desired system speed" is the setting of speed control knob 121, whereby the operator can select or limit the motions allowed by infant calming/sleep-aid device 10, 100. The desired motion state signal goes to lookup within motion generation module 128, which outputs a reference motor command based on a desired motion state. If the currently active motor commands are close to the reference motor commands, then the motor commands are actively adjusted within an allowable envelope via a gradient ascent based on observed motion frequency and amplitude. If the current motor commands are not close to the reference motor commands, then the motion generation module will set desired motor commands via path planning in a motor command space. "Path planning" transitions motor settings to desired motor settings by inserting intermediate motor settings as necessitated by nest dynamics to ensure that motion stays in a desirable range during transition. If the desired system speed is less than "full," then a signal is sent to adjust the desired motor commands in proportion to the desired system speed. "Full" is the fully-on position of the knob, and means that infant calming/sleep-aid device 10, 100 is not being limited by this knob and is allowed to perform all of the motions it determines to be relevant. If speed control knob 121 is turned down from "full," motions of infant calming/sleep-aid device 10, 100 starts to become constrained, so speed control knob 121 acts as an operator to override the normal motion behavior of infant calming/sleep-aid device 10, 100. If not, then a comparison is made as to whether the observed motion is nominal. If it is not, then motor output is disabled. If it is nominal, then an output signal of desired motor commands is given to target motor positions and speeds of the actuator of the multichannel USB motor controller. In some embodiments, sound is delivered to an infant but not motion if an infant is in the device but not securely attached. The level of motion and or sound output may also be modified by the caregiver's choice of a special boost function.

In an alternative embodiment of motion generation module 128, shown in FIG. 16, there is no receipt by the module of signals related to motion frequency and amplitude. Therefore, it is only necessary to set desired motor commands by interpolating from a current command based on a look up table of motor commands based on a desired motion state in response to receiving a signal with respect to the desired motion state. All of the other components of motion generation are the same as represented in FIG. 15.

In one embodiment, the motion generation module 128 receives a motion state input of an abnormal signal, for example that an infant is not breathing, from the biometric sensor module 1002 (FIG. 10). The resultant programmed vigorous motion (such as jiggly motion, vibration, etc.) may continue until the abnormal biometric signal is discontinued, for example when an infant begins breathing again, or the device is shut off.

Another exemplary embodiment of an infant calming device is shown in FIGS. 17-21. In this example, the infant calming device includes a main moving platform with an integral head support portion, that is, the head support portion is contiguous with and rigidly fixed to the main moving platform, in essence creating a single platform supporting the head and body of the infant.

Figure 17:
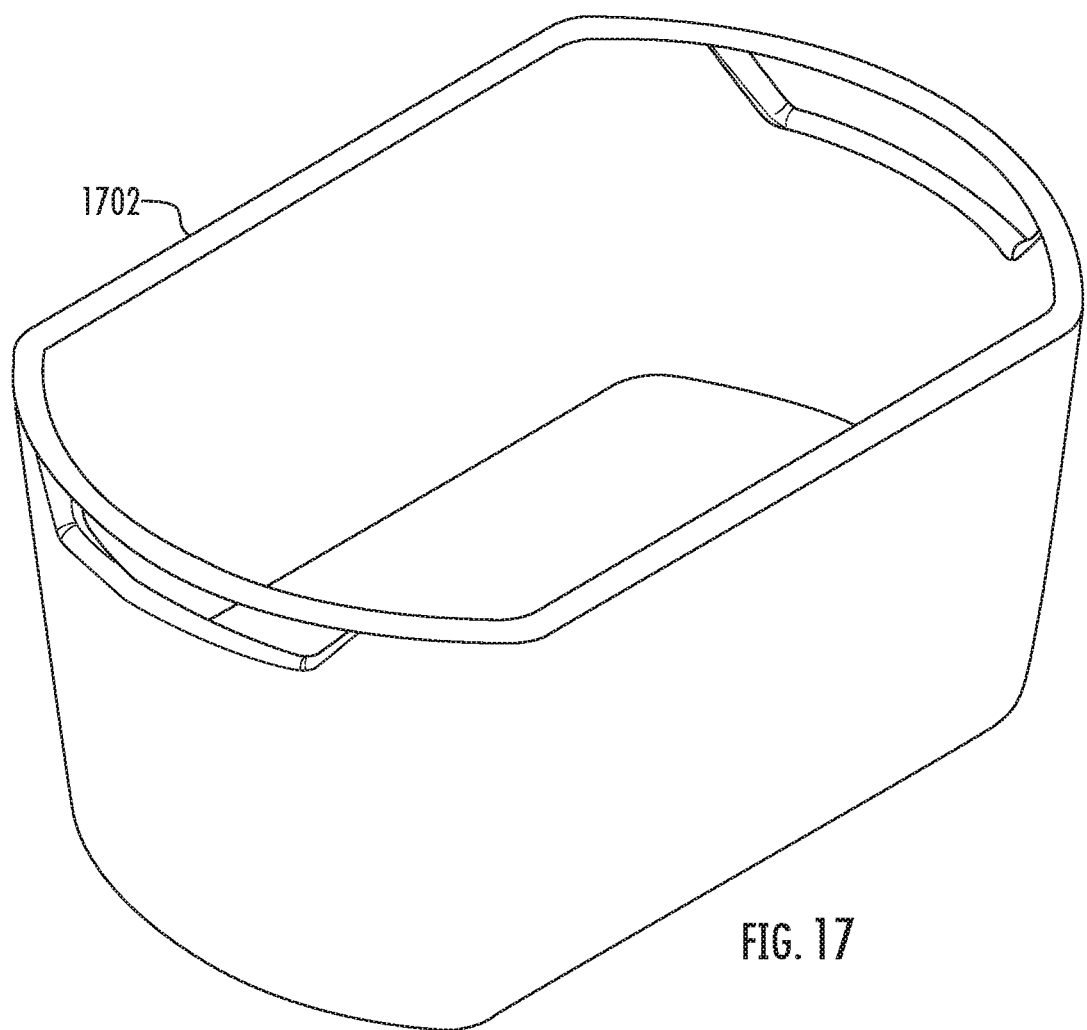
FIGS. 17-21 illustrate another exemplary embodiment of an infant calming device having a moving main platform with an integral head platform portion.
Figure 19:
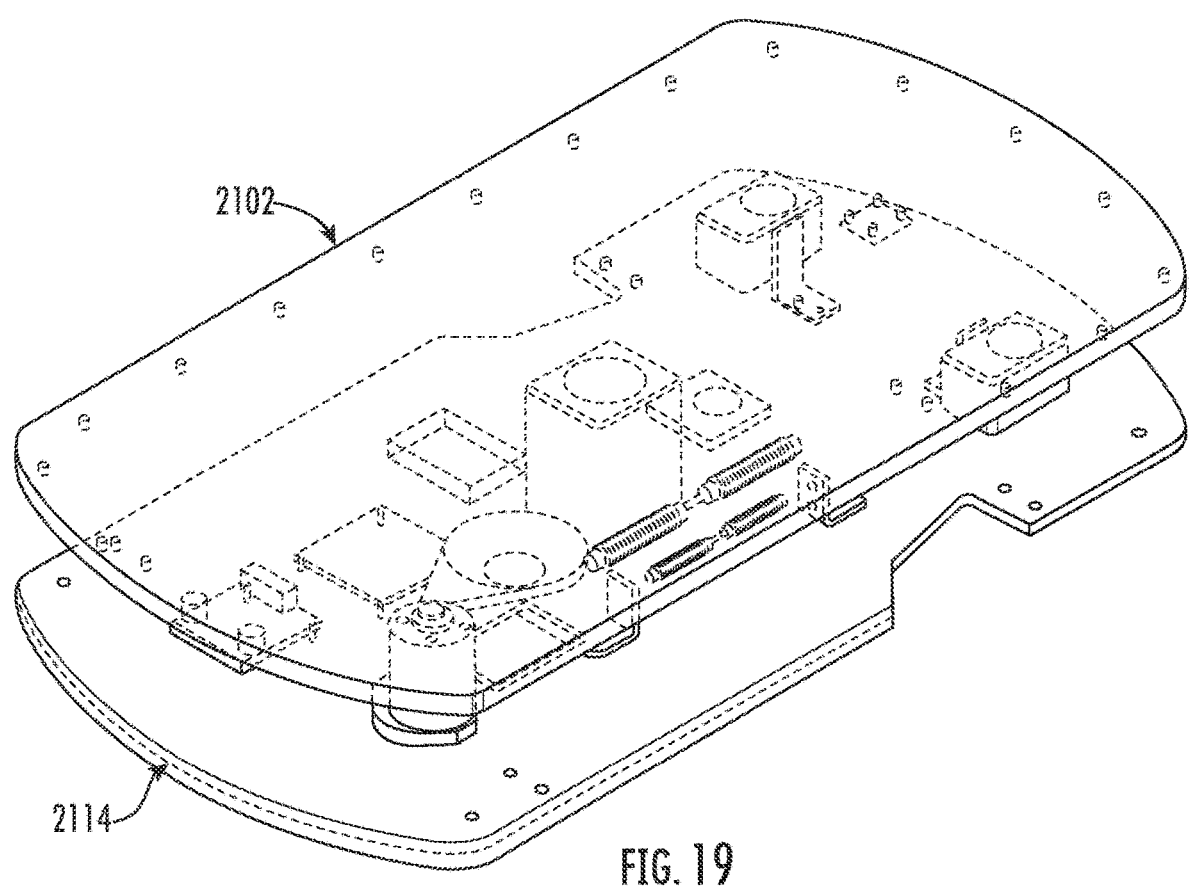
Figure 20:
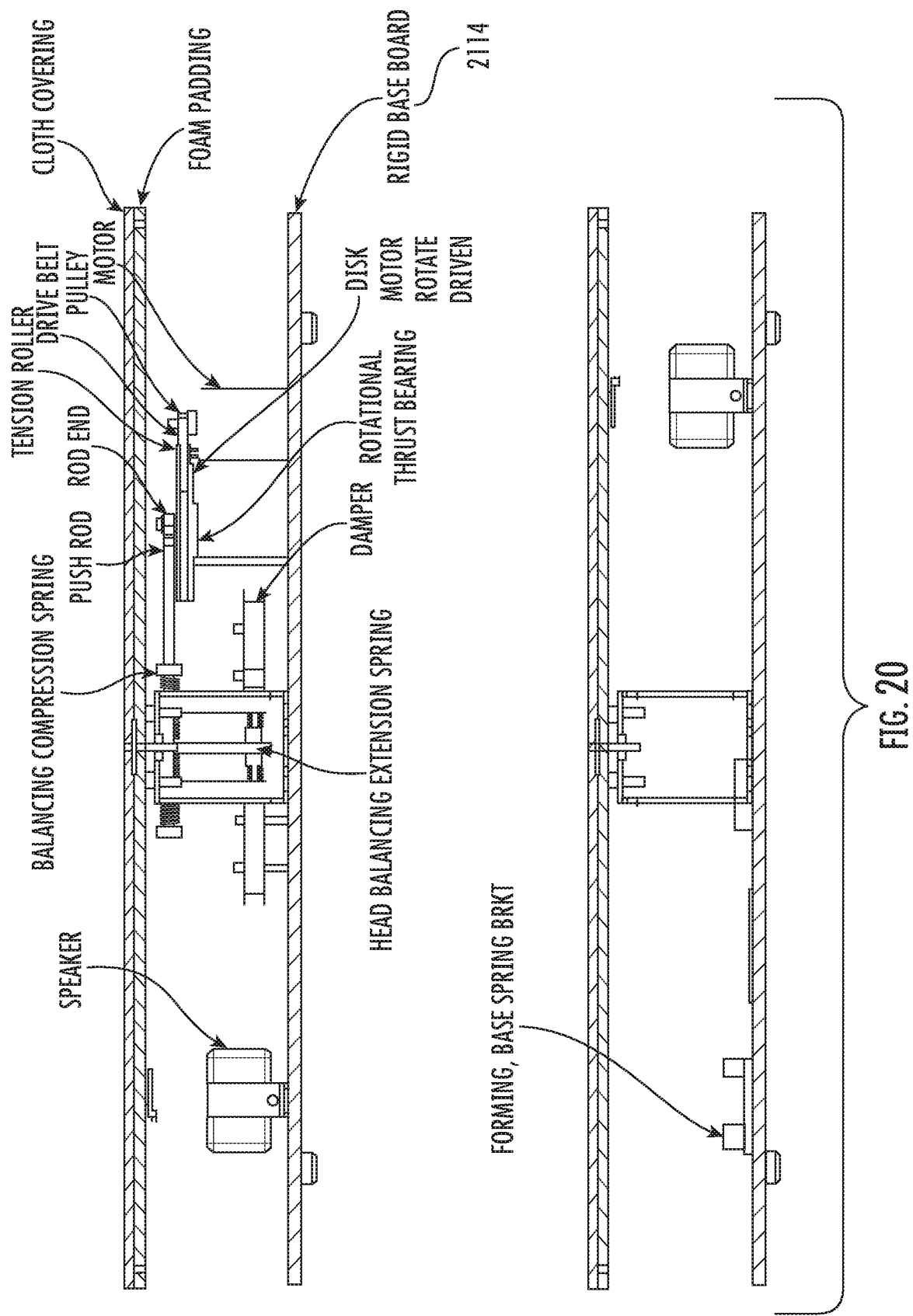

An enclosure 1702 for an infant calming device using a single main moving platform is shown in FIG. 17. Single main moving platform 2102 and rigid base 2114 of this device are shown in FIGS. 18 and 19, where FIG. 19 also shows the other components of the device, as seen looking through main moving platform 2102. FIG. 20 shows cross sectional views of the embodiment of an infant calming device using a single main moving platform.

Figure 21:
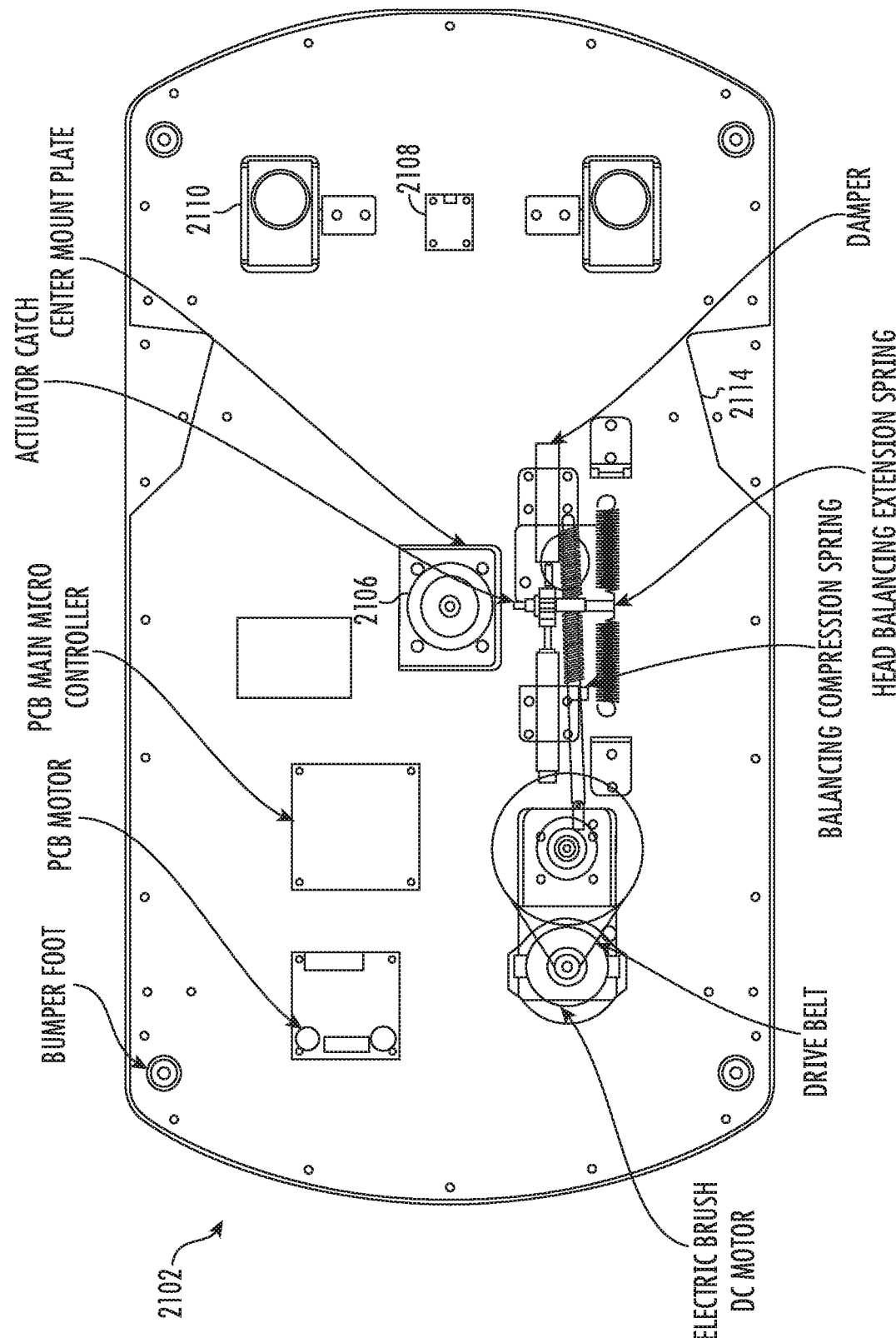

As shown in FIG. 21, main moving platform 2102 is supported by main support shaft at main rotation bearing 2106. The main rotation bearing 2106 may be comprised of several vertical pieces of plastic or spring steel that do the job of supporting the upper surface, while also flexing to replace the springs and dampers described above.

Motion sensing device 2108, such as an accelerometer, underneath main platform 2102 detects motion of main platform 2102. Microphones (not shown) detect sound emitted by the infant (not shown) when supported by infant aid sleep device. One or more speakers 2110, supported by brackets 2112 mounted on rigid base 2114, may be located directly beneath head position of infant on main moving platform 2102. Secure sleep sack fastening clips may be attached to main moving platform 2102 for securing an infant in suitable swaddling clothes.

The exemplary embodiment shown in FIGS. 17-21 operates similarly to the embodiment shown in FIGS. 1-16, described above. The embodiment in FIGS. 17-21 differs from that shown in FIGS. 1-16 in that the separate head and body boards are replaced by a single moving board. Along with the replacement of the separate head and body boards by a single moving board, the secure sleep sack fastening straps are replaced by clips integral to the baby swaddle wrap. The head rotation bearing, rotating head platform, head board support U bracket, head balancing extension spring, and weight sensors are also absent.

In embodiments, the main moving platform 16, 2102 may hang from the framing that is above the main moving platform via fabric and/or cables. The main moving platform 16, 2102 would then be free to rotate or swing as needed. A motor and offset wheel would deliver the needed input to create the desired motion, such as a smooth sinusoidal motion of the main moving platform at low frequencies and the rapid accelerating motion at high frequencies.

As discussed above, two versions of the infant calming/sleep-aid device are shown in FIGS. 2 through 9, with microphones to detect infant crying, motion and sound actuators, a swaddling system to keep the baby in optimal position and a gel pad to reduce the pressure on the back of the skull (thereby avoiding possible plagiocephaly). The device also may contain a logic board to accomplish two tasks; delivering staged interventions of specially engineered sound and delivering motion created by two linked platforms attached to a motor and rod actuator (as well as a series of springs and dampeners to modulate the activity.) These platforms may act in a reciprocating manner about an axis that intersects the infant and is orthogonal to a major plane of the surface supporting the infant to provide a motion that varies from slow smooth rocking (0.5-1.5 cps) to keep babies calm- and promote sleep, and ramping up to a faster, smaller, jiggling motion (2-4.5 cps) with a more spiked waveform to deliver a sufficiently abrupt acceleration-deceleration action to stimulate the vestibular mechanism of the inner ear, trigger a calming reflex and soothe the baby, such as when the baby cries (e.g., head rocking back and forth in excursions of less than 1'). The sound in the device may be adapted to respond to the baby's upset by starting a specially engineered high-pitched sound, then stepping down to quieter, lower pitched white noise over several minutes. A wide variety of sound patterns may be enabled. The device may be adapted to gradually increase the intensity of the sound and/or motion during the early weeks of life and to gradually reduce (i.e. wean) the intensity of the sound and/or motion over a suitable time period, such as several weeks or several months later in infancy.

Another exemplary embodiment of an infant calming/sleep-aid device is shown in FIGS. 22 through 27.

As shown in FIG. 22A, infant calming/sleep-aid device 2258 may include various control system related components including a control system 2216 for receiving and processing inputs 2200 and generating outputs 2246, a user interface 2201, and a communication facility 2214. It is to be appreciated that the control system 2216 may include various components depending on implementation needs, include various combinations of a motor, driver, sensory circuit, and microprocessor. Components of the control system and the user interface can be located on-board or remotely from the enclosure/platform portion of infant calming/sleep-aid device 2258. Inputs 2200 may include data or control signals from various types of sensors or devices such as microphone or sound sensor 2202, motion control sensor 2206, accelerometer or motion sensor 2208, user interface 2201, biometric sensor, and the like. In an embodiment, biometric sensor could be an accelerometer or other vibration sensor, and act to measure the breathing of an infant by measuring vibrations in the main moving platform. Outputs from the control system 2216 are directed to devices such as one or more speakers 2248 for controlling the generation of sound, motion controller 2250 for controlling the motion of a platform or structure on which the infant is placed, call to emergency services using Wi-Fi connection, and status light facility 2252 for controlling illumination of various status lights.

Other inputs may also be provided by other sensors such as visual sensors, including cameras, pressure sensors, sensors located in a swaddle or sleep sack, third party sensors, including monitors, sensors embedded in fabrics, and the like. Sensors embedded in fabrics may be flexible sensors. Sensors may be used for detecting child physiological parameters. Sensors may be used to provide inputs and feedback for mode selection for a mechanism that activates the calming reflex of an infant or, in certain circumstances, increases a baby's arousal. Microphone or sound sensor 2202 may be in communication with user interface 2201. Motion control sensor 2206 may be controlled by user interface 2201. Motion control sensor 2206 may be in communication with motion generation module 2232. Motion control sensor 2206 may send desired system speed input 2220 to motion generation module 2232.

User interface 2201 may be in communication with inputs such as microphone or sound sensors 2202, cry/state detection module 2218, motion analysis module 2222, accelerometer or motion sensor 2208, and the like. User interface 2201 may allow a user to input data such as the date of birth of an infant, the due date of an infant, the name of the infant, the weight of the infant, and the like. The weight of the infant may be input manually or automatically. The weight of the infant may be input automatically from a scale that is integrated with the infant calming/sleep-aid device 2258. The user interface 2201 may be used to provide a diary. The diary may be a sleep diary, cry diary, and the like. The user interface 2201 may be used to boost baseline stimulation by providing more motion and sound. For example, an extra fast and/or strong sound could be provided for infants that are difficult to calm. This extra fast and/or strong sound could be called Intervention4. Intervention4 may only be able to be activated two consecutive times, until the device is reset. Intervention4 may be limited to about two minutes of operation. The infant calming/sleep aid device may turn off after Intervention4 has been operating for about two minutes.

User interface 2201 may be an integral part of the infant calming/sleep-aid device 2258, or a separate piece, such as on a mobile peripheral device, which may be connected by a wired connection, a wireless connection, and the like to the infant calming/sleep aid device 2258. The wireless connection may be a Wi-Fi connection, Bluetooth connection, and the like.

The user interface 2201 may have controls, set-up information input, and other input data that can be sent to the control system of the device. Controls may include an on/off control, sound control, motion control, light control, and the like. Controls may be enabled or disabled. Motion control may have an extension option that automatically extends the sound, extends the basic motion of the device, and the like. The option that extends the basic motion of the device may be used after an infant is older than four months. Light control may have a dim option, be used to turn and LED alarm light on or off, and the like.

The user interface 2201 may allow a user to input set-up information, other information, and the like. Set-up information may include due date, birthdate, name, nickname, date/time setup, and the like. Other input information may include information related to shots the infant has had, feedings, travel, dirty diapers, and the like.

The user interface 2201 may provide various functions, such as Session, Session 'Super', History, Profile, Settings, Customization, Journaling, and the like. Session may include start/stop session, track session duration, track cry and sleep duration, track mode position, session summary, period summary, track epic position, contextual and expert tips messaging, alert messaging, AM/PM model, night light, and the like. Period summary may be for a 12-hour clock or 24-hour clock setup. Session 'Super" may include track mode position, track mode duration, volume control, editable mode position, and the like. History may include compare periods, display AM vs. PM sessions, share data and epic position via email and social, add sleep note to session, add weight note to session, and the like. Compare periods may compare periods over a 12-hour period, a 24-hour period, and the like. Profile may include name/nickname, due date, birth date, and the like. Settings may include overview, getting started, sleep library, level 4 on/off, notifications, push start, milestones, sleep facts, social network setup, sync on/off, and the like. Customization may include editable session data, manual entry, sound on/off, customize sound, customize mode, show weight in profile, allow weight input via external API, light control, and the like. Overview may include content from Epic Education, and the like. Getting Started may include content from First Use Coaching, and the like. Sleep library may include content from eBooks, and the like.

The user interface 2201 may provide cloud based functions. Cloud based functions may include account management, the ability to invite other account holders to manage profile, add friends, compare session data with friends, anonymously post to world data, compare session/period/epic with world data, social commenting, web view of data, and the like.

Figure 26B:
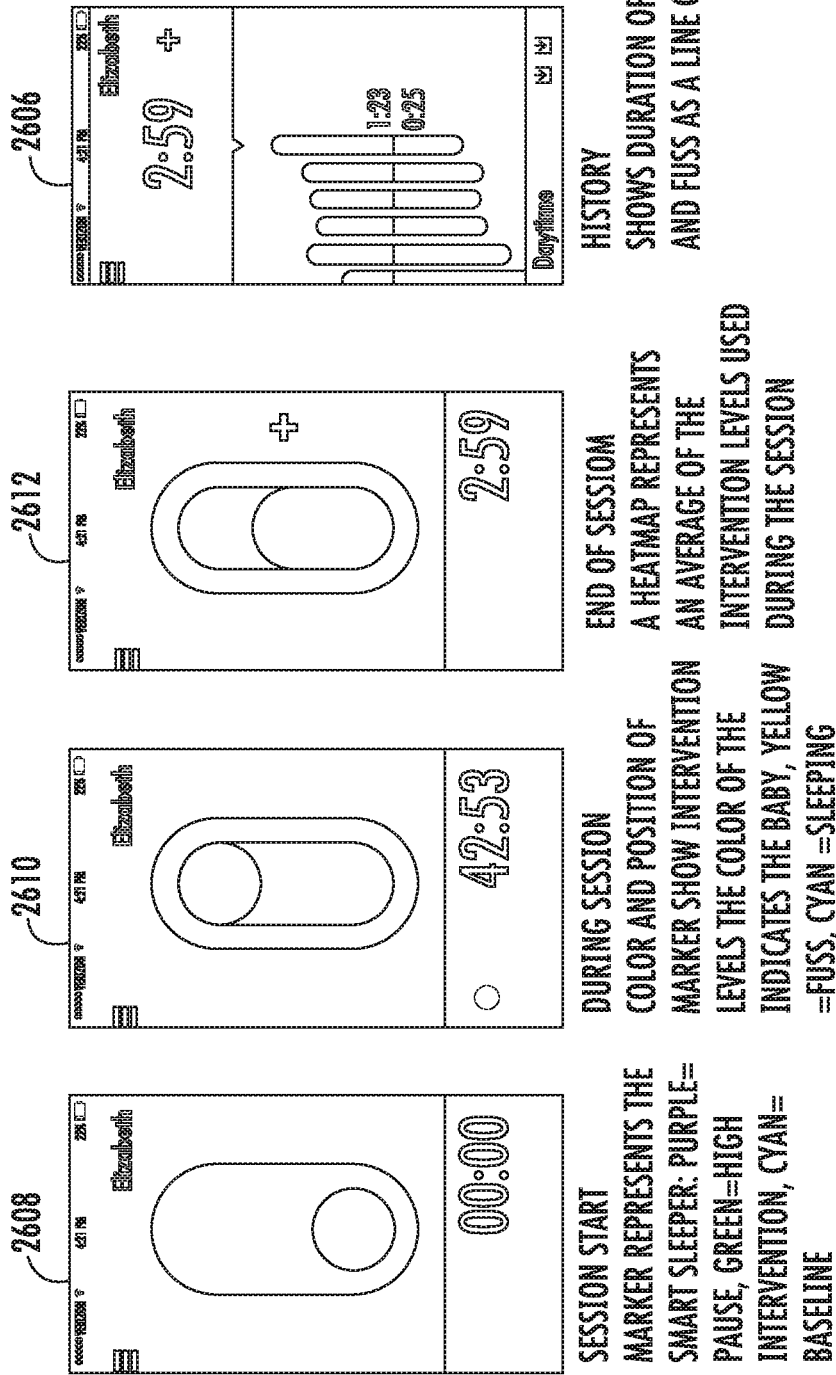
FIG. 26B illustrates views of sliders displayed by a user interface for use with the infant calming/sleep-aid device of FIG. 22A.

FIGS. 26A-26D illustrate a user interface 2201 in exemplary and non-limiting embodiments. FIG. 26A illustrates layers of the user interface 2201. Layers include the shape which represents the top view of the infant calming/sleep-aid device 2258. Layers may also include icons. Icons may include a baby icon, a baseline indicator icon, and the like.

Icons may be placed at the center of the display. Layers may include views. Views may include before session 2600, during session 2602, end of session 2604, history 2606, and the like. Before session 2600 may include a center dot that represents the child. The center dot may be color coded with color codes. Color codes may include purple for pause, yellow for fuss, cyan for sleeping, and the like. During session 2602 may include a ring. A ring may represent levels of wiggle/sound. Center may be baseline. Color may move out as intensity increases. End of session 2604 may include color. Color may represent an average of the levels of wiggle/sound used during the session. History may show duration of sleep and fuss as a line chart.

FIG. 26B illustrates sliders of the user interface. Sliders may include a focus on the current state of the infant calming/sleep-aid device 2258. Sliders may include a marker. The marker may indicate the current level of motion and sound of the infant calming/sleep-aid device 2258. Sliders may include views. Views may include session start 2608, during session 2610, end of session 2612, history 2606, and the like. Session start 2608 may include a marker that represents the infant calming/sleep-aid device 2258. The marker may be color coded with color codes. Color codes may include purple for pause, green for high intervention, cyan for baseline, and the like. During session 2610 may include a marker. The color and position of the marker may show intervention levels. During session 2610 may include a notch. The notch may indicate the baby. The notch may be color coded with color codes. Color codes may be yellow to indicate fuss, cyan to indicate sleeping, and the like. End of session 2612 may be a heat map that represents an average of the intervention levels used during the session.

Figure 26C:
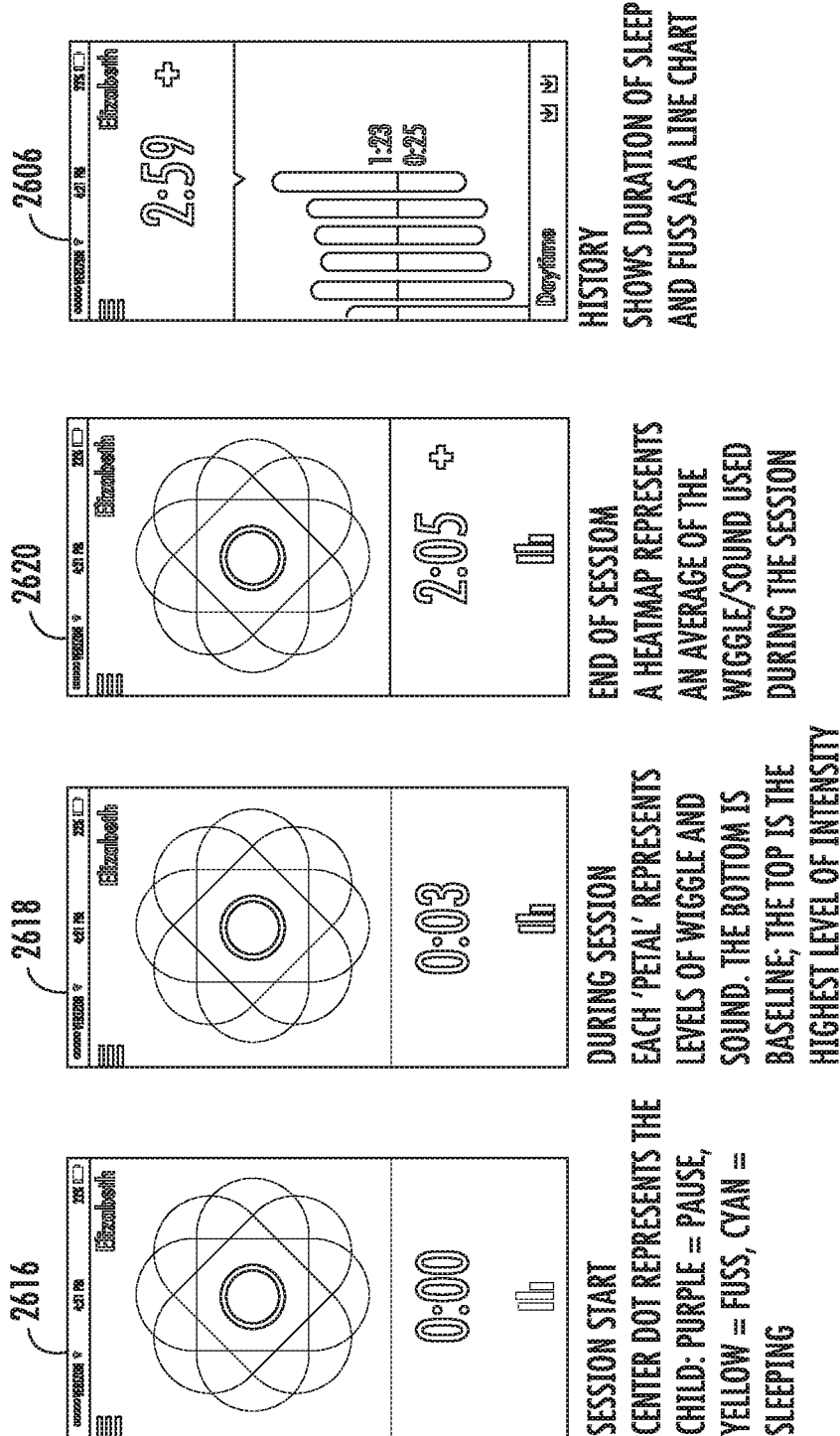
FIG. 26C illustrates views of blossoms displayed by a user interface for use with the infant calming/sleep-aid device of FIG. 22A.

FIG. 26C illustrates blossoms of the user interface. Blossoms may include an icon for the infant at the center of the experience while different intervention levels of the infant calming/sleep-aid device 2258 are shown in a trajectory around it. Blossoms may include views. Views may include session start 2616, during session 2618, end of session 2620, history 2606, and the like. Session start 2608 may include a center dot that represents the infant. The dot may be color coded with color codes. Color codes may include purple for pause, yellow for fuss, cyan for sleeping, and the like. During session 2618 may include petals. Each petal may represent levels of motion and sound. The bottom petal may be baseline, the top petal may be the highest level of intensity, and the like. End of session 2620 may include a heat map. The heat map may represent an average of the levels of motion and sound used during the session.

Figure 26D:
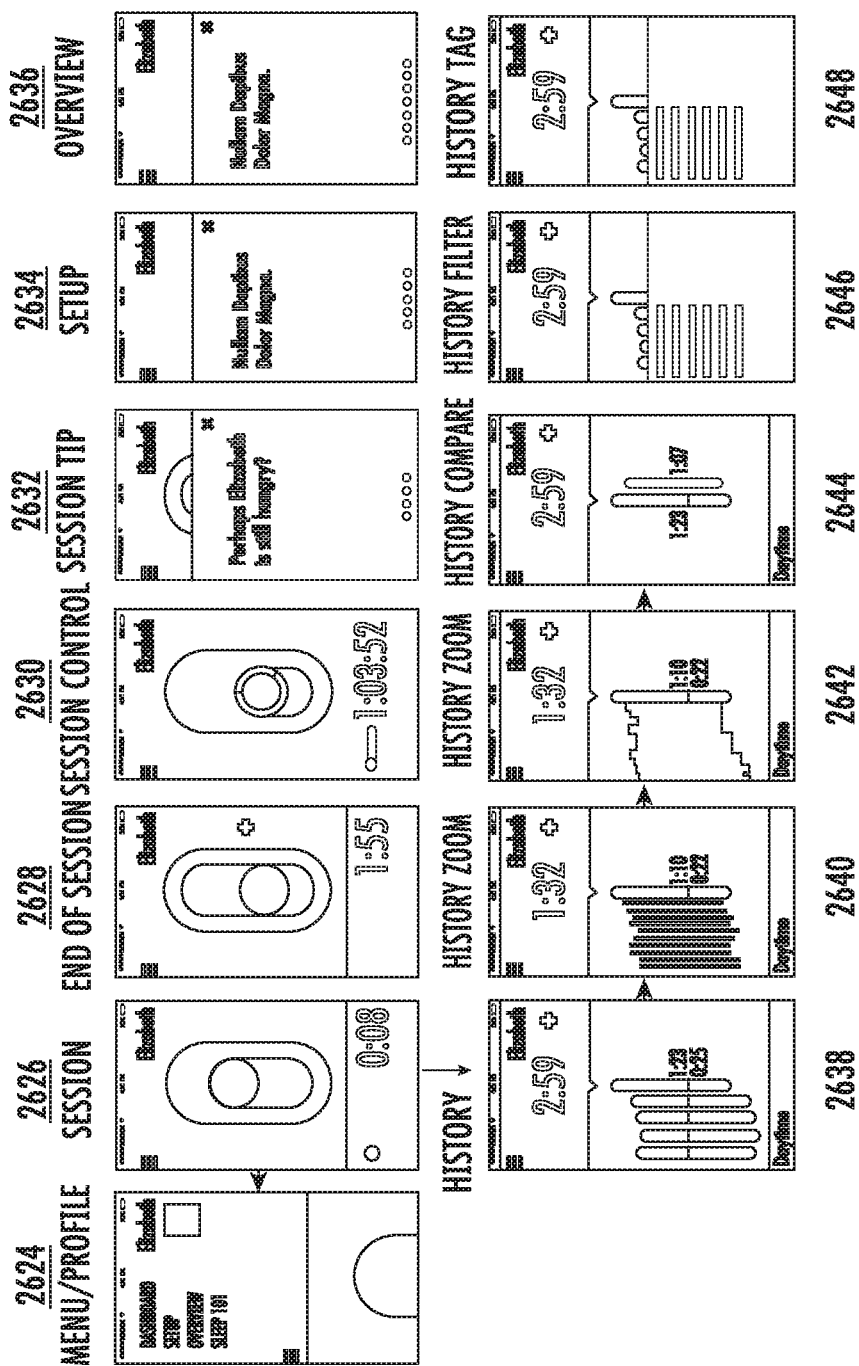
FIG. 26D illustrates additional views displayed by a mobile application user interface for use with the infant calming/sleep-aid device of FIG. 22A.
Figure 27A:
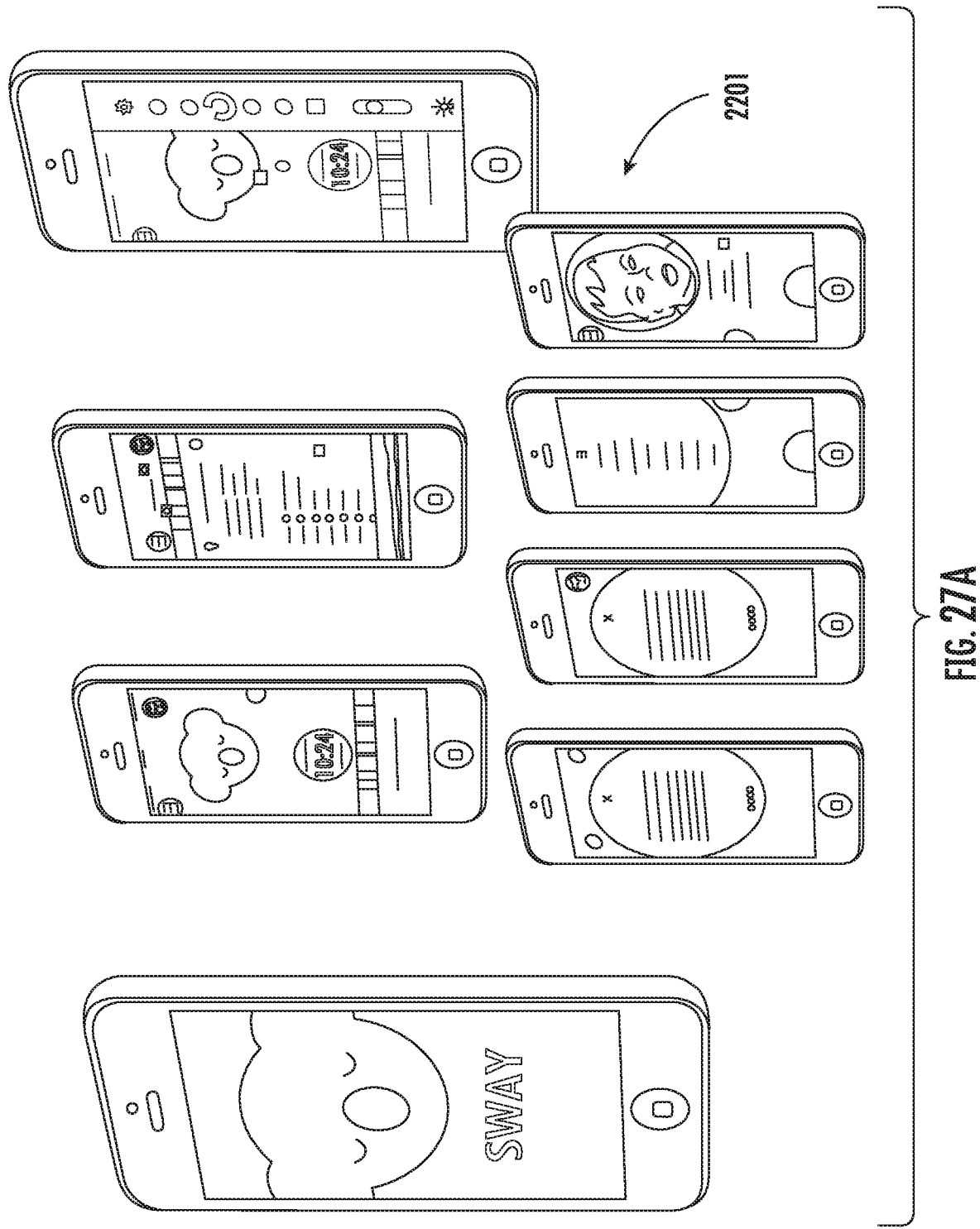
FIG. 27A illustrates additional views displayed by an exemplary mobile device application user interface for use with the infant calming device.
Figure 27B:
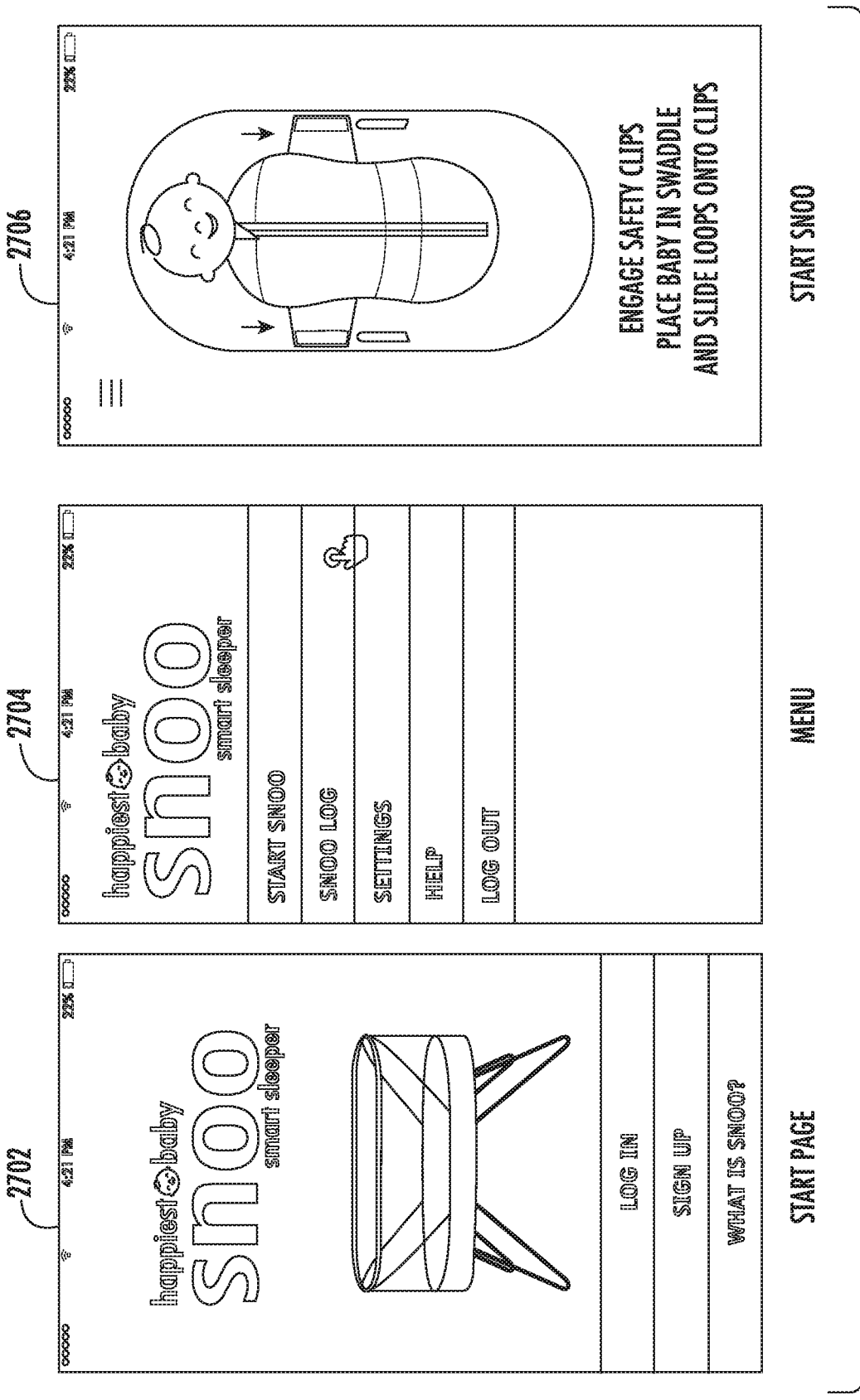
Figure 27C:
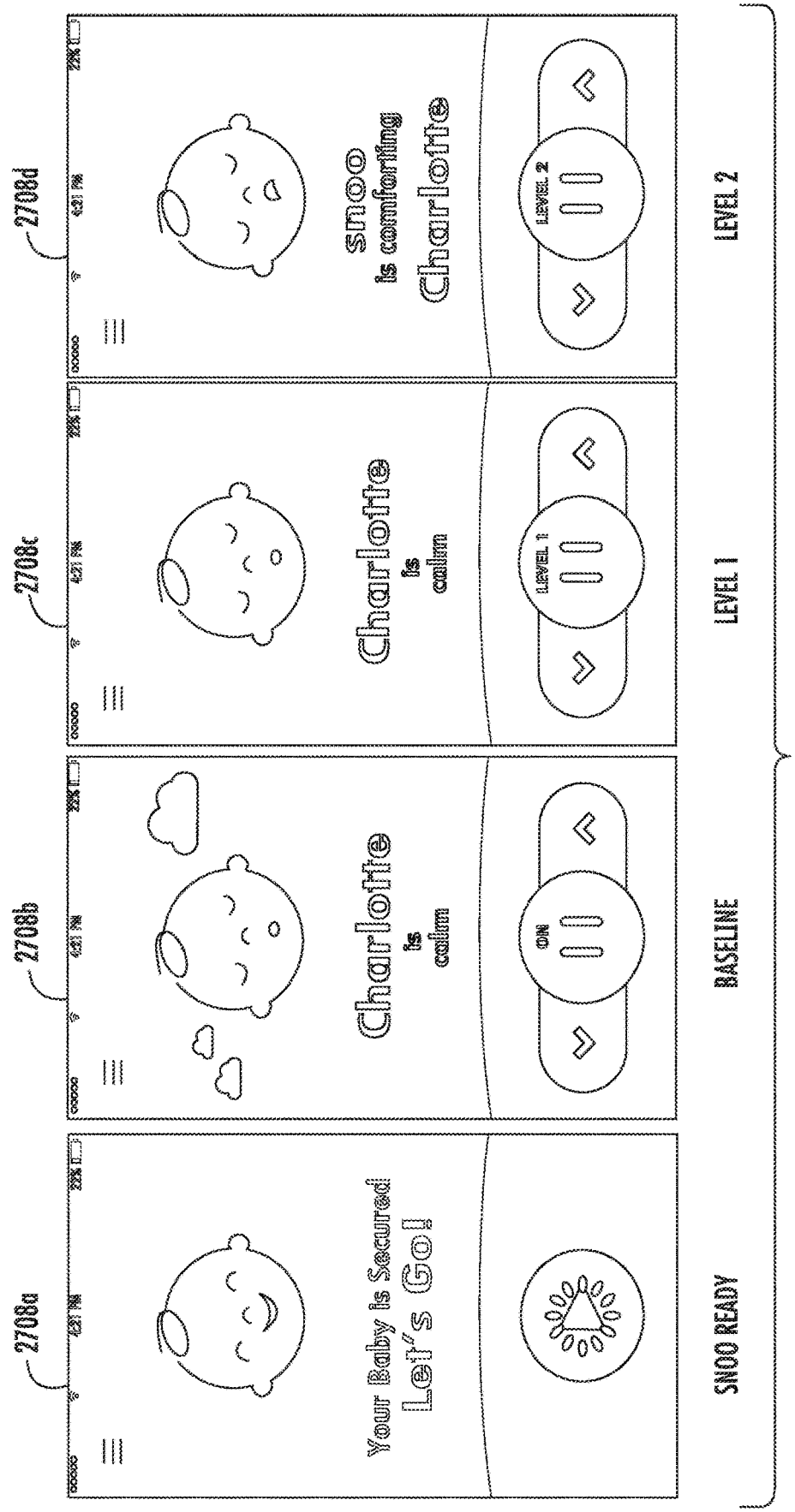
Figure 27D:
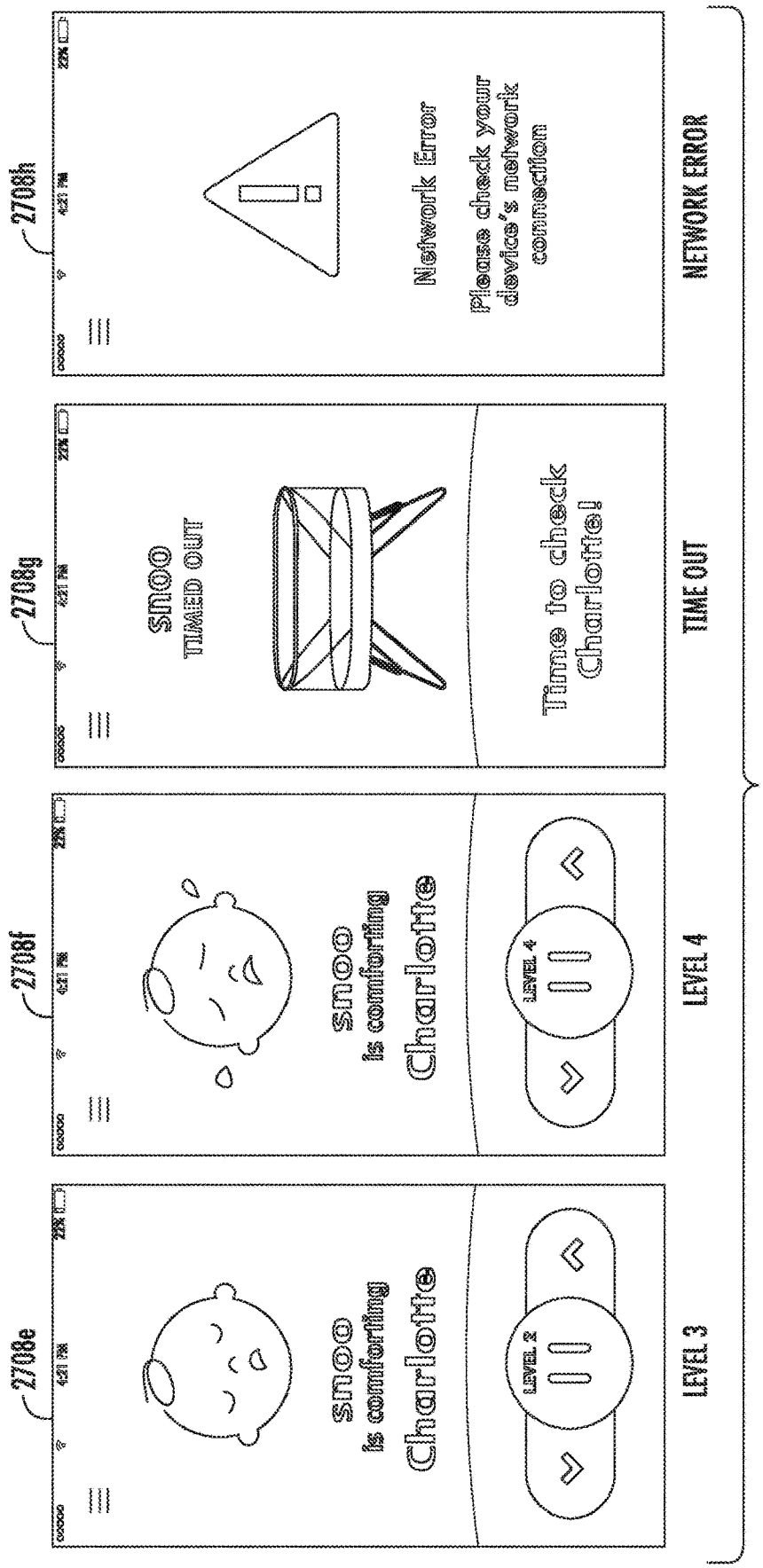

FIG. 26D illustrates additional views of the user interface. Additional views may include menu/profile 2624, session 2626, end of session 2628, session control 2630, session tip 2632, setup 2634, overview 2636, history 2638, history zoom 2640, history compare 2644, history filter, 2646, history tag 2648, and the like. A user may move from one screen to the next, such as by swiping, such that a user may swipe to see a day view, swipe again to see a week view, etc.

FIGS. 27A-27E illustrate additional views of a user interface of a mobile device for use with the infant calming/sleep aid device. FIGS. 27B-27E illustrate an exemplary home screen 2702, an exemplary menu screen 2704, an exemplary instructional screen 2706 to instruct a user to secure the infant, various status screens 2708*a*-2708*l* indicating the level or state of the infant calming device, a network error screen, and the like. In one embodiment, an infant calming/sleep aid device can further include a mobile device having a user interface 2201 in communication with the infant calming/sleep aid device such that the user interface 2201 can be configured to provide a state of infant cry to the mobile device.

User interface 2201 may be provided as a mobile application. The mobile application may provide data inputs to the control mechanism of the infant calming/sleep aid device 2258. Data may include monitoring data, feedback data, control data, reporting data, analytics data, and the like. The mobile application may be installed on a mobile device. The device may be a smartphone, tablet computer, and the like. The mobile device may have an operating system that may be iOS, Android, and the like. The mobile application may enable interactions with the device. Interactions may be enabled through a communication interface. The communication interface may be a universal serial bus (USB) interface, Wi-Fi interface, Bluetooth interface, and the like. Interactions may be control interactions. Control interactions may be similar to the interactions that may be enabled directly from the infant calming/sleep aid device 2258, only available on the mobile application, and the like. Examples of control interactions may include the ability to turn on Intervention4 using four fast taps of the on/off button within two seconds, turn on/off the infant calming/sleep aid device 2258 by pressing and holding the on/off button for three seconds, and the like.

Other mobile device interactions may include reports and statistics, sharing and group interactions, benchmarking and comparison interactions, graphic interactions, acoustic signature of a cry interactions, data upload to a third party interactions, feedback from a subject matter expert interactions, warning alert interactions, overtone customization of white noise interactions, other input interactions, journal sharing/printout interactions, weight interactions, breastfeeding interactions, camera interactions, and the like. Other input interactions may include photo input interactions, video input interactions, audio input interactions, and the like.

Additional inputs may include information inputs. Information inputs may include baby weights, baby lengths, baby circumferences, frequencies, travel, immunizations, illness, heart rate, respiratory rate, blood oxygenation, and the like. Baby weights may include weight at birth, baby weights at different weightings, and the like. Baby length may include baby length at birth, baby length at different measuring's, and the like. Baby circumference may include baby circumference of the head at birth, baby circumference of the head at different measuring's, and the like. Frequencies may include frequency of feeding, frequency of diaper changes/pee or poop, and the like. Information inputs may be added to a mobile device journal.

Microphone or sound sensor 2202 may send data to cry/state detection module 2218. Accelerometer or motion sensor 2208 may send motion data to motion analysis module 2222. Communication facility 2214 may be used to establish communication between inputs 2200 and control system 2216. Communication may be established via direct control, remote control, and the like. Direct control may include providing control inputs to the communication facility from input devices directly integrated with the infant calming/sleep-aid device 2258. Remote control may include providing control inputs to the communication facility from input devices remotely connected to the infant calming/sleep-aid device 2258. Remote connectivity may include wired and wireless connectivity. Wireless connectivity may include Wi-Fi connectivity, Bluetooth connectivity, and the like. Journaling may include track feedings, track diapers, and the like.

Control system 2216 may include various modules. Modules may include cry/state detection module 2218, behavior state module 2230, biometric detection module, audio generation module 2238, motion generation module 2232, motion analysis module 2222, status light module 2234, and the like. Cry/state detection module may be in communication with microphone or sound sensor 2202, motion control sensor 2206, behavior state module 2230, and the like. Cry/state detection module 2218 may send an infant crying/not crying status input, along with a quantification of a crying episode to behavior state module 2230. Biometric detection module may be in communication with motion generation module 2232, audio generation module 2238, and the like. Biometric detection module may send desired motion state input 2260 to motion generation module 2232, desired audio track, desired volume/equalizer settings input 2236 to audio generation module 2238, and the like. Behavior state module 2230 may be in communication with crying detection module 2218, motion generation module 2232, audio generation module 2238, and the like. Behavior state module may send desired motion state input 2260 to motion generation module 2232, desired audio track, desired volume/equalizer settings input 2236 to audio generation module 2238, and the like. Motion generation module 2232 may be in communication with behavior state module 2230, motion control sensor 2206, user interface 2201, motion analysis module 2222, motion controller 2250, and the like. Motion analysis module 2222 may be in communication with accelerometer or motion sensor 2203, user interface 2201, motion generation module 2232, status light module 2234, and the like. Motion analysis module 222 may send motion frequency/amplitude and motion is safe/is not safe input 2226 to motion generation module 2232. Motion analysis module 2222 may send motion is safe/not safe input and motion is soothing/is not soothing input 2228 to status light module 2234. Motion generation module may send target motor positions/speeds input to motion controller 2250 and the like. Audio generation module 2238 may be in communication with behavior state module 2230, one or more speakers 2248, and the like. Audio generation module 2238 may send audio generation module input to one or more speakers 2248. Status light module 2234 may be in communication with motion analysis module 2222 status lights color display facility 2252 and the like. Status light module 2234 may send target status light colors input 2244 to status lights color display facility 2252 and the like.

Control system 2216 may also be in communication with data storage facility 2254, rules engine 2256, and the like. Data storage facility 2254 may store information that may be accessed by other modules of the control system, and the like. Rules engine 2256 may provide rules for inputs and triggers to a mechanism to activate the "calming reflex" of an infant.

Figure 23C:
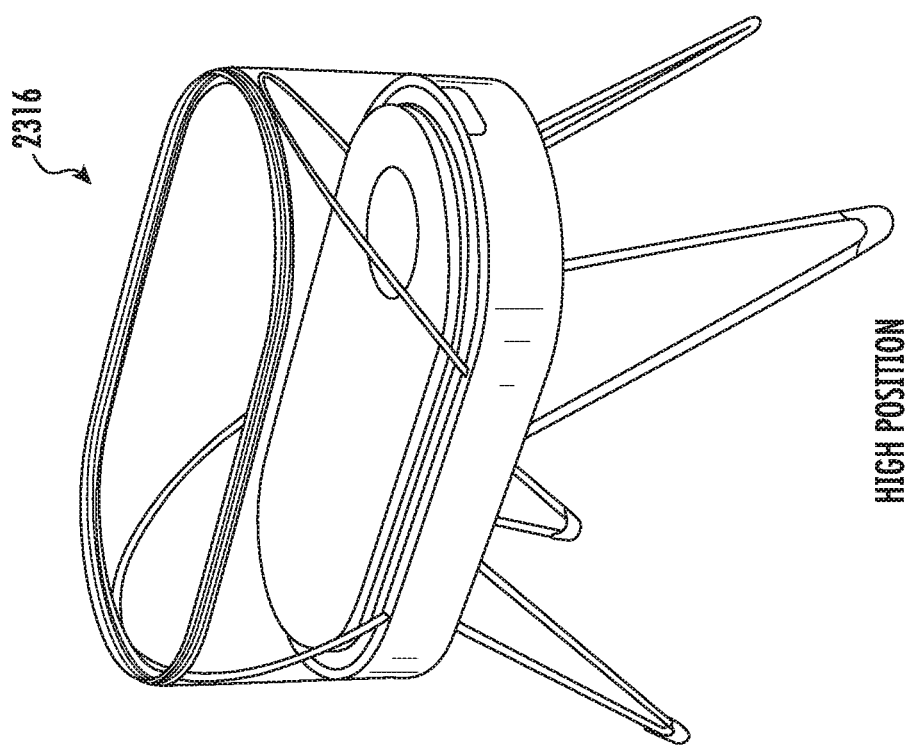
FIGS. 23C and 23D are perspective views of the infant calming/sleep-aid device of FIG. 23B.
Figure 23D:
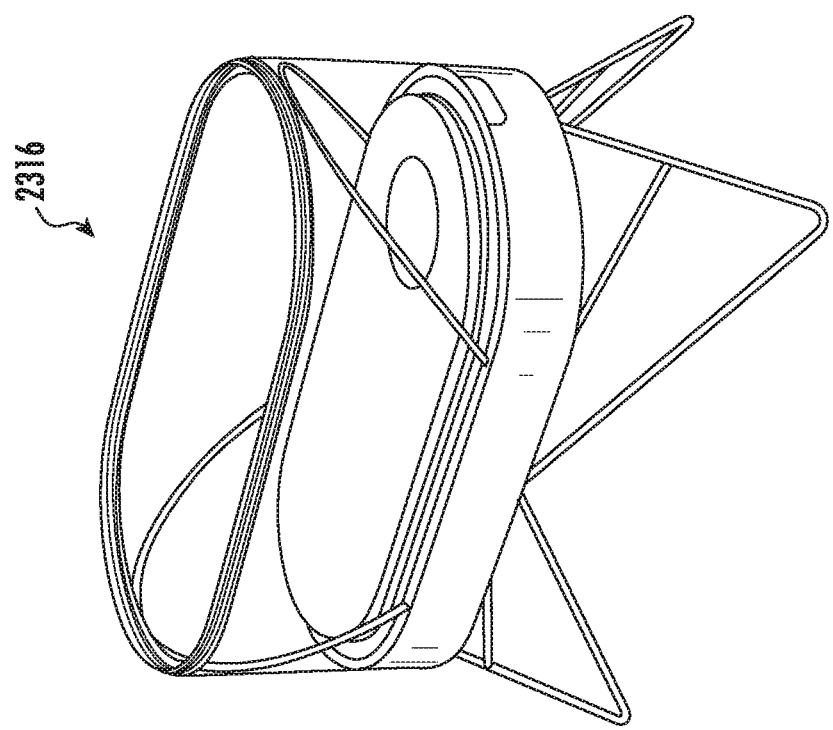
Figure 23E:
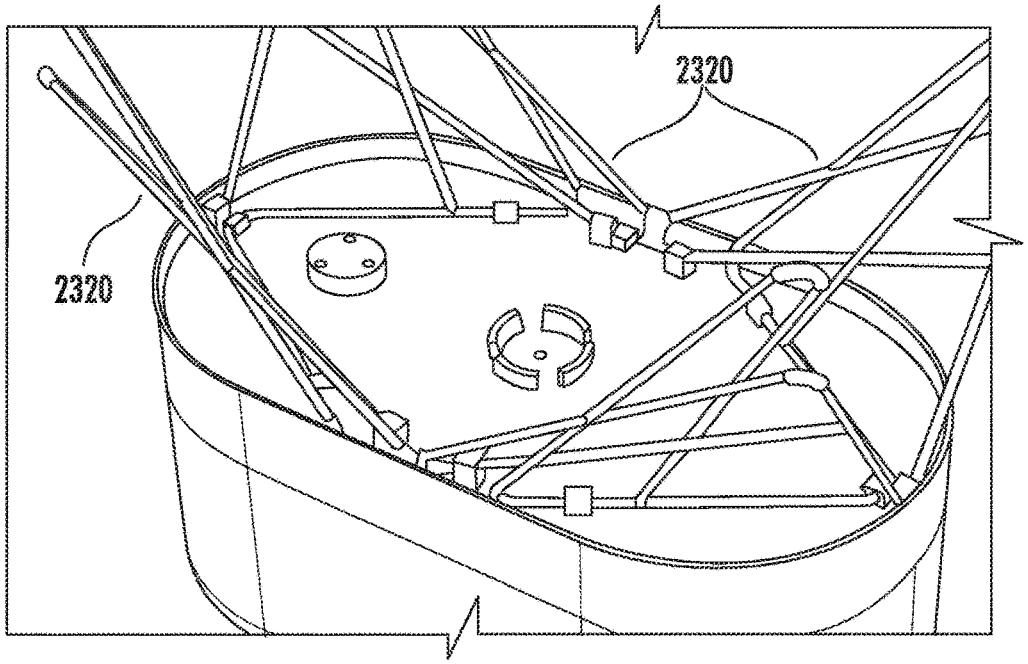
FIGS. 23E-23H illustrate exemplary embodiment of leg connectors of the infant calming/sleep aid device of FIG. 23B, which are used to attach legs.
Figure 23F:
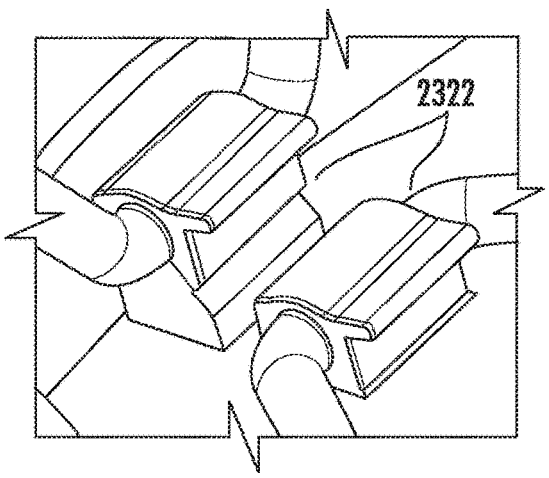
Figure 23G:
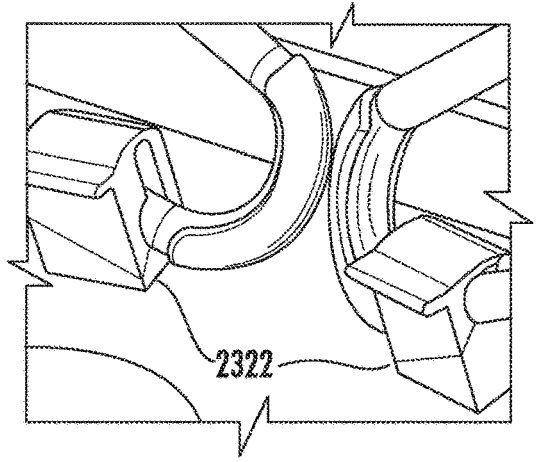
Figure 23H:
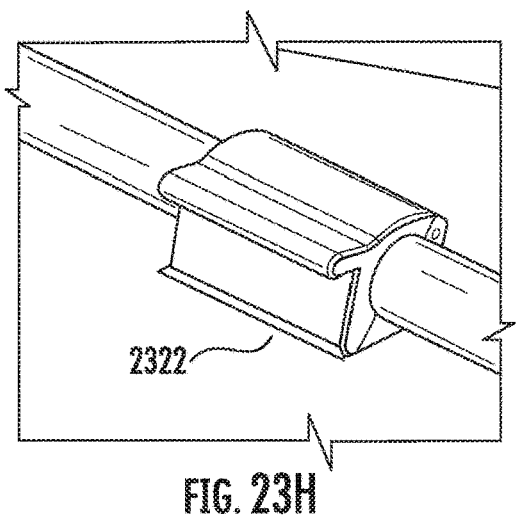
Figure 23I:
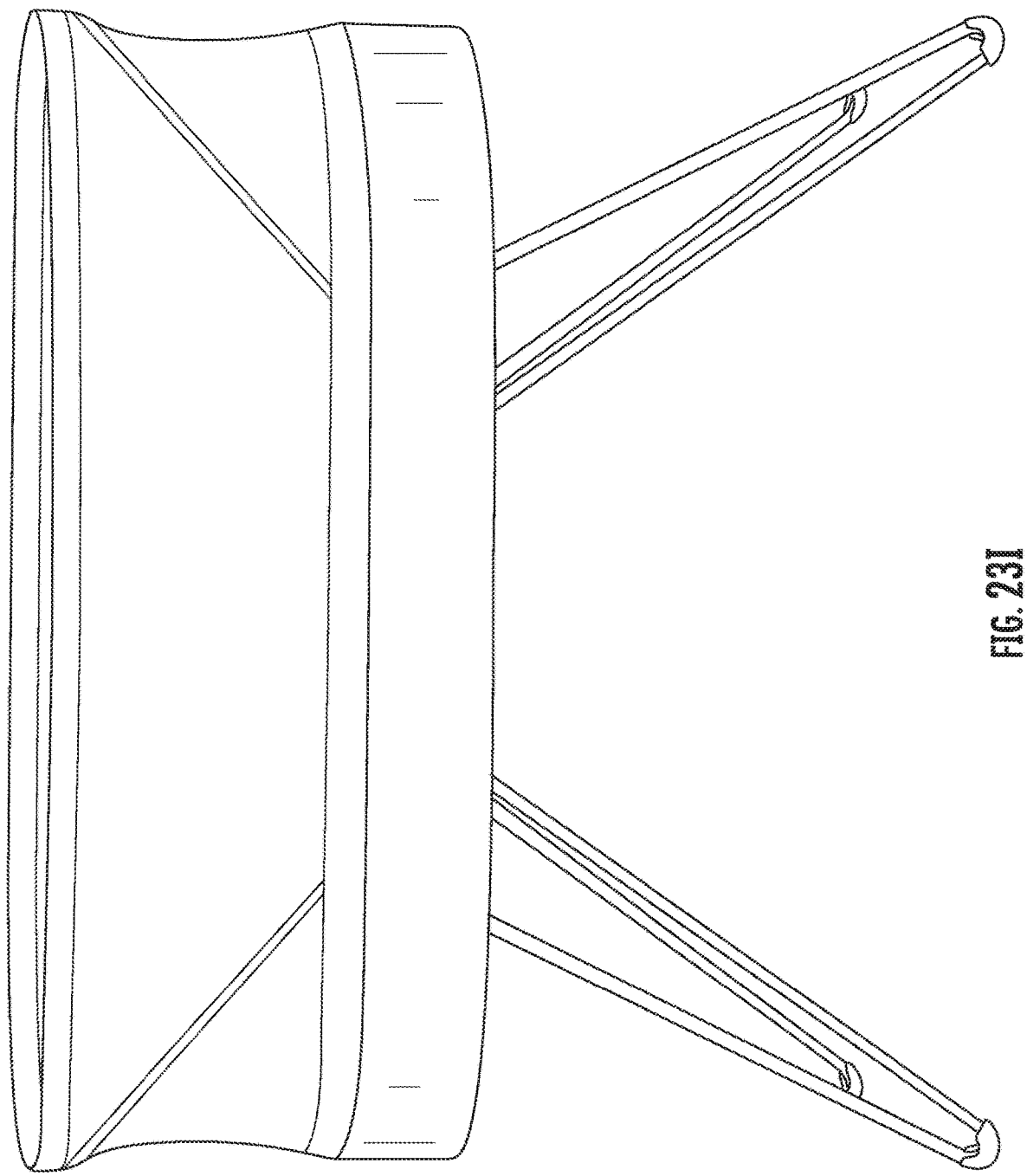
FIG. 23I illustrates an exemplary infant calming/sleep aid device having an inside mesh and an outside mesh fabric.
Figure 23J:
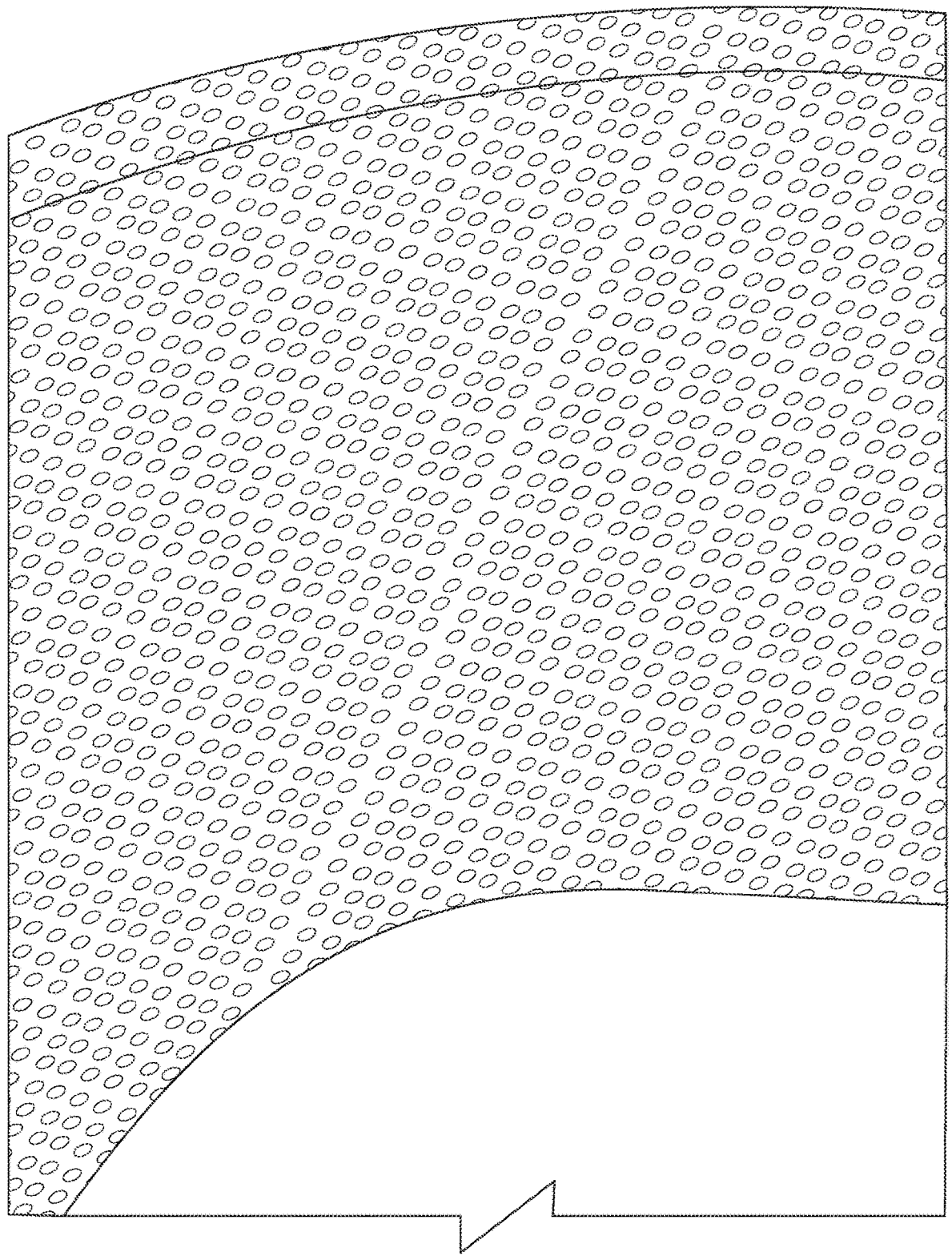
FIGS. 23J-L illustrate various views of the exemplary double mesh infant calming/sleep aid device.
Figure 23K:
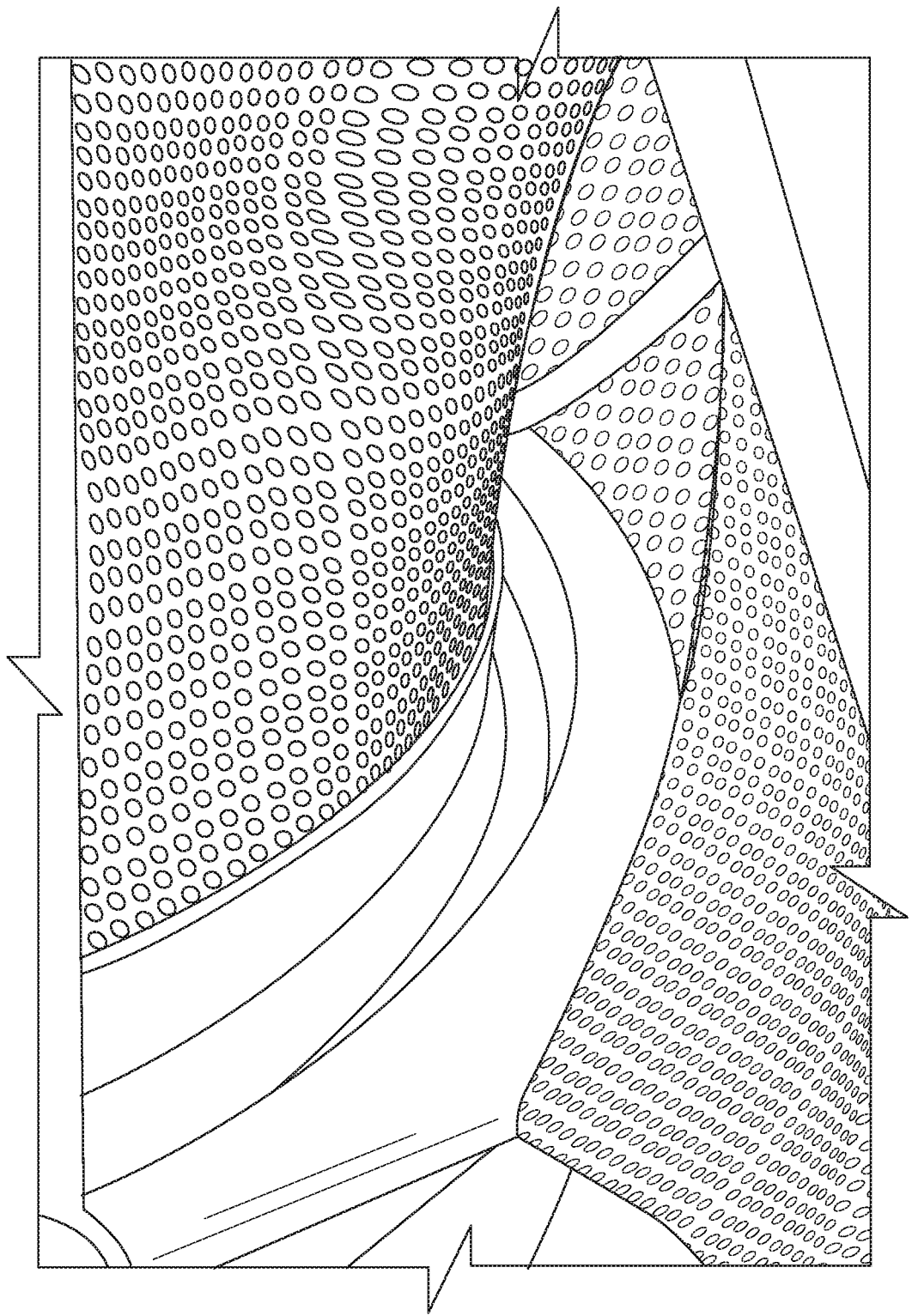

FIGS. 23A and 23B illustrate the infant calming/sleep aid device 2258 in exemplary and non-limiting embodiments. FIG. 23A is a partially cut-away perspective view of the infant calming/sleep aid device 2258. FIG. 23B is an exploded perspective view that illustrates components of the infant calming/sleep aid device 2258. Components of the infant calming/sleep aid device 2258 may include outer fabric 2300, structure 2302, inner fabric/mattress cover 2304, mattress 2306, lower wall 2308, veneer/felt cosmetic layer 2310, stand 2312, and foot pad/wheel 2314. The height of the infant calming/sleep aid device 2258 may be adjustable. FIGS. 23C and 23D are perspective views of the infant calming/sleep aid device 2258 in a low position 2316 and in a high position 2318. FIG. 23E illustrates a bottom view of the infant calming/sleep aid device 2258 with legs attached to the bottom of the infant calming/sleep aid device 2258. FIGS. 23F-23H illustrate leg connectors 2322 used to attach the legs 2320 to the infant calming/sleep aid device 2258. The legs may be unsnapped and reversed to allow a high or low position of the platform/structure on which the infant is secured.

Infant calming/sleep aid device 2258 may provide a mechanism to activate the calming reflex of an infant, such as via the control system described with respect to FIG. 22A. The mechanism may use stereotypical sensory input, stereotypical behavioral output, and the like to trigger the calming reflex. The activation mechanism may be programmed to wane after 3-5 months or the like. The mechanism may exhibit threshold variations that vary between higher and lower thresholds based on the individual infant. The mechanism may vary by biometric evaluation or state of the infant and may call for higher or lower levels of stimulation based on the state of the infant. The state may be a quiet sleeping state, active sleep state, drowsiness state, quiet alert state, fussing state, crying state, and the like. The state may be matched to the optimal stimulus level of an individual infant. Levels may also be adjusted to match the age of the infant, for example during the first month of the life of the infant. Failure to exceed the optimal stimulus level may result in an absence of response by the infant to the mechanism. The mechanism may be activated by sound generated by the infant, movement generated by the infant, abnormal biometric signals, and the like. The output of the mechanism may cause reductions in motor output levels. The infant calming/sleep aid device 2258 may automatically shut down if an infant is not calmed by higher levels of motion and sound. Higher levels of motion and sound may be called Intervention3 and Intervention4. The infant calming/sleep aid device may teach infants to sleep better by training the sleep pattern of the infant using sleep cues. Sleep cues may be swaddling, effective motion, optimal sound, and the like. Motion may take on characteristics of a more square-shaped wave as the platform moves more quickly.

The mechanism to activate the calming reflex or the conditioned response of an infant may be activated by a feedback based control mechanism. The feedback based control mechanism may select modes, parameters, parameter ranges, and the like. Modes may be motion modes, sound modes, and the like. Parameters may be motion parameters, sound parameters and the like. Parameter ranges may be motion parameter ranges, sound parameter ranges, and the like. The feedback based control mechanism may provide motion feedback to control the motion of the swing of the infant calming/sleep aid device 2258. The motion feedback may activate a calming reflex of the infant to provide vestibular stimulation in the inner ear of the infant. The feedback based control mechanism may operate as a feedback loop. The feedback loop may result in a reduction overtime of the mechanism to activate the calming reflex or conditioned response of an infant. For example, it may be desirable to wean an infant from the motion of the infant calming/sleep aid device 2258 starting when the infant is of the age 3-4 months. The feedback based control mechanism may be activated by a remote control, a camera mounted on the infant calming/sleep aid device 2258, and the like. The remote control may be operated by a caregiver. The caregiver may be in the same room as the infant calming/sleep aid device 2258, or a different room than the infant calming/sleep aid device 2258.

In one embodiment, an infant calming/sleep-aid device may include a movable platform 2102 similar to that described in FIG. 19 or other movable platform described throughout this disclosure. The movable platform 2102 can be configured to support an infant within the infant calming/sleep-aid device. In one embodiment, the infant calming/sleep-aid device includes a sound output device 2248 configured to provide a sound for soothing the infant. In some embodiments, a sleep sack, similar to those shown in FIGS. 25A-25L and 25P-25R, may be connected to the movable platform 2102 such that the sleep sack is configured to secure the infant's head at a position inside the device.

In another embodiment, an infant calming/sleep-aid device includes a sensor system 2202 (e.g., microphone sensor or sound sensor) similar to that described in FIG. 22A and in other places throughout the disclosure. The sensor system 2202 may be disposed above or below the moveable platform 2102 but proximate to the movable platform 2102 such that the sensor system 2202 is operable to detect a noise. In another embodiment, the infant calming/sleep-aid device may include a cry/state detection module 2218 that acts to detect baby cries originating from within the infant calming device, to detect cries that are above various threshold values, such as 65 dB or greater.

In one embodiment, the sensor system 2202 is configured to generate measurement data for the noise detected. For example, the measurement data may include a digital recording of a sound pattern for the noise detected. Based on the recorded sound pattern, the cry/state detection module 2218 may be configured to identify noise detected from the infant, noise detected from within the device, or noise detected from the ambient environment outside of the device. In an embodiment, the recorded sound pattern may also be used by the cry/state detection module 2218 to determine whether the noise inside the device is coming from the infant or from other noises within the device (e.g., infant moving about and making non-crying noises within the device). In an embodiment, the recorded sound pattern may be used by a cry/state detection module 2218 to determine a state of infant cry based on whether the infant cry is 50 dB or greater, 55 dB or greater, 60 dB or greater, 65 dB or greater, 70 dB or greater, 75 dB or greater, 80 dB or greater, 85 dB or greater, 90 dB or greater, 95 dB or greater or 100 dB or greater.

In one embodiment, the infant calming/sleep-aid device includes a control system 2216 communicatively connected to the sensor system 2202. The control system 2216 may be configured to receive the measurement data generated by the sensor system 2202. In operation, the control system 2216 may determine, based on a first parameter of the measurement data, whether the noise detected originates from inside or outside the device. It is to be appreciated that the first parameter of the measurement data may be a parameter obtained by processing the measurement data. In an embodiment, the first parameter may be a location of the noise detected as determined by applying a directional filter to the measurement data. For example, the location of the noise detected may be coming from inside the device. In yet another example, the first parameter may be a location of the noise detected coming from ambient environment outside of the device. In one embodiment, if the noise detected is determined to originate from outside the device, a no cry state is determined.

If the control system 2216 determines that the noise detected is determined to have originated from inside the device, the control system 2216 is further configured to determine, based at least on a second parameter of the measurement data, whether the noise is that of an infant cry or not. It is to be appreciated that the second parameter of the measurement data may be a parameter determined by processing the measurement data. In one example, the second parameter may be the frequency of the noise detected as determined by applying a frequency filter to the measurement data. In an embodiment, the control system 2216 is able to determine, based on the frequency of the noise and its re-occurrence over a period of time, whether the noise detected is that of the infant cry or simply other non-cry noises being made by the infant within the device. In an embodiment, the reoccurrence of the frequency of the noise may be determined using a pattern recognition algorithm or filter.

If the control system 2216 determines that the noise detected is that of an infant cry, the control system 2216 is further configured to determine, based at least on a third parameter of the measured data, a state of infant cry. In one embodiment, the state of infant cry can be determined by a threshold value. It is to be appreciated that the third parameter of the measurement data may be a parameter determined by processing the measurement data. In one example, the third parameter may be the intensity of the noise detected as determined by applying a threshold filter 2286 to the measurement data to determine the state of infant cry. In an embodiment, after confirming that the noise detected is that of an infant cry, the control system 2216 is configured to determine a state of infant cry based on whether the infant cry threshold value is 50 dB or greater, 55 dB or greater, 60 dB or greater, 65 dB or greater, or 70 dB or greater.

In some embodiments, the state of infant cry can be determined by comparing the intensity of the noise detected to a plurality of threshold values. This can be carried out by the control system 2216, which is configured to compare the intensity of the noise detected to threshold values of 50 dB or greater, 55 dB or greater, 60 dB or greater, 65 dB or greater, or 70 dB or greater. In operation, if the noise detected does not reach the state of infant cry as determined by a threshold value, then a no cry state is determined.

In one embodiment, after the state of infant cry has been determined against a threshold value, the control system 2216 is further configured to provide a control signal to operate at least one of the movable platform 2102 or the sound output device 2248 to soothe the infant. In some embodiments, the control signal may be configured to control the movable platform 2102 to undergo a predetermined, oscillatory motion for soothing the infant or to control the sound output device 2248 to output a sound for soothing the infant.

In one embodiment, the control signal from the control system 2216 may include a command to the movable platform 2102 to change at least one of a frequency or an amplitude of an oscillatory motion of the movable platform. In another embodiment, the control signal from the control system 2216 may include a command to the sound output device 2248 to change an intensity of the sound for soothing the infant.

In one embodiment, the infant calming/sleep-aid device may further include a sleep sack similar to those shown in FIGS. 25A-25L and 25P-25R. The sleep sack may be connected to the movable platform 2102 such that the sleep sack is configured to secure the infant's head at a position inside the device. It is to be appreciated that the position of the infant's head may be predetermined and programmed into the control system 2216. Since the predetermined position of the infant's head may be known to the control system 2216, the control system 2216 may use it as a basis for comparison to more accurately make cry/state detection determinations as discussed in the present disclosure.

In one embodiment, the infant is assumed to be positioned correctly in the infant calming device (as described elsewhere herein), such as with safety clips, such that the baby is positioned proximate to the microphones. Further, the cries are detectable while the device is playing calming sounds, such as in the form of various white noise tracks. The device rejects sounds originating from outside of the infant calming device, such as human speech, sounds from other children, or ambient noise from sources such as music sources, television, and pets, and other common household sounds. Baby cry events are recognized and appropriate action is undertaken, such as responding via movement of the platform, or modifying the characteristics of the sound or logging the events for further analysis.

In particular, the module 2218 may include a directional filter 2282, a frequency filter 2284, and a threshold filter 2286. The directional filter 2282 may be applied to the measurement data to determine the location of the noise detected. This location may help determine, whether the noised detected by the microphones emanated from inside or outside the infant calming device. The frequency filter 2284 may be applied to the measurement data to determine the frequencies and reoccurrence of such frequencies within a specified amount of time of the noise detected. This frequency may help determine whether sound from inside the infant calming device is actually a cry. The threshold filter 2286 may be applied to the measurement data to determine the state of infant cry.

Figure 22B:
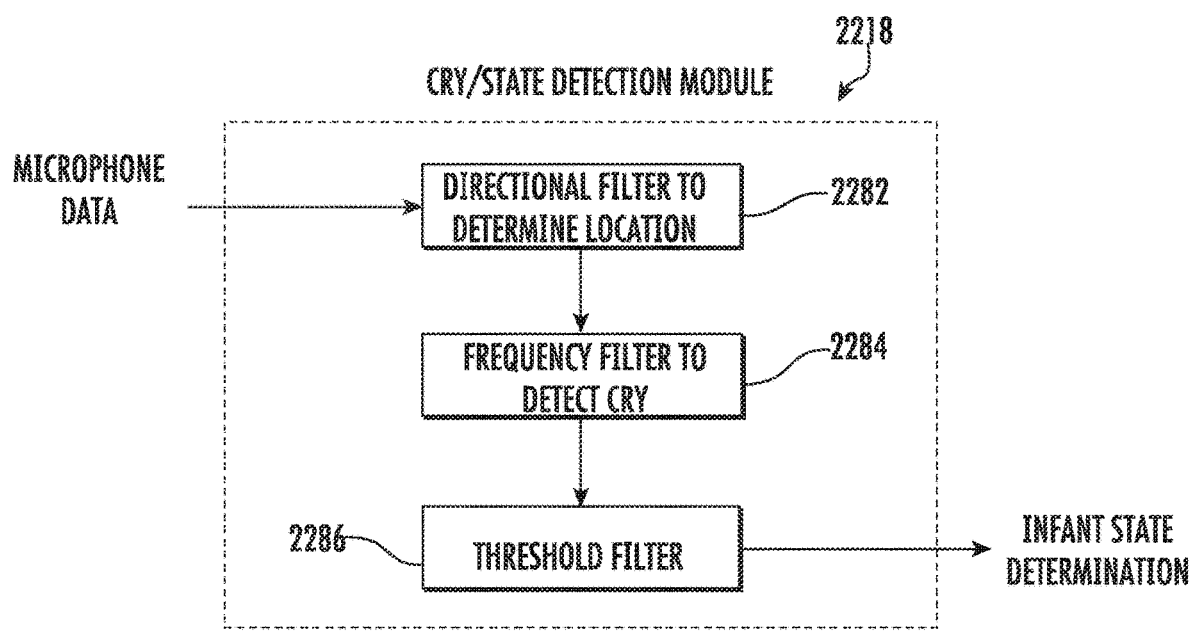
FIG. 22B is a representation of an exemplary cry/state detection module of the exemplary infant calming/sleep-aid device.

FIG. 22B is a representation of an/state detection module 2218 of the infant calming/sleep-aid device, which receives signals (data) from a plurality of microphones, such as three microphones, in the infant calming device. In one embodiment, the sensor system 2202 may include at least three microphones disposed proximate to the left side of, the right side of, and above the position of the infant's head. In another embodiment, each of the three microphones may be an omnidirectional microphone. In another embodiment, the microphone(s) may be placed below the infant to minimize the microphones picking up outside noise.

Figure 22C:
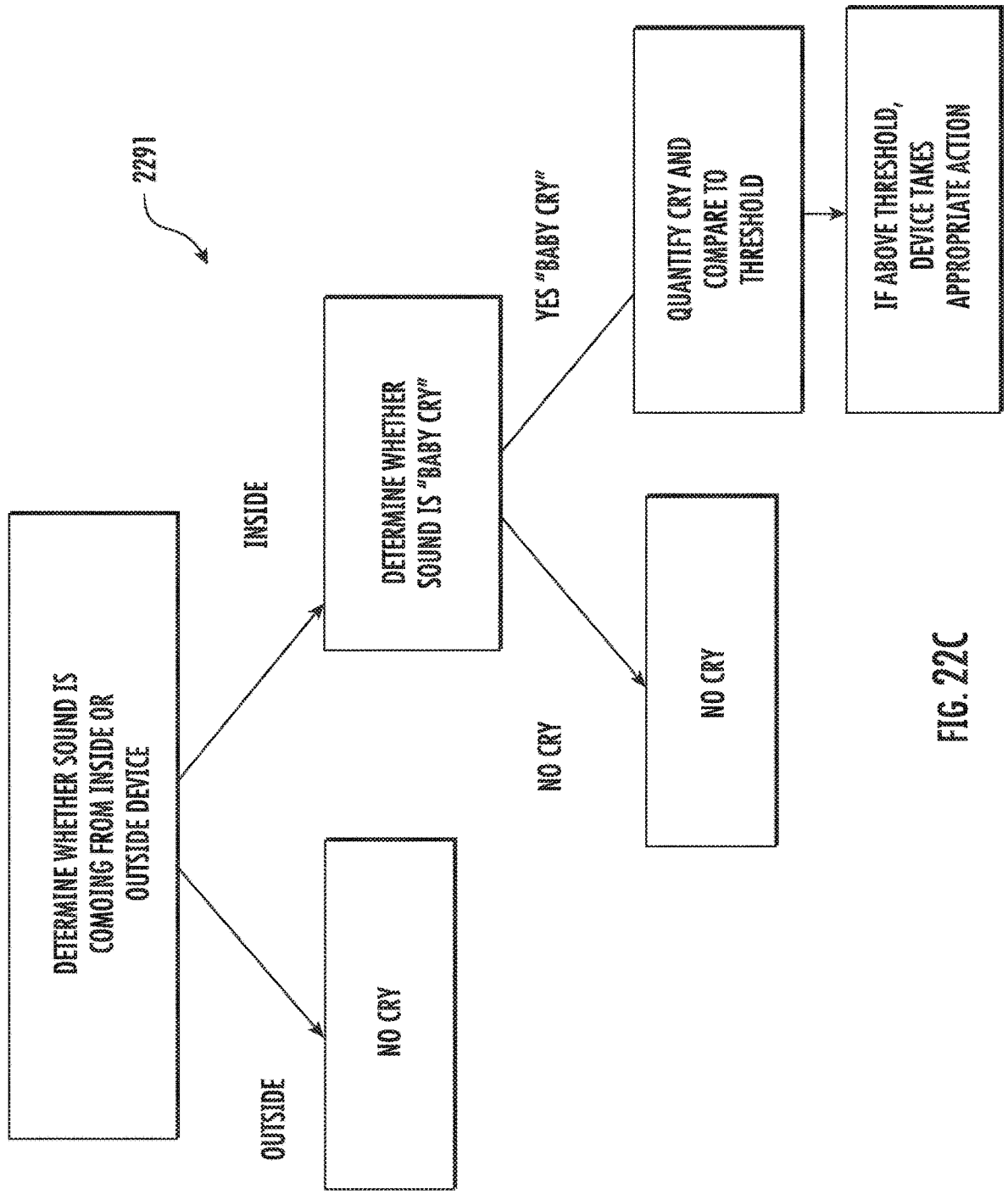
FIG. 22C is an exemplary process for the cry/state detection module.

FIG. 22C illustrates in further detail operation 2291 of the cry/state detection module 2218 and its interaction with the behavior state module 2230, which may be operable to provide soothing or comforting actions to a baby in a series of levels. In particular, a determination is first made as to whether the sound signals from the microphones represent sound coming from inside of the infant calming device, or outside of the device. If a determination is made that sound is coming from outside the device, then a determination may be made that no cry is detected. If a determination is made that sound is coming from the inside of the device, then processing proceeds to the frequency filter, and the signals are evaluated in a specified frequency band (depending on what white noise track is playing) and the number of times such frequencies appear within a specified amount of time to determine whether the sound is a baby cry. If frequency does not match a predetermined range, then it may be determined that no baby cry detected. If a determination is made that there is a baby cry, then a threshold analysis is performed to quantify the cry and compare it to a threshold value. If the cry is above a specified threshold, which may depend on the current level of operation of the device, the device takes appropriate action. The purpose of a threshold value, which may change depending on the current level of device operation, is to distinguish between different variations/levels of crying/upset, such as grunts, fussing, hard crying, screaming, and the like.

Figure 22E:
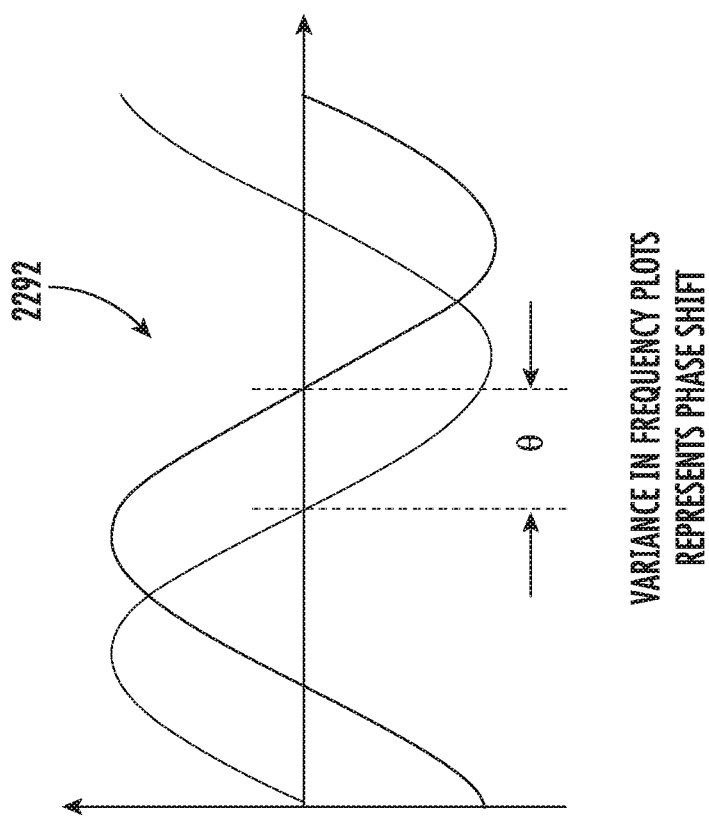
FIG. 22E illustrates an exemplary phase shift analysis of data from different microphones.
Figure 22D:
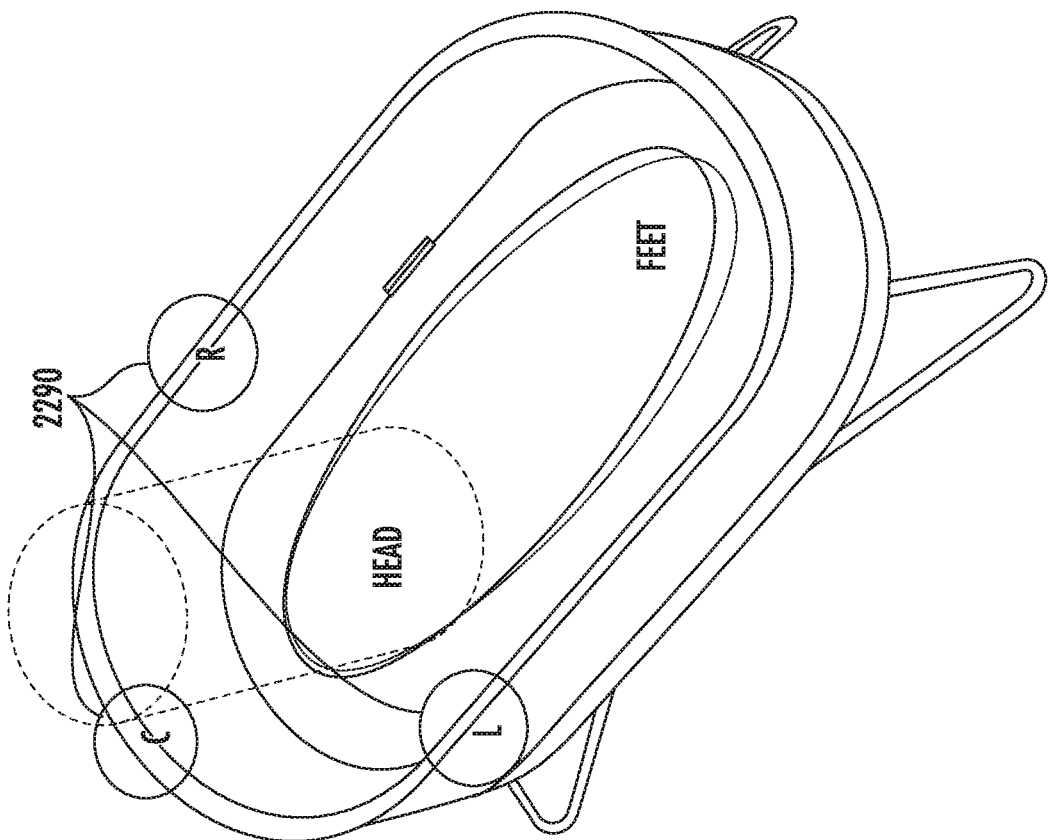
FIG. 22D illustrates an exemplary placement of various microphones within the infant calming device and with respect to the head of the infant.

In particular, FIG. 22D illustrates an exemplary placement of three microphone boards 2290 around the head of the infant, such as at a left position (L), a right position (R), and a center position (C). Each microphone board 2290 may include an omnidirectional microphone (such as −44 dB; size 2.7 mm×6 mm), one or more pre-amplifiers, and various connections. In this arrangement, a 'zone of sound detection' is a vertical cylinder that emanates upward from the infant's head. In one embodiment, the sensor system 2202 includes at least three microphones disposed proximate to the left side of, the right side of, and above the position of the infant's head as best illustrated in this figure. In another embodiment, each of the three microphones is an omnidirectional microphone. With this arrangement, the three microphones each measure sound and provide signals that may be analyzed by a directional filter configured to perform a phase shift analysis 2292, such as schematically represented in FIG. 22E. In particular, FIG. 22E shows how the signals from two different microphones may be shifted in phase with respect to each other. By analyzing the phase shifts between the signals, and analyzing the signal strengths from the microphones such as by triangulation, a determination can be made as to whether the detected sound emanates from inside the device or from outside the device. In another embodiment, microphones may be placed below the moving platform, where outside noise is naturally muted.

It is to be appreciated that the embodiments of the present disclosure are contemplated for implementation with the above disclosed approach or any other sound location determination approach known in the art.

Figure 22F:
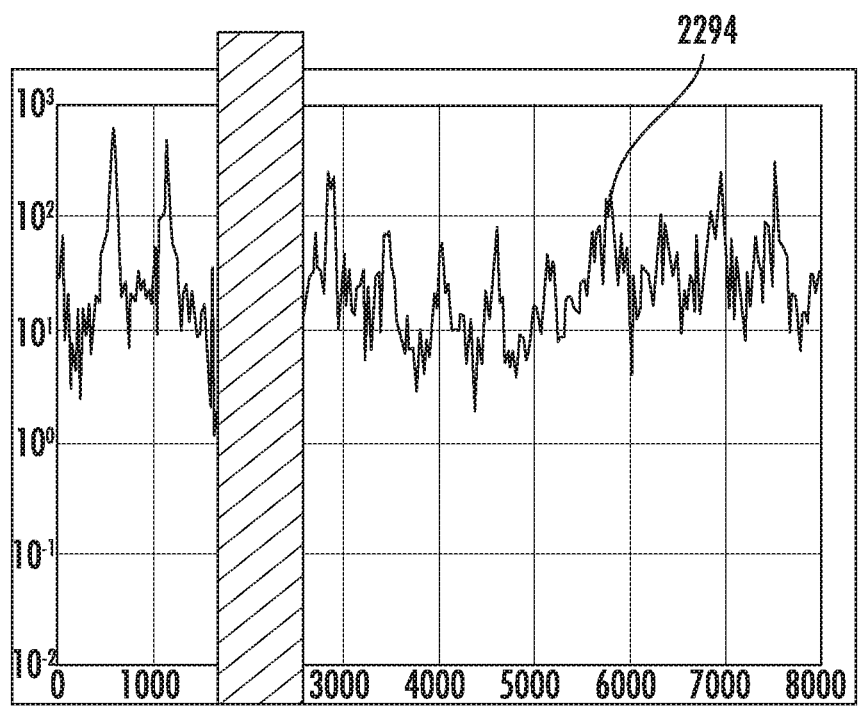
FIG. 22F illustrates a white noise file with an exemplary frequency band removed.

If the detected sound emanates from inside of the device, a frequency analysis is next performed with a frequency filter to determine whether the baby is crying. Each of the white noise audio tracks available to be played has a corresponding frequency band removed (that is, there are no components at frequencies in the frequency band in the white noise audio track), such as illustrated in FIG. 22F for a particular white noise audio track 2294. The removed frequency bands for the various white noise audio tracks 2294 may be different from each other, and each should be within the range of audible baby cries, around 800-5000 Hz. By looking at the detected signals from the microphones at the frequencies in the removed band corresponding to the white noise track being played (where no white noise sound frequency components exist), a determination can be made regarding the strength (intensity) of sound in the removed frequency band, and the presence of a baby cry can be established if sufficient intensity is detected.

It is to be appreciated that the embodiments of the present disclosure are contemplated for implementation with the above disclosed approach or any other frequency determination approach known in the art.

Figure 22G:
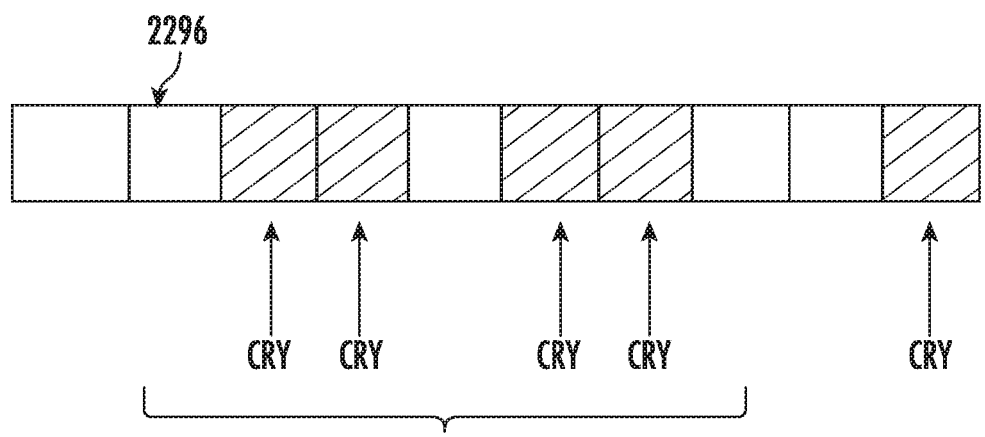
FIG. 22G illustrates an exemplary process for quantifying an infant cry.

FIG. 22G illustrates an exemplary process 2296 for quantifying an infant cry with a threshold filter. An average of amount of energy, or sound intensity, during a specified time period may be determined. For example, an average sound intensity over a rolling six second period may be obtained. The number of peaks may be tracked, intensity of peaks may be tracked, duration of cry periods may be tracked, and the like, to inform the behavior state machine to transition from one level of platform movement to another.

It is to be appreciated that the embodiments of the present disclosure are contemplated for implementation with the above disclosed approach or any other infant cry quantification approach known in the art.

Figure 22H:
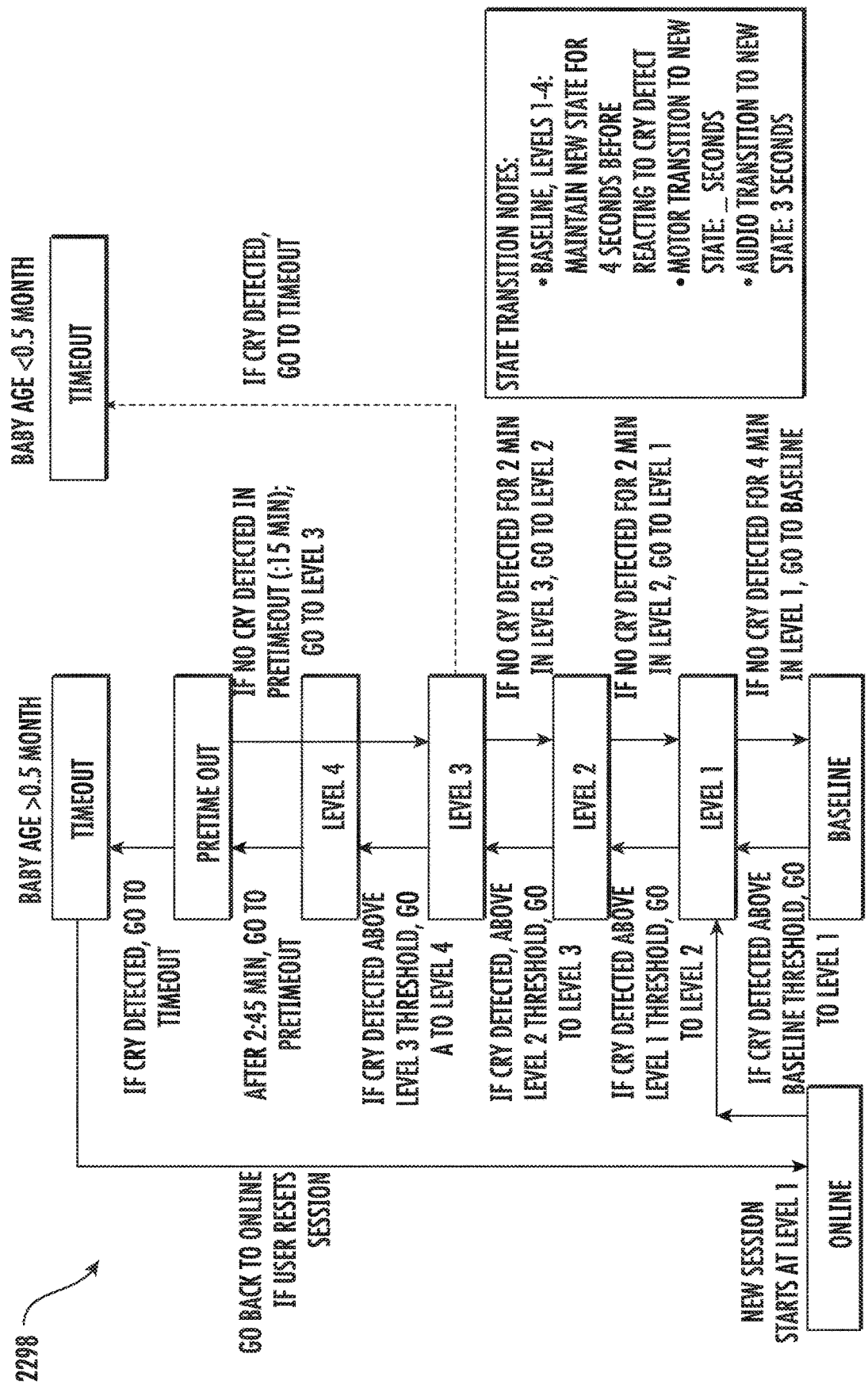
FIG. 22H illustrates an exemplary process of behavior state module.

FIG. 22H illustrates an exemplary process 2298 of a behavior state module 2230 for operating an infant calming device with various levels of operation. In operation, the behavior state module 2230 can be configured to receive the state of infant cry as determined by the detection module 2218. In one embodiment, the detection module 2218 can be configured to determine whether the noise detected originates from inside or outside the infant calming device, and whether the noise detected is that of an infant cry, and a state of infant cry as discussed above. In another embodiment, the behavior state module 2230 can be configured to receive the state of infant cry as determined by the detection module 2218 and configured to provide at least one output for generating a control signal to operate at least one of the movable platform 2102 and the sound output device 2248 to soothe the infant.

The state of infant cry may be received in the form of a logic input and may include various levels of cry state determination as will be discussed further below. In one embodiment, the behavior state module 2230 can be configured to provide at least one logic output to a motion generation module 2232 and/or an audio generation module 2238 of the control system 2216. In operation, the motion generation module 2232 can be configured to receive the at least one logic output from the behavior state module 2230 for operating the movable platform 2102. This can be achieved by sending a control signal from the motion generation module 2232 to the motion controller 2250 for operating the movable platform 2102. Alternatively, this can be accomplished by the control system 2216 sending a control signal to operate the motion controller 2250 for operating the movable platform 2102. In addition, in operation, the audio generation module 2238 can be configured to receive the at least one logic output from the behavior state module 2230 for operating the sound output device 2248. This can be achieved by sending a control signal from the audio generation module 2238 to the sound output device 2248 for outputting the sound to soothe the infant. Alternatively, this can be accomplished by the control system 2216 sending a control signal to operate the sound output device 2248 to output the sound to soothe the infant.

In one embodiment, the detection module 2218 can be configured to apply a threshold filter 2286 to the measurement data to determine the third parameter, the third parameter of the measurement data being an intensity of the noise detected. The state of infant cry can be determined by comparing the intensity of the noise detected to a plurality of threshold value as described herein.

As shown in FIG. 22H, a first state of infant cry can be triggered by a first threshold value (e.g., Level 1), and a second state of infant cry can be triggered by a second threshold value (e.g., Level 2), the second threshold value being greater than the first threshold value. Additionality, such trigger can also be invoked manually by the user via the device's physical control panel or through its application.

In operation, when the behavior state module 2230 receives a determination of the first state of infant cry, and subsequently receives a determination of the second state of infant cry, the behavior state module provides a first output for the first state of infant cry then a second output for the second state of infant cry, respectively. In doing so, the change from the first output to the second output causes at least an increase in a frequency or a decrease in an amplitude of an oscillatory motion of the movable platform 2102. This can also be known as a step-up between levels and is best illustrated in the table in FIG. 22I and described in more detail below. In some embodiments, when the infant cry is detected by the detection module 2218 for a predetermined period of time after the determination of the second state of infant cry, the behavior state module 2230 may provide a stop output to cease the oscillatory motion of the movable platform 2102. This can also be known as a time out where the caregiver is notified to attend to the infant.

Optionally, when the behavior state module 2230 receives a determination of the first state of infant cry, and subsequently receives a determination of the second state of infant cry, the behavior state module provides a first output for the first state of infant cry then a second output for the second state of infant cry, respectively. In doing so, the change from the first output to the second output may causes an increase in intensity of the sound for soothing the infant. In one embodiment, when the infant cry is detected by the detection module for a predetermined period of time after the determination of the second state of infant cry, the behavior state module 2230 provides a stop output to cease the sound for soothing the infant. Like above, this means that the infant needs to be attended and appropriate notification, accordingly, is provided.

In another operation, when the behavior state module 2230 receives a determination of the second state of infant cry, and subsequently receives a determination of the first state of infant cry, the behavior state module provides a first output for the second state of infant cry then a second output for the first state of infant cry, respectively. In this instance, a first state of infant cry can be triggered by a first threshold value (e.g., Level 2), and a second state of infant cry can be triggered by a second threshold value (e.g., Level 3), the second threshold value being greater than the first threshold value. In doing so, the change from the first output to the second output causes at least a decrease in a frequency or an increase in an amplitude of an oscillatory motion of the movable platform 2102. This can also be known as a step-down between levels and is best illustrated in the table in FIG. 22I and described in more detail below. In one embodiment, the determination of the first state of infant cry can be based on a determination of no cry.

Optionally, when the behavior state module 2230 receives a determination of the second state of infant cry, and subsequently receives a determination of the first state of infant cry, the behavior state module provides a first output for the second state of infant cry then a second output for the first state of infant cry, respectively, the second state of infant cry triggered by a second threshold value greater than a first threshold value that triggers the first state of infant cry. In doing so, the change from the first output to the second output may causes a decrease in intensity of the sound for soothing the infant. Like above, in one embodiment, the determination of the first state of infant cry can be based on a determination of no cry.

FIG. 22I illustrates exemplary calming responses 2299 that the device can take, in this case defined by amplitudes and frequencies of movement of the platform and audio file types and volumes at the various levels, which can be altered according to various age ranges, size of baby, or other infant characteristics. The movement generally starts at level one (though this may be overridden by input of a desired starting level). The motion of the platform is faster and shorter as the levels are increased. The volume of sound is also increased during a step up between levels. After a certain period of time at the highest level, if a baby continues to cry, the motion may be stopped and a time out may occur, and appropriate notifications may be provided to the caregiver so the caregiver may attend to the infant. The decision to change between levels or states occurs after a specified period if the current level threshold is exceeded (e.g., the baby continues to cry with more intensity). On the other hand, in an embodiment, if the behavior state module 2230 receives a no cry state determination from the detection module 2218 for a predetermined amount of time, the behavior state module 2230 may be configured to step down a level of operation until the baseline is reached. FIG. 22I also shows various LED status colors on the infant calming/sleep aid device may be used to indicate the various different levels or operation states of the device.

In one embodiment, an infant calming system may include an infant calming device, optionally in combination with a sleep sack, and a mobile device similar to those shown in FIGS. 27A-27E. The mobile device includes a user interface 2201 that can be in communication with the infant calming system where the user interface 2201 is configured to provide the state of infant cry to the mobile device. In another embodiment, the user interface 2201 can be configured for a user to use the infant calming system.

In one embodiment, a method for sleep aid and infant calming includes providing a device configured to receive an infant therein, the device being an infant calming/sleep aid device as described herein. In this embodiment, the device includes a movable platform 2102 and a sound output device 2248 to provide a sound for soothing the infant. Next, the method includes detecting a noise with a sensor system 2202 of the device followed by generating measurement data for the noise detected, the measurement data similar to those described above.

In one embodiment, the sensor system 2202 includes at least three microphones 2202 proximate to a left side of, a right side of, and above the position of the infant's head. In an embodiment, one or more of the at least three microphones may be positioned below the infant such that the breathing of the infant may also be monitored. In another embodiment, each of the three microphones 2202 is an omnidirectional microphone 2202.

In one embodiment, the method includes providing the measurement data to a control system 2216 of the device. Next, the method includes determining, based at least on a first parameter of the measurement data, whether the noise detected originates from inside or outside the device. In one embodiment, the first parameter of the measurement data can be determined by applying a directional filter 2282 to the measurement data. In operation, if the noise detected is determined to originate from outside the device, a no cry state is determined.

In one embodiment, if the noise detected is determined to originate from inside the device, determining, based at least on a second parameter of the measurement data, whether the noise detected comprises an infant cry. In one embodiment, the second parameter of the measurement data is determined by applying a frequency filter 2284 to the measurement data. In another embodiment, the second parameter of the measurement data may be that of the frequency of the noise detected, and that the noise detected comprises an infant cry if it achieves a certain frequency level. In the alternative, if the noise detected does not reach a certain frequency level or fall within a predetermined frequency range to constitute the infant cry, then a no cry state is determined.

Next, if the noise detected is determined to comprise the infant cry, determining, based at least on a third parameter of the measurement data, a state of infant cry. It is to be appreciated that the third parameter of the measurement data may be a parameter determined by processing the measurement data. In one example, the third parameter may be the intensity of the noise detected as determined by applying a threshold filter 2286 to the measurement data to determine the state of infant cry. In one embodiment, after the state of infant cry has been determined by a threshold value, the control system 2216 is configured to determine a state of infant cry based on whether the infant cry is 50 dB or greater, 55 dB or greater, 60 dB or greater, 65 dB or greater, or 70 dB or greater.

In operation, depending on the state of infant cry as determined by a threshold value, the method includes providing a control signal from the control system 2216 to operate at least one of the movable platform 2102 and the sound output device 2248 to soothe the infant. In one embodiment, for a state of infant cry, the control signal includes a command to the movable platform 2102 to change at least one of a frequency or an amplitude of an oscillatory motion of the movable platform 2102. In another embodiment, the control signal includes a command to the sound output device 2248 to change an intensity of the sound for soothing the infant. In one embodiment, the method may optionally include connecting a sleep sack similar to those shown in FIGS. 25A-25L and 25P-25R to the movable platform 2102 where the sleep sack is able to secure the infant's head at a position inside the device.

In one embodiment, an infant calming/sleep aid device includes a moving platform 2102 rotatable in an oscillatory manner and a plurality of microphones 2202. The device may further include a control system 2216 for controlling a movement of the moving platform 2102, where the control system 2216 includes a cry detection module 2218. In an embodiment, the platform 2102 is rotatable in an oscillatory manner on horizontal axis, vertical axis, or any combination thereof. As such, platform 2102 may be rotatable in a horizontal plane, vertical plane, or in a volumetrically defined space.

In one embodiment, the cry detection module 2218 includes a directional filter 2282, a frequency filter 2284 and a threshold filter 2286. In operation, the directional filter 2282 of the cry detection module 2218 can be configured to process a sound signal detected by the plurality of microphones 2202 for determining whether the sound signal originated from within the infant calming/sleep aid device. This sound signal may also correspond to measurement data having parameters similar to those discussed above. The frequency filter 2284 of the cry detection module 2218 can be configured to process the sound signal for determining whether the sound signal is a predetermined frequency of infant cries. Similarly, this sound signal may also correspond to measurement data having parameters. The threshold filter 2286 of the cry detection module 2218 can be configured to process the sound signal for determining an intensity of the sound signal. In an embodiment, the recorded sound pattern may be used by a cry detection module 2218 to determine a state of infant cry based on whether the infant cry is 50 dB or greater, 55 dB or greater, 60 dB or greater, 65 dB or greater, 70 dB or greater, or 75 dB or greater.

In one embodiment, when the cry detection module 2218 determines a state of infant cry based on whether the sound signal originated from within the infant calming/sleep aid device, whether the sound signal is in a predetermined frequency of infant cries, and a comparison of the intensity of the sound signal to a plurality of threshold values, the control system can operably control the moving platform 2102 based on determinations of the cry detection module 2218.

In one embodiment, based on determinations of the cry detection module 2218 and the filters 2282, 2284, 2286 discussed above, the control system 2216 may operate the moving platform 2102 to facilitate soothing the infant. In another embodiment, the control system 2216 may operate a sound output device 2248 to direct a predetermined sound at the infant for purposes of calming or soothing the infant.

In an embodiment, the sensor system 2202 comprises at least one biometric sensor configured to measure a physiological parameter as discussed in paragraphs 110 and 166 above, and the control system 2216 is further configured to provide, based on the physiological parameter, a control signal to operate at least one of the movable platform 2102 and the sound output device 2248 as discussed in various embodiments of the present disclosure.

In one embodiment, the infant calming/sleep aid device further includes a sleep sack similar to those described above and herein, the sleep sack having an upper portion and a lower portion. The upper portion can be adapted to enclose the infant's torso and arms, the lower portion adapted to enclose the infant's hips, legs and feet, where the upper portion of the sleep sack is wider than the lower portion to allow for infant to be swaddled while wearing a sleeping garment.

In one embodiment, the plurality of microphones 2202 of the infant calming/sleep aid device may include microphones 2202 positioned in a left position, a center position, and a right position within the device. In an embodiment, one or more of the at least three microphones may be positioned below the infant such that the breathing of the infant may also be monitored. In some embodiments, each of the microphones 2202 may be an omnidirectional microphone 2202. In operation, the plurality of microphones 2202 can detect a zone of sound detection in a vertical cylinder that emanates upwards from the infant's head.

In one embodiment, the cry detection module 2218 of the infant calming/sleep aid device rejects sounds originating outside the device. The types of sounds originating from outside the device may include human speech, sounds from other children, or ambient noise from music, television, pets, or other common household sounds, among others. In some embodiments, the combination of the location/directional filter 2282 and the plurality of microphones 2202 may be used to determine location of the sound inside or outside the device. In other embodiments, the frequency filter 2284 can be used to determine whether the sound coming from inside the device is an infant cry. In yet another embodiment, the threshold filter 2286 can make an infant state determination by quantifying the infant cry via an analysis of the plurality of microphones 2202.

The infant calming/sleep aid device 2258 may provide analytics and algorithms. The analytics and algorithms may be based on readings from microphone, sensors and the like. The analytics and algorithms may provide feedback input to the mechanism to activate the calming reflex of an infant. The algorithms may analyze combinations, store combinations, replicate combinations and the like. Sensors may provide sensor readings. Sensor readings may have ranges. A range may be a sound range, a motion range, and the like. A sound range may be based on the blood flow/heartbeat of a mother. The heartbeat may be 80 bpm, 160 bpm, 240 bpm, and the like. The motion range may be between 0.5-4.25 Hz.

The analytics and algorithms may be used to detect if an infant is upset or has apnea. The detection may be based on visual inspection, continuous detection, and the like. Visual inspection may be used to initiate a calming mechanism involving a relatively step wise and high frequency motion. Continuous detection may shift into a remain calm protocol, may use a sensor, and the like. A sensor may detect if the infant is in the infant calming/sleep aid device 2258, detect if the secure sleep sack is properly attached to the infant calming/sleep aid device 2258 and the like. The mechanism may only turn on if the sensor detects that the sleep sack is properly installed in the infant calming/sleep aid device 2258.

The infant calming/sleep aid device 2258 may provide an application programming interface (API). The API may allow integration of the infant calming/sleep aid device 2258 with external devices and system. External devices and systems may provide additional control inputs to activate the mechanism to activate the calming reflex or conditioned response of an infant. The mechanism to activate these infant responses may provide inputs to the external devices and systems. Control inputs may include sound control inputs. Sound control inputs may be used to turn on and off external sound sources, turn on and off sound sources internal to the infant calming/sleep-aid device mechanism, and the like. The sound control inputs may provide the user the ability to choose which sound sources to activate and even to introduce their own novel sounds, such as a recording of a parent's voice. Integration may be by wired or wireless connectivity. Wired connectivity may include the use of a hard-wired splitter. Wireless connectivity may include Wi-Fi connectivity, blue-tooth connectivity, and the like. External devices and systems may be home automation network external devices and systems and allow integration of the infant calming/sleep-aid device 2258 with a home automation network. Integration with the home automation network may enable the infant calming/sleep-aid device 2258 to report to a user or allow the user to remotely control the infant calming/sleep-aid device 2258. Integration may include integration with monitors. Monitors may include carbon monoxide monitors, oxygen level monitors, breathing monitor, oxygen saturation monitors, motion monitors, temperature monitors, smoke monitors, heart rate detector monitors, respiratory rate monitors, and the like. Monitors may provide an input to activate the infant calming/sleep-aid device 2258 that may activate the infant calming/sleep-aid device 2258. The infant calming/sleep aid device 2258 may be activated to attempt to wake an infant, such as by stimulation with vigorous motion or loud sound or both. An infant may be stimulated to prevent sudden infant death syndrome (SIDS). Integration may also include integration with safety systems. Safety systems may include home safety systems, infant safety systems, child safety systems, and the like.

The infant calming/sleep-aid device may also include collapsible walls and legs, handles, cord, wheels, and the like. Collapsible walls may enable portability and adjustability. Portability may include ease of moving the infant calming/sleep-aid device around a room, facilitate shipping, travel, aging of the baby, a standing position, user or stroller height, and the like. Cord may be a retractable cord, a break-away cord, and the like. Wheels may be implemented when collapsed, and the like. Legs may be extendable, telescoping, collapsible or removable and rotated/reinserted to be a different height, and the like. The infant calming/sleep-aid device 2258 may be made available in a lightweight embodiment, include a stand trolley, and the like. Stand trolley may include wheels for inside transport, make the infant calming/sleep aid device 2258 reconfigurable into a stroller, provide stability, motor removal, enable transportability, and the like. Stability may include stability during motion, stability during strolling, and the like. The infant calming/sleep-aid device 2258 may be made available in a variety of colors and color combinations. Color and color combinations may be user selectable and may be changeable via alternative veneers, alternate ornamental fabric decoration strips, mesh color/design, sleep sack color/design, and the like. The infant calming/sleep-aid device 2258 may be made available in organic materials, appealing designs, and the like. The infant calming/sleep-aid device 2258 may be certified for safety, certified for safety in many categories, and the like. The infant calming/sleep-aid device 2258 may have removable mesh that allows for creating individually selected designs printed on the outside mesh. The accelerometer 2223 of the infant calming/sleep-aid device may measure head excursions to prevent excessive motion, and the like. The infant calming/sleep-aid device 2258 may be made include flexible mesh. Flexible mesh may provide better airflow and allow broader excursions of the main moving platform 16. The flexible mesh must be made stiff enough to prevent a pocket forming to potentially suffocate an infant who rolls into it, however flexible enough to allow for give so the top platform may sway back and forth.

Figure 23L:
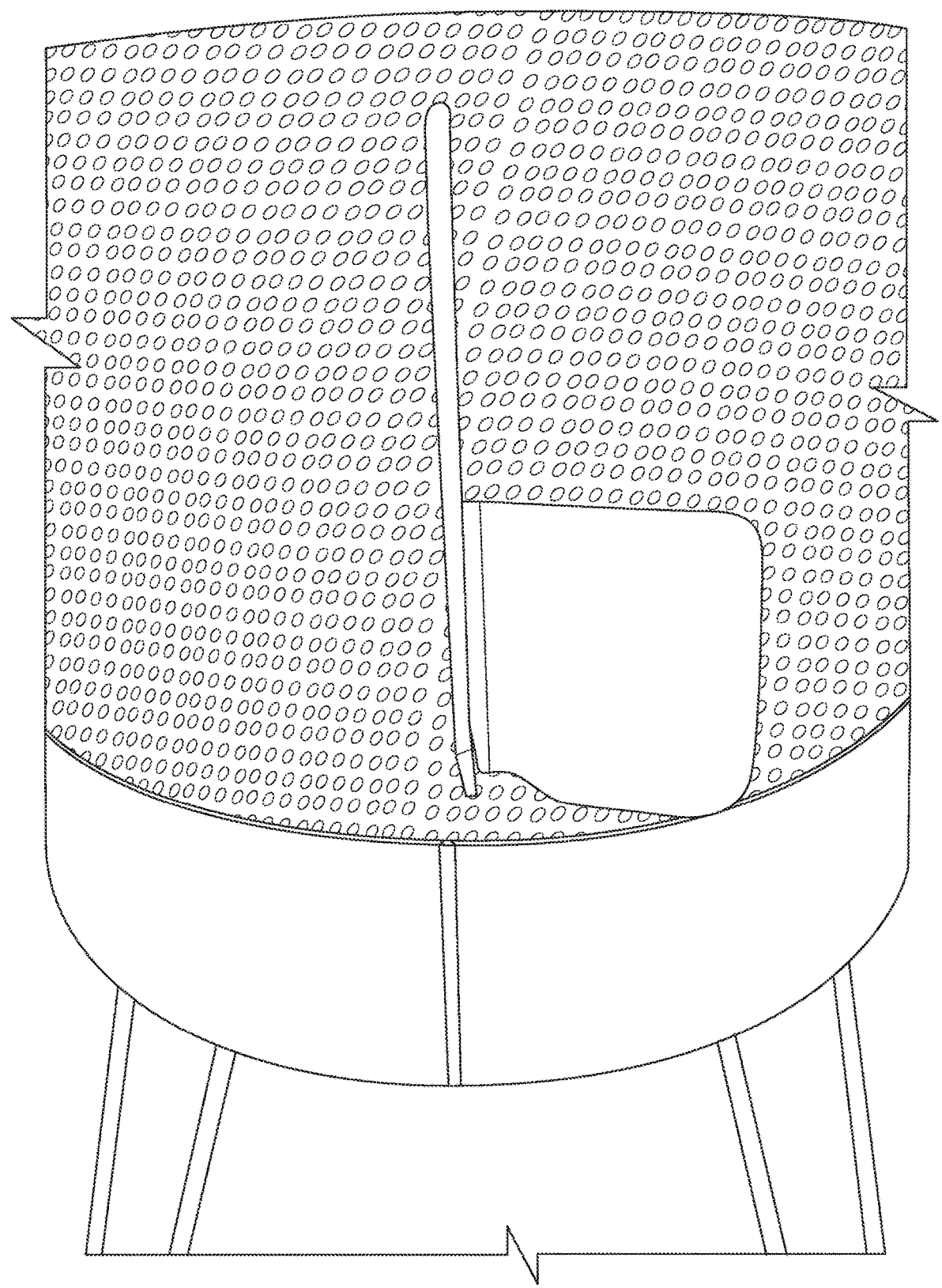

FIGS. 23-23L illustrates an exemplary infant calming/sleep aid device having an inner mesh and an outer mesh layers allowing for air flow while protecting the infant from being able to reach outside of the movable platform and protecting against pinched extremities and other hazards, as well as protecting children and adults to reach into the moveable area of the device from the outside while in operation. The inside mesh fabric extends upward from the outer periphery of the movable platform and are spaced apart thereby creating a gap therebetween. As the platform of the infant calming/sleep aid device moves, air flow is generated through the inner and out mesh layers. FIGS. 23J and 23K show detailed inside views between the inside mesh and the outside mesh, and FIG. 23L illustrates that a zipper on the outside mesh allows access to the area between the inside mesh and outside mesh and components outside of the movable platform, without creating any risk of an infant falling out of the device or entering into an otherwise risky position. It is to be appreciated that the configuration of the inner and outer mesh layers of FIGS. 23-23L may be implement with any embodiments of infant calming/sleep aid devices of the present disclosure.

A mattress may include a gel pad or other mechanism on which the head of the infant may rest. A weight sensor may be underneath the gel pad. The infant calming/sleep-aid device 2258 may not activate or may shut off if the weight sensor under the gel pad does not indicate that the head of the infant is resting on the gel pad.

Figure 24B:
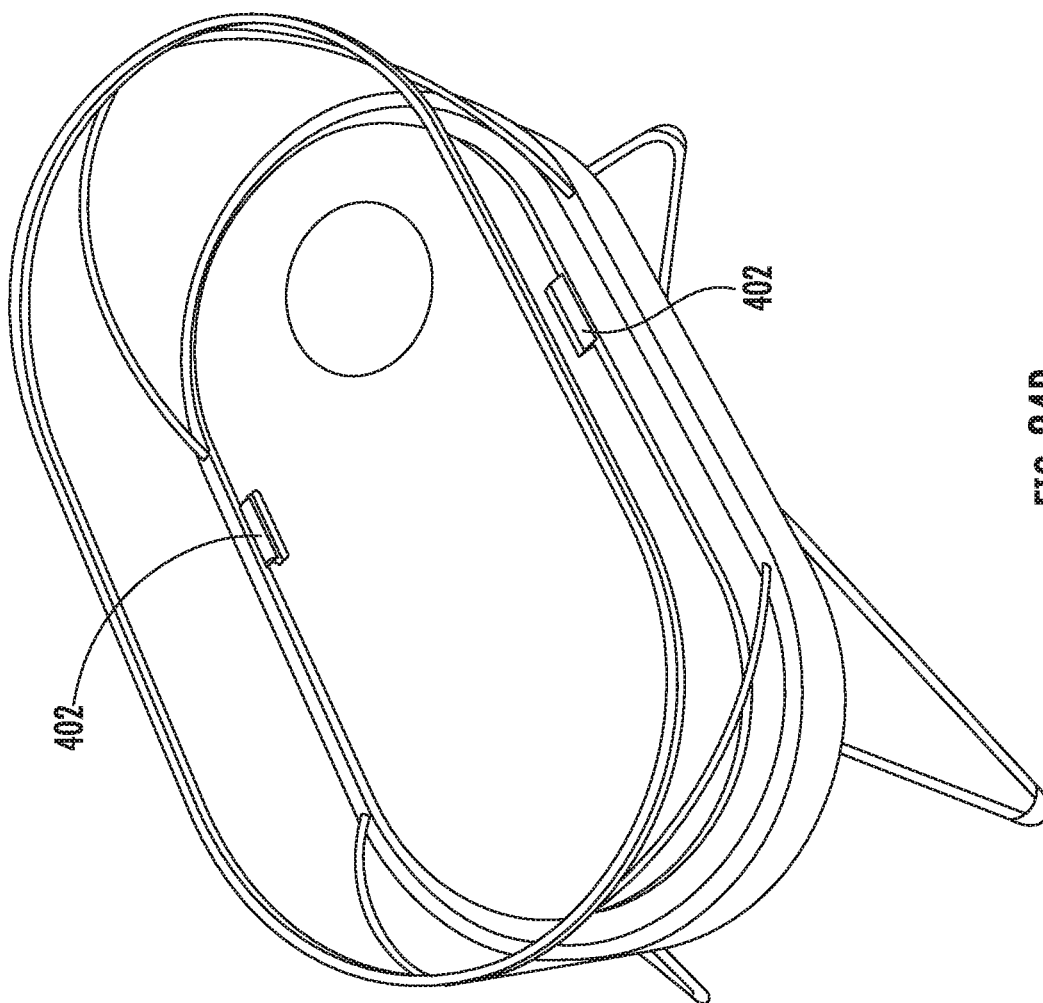
FIG. 24B is a top perspective view of the infant calming/sleep-aid showing the part of the attachment mechanism that allows a secure sleep sack to be attached to the infant calming/sleep-aid device of FIG. 23B.
Figure 24A:
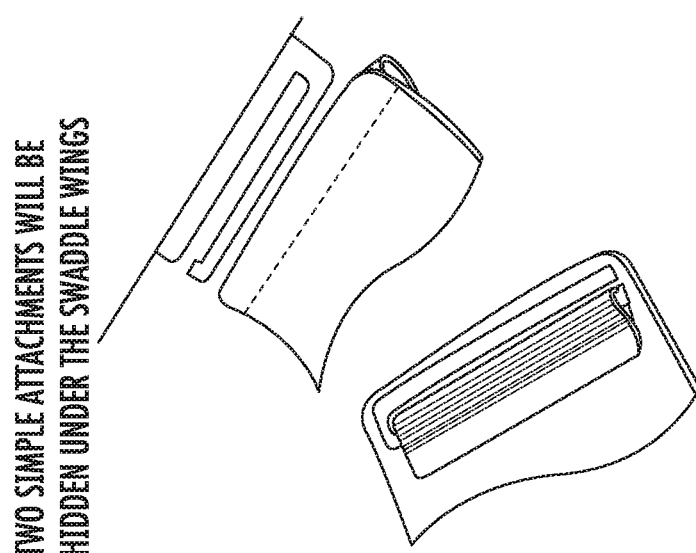
FIG. 24A is a view of the attachment mechanism to attach a secure sleep sack to the infant calming/sleep aid device of FIG. 23B.
Figure 28:
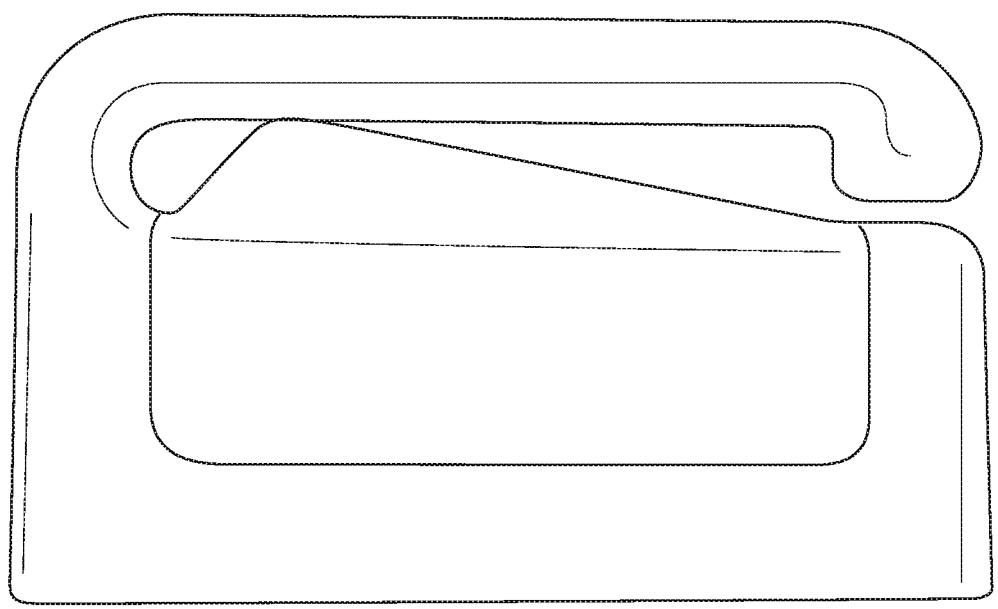
FIGS. 28 and 29 illustrate exemplary embodiments of a clip or switch for control purposes of the device.
Figure 29:
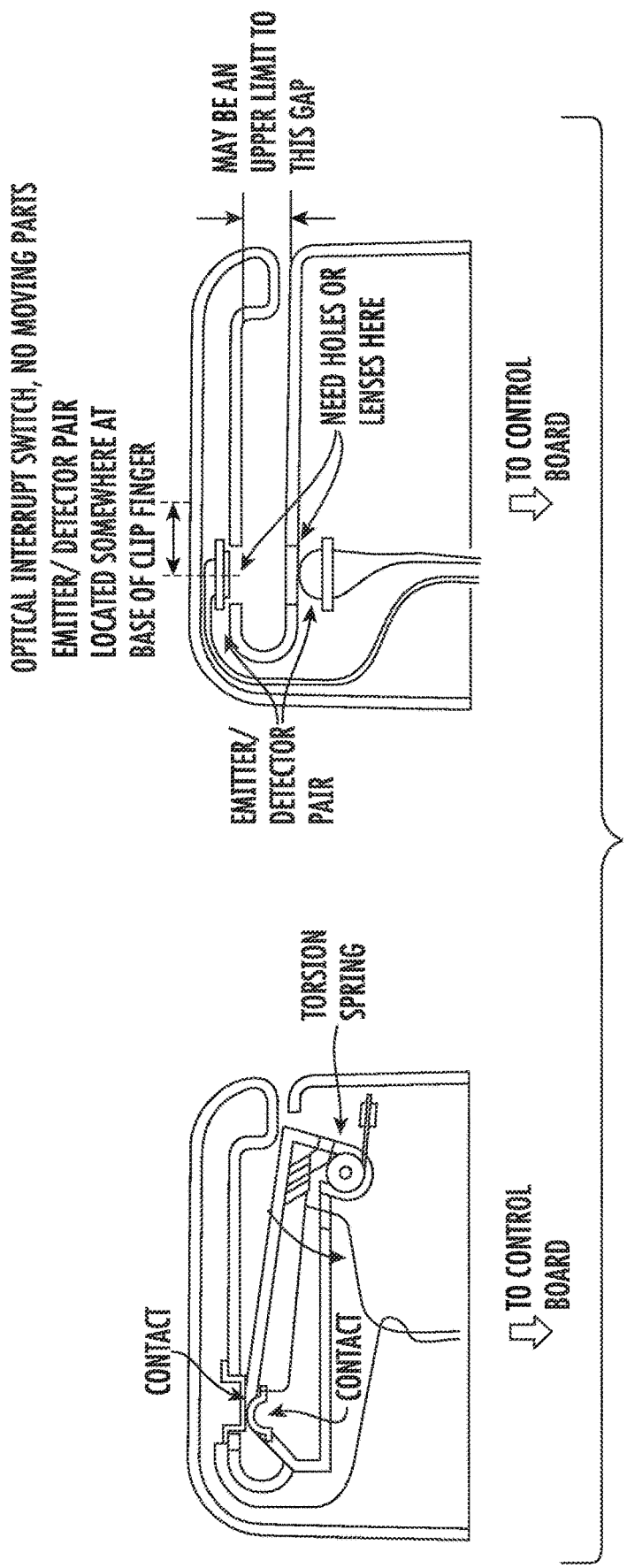

The infant calming/sleep-aid device 2258 may include a sleep sack that may take various forms and may have an attachment. The attachment may attach the sleep sack to a main moving platform. FIG. 24A illustrates an illustrative and non-limiting embodiment of the attachment. FIG. 24B illustrates an exemplary and non-limiting embodiment of the infant calming/sleep-aid device 2258 with an attachment mechanism 2402. Attachment mechanism 2402 may secure the sleep sack to the infant calming/sleep-aid device 2258. Attachment may be via a one-handed attachment mechanism, and the like. Infant calming/sleep-aid device 2258 may not switch on if the sleep sack is not properly secured to the infant calming/sleep-aid device 2258. In this regard, FIG. 28 illustrates an exemplary embodiment of a clip for detecting if an infant is properly secured, in order to control operation of the device. In embodiments, two clips may act to sense when attachment pieces of a sleeping sack are in place to indicate that an infant is securely fastened on a support surface of the infant calming/sleep aid device. Various control modes can follow. For example, motion of the device may be prohibited/disabled if an infant is not properly secured while allowing sound to still be generated. Other sensors are also envisioned for detecting if an infant is properly secured, such as a contact switch, or optical switch, or the like, such as shown in FIG. 29. For example, safety clips that the secure sleep sack attaches to may contain a switch that enables the motion mechanism. Failure to properly attach the secure sleep sack will result in the device delivering sound, but no motion when it is turned on. Motion will only be delivered if the secure sleep sack is properly attached on each clip.

The location of the sleep sack attachment may be adjustable. For example, the location of the sleep sack attachment may be adjustable by two to three inches or so.

The sleep sack may allow enough room in the sack for the hips of the infant to flex and open. The sleep sack may keep the arms of the infant at the sides of the infant. An internal band may be used to keep the arms of the infant at the sides of the infant. The secure sleep sack may have arm openings, which are able to be opened and closed. The sleep sack may have a zipper closure. The zipper may open in an upwards direction, a downwards direction, and the like. The sleep sack may have an adjustable area on the back. The sleep sack may have a narrow sleeve or light elastic at the end of the sleep sack wing, on the clip attached to the infant calming/sleep-aid device 2258, and the like.

Figure 25A:
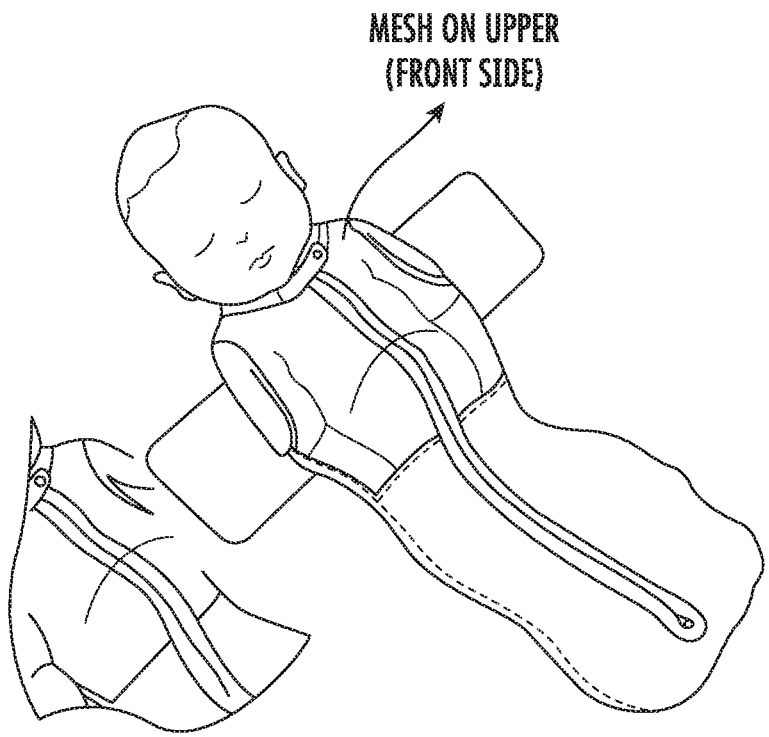
FIGS. 25A-25L are views of exemplary secure sleep sacks.
Figure 25B:
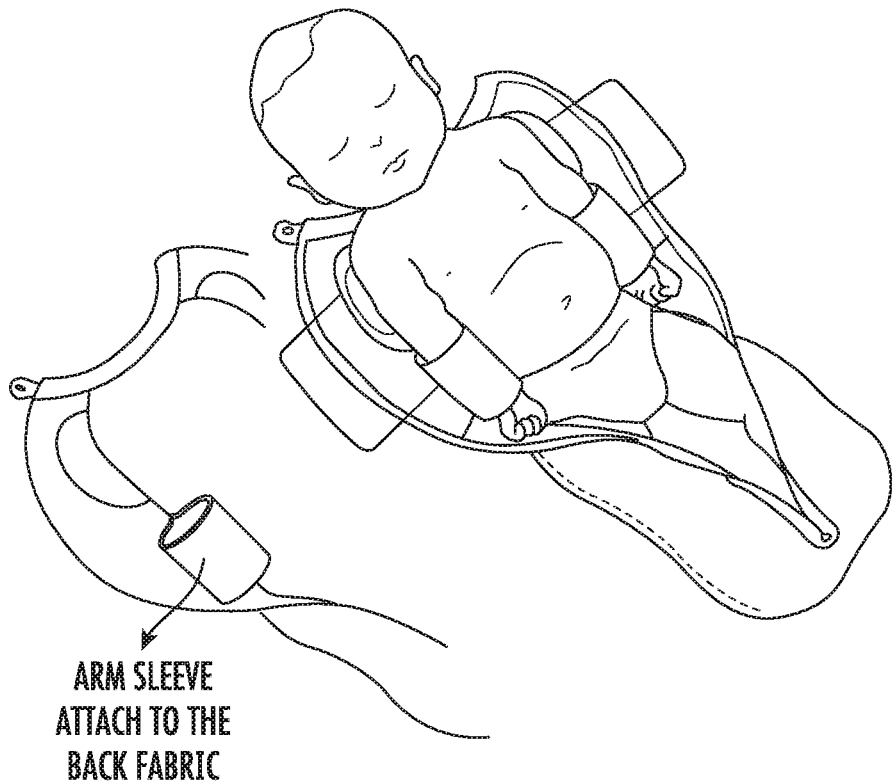
Figure 25C:
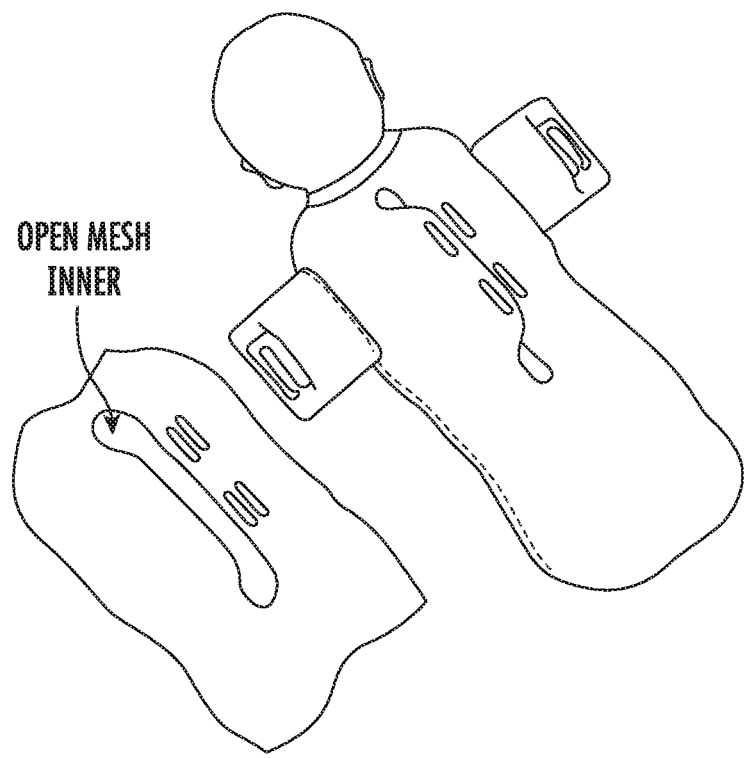
Figure 25D:
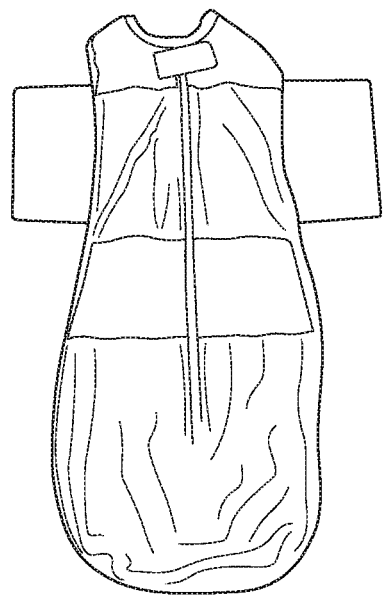
Figure 25E:
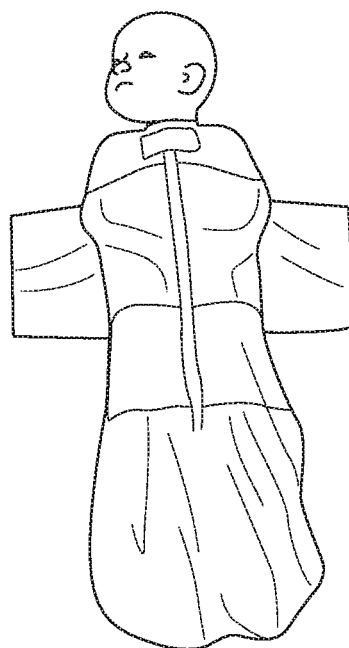
Figure 25G:
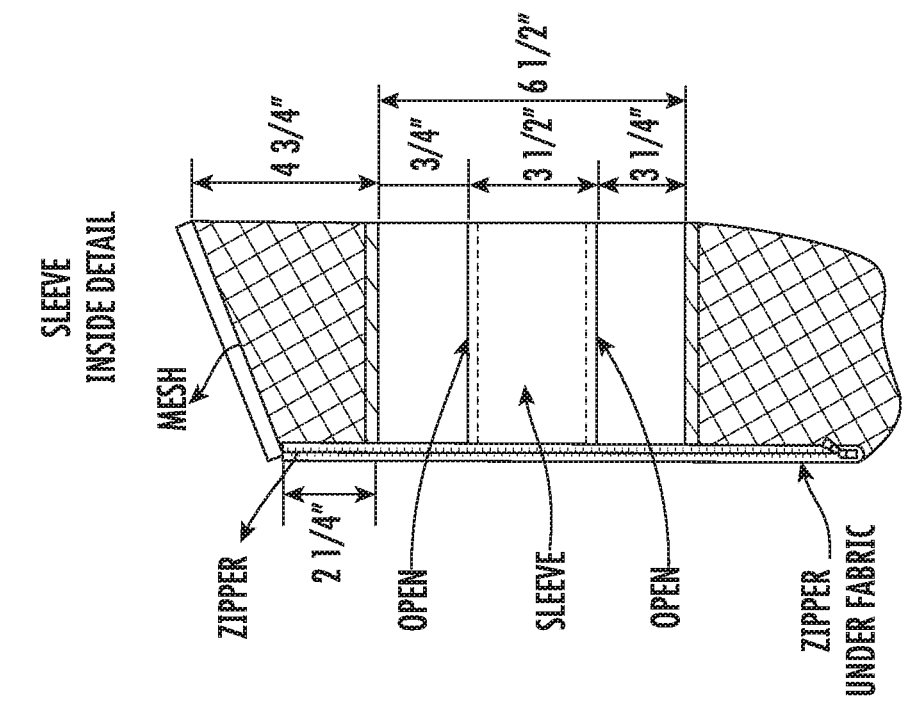
Figure 25F:
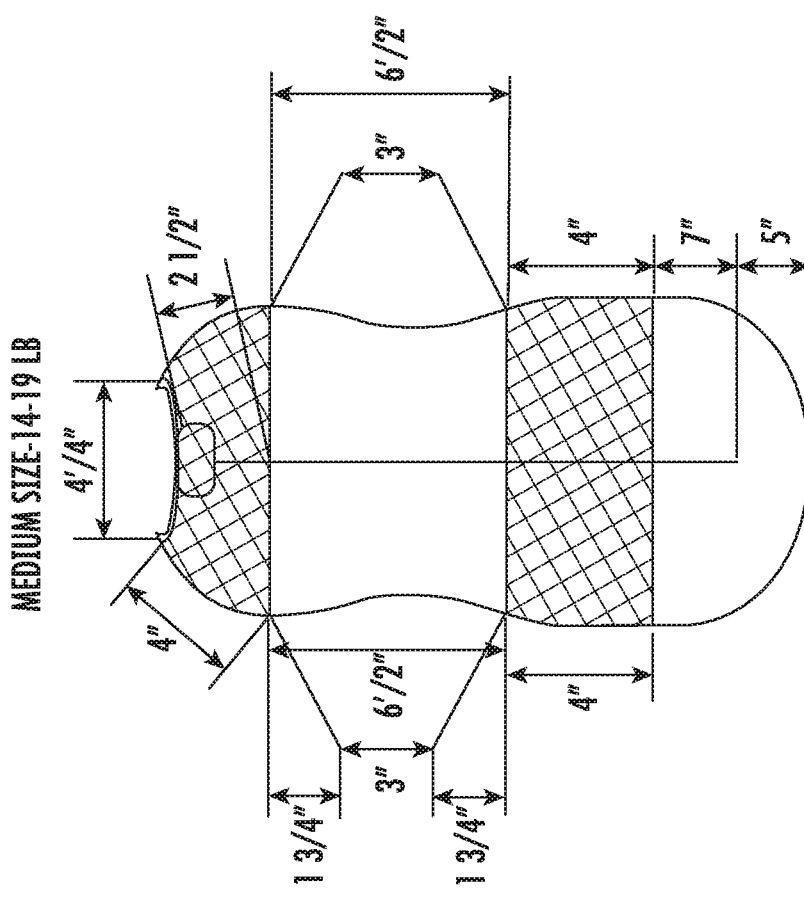
Figure 25J:
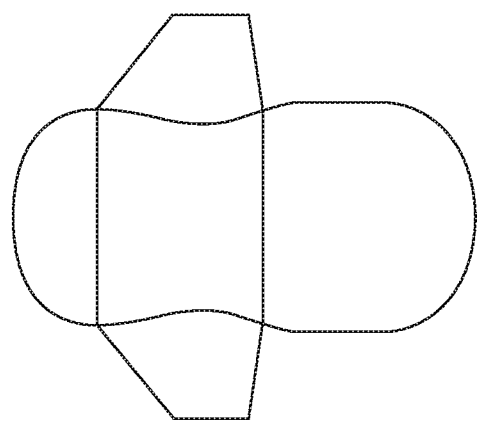
Figure 25I:
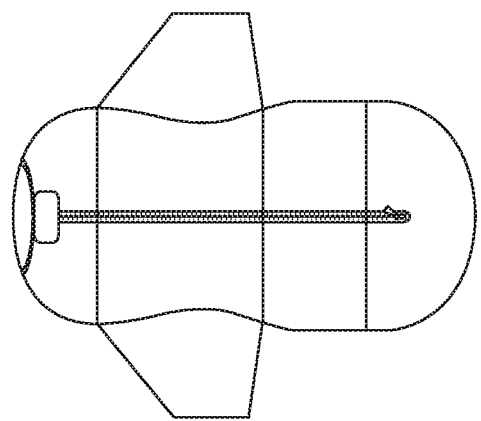
Figure 25H:
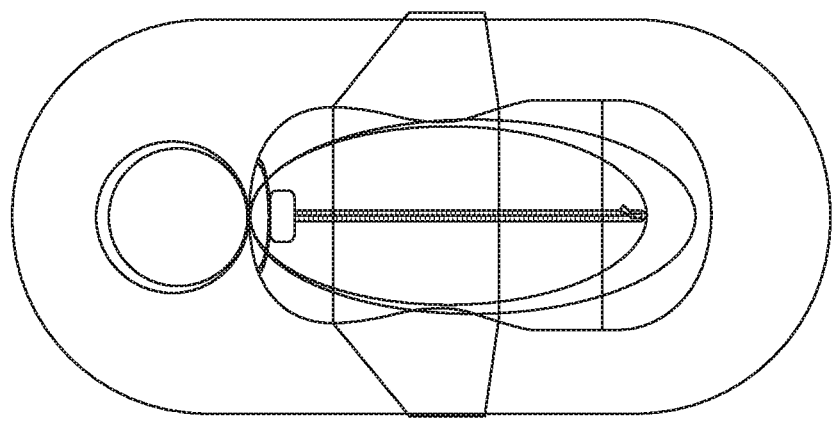
Figure 25K:
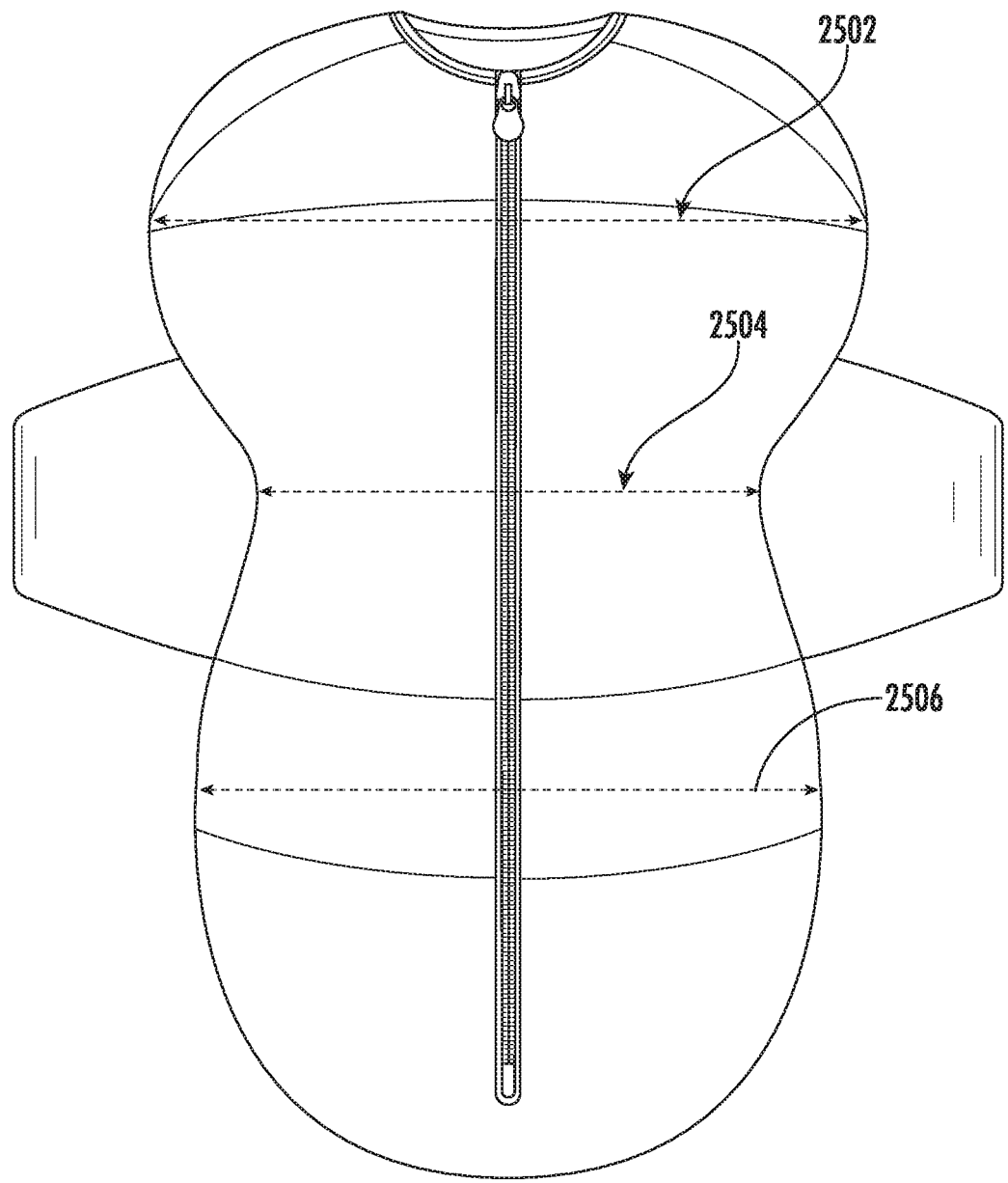
Figure 25L:
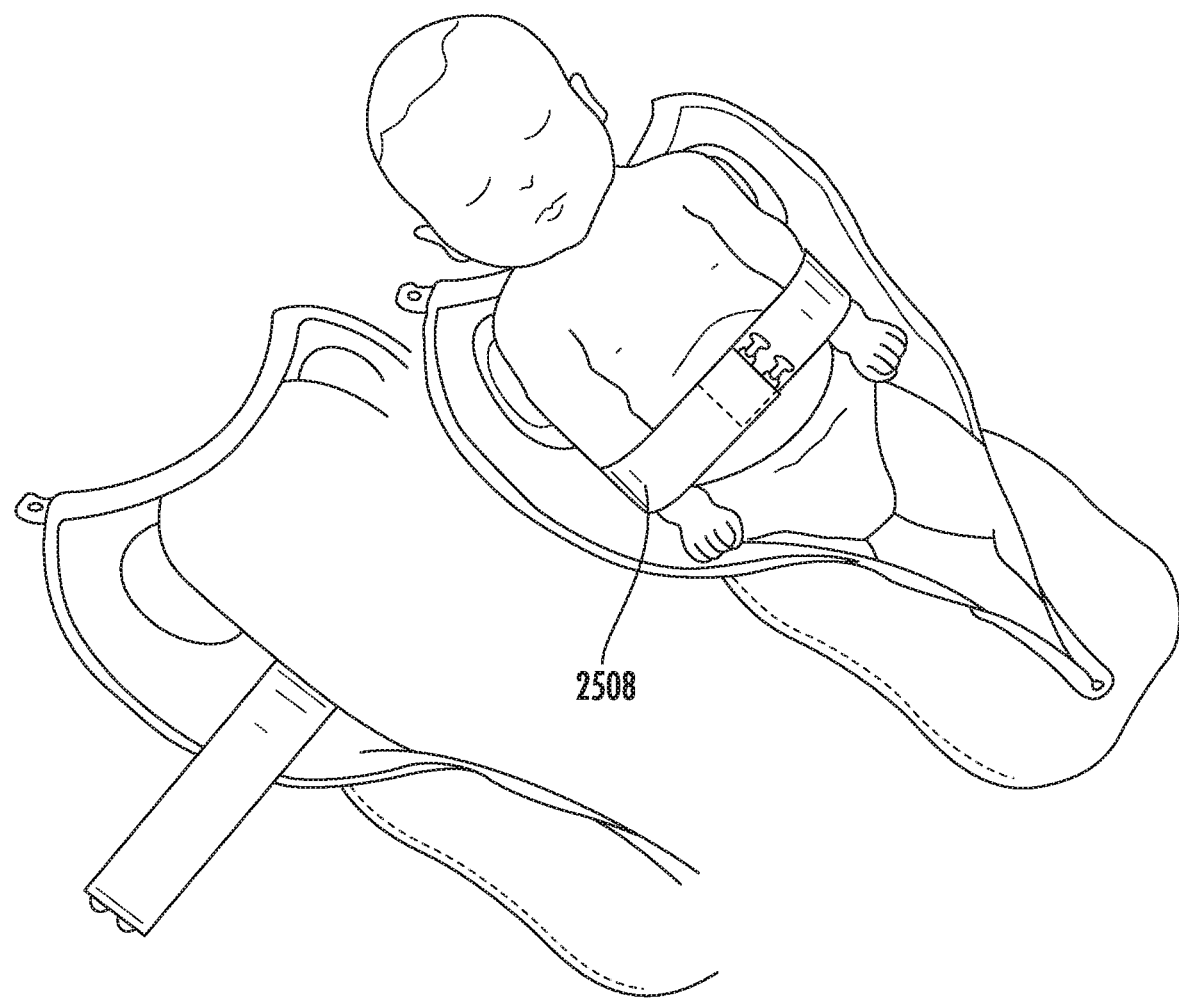

FIGS. 25A-25L illustrate various features of sleep sacks according to illustrative and non-limiting embodiments. FIG. 25A illustrates a front view of a sleep sack in a closed position with an infant inside of the sleep sack. FIG. 25B illustrates a front view of the sleep sack in an open position with an infant inside the sleep sack. FIG. 25C illustrates a back view of the sleep sack with an infant inside the sleep sack. FIGS. 25D-25E illustrate front views of the sleep sack in a closed position. FIG. 25F illustrates a front view of the sleep sack where the sleep sack is wider in the upper portion of the lower half (in the hip region) to allow for the hips of the infant to flex and open. FIG. 25H illustrates an infant in the sleep sack and the sleep sack attached to the main moving platform 16. FIG. 25I illustrates a front view of the sleep sack. FIG. 25J illustrates a rear view of the sleep sack. FIG. 25K illustrates a sleep sack having an upper portion that is wider at its widest point than the maximum width of the lower portion. FIG. 25L illustrates a sleep sack have an internal sash to secure the infant's arms at the infant's side.

As illustrated in FIG. 25K, the sleep sack may have an upper portion and a lower portion separated by a center indentation 2504 near a midpoint of the vertical length. The center indentation may be located approximately 10 inches up from the bottom of the sleep sack. At a widest point of the upper portion 2502, the upper portion may be wider than a widest point of the lower portion 2506. The greater width of the upper portion, which may be in the order of approximately 0.5 inches greater between the widest points of the upper and lower portions, may facilitate swaddling an infant with their arms at their side even if the infant is also wearing a sleeper (for example, in a cold climate or unheated room). In an illustrative and non-limiting example, this may mean that the sleep sack is approximately 11 inches at the widest point in the upper half, 10.5 inches at the widest point on the bottom half and approximately 9 inches in width at a center indentation.

As illustrated in FIG. 25L, the sleep sack may have a two-part internal sash 2508 with a hook and eye closure that may be used to secure an infant's arms at the infant's side.

The sleep sack is intended to be closed once the infant's arms are secured to his or her side.

Figure 25M:
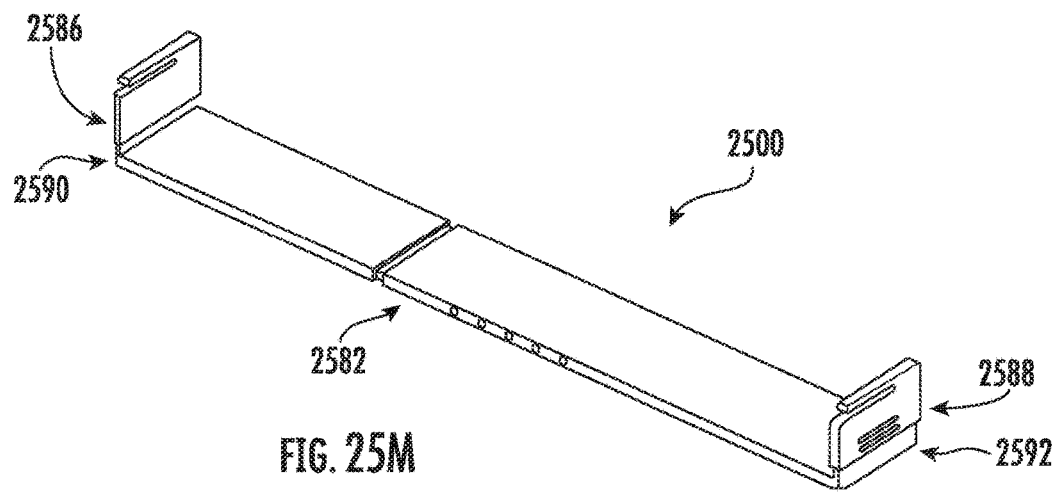
FIG. 25M is an exemplary sleep sack attachment device.
Figure 25N:
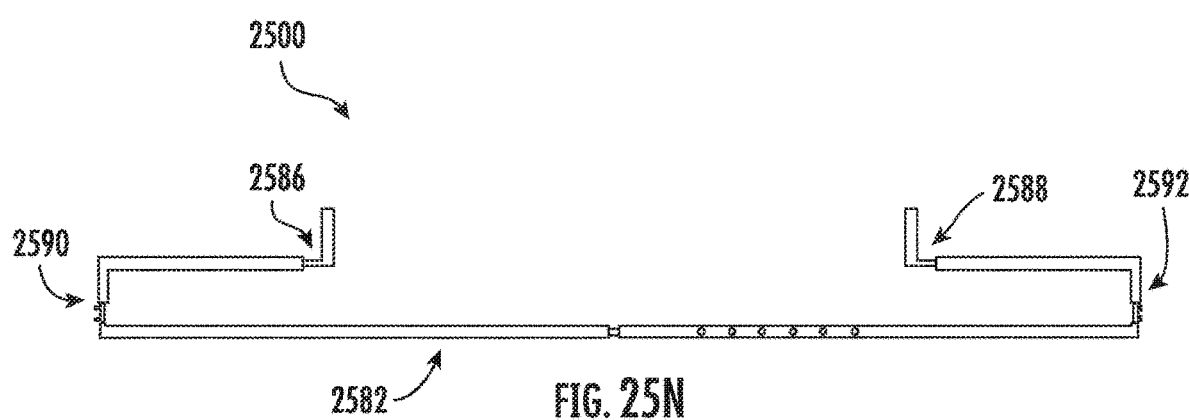
FIGS. 25N-O illustrate another exemplary sleep sack attachment device.
Figure 25O:
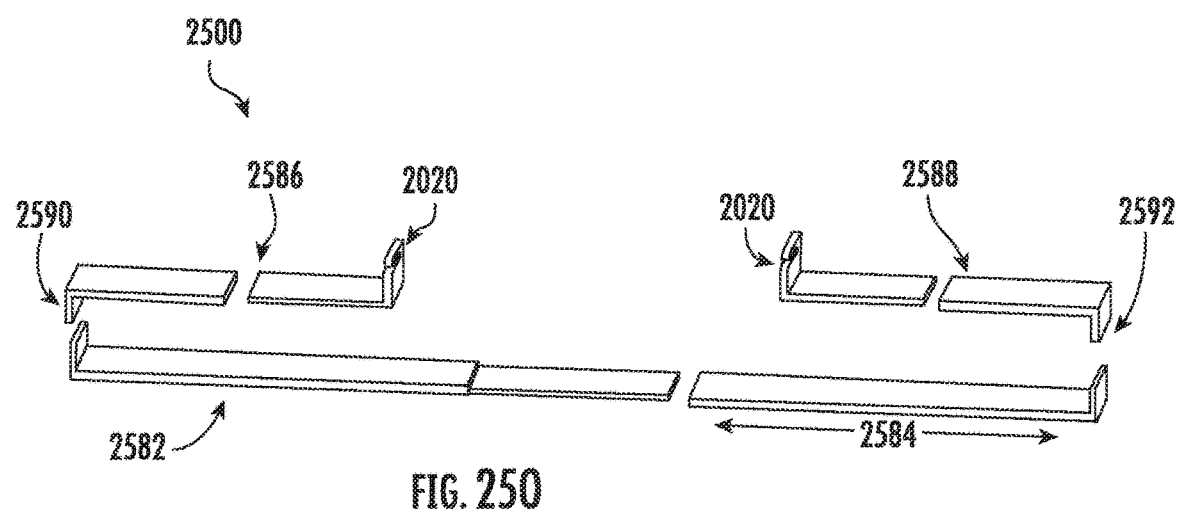
Figure 25R:
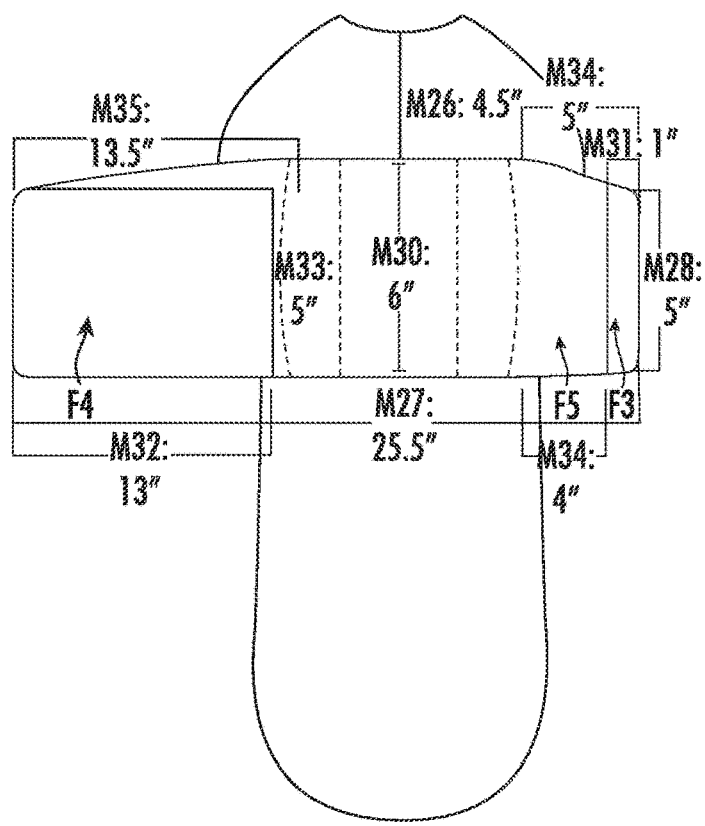
Figure 25S:
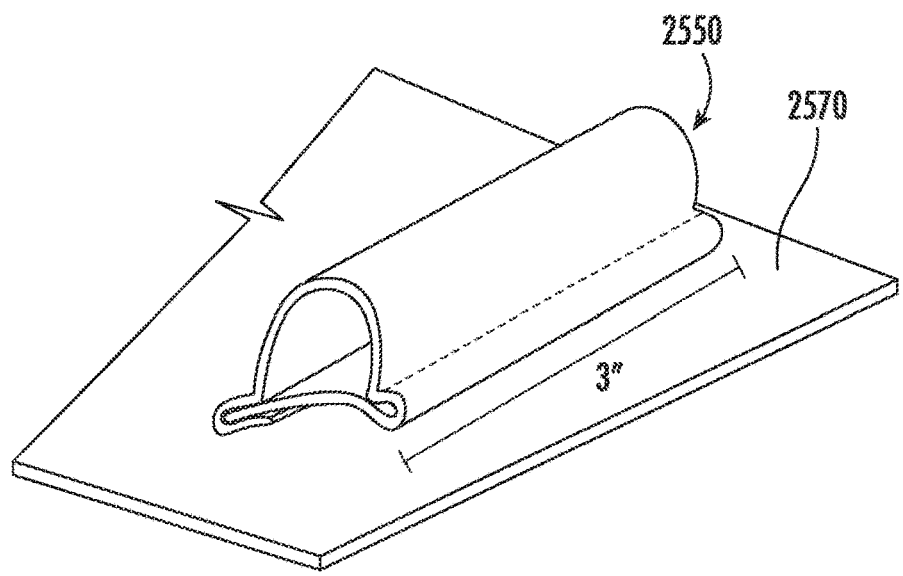

FIG. 25P through FIG. 25R illustrate another exemplary sleep sack, where F1 indicates a cotton material, F2 indicates a mesh polyester material, F3 indicates male Velcro, F4 indicates female loop fabric, F5 indicates cotton poplin material, F6 and F7 indicate cotton bindings. FIG. 25S illustrates an exemplary elastic wing attachment mechanism.

The sleep sack may be available in different designs. Designs may be printed designs. Printed designs may non-threatening designs. Non-threatening designs may be animal designs, angel designs, wings, and the like. Designs may be available with options, changeable, engaging, and the like. The sleep sack may be available in various materials. Material may include a woven jersey cotton spandex material. Materials may include a mesh component, be adapted for the seasons, and the like. A mesh component may be a cooling component, a breathable component, and the like. Mesh may prevent overheating and reduces the risk of suffocation. The breathable component may include active airflow to increase breathability. Adaptability for the seasons may include adaptability for warm temperatures, cold temperatures, and the like. The sleep sack may include interior sleeves.

The sleep sack may be used in a regular crib or bassinet with a sleep sack attachment device 2500, such as shown in FIGS. 25M through 25O, to prevent a baby from rolling over and keep the baby sleeping on his or her back, as recommended the American Academy of pediatrics as the safest position. For example, FIG. 25M and FIGS. 25N-25O illustrate two different example configurations of a sleep sack attachment device. Referring to FIG. 25M-O, which are a perspective view, a side view, and an exploded view of the device 2500 respectively, an embodiment may include a lower portion 2582 configured to be disposed beneath a mattress (not shown), the lower portion 2582 slidably extendible in a lateral direction 2584. The sleep sack attachment device 2500 may further include first and second upper portions 2586 and 2588 configured to be removably coupled to the attachment mechanism 2550 of the sleep sack 2560, which is illustrated in FIG. 25P-S. The sleep sack attachment device 2500 may further include first and second side portions 2590, 2592 extending generally in a direction perpendicular to the lateral direction 2584 and connecting the respective first and second upper portions 2586, 2588 to the lower portion 2582. In an embodiment, the first and second upper portions 2586, 2588 may have attachment means 2020 to engage with the sleep sack 2560. In an embodiment, the attachment means 2020 may comprise safety clips as illustrated to engage with a sleep sack 2560 having wings 2570 with loops 2550 as illustrated. In an embodiment, a configuration of the sleep sack attachment device 2500 allows for adjustment of the width of the device, in order to accommodate various widths of mattresses in different cribs or bassinets. For example, a lateral adjustment of an extension of the lower portion 2582 adjusts lateral positions of the first and second side portions 2590, 2592 whereby the mattress (not shown) would fit between the first and second side portions 2590, 2592. As shown in FIGS. 25N-25O, the sleep sack attachment device may also include other adjustable dimensions, in order to accommodate various widths/sizes of the sleep sack itself. For example, the first and second upper portions 2586, 2588 and the first and second side portions 2590, 2592 are slidably connected, respectively, such that lateral positions of the first and second upper portions 2586, 2588 are adjustable independent of the extension of the lower portion 2582. Various different types of securing means or safety clips to secure the sleep sack to the attachment device are also envisioned. For example, the attachment device may include loops such that the loops can be secured to safety clips on a sleep sack.

The infant calming/sleep-aid device 158 may have selectable modes. Selectable modes may be selected with an algorithm. The algorithm set point may be based on the age of the infant. The infant calming/sleep-aid device 158 may ask for dates of the infant from a user. Dates of the infant may be due date, birth date, and the like. The infant calming/sleep-aid device may ask the user if the infant was born early, late, and the like. Age of the infant may be based on the age inputs. Age inputs may be dates of the infant, if the infant was born, early, late, and the like. Algorithm set point may be calculated by asking the age of the infant, then subtracting the age of the infant from the birth date of the infant. Algorithm set point may also be calculated by setting the birth date of the infant to the due date of the infant. Age of the infant may be provided in months, weeks, days, and the like.

The infant calming/sleep-aid device 158 may have a start mode. Start mode may be initiated when the infant calming/sleep-aid device 158 is turned on to operate and may be based on the age of the infant. Start mode for an infant less than 0 months old may be Baseline and may not go higher than Intervention2. Start mode for an infant that is between 0 and 0.5 months may be Initial1 and may not go higher than Intervention2. Start mode for an infant that is between 0.5 and 3 months may be Initial1. Start mode for an infant between 3 and 4 months may be Baseline or Initial1 if Baseline Boost is active. Start mode for an infant that is older than 4 months may be initial 1 with 1.0 Hz motion and may then use no motion and normal sound in Baseline. Normal sound may be 68 dB Rain on the Roof.

Selectable modes may be modified by a Baseline Boost setting. Baseline Boost setting may be based on the age of the infant. Baseline boost for an infant that is younger than 0 months may not be activated. Baseline Boost setting for an infant that is between 0 and 1 month may cause the infant calming/sleep-ad device 158 to start in Initial1 when switched on and may use Initial1 settings in Baseline. Baseline Boost setting for an infant that is between 1 and 3 months may cause the infant calming/sleep-ad device 158 to start with a more robust level of sound, or motion, or both. This level may be equivalent to Initial1 when the device is switched on and may use 1.0-2.0 Hz motion and 70 dB sound settings in Baseline. Baseline Boost setting for an infant that is between 3 and 4 months may cause the infant calming/sleep-ad device 158 to start in Initial1 with 1.0-2.0 Hz motion setting when switched on and may then use normal settings in Baseline. Baseline Boost setting for an infant that older than 4 months may cause the infant calming/sleep-ad device 158 to start in Initial1 with 0.5-1.5 Hz motion when switched on and may use no motion and normal sound settings in Baseline. Normal sound may be 68-74 dB Rain on the Roof sound.

When Baseline Boost is set for an extended setting, it may automatically revert to default after 14 days of activation, immediately, and the like. Revert to default immediately may occur when the infant calming/sleep-aid device 158 is reset for a new infant.

Selectable modes may include Baseline, Intervention1, Intervention2, Intervention3, Intervention4, and the like. Baseline mode settings may be based on the age of the infant. Baseline mode settings for an infant between 0 and 1 month may be 1.0 Hz motion and Rain on the Roof at 70 dB sound, for an infant between 1 and 4 months 1.0 Hz motion and Rain of the Roof at 68 dB sound, for an infant older than 4 months 0.0 Hz motion and Rain on the Roof at 68 dB sound, and the like. Baseline when Baseline Boost is activated for an infant between 0 and 1 month may be 2.0 Hz motion and Rain on the Roof at 72 dB sound, for an infant between 1 and 3 months 2.0 Hz motion and 70 dB Rain on the Roof sound, and the like. Baseline may step up to Intervention1 if Crying_D1 is detected. Crying_D1 may trigger at 0.6 accumulated seconds of Crying Audio Classification time during a period of 6 seconds, and the like.

Intervention1 may be 2.5 Hz motion and Rain on the Roof at 72 dB sound. Intervention1 may step up to Intervention2 if Crying_D1 is detected, otherwise go to CoolDown3 after 8 minutes.

Intervention2 settings may be based on the age of the infant. Intervention2 settings for an infant younger than 0.5 months may be 2.8 Hz motion and Strong Hair Drier sound at 75 dB, may switch to Timeout if Crying_D2 is detected in the last 10 seconds (3:50 to 4:00), otherwise step to CoolDown2 after 4 minutes, and the like. Crying_D2 may trigger at 1.2 accumulated seconds of Crying Audio Classification time in a period of 6 seconds, and the like.

Intervention2 settings for an infant between 0.5 and 1 month may be 2.8 Hz motion and Strong Hair Drier sound at 75 dB, may step up to Intervention3 if Crying_D2 is detected, otherwise go to CoolDown2 after 4 minutes, and the like. Intervention2 settings for an infant older than 1 month may be 3.0 Hz motion and Strong Hair Drier sound at 75 dB, may step up to Intervention3 if Crying_D2 is detected, otherwise go to CoolDown2 after 4 minutes, and the like.

Intervention3 settings may be based on the age of the infant. Intervention3 settings for an infant between 0.5 and 1 month may be 2.8 Hz motion and Fast and Vigorous sound at 79 dB, and the like. Intervention3 settings for an infant older than 1 month may be 3.25 Hz motion and Fast and Vigorous sound at 79 dB, may switch to Timeout if Crying_D2 is detected in last 10 seconds (2:20 to 2:30), present user option to use Intervention4, otherwise Step to CoolDown1 after 2.5 minutes, and the like. CoolDown1 settings may be based on the age of the infant. CoolDown1 settings for an infant between 0.5 and 1 month may be 2.8 Hz motion, Strong Hair Drier 75 dB sound, for an infant older than 1 month 3.0 Hz motion and Strong Hair Drier 75 dB sound, and the like. CoolDown1 may step up to Intervention3 if Crying_D2 is detected, otherwise go to CoolDown2 after 4 minutes, and the like. CoolDown2 may be 2.5 Hz motion and Strong Hair Drier sound at 72 dB and the like. CoolDown2 may step up to Intervention2 if Crying_D2 is detected, otherwise go to CoolDown3 after 8 minutes, and the like. CoolDown3 settings may be 1.8 Hz, Rain on the Roof sound at 70 dB, and the like. CoolDown3 may step up to Intervention1 if Crying_D2 is detected, otherwise got to Baseline after 12 minutes, and the like.

Intervention4 may be only manually activated. Intervention4 settings may be based on the age of an infant. Intervention4 settings for an infant between 0.5 and 1 month of age may be 2.8 Hz Fast and Vigorous at 81 dB sound, for an infant older than 1 month 3.25 Hz Fast and Vigorous sound at 85 dB, and the like. Intervention4 may switch to Timeout if Crying_D2 in last 10 seconds (1:50 to 2:00) is detected, otherwise return to regular operation by autostepping to Intervention3 after 2 minutes, and the like.

Timeout may be no alarm, alarm noise then silence, and the like. Alarm noise may be 6 beeps with 1 second timing between beeps, 4 second pause, 3 beeps with 1 second timing between the beeps, and the like. Timeout may also include an LED. LED may be a red LED, flashing until the infant calming/sleep-aid device 158 is reset by the user, and the like.

The infant calming/sleep-aid device 2258 may include other safety mechanisms that may impact the selection and activation of the operational modes. Other safety mechanisms that may impact the selection and activation of the operational modes may include shutting off if Intervention3 has ended and the infant is still crying, shutting off if Intervention4 has ended and the infant is still crying, not starting if the sleep sack is not properly engaged, not starting if the infant's head is not sensed to be in the proper location, stopping if the infant's head is sensed to no longer be in the proper location, not starting if the infant calming/sleep-aid device 2258 has been activated for longer than 6 hours in the day for the first two months, may not start if a sensor detects that the baby is not aligned properly in the infant calming/sleep-aid device 2258, and the like. If the infant calming/sleep-aid device 2258 has shut off because either Intervention3 or Intervention4 has ended and the infant is still crying, the infant calming/sleep-aid device 2258 may be reset, in order to allow the infant calming/sleep-aid device 2258 to be activated again.

The infant calming/sleep-aid device 2258 may include protocols, profiles, components, and add-on's. Protocols may be based on the age of the infant and how upset the infant is. Protocols may be based on functions. Functions may be motion functions, sound functions, light indicator functions, ambient light sensor functions, light generation functions, or combinations of functions. Light indicator functions may be a night light, an indicator to provide a warning to a user when the user is shaking the infant calming/sleep-aid device 2258, an indicator to signal which intervention levels are being delivered, and the like. The indicator to provide a warning to a user when the user is shaking the infant calming/sleep-aid device 2258 may indicate that the level of shaking may be unsafe. Light indicator functions may be integrated with the infant calming/sleep-aid device 2258, displayed on a connected device, and the like. A connected device may be a smartphone, tablet computer, and the like. Ambient light sensor functions may be integrated with the infant calming/sleep-aid device 2258, located on a connected device, and the like. Light generation functions may be functional, aesthetic, and the like. Functional light generation functions may illuminate the user interface of the infant calming/sleep-aid device 2258, provide an orange melatonin inducing night light, and the like. Profiles may be based on knowledge of an infant profile, user override using preferences, and the like. User override may provide the user with several choices to override and raise the baseline intervention. Components may be cords, batteries, motors, and the like. Cords may be breakaway cords, retractable cords, and the like. Batteries may be rechargeable as an option for sound, and the like. Add-on's may be cameras, scales, measuring devices, a kit for turning the infant calming/sleep aid device 2258 into a crib, playpen, or the like, extra blankets, sheets, skins, parts, a travel bag, and the like.

The infant calming/sleep-aid device 2258 may facilitate interface integration. Interface integration may facilitate integration with interfaces such as Bluetooth interfaces, hard-wired interfaces, home automation network interfaces, monitors, and the like. Hard-wired interfaces may include hard-wired splitter interfaces. Monitors may include carbon monoxide monitors, safety monitors, and the like. Safety monitors may include home safety monitors, baby safety monitors, child safety monitors, and the like.

The infant calming/sleep-aid device 2258 may comprise a user interface. The user interface may comprise a control panel. The control panel may control options such as motor speed, modulation, speaker output, and the like. The control panel may comprise knobs, switches, lights, motion activation, sound activation, interfaces to drive electronics and other I/O methods.

The infant calming/sleep-aid device 2258 may comprise sub-assembly components. Such components may comprise amplitude modulation components, screws, gears, nut frames, springs, and the like.

The infant calming/sleep-aid device 2258 may comprise a head platform. The head platform may passively rotate. The head platform may comprise a spring system using injection molded plastic as the spring/damper to reduce noise and parts required. The head platform may comprise a plurality of dampers. The head platform may comprise a covering. The cover may be flexible, cloth, foam, or the like. The head platform may comprise joint connectors, such as, but not limited to, hinge and rod connectors. The head platform may comprise bearings such as, but not limited to rotation and head rotation bearings. The head platform may comprise wraps. The wraps may comprise swaddling wraps, fastening wraps, and the like.

The infant calming/sleep-aid device 2258 may comprise an enclosure around a sleep surface. One embodiment may have a light mesh veil/mosquito netting over the top of the device. One embodiment may have an ornamental animal head and tail that may be attached onto the device. The sleep surface may comprise a position stabilizer. The surface may secure a baby in supine position to prevent unraveling or rolling and to maintain optimal stimulation positioning. The infant calming/sleep-aid device 2258 may comprise a single head platform which may passively rotate and which may be constrained by springs or dampers. The sleep surface body platform made from flexible cloth covering or flexible foam padding. In embodiment, the sleep surface may comprise a movable joint connector using hinges, rods, or the like. In embodiments, the sleep surface may comprise a support platform. In embodiments, the sleep surface may comprise bearings. In embodiments, the sleep surface may comprise a special head insert to reduce pressure on back of skull. In embodiments, the infant calming/sleep-aid device may comprise adjustable legs allowing variable height configurations. In embodiments, the sleep surface may comprise a secure sleep sack. In embodiments, the sleep surface may interact with an electronically programmable interface system. The interface system may comprise a control panel. The control panel may comprise switches, lights, and other I/O interface capabilities. The interface system may comprise automated programming selections or may allow a user to select device settings, such as duration. In embodiments, the sleep surface may comprise drive electronics to control drive motor speed, an amplitude modulation motor, and speaker audio output. Speaker outputs may comprise specified equalizer settings i.e. the use of special sound profiles to promote sleep and reduce crying. In embodiments, the sleep surface may comprise plates such as drive plates or swing arm plates, among others. In embodiments, the sleep surface may comprise a push or pull rod. In embodiments, the sleep surface may comprise drive motor connections to different drive types such as clamps, bearings, pins, among others. In embodiments, the sleep surface may comprise an elastic actuator catch bracket. In embodiments, the sleep surface may comprise a sub-assembly to directly control the amplitude output of the main rotating platform. The sub-assembly may comprise components such as, but not limited to, amplitude modulation rotational bearings, acme screws, acme nuts, acme nut frames, and gears. In embodiments, the sleep surface may comprise an amplitude modulation motor.

The infant calming/sleep-aid device 2258 may comprise a motion generation and drive mechanism for a crib. The mechanism may comprise an electronic motor. The motor may be isolated from proximity to the baby for EMR shielding. The mechanism's movement may take into account wear and tear. The mechanism may comprise elastic walls to move with the mattress. The mechanism may comprise a swing arm crank shaft either directly or indirectly attached to the motor. The mechanism may comprise a plurality of springs such as injected plastic springs. The mechanism may have stability components in order to compensate for interactions with the stand and the environment. The mechanism may move in a sinusoidal motion when the infant is asleep and a non-sinusoidal motion when the infant is awake or crying, to attempt to calm the child down. The mechanism may operate with a direct amplitude adjustment or may operate without such direct adjustments. Direct amplitude adjustment settings may comprise a slow and large amplitude setting (e.g. 30 cycles per minute and 6 cm/cycle at the head), a fast and short amplitude setting (e.g. 150 cycles per minute and 3 cm/cycle at the head), a rapid and short amplitude setting (e.g. 180 cycles per minute and 2 cm/cycle at the head), among other combinations (e.g. 4.5 Hz, 270 cpm, range 150-270 cpm). The mechanism may comprise an accelerometer in order to measure head movement. In embodiments, the mechanism may work in conjunction with sensors placed under a mattress to detect when or if an infant is in the crib without being secured in the sleep sack. The mechanism may stop movement if the sensors detect that the infant is in a compromised position or if the infant is no longer in the sleep sack. Movement may also stop when a calming movement mode has been completed and the infant is still crying. In embodiments, users may not be able to manually select movements and may warn users if safety parameters are not met, such as excessive acceleration or unsafe frequency. In embodiments, a manual override may be provided to uncouple the motion generator if a motion is undesirable The infant calming/sleep-aid device 2258 may comprise a crib sound system. In embodiments, equalizer settings may be provided for optimal pitch profiles (e.g. sound levels are mixed with increasing high pitch profiles as a baby cries more). The sound system may comprise one or more speakers and may generate sounds similar to those hard by the babies in utero. For example, sounds may be generated to replicate the turbulence of blood flowing through uterine and umbilical arteries. In embodiments, the high frequency component may be diminished (e.g. 65 to 70 dB with a profile predominantly about <500 Hz). In other embodiments, the system may be capable of a harsher sound (e.g. 70 to 75 dB with a profile predominantly about <1000 Hz) or a multi-frequency sound (e.g. 75 to 80 dB with a profile from 0 to 16000 Hz). In embodiments, the system may be calibrated not to exceed 85 dB at the infant's head, not to exceed more than 18 hours a day to prevent overuse and not to exceed 85 dB for longer than 20 minutes of an hour. If such levels are exceeded, a notification may be provided to a user in order to stop usage. In embodiments, the speaker may make an alarm sound when the device times out. In embodiments, the sound system may comprise variable volume controls. In embodiments, the sound system may be able to detect sounds. Such detections may be conducted by microphones to sense warnings, to hear a child, or to indicate the duration a child has been crying, among other uses. The sound system may be used to conduct analysis on such detections. In embodiments, the sound system may be battery operated. Sounds may be imported into sound interface applications, such as Dolby Advanced Audio v2, to provide music, voices, singing as an overtone, or interactively talk to the infant via the application API. In embodiments, the sound system may be removed or dampened.

In embodiments, the infant calming/sleep-aid device 2258 may comprise microprocessors for use in the crib. Microprocessors may be used to differentiate sounds, such as infant sounds, system sounds, or ambient noise. Microprocessors may be used to record and analyze sounds. Such sounds may include sounds which reflect a baby's state (e.g. sleeping, crying) or to provide feedback. Microprocessors may be used to generate responses and deliver the optimal mix of sound and motion for a specific. For example, a user may implement an initial combination of sound and motion for the first few uses, then switch to a different program based on a child's reaction to the uses. Microprocessors may be used to respond to changing states, such as to calm crying, reduce sleep latency, increase sleep efficiency, among others. Microprocessors may also be used to wean infants off of motion and sound as they age. For example, the device may increase sound and motion as child gets older and then automatically wean the baby off motion as he or she gets over 4 months. The device may also react to incidents of waking and reduced crying. Microprocessors may take in inputs such as the weight of an infant, age of infant, whether the infant was delivered on time, the duration of detected sound made by infant, the duration of detected motion of infant, the desired motion state, the sensed motion frequency, the amplitude of main platform, the desired system speed, whether motion of main rotating platform exceeds safety threshold, and the like. The microprocessor may generate outputs such as motor control, audio responses and visual signals.

The infant calming/sleep-aid device 2258 may comprise a mechanism for the more square waveform generation for a crib. Such a mechanism may be enabled by flexible joint connecting head and body platform. The main rotating platform may use a variety of variables to determine the waveform generation, such as weight of infant, drive motor frequency, balancing compression spring force constant, as well as other variables.

The infant calming/sleep-aid device 2258 may rely on several algorithms in order to generate outputs to calm an infant. The device may analyze certain output combinations that have succeeded, store such combinations, and then replicate these combinations. The device may create profiles based on knowledge of a child's physiological or behavioral parameters or based on a parent or user's overrides and preferences, among a variety of other parameters.

The infant calming/sleep-aid device 2258 may comprise a motion analysis module. The module may comprise a motion amplitude estimate signal, a threshold-crossing based motion frequency estimator, a time-based filter, a digital filter bank, a filtered accelerometer data signal, and a motion frequency estimate signal among others. The infant calming/sleep-aid device 2258 may comprise a behavior state machine module, an audio generation module, a crying detection module, and the like. The crying detection module may comprise a digital band-pass filter and a time-based filter.

The infant calming/sleep-aid device 2258 may comprise a mattress for a crib. The mattress may be made from organic materials such as organic latex, coconut fiber, or polyethylene, and may comprise a gel pad for the head. The mattress may be created for firmness or softness preferences, and may also be waterproof. Compatible sheets may be used for the mattress and the mattress may contain circuitry so that it may maintain connectivity with walls, the mattress, and the platform.

The infant calming/sleep-aid device 2258 may be controlled remote by smartphone or other mobile device using communication standards such as Bluetooth. The infant calming/sleep-aid device 2258 may comprise variable motion and sound capabilities as well as a feedback loop and mechanisms to reduce functionality over time. The infant calming/sleep-aid device 2258 may comprise a moving platform and may have a dual range of motion. The infant calming/sleep-aid device 2258 may comprise a plurality of collapsible walls and legs. Such functionality may aid in shipping, travelling, aiding a child to stand, among other uses. The functionality may change depending on the age of the infant or the stroller height/height of the baby's mother. The infant calming/sleep-aid device 2258 may comprise handles, wheels, and legs that may be extendable, adjustable, or collapsible. The infant calming/sleep-aid device 2258 may comprise trolley functionality to transform the device into a stroller or it may comprise a crib functionality to transform the device into a crib. The infant calming/sleep-aid device 2258 may comprise wheels for transport. The infant calming/sleep-aid device 2258 may comprise a removable motor. The infant calming/sleep-aid device 2258 may comprise flexible and removable mesh components. One embodiment envisions the ability to re-obtain back units and refurbish them to resell on a secondary market.

In embodiments, the infant calming/sleep-aid device 2258 may generate a plurality of outputs. Such outputs may be user modes such as movement modes. Movement modes may comprise short and large amplitude modes, fast and short amplitude modes and rapid and short amplitude modes, among others. Outputs may also comprise sound modes such as modes where the high frequency component is diminished, modes that produce a harsher sound and modes that produce a multi-frequency sound.

The infant calming/sleep-aid device 2258 may comprise sensors such as, but not limited to, audio sensors, motion sensors, biometric, a camera, other third-party sensors, flexible sensors, accelerometers, a warning system, and a manual override. The infant calming/sleep-aid device 2258 may comprise certain product add on components such as a camera, a scale, an ambient temperature thermometer, a heart rate monitor, a respiratory rate monitor, an oxygen monitor, a measuring device, a kit for turning the device into a crib, a kit for turning the device into a playpen, extra accessories, a microphone, and sound importing capabilities, such as music, voices, singing, and interactive talking via an API. In embodiments, device components may be removable. The infant calming/sleep-aid device 2258 may comprise an electrical cord that may be able to break away or may be retractable. The infant calming/sleep-aid device 2258 may comprise batteries, and in embodiments, batteries which may be rechargeable. The infant calming/sleep-aid device 2258 may comprise light indicators such as a night light, or a shaking detection light, ambient light sensors, functional lights (e.g. to light up the user interface, to induce melatonin, to assess manual jiggle, to function as a stroller light), and lights to signal that an intervention level is being delivered. The infant calming/sleep-aid device 2258 may comprise several different aesthetic features, such as changing designs.

The infant calming/sleep-aid device 2258 may employ a plurality of different parameters. In embodiments, sound and motion ranges may be restricted. In embodiments, the device may use different thresholds or triggers to deliver output. Such triggers may include sensory inputs, behavioral inputs, variational inputs, head movement, acceleration, frequency, amplitude, rotation, safety, number of waking incidents, number of crying incidents, abnormal biometric readings and an infant's measurements, among others. Variational inputs may include individual variations, optimal stimulus level data, and state data such as type of sleep, drowsiness, quietness, fussing, or crying. The infant calming/sleep-aid device 2258 may rely on duration inputs for sound and motion. The infant calming/sleep-aid device 2258 may rely on target inputs such as desired motion state or desired system speed. The infant calming/sleep-aid device 2258 may rely on noise detection from the system, infant, or ambient noise and also rely on biometric sensors. The device may differentiate between multiple types of noise. The infant calming/sleep-aid device 2258 may rely on filters such as band-pass, digital band-pass, time-based, a filter bank, or a digital filter bank, among others.

The infant calming/sleep-aid device 2258 may comprise materials such as flexible mesh and seasonal materials. Such materials may be warm, light, or breathable depending on the environment in which the device is deployed.

The infant calming/sleep-aid device 2258 may be deployed for several uses such as, but not limited to monitoring, reporting, control, analytics, reports/statistics, sharing/groups, benchmarking/comparison, graphics, acoustic signature of the cry, organizational data, expert feedback, communications (e.g. walkie-talkie), providing alerts (e.g. warning alerts, health concern alerts), overtone customization of the white noise, photo/video/audio input, journal sharing/printout, automatize diaper/formula ordering online, weight determination, breastfeeding determination, and image capturing uses, among others.

The infant calming/sleep-aid device 2258 may be integrated to work with a smartphone or other similar mobile device. The device may communicate with the mobile device using methods such as USB, Bluetooth, and Wi-Fi, among others. The mobile phone may be used to input information such as weight (at birth and longitudinal weight), length (at birth and longitudinal), head size (at birth and longitudinal), the frequency of feeding, frequency of diaper changes and sleep behavior, among others. User may be able to use their mobile device to instantly create and share graphic displays of their baby's sleep pattern over different periods of time, among many other uses.

While this disclosure has been particularly shown and described with references to example embodiments thereof, it will be understood by those skilled the art that various changes in form and details may be made therein without departing from the scope of the disclosure encompassed by the appended claims.

While the disclosure has been disclosed in connection with the preferred embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

The use of the terms "a" and "an" and "the" and similar referents in the context of describing the disclosure (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above described embodiment, method, and examples, but by all embodiments and methods within the scope and spirit of the disclosure.

All documents referenced herein are hereby incorporated by reference.

What is claimed is:

1. A sleep sack attachment system for securing a sleep sack, the system comprising:
    an attachment device configured to removably attach to the sleep sack to stably secure the sleep sack along a surface of a mattress, the attachment device comprising:
        a lower portion having a lateral extending length and configured to be disposed beneath the mattress, the lower portion slidably extendible to adjust the lateral extending length of the lower portion;
        first and second upper portions configured to be removably coupled to the sleep sack; and
        first and second side portions extending generally in a direction perpendicular to the lateral extending length of the lower portion and connecting the respective first and second upper portions to the lower portion;
        wherein a lateral adjustment of an extension of the lateral extending length of the lower portion adjusts lateral positions of the first and second side portions whereby the mattress fits between the first and second side portions.

2. The system of claim 1, wherein the system further includes the sleep sack comprising a body for receiving an infant and wings that laterally extend from the body, wherein the first and second upper portions are configured to attach to an attachment mechanism positioned on each of the wings, wherein the first and second upper portions and the respective first and second side portions are slidably connected such that lateral positions of the first and second upper portions are adjustable independent of a lateral adjustment of the extension of the lower portion.

3. The system of claim 1, wherein the first and second upper portions and the respective first and second side portions are slidably connected such that lateral positions of the first and second upper portions are adjustable independent of a lateral adjustment of the extension of the lower portion.

4. The system of claim 1, wherein the first and second upper portions each comprise a clip configured to engage with an attachment mechanism of the sleep sack.

5. The system of claim 4, wherein the system further includes the sleep sack, wherein the sleep sack comprises wings that extend laterally from a body of the sleep sack that is configured to receive an infant, and Wherein the attachment mechanism comprises a loop positioned on the wings.

6. The system of claim 1, wherein the first and second upper portions each comprise a loop configured to engage with an attachment mechanism of the sleep sack.

7. The system of claim 6, wherein the system further includes the sleep sack, wherein the sleep sack comprises wings that extend laterally from a body of the sleep sack that is configured to receive an infant, and wherein the attachment mechanism comprises a clip positioned on the wings.

8. The system of claim 1, wherein the first and second upper portions extend laterally inward from the respective first and second side portions such that the first and second upper portions extend laterally above the lower portion.

9. The system of claim 8, wherein the first and second upper portions and the respective first and second side portions are slidably connected such that lateral inward positions of the first and second upper portions are adjustable independent of a lateral adjustment of the extension of the lower portion.

* * * * *